United States Patent [19]
Busch

[11] Patent Number: 4,888,032
[45] Date of Patent: Dec. 19, 1989

[54] SALTS OF CATIONIC-METAL DRY CAVE COMPLEXES

[75] Inventor: Daryle H. Busch, Columbus, Ohio

[73] Assignee: The Ohio State University Research Foundation, Columbus, Ohio

[21] Appl. No.: 571,812

[22] Filed: Jan. 18, 1984

Related U.S. Application Data

[63] Continuation-in-part of Ser. No. 114,670, Jan. 23, 1980, abandoned.

[51] Int. Cl.$^4$ .................. C01B 13/0; C01B 21/04; B01D 19/00; B01D 53/34
[52] U.S. Cl. .................... 55/38; 55/43; 55/53; 55/68; 252/181.6; 252/181.7; 252/188.28; 423/219; 423/579; 502/34; 556/45; 556/50; 556/110; 556/138
[58] Field of Search ............ 55/16, 68, 75, 97; 252/181.6, 181.7, 188.28; 423/219, 579; 502/34; 556/45, 50, 110, 138

[56] References Cited

U.S. PATENT DOCUMENTS 3,396,150  8/1968  Ward et al. .............. 528/53
4,451,270  5/1984  Roman .................... 55/38

OTHER PUBLICATIONS

Chem. Eng., 7-13-81, 63.
Parell, Technology, Mar./Apr. 81, p. 16.
Scholander, Science, 131,585 (1960).
Basselt et al., Biochim. Biophys. Acta., 211, 194 (1970).
Science News, 3-6-82, p. 151.
Bend Research, Technical Brief, Oxygen Enrichment, (Autumn 1981).
Jones et al., Chemical Review 79(2), 139-179 (1979).
Schammel Ph.D. Thesis (1976).
Busch et al., Reprint of ACS Symposium Series #38, p. 3, ACS (1977).
Jager, Z. Anorg. Allg. Chem 346, 76 (1976).
Jager, Z. Chem. 8, 30, 392 (1968).
Riley et al., Inorganic Synthesis 18, 36 (1978).
Strecky, Thesis (1979).
Corfield et al., J.A.C.S., 95, 4465 (1973).
Eilmex et al., Bultelin de L'Academic Polonaise . . . 6, 441 (1978).
Hiller et al., Liebigs Ann. Chem, 717, 137 (1968).
Tang, Inorg. Chem., 12, 2589-95 (1973).
Crumbliss et al., Science 164, 1168 (1969).
Crumbliss et al., J.A.C.S. 92, 55 (1970).
Pignatello et al., J.A.C.S., 101; 5929 (1970).
Wallace et al., J. Biol. Chem., 257, 4966 (1982).
Hoffman et al., J.A.C.S., 92, 61 (1970).

(List continued on next page.)

Primary Examiner—John Kight
Assistant Examiner—Nathan M. Nutter
Attorney, Agent, or Firm—Sidney W. Millard

[57] ABSTRACT

Salts containing cations of the formula:

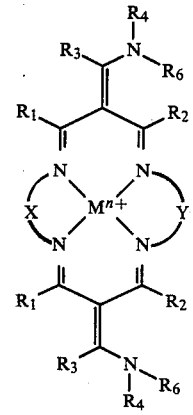

(in which M is Co, Fe, Cr or Mn, X, Y, $R_1$, $R_2$ and $R_4$ are hydrogen, alkyl or substituted groups, and the two $R_3$ groups and/or the two $R_6$ groups form an organic bridging group), and derivatives of these compounds having various axial ligands attached to the metal atom, complex oxygen reversibly and are thus useful for oxygen scavenging and separating oxygen from air. Other types of compounds having similar bridging groups are also useful for the same purpose.

208 Claims, 10 Drawing Sheets

OTHER PUBLICATIONS

Hoffman et al., J.A.C.S., 97, 61 (1970).
Goedker et al., J. Coord. Chem., 7, 89 (1977).
Taylor et al., J.A.C.S., 91, 1072 (1969).
Katovik et al., Inorg. Chem., 10, 458 (1971).
Katovik et al., J.A.C.S., 91, 2122 (1969).
Kamenar et al., Inorg. Chem., 18, 815 (1979).
Madden, Ph.D. Thesis (1975).
Barefiled et al., Inorg. Chem. 12, 2435 (1973).
Barefiled et al., Inorg. Chem., 15, 408 (1976).
Ranasabbu et al., J. Chem. Soc. Chem. Commum. 1982, 277.
Wainwright, J. Chem. Soc., Dalton Trans. 1980, 2117.
Kegpour et al., Inorg. Chem. Acta, 33, L149 (1979).
Green et al., J. Chem. Soc. Chem. Commun., 1968, 518.
Green et al., Inorg. Chim. Acta, 5, 17 (1971).
Black et al., Aust. J. Chem. 23, 2039 (1970).
Lindoy et al., Inorg. Nucl. Chem. Lett. 5, 525 (1969).
Fleischer et al., Inorg. Nucle. 9, 10610 (1973).
Martin et al., J. Chem. Soc., Dalton Trans, 1979, 1497.
Martin et al., J. Chem. Soc., Dalton Trans. 1970, 1503.
Riley, Helo. Chim. Acta 54, 2747 (1971).
Bartlett et al., Helo. Chim. Acta 54, 2753 (1971).
Busch et al., J.A.C.S., 103, 1472 (1981).
Busch et al., Inorg. Chem. 20, 2834 (1981).
Stevens J. C. Ph.D., Dissertation (1979).
Kojima, Post-Doctoral Report (1980).
Zimmer, Ph.D., Thesis (1979).
Jackson, Ph.D., Dissertation (1981).
Dazkiewicz, Post-doctoral Report (1978).
Takeuchi, Ph.D., Dissertation (1981).
Riley, Ph.D. Thesis (1975).
Schammel et al., Inorg. Chem., 19, 3159 (1980).
Busch et al., J.A.C.S., 103, 5107 (1981).
Stevens et al., J.A.C.S., 102, 3285 (1980).
Kunz, Chem. Ber. 60, 367 (1927).
Larkworthy, J.A.C.S., 1981, 4025.
Draker, Nature, 182, 1084.

XVII

XVII A

I

IA

II

II A

III

IIIA

XVIII

XVIIIA

XXII B

XXII C

XXII D

XXII E

SALTS OF CATIONIC-METAL DRY CAVE COMPLEXES

The Government has rights in this invention pursuant to Contract Number CHE-75-14837 awarded by the National Science Foundation.

This application is a continuation-in-part of my copending application Ser. No. 114670 filed Jan. 23, 1980 and now abandoned.

BACKGROUND OF THE INVENTION

Oxygen is produced industrially in enormous quantities from air. Hitherto, substantially all industrially-produced oxygen has been separated from air by condensing the air and then fractionally distilling the liquid air to separate the oxygen from nitrogen and other gases. This liquification procedure consumes very large amounts of energy, since the boiling point of oxygen at atmospheric pressure is only 77° K.

The industrial demand for oxygen is growing and is expected to increase greatly if and when large-scale production of synthetic fuels begins, since most of the processes for liquification of coal and similar methods of producing synthetic fuels require large quantities of oxygen. In view of the known disadvantages of the air liquification process, attention has recently been directed toward methods for the separation of oxygen from air at temperatures much closer to ambient. In principle, such separation methods are very simple; a solution is prepared containing a compound which can complex molecular oxygen in a manner similar to that of the known biological oxygen-containing proteins, myoglobin and hemoglobin, this solution is exposed to air or a similar oxygen-containing gas so that a large proportion of the oxygen-containing compound becomes complexed with oxygen, then the solution is removed from contact with the air and exposed to an environment in which the oxygen partial pressure is less than that in equilibrium with the oxygen-complexed compound, so that the oxygen-complexed compound gives up at least part of its oxygen, thereby releasing into the environment a gas much richer in oxygen than the air with which the solution was originally in contact (a small amount of nitrogen and other gases almost invariably comes over with the oxygen because of the solubility of the other gases in the solution). If further purification is desired, the process can be repeated to yield a gas even richer in oxygen.

Perhaps the most promising techniques for thus separating oxygen from air involve the use of so-called "immobilized liquid membranes". Such immobilized liquid membranes comprise a solid support, typically a synthetic polymer, which is inert to oxygen, together with liquid immobilized on the inert support. The support may have very fine holes therein so that the liquid cannot run through the porous material, a polymer film acting as the support may be swollen by contact with the liquid, or various other techniques may be used for immobilizing the liquid on the support. Air or some other oxygen-containing gas is passed over one side of the immobilized liquid membrane, while the gas which passes through the membrane is removed by pumping on the opposite side of the membrane. The oxygen "diffuses selectively" through the liquid membrane; in fact, since there is an oxygen partial pressure gradient between the two sides of the membrane, the oxygen molecules are carried in the form of a metal complex through the immobilized liquid membrane at a much greater rate than the rate at which other gases pass through the membrane. More detailed descriptions of such immobilized liquid membrane gas separation techniques are given in U.S. Pat. No. 3,396,510 issued August 13, 1968 to Ward et al; Chemical Engineering, July 13, 1981, page 63; Parrett Membranes Succeeding by Separating, Technology, March/April 1982, page 16; Scholander, Science, 131, 585 (1960), Bassett et al, Non-Equilibrium Facilitated Diffusion of Oxygen Through Membranes of Aqueous Cobaltodihistidine, *Biochim. Biophys. Acta.*, 211, 194 (1970); Science News, March 6, 1982, page 151; and a Technical Brief, Oxygen Enrichment, published by Bend Research, Inc., 64550 Research Road, Bend, Oregon 97701 (Autumn 1981): the disclosures of all these documents are herein incorporated by reference.

Heretofore, synthetic oxygen carriers have proven unsuccessful in aqueous solutions. For instance, the many well-known 1:1 dioxygen adducts of cobalt(II) suffer from at least one of four major limitations when compared to the coboglobins: they exist only at low temperature, they do not exist in aqueous solutions, they rapidly react further to form the 2:1 $\mu$-peroxo complexes, and they do not approach coboglobin in stability (as measured by the equilibrium constant Keq). A good understanding of this area can be gained by reading Jones et al, *Synthetic Oxygen Carriers Related to Biological Systems,* Chemical Reviews, 79(2), 139–179 (1979).

The present invention relates to salts of metal dry cave complexes useful for complexing molecular oxygen. For present purposes, a "dry cave" is a cavity in the vicinity of a vacant metal coordination site of the complex which can reversibly accommodate molecules. Such cavity can be made hydrophobic by providing interior walls consisting almost entirely of filled $\pi$-orbitals. Thus, the metal dry cave complexes can reversibly bind small molecules such as dioxygen even in aqueous solutions. As such, the metal dry cave complexes can effectively emulate various protein complexes such as, for example, myoglobin, hemoglobin, and the like.

Heretofore, nickel dry cave complexes have been proposed (Schammel, Thesis, The Ohio State University, Columbus, Ohio, 1976; Busch et al, *Control of Potentials of Metal Ion Couples in Complexes of Macrocyclic Ligands by Ligand Structural Modifications,* Reprint of ACS Symposium Series, No. 38. Electrochemical Studies of Biological Systems, American Chemical Society, 1977). Cobalt and iron derivatives were attempted, but it is now known that such attempts were fruitless.

SUMMARY OF THE INVENTION (Since the formulae shown in the accompanying drawings are formulae showing only the cation of a salt, references hereinafter to a compound or salt of Formula—are to a compound or salt containing a cation of the specified formula.)

In one aspect this invention provides a salt of a cationic metal complex of Formula XVII in FIG. 1 of the accompanying drawings wherein:

M is Co, Fe, Cu or Mn;

$n^+$ is a positive oxidation state of M, n being not greater than 3;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;

each $R_4$ independently is hydrogen, an alkyl group containing not more than about 4 carbon atoms, a cyanoalkyl group containing not more than about 4 carbon atoms, a phenyl group or a benzyl group;

each $R_6$ independently is hydrogen or a methyl group; or the two $R_6$ groups together form a nitrogen-nitrogen bridge, said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula:

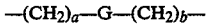
—(CH$_2$)$_a$—G—(CH$_2$)$_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group, subject to the proviso that when G is a sulfur atom, an imino group or a methylimino group, the sum of a and b is at least 4;

or the two $NR_4R_6$ groups together form a bis-piperazino bridge of the formula

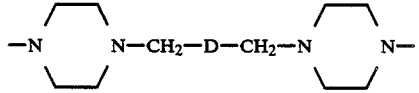

where D is a 1,3-phenylene group, a 1,4-phenylene group, a 1,4-phenylene group substituted by one or more methyl groups, a 9,10-anthracene group or a 2,6-pyridylene group, subject to the proviso that when the two $R_3$ groups do not form a carbon-carbon bridge, either the two $R_6$ groups must form a nitrogen-nitrogen bridge or the two $NR_4R_6$ groups must form a bis-piperazino bridge.

In another aspect, this invention provides a salt comprising a cationic metal complex of Formula XVIIA in FIG. 1 of the accompanying drawings, wherein M,n+, X, $R_1$, $R_2$, $R_3$, $R_4$ and $R_6$ have the same definitions as in Formula XVII and Z is an electron donor selected from the group consisting of the halide ions, cyanate, thiocyanate, azide, acetonitrile, water, an alkanol containing not more than about five carbon atoms, pyridine, 4-aminopyridine, imidazole and N-methylimidazole.

The invention extends to an adduct of the salts of Formulae XVII and XVIIA in FIG. 1 of the accompanying drawings and molecular oxygen or carbon monoxide.

In a further aspect, the invention provides a salt of Formula III in FIG. 1 of the accompanying drawings wherein:

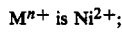
$M^{n+}$ is $Ni^{2+}$;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_4$ independently is hydrogen, an alkyl group containing not more than about 4 carbon atoms or benzyl;

each $R_6$ independently is hydrogen or a methyl group; and $R_5$ is a polymethylene group containing from 7 to about 12 carbon atoms or a m- or p-xylylene group.

In yet a further aspect, the invention provides a salt of Formula II in FIG. 1 of the accompanying drawings wherein:

$M^{n+}$ is $Ni^{2+}$;

X and Y are each independently an o-phenylene, ethylene, trimethylene, 2-(2-pyridyl)-trimethylene; 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_4$ independently is hydrogen or a methyl group;

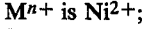
R is a polymethylene group containing from 4 to about 12 carbon atoms, a polymethylene group containing from 4 to about 12 carbon atoms and substituted by a methyoxycarbonyl group, or a grouping of the formula —(CH$_2$)$_a$—G—(CH$_2$)$_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, an imino group or a methylimino group, the sum of a and b is at least 4; and $R_5$ is a polymethylene group containing from 7 to about 12 carbon atoms or an m- or p-xylylene group.

In yet a further aspect, the invention provides a salt of Formula XVIII in FIG. 1 of the accompanying drawings wherein:

$M^{n+}$ is $Ni^{2+}$;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, a methyl group or a phenyl group; and

D is a 1,3-phenylene group, a 1,4-phenylene group, a 1,4-phenylene group substituted by one or more methyl groups, a 9,10-anthracene group or a 2,6-pyridylene group.

In yet a further aspect the invention provides a method for removing molecular oxygen from a gaseous mixture, which comprises exposing a salt of Formula XVII or XVIIA in FIG. 1 to the gaseous mixture thereby allowing the cationic metal complex of the salt to complex molecular oxygen and thus to absorb oxygen from the gaseous mixture.

The invention also provides a method for increasing the proportion of molecular oxygen in a gaseous mixture, which comprises:

passing the gaseous mixture over one face of an immobilized liquid membrane containing an oxygen-containing compound of Formula XVII or XVIIA in FIG. 1 of the accompanying drawings;

allowing molecular oxygen to diffuse selectively through said immobilized liquid membrane;

removing from adjacent the opposed face of the immobilized liquid membrane an oxygen-enriched gas containing a higher proportion of molecular oxygen than the original gaseous mixture.

The invention also provides an oxygen-binding polymer comprising a polymeric support having attached thereto bridging groups or molecules of the Formula XIX, XIX A or XIXB shown in FIG. 6 of the accompanying drawings wherein:

M is Co, Fe, Cu or Mn;

$n^+$ is a positive oxidation state of M, n being not greater than 3;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R'_3$ independently is hydrogen, an alkyl group containing not more than about 17 carbon atoms, a benzyl group, a phenyl group, or a phenyl group substituted by a halogen atom or by one or two methoxy groups;

each $R_4$ independently is hydrogen, an alkyl group containing not more than about 4 carbon atoms, a cyanoalkyl group containing not more than about four carbon atoms, a phenyl group or a benzyl group;

each $R'_6$ independently is hydrogen or a methyl group; and

Z is an electron donor selected from the group consisting of the halide ions, cyanate, thiocyanate, azide, acetonitrile, water, an alkanol containing not more than about five carbon atoms, pyridine, 4-aminopyridine, imidazole and N-methylimidzole.

In the case of the molecules of Formula XIX B, the polymer must be provided with electron-donating groups which can coordinate with the metal ion $M^{n+}$, thereby securing the molecule of Formula XIX B to the polymer. In effect, the electron-donating group and attached polymer function as does the ligand Z in other compounds of the invention.

The invention also provides a compound of Formula XX shown in FIG. 7 of the accompanying drawings wherein $R_7$ is a polymethylene group containing from 7 to about 16 carbon atoms or a group of the formula:

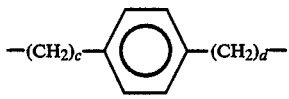

where $c+d$ equals an integer of from 4 to about 12; and $R_8$ is a polymethylene chain containing from 1 to about 10 carbon atoms, or a complex of such a compound with a nickel, cobalt, iron, copper or manganese ion in a +2 or +3 oxidation stage, this ion being co-ordinated by the two nitrogen atoms and the two oxygen atoms of the compound and displacing the two hydroxyl protons thereof.

The invention also provides a compound of the Formula XXI shown in FIG. 7 of the accompanying drawings wherein M is cobalt, iron, copper or manganese, $n^+$ is a positive oxidation state of M, n being not greater than 3, and $R_9$ is a bridging group of the formula

wherein each Q independently is a methylene group, an imine group or an oxygen or sulfur atom and and e is from 5 to about 10, or a bridging group of the formula

wherein Q is as defined above, $f+g$ equals from 3 to about 9 and $C_6H_4$ represents a phenylene group, M is nickel, cobalt, iron, copper or manganese and $n^+$ is a positive oxidation state of M, n being not greater than 3.

The invention also provides a compound of one of the Formulae XXIIA-XXIIE shown in FIG. 7 of the accompanying drawings wherein q is 2 or 3; and $R_{10}$ is a bridging group of the formula

where each Q independently is a methylene group, an imine group or an oxygen or sulfur atom and r is from 4 to about 10 or a bridging group of the formula

where Q is as defined above, $h+i$ equals from 2 to about 7 and $C_6H_4$ represents a phenylene group, or a complex of such a compound with a nickel, cobalt, iron, copper or manganese ion in a +2 or +3 oxidation state, this ion being coordinated by the four central nitrogen atoms.

The invention also provides a compound of Formula XXIII in FIG. 7 of the accompanying drawings wherein, $R_{11}$ is hydrogen or an alkyl group; and $R_9$ is as defined above with reference to Formula XXI, or a complex of such a compound wherein a single nickel, cobalt, iron, copper or manganese ion in a +2 or +3 oxidation state is coordinated with all four nitrogen atoms.

The invention also provides a compound of Formula XXIV in FIG. 7 of the accompanying drawings wherein $R_{10}$ is as defined above with reference to Formula XXII; and $R_{12}$ is hydrogen or an alkyl group.

The invention also provides a compound of the Formula XXV in FIG. 7 of the accompanying drawings wherein:

m is 2 or 3;

$R_{13}$ is hydrogen or an alkyl group; and $R_{15}$ is a polymethylene group containing at least about 8 carbon atoms, a grouping of one of the formulae:

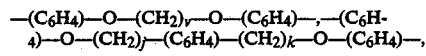

$-(C_6H_4)-O-(CH_2)_v-O-(C_6H_4)-, -(C_6H_4)-O-(CH_2)_j-(C_6H_4)-(CH_2)_k-O-(C_6H_4)-,$ $(1,7\text{-naphthylene})-O-(CH_2)_v-O-(1,7\text{-naphthylene})$- and -$(1,7\text{-naphthylene})-O-(CH_2)_j-(C_6H_4)-(CH_2)_k-O-(1,7\text{-naphthylene})$- where $(C_6H_4)$ represents a phenylene group (which may be the ortho, meta or para-isomer) group, v is an integer from about 4 to about 10 and, and j and k are two integers whose sum is from about 4 to about 10;

or a complex of such a compound wherein the two protons of the central imine groups are replaced by a single nickel, cobalt, ion, copper or manganese ion in a +2 or +3 oxidation state, this ion also being co-ordinated with the remaining three nitrogen atoms.

Finally, the invention also provides a process for complexing oxygen using a compound of Formula XXVI in FIG. 7 of the accompanying drawings wherein M, n+ and $R_9$ are as defined above with reference to Formula XXI.

DETAILED DESCRIPTION OF THE INVENTION

Figure 1A:
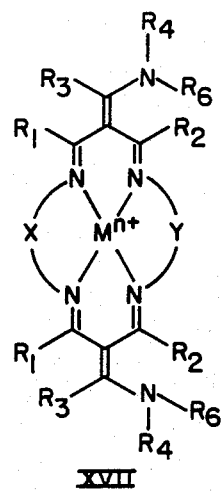
FIG. 1 shows Formulae XVII and XVIIA, together with the further Formulae I, IA, II, IIA, III, IIIA, XVIII and XVIIIA which represent sub-groups of compounds falling within Formulae XVII and XVIIA.
Figure 1A:
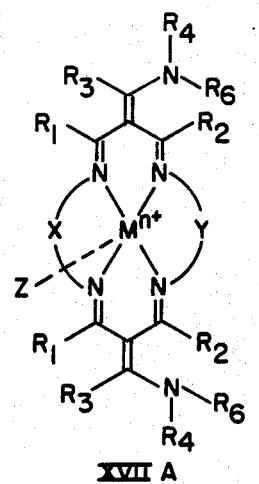
Figure 1A:
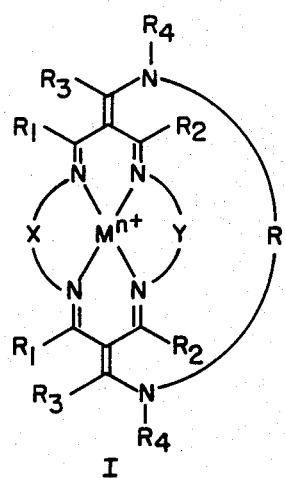
Figure 1A:
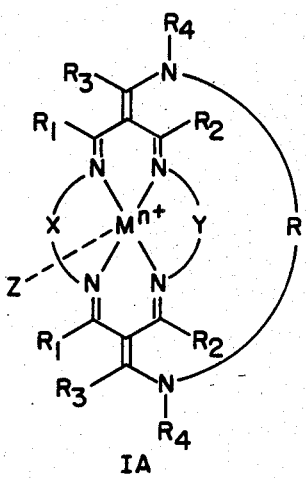
Figure 1A:
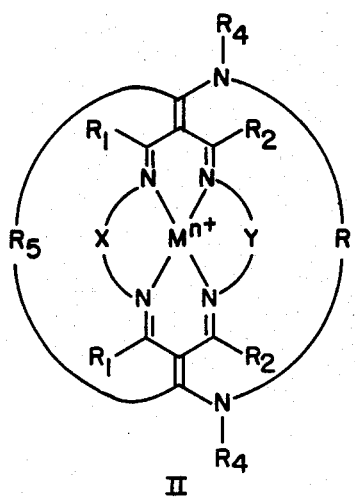
Figure 1A:
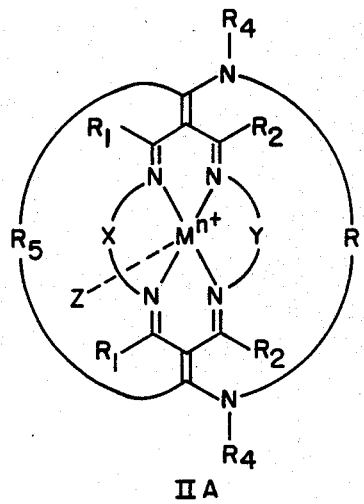
Figure 1B:
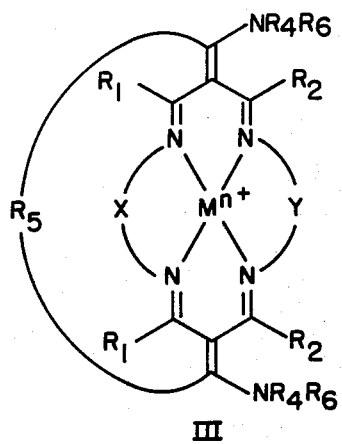
Figure 1B:
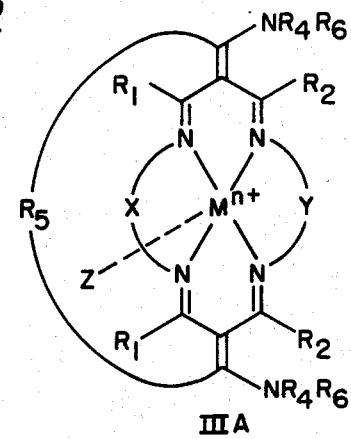
Figure 1B:
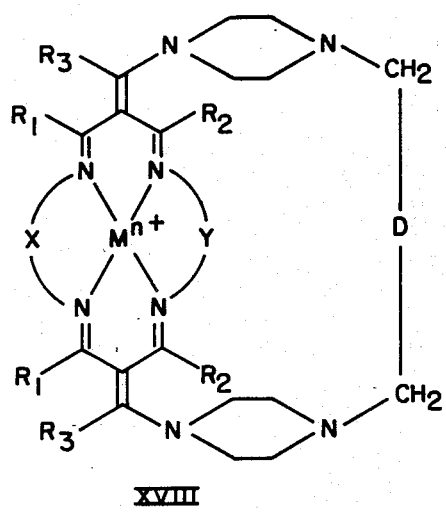
Figure 1B:
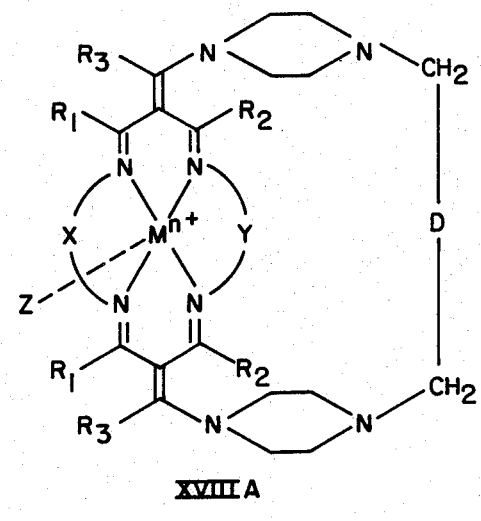

Compounds of Formulae I-XVIII and I A-XVIII A

It will be observed that the compounds of Formula XVIIA differ from the closely-related compounds of Formula XVII only by the presence of a fifth ligand coordinated to the metal atom. This fifth ligand is an electron donor which serves to donate electrons to the metal atom.

In the instant compounds of Formula XVII, the preferred anions are hexafluorophosphate, tetrachlorozincate, perchlorate, hexafluoroarsenate, fluoroborate, trifluoromethylsulfonate and the halides, hexafluorophosphate and chloride anions being especially preferred. The preferred metal ions $M^{n+}$ are $Co^{2+}$, $Co^{3+}$, $Fe^{2+}$, $Fe^{3+}$, $Cu^{2+}$, $Mn^{2+}$ and $Mn^{3+}$, the $Co^{2+}$ and $Fe^{2+}$ ions being especially preferred. The group $R_1$ is preferably hydrogen, while the group $R_2$ is preferably methyl. When two separate groups $R_3$ are present, each group is preferably hydrogen, a methyl group, a phenyl group, a t-butyl group, an n-heptyl group, a 4-methoxyphenyl group, a 4-chlorophenyl group, a 4-fluorophenyl group or a 3,5-dimethoxyphenyl group; when the two $R_3$ groups together form a carbon-carbon bridge, this bridge is preferably a polymethylene group containing 7 to 10 carbon atoms or a m-xylylene group.

The preferred $R_4$ groups in Formula XVII are hydrogen, a methyl group, an n-propyl or n-butyl group, a 2-cyanoethyl group or a benzyl group.

When the two $R_6$ groups in Formula XVII together form a nitrogen-nitrogen bridge, this bridge preferably comprises a polymethylene bridge of 4 to about 12 carbon atoms, an m- or p-xylylene group, a (5-methoxy)-m-xylylene group, a $-(CH_2)_3-(9,9\text{-flourylene})-(CH_2)_3-$ group, a $-(CH_2)_4CH(COOCH_3)(CH_2)_4-$ group, a $-CH_2-(1,3\text{-cyclohexylene})-CH_2-$ group, a $-(CH_2)_2C(CH_3)_2(CH)_2-$ group, a 3-thiapentamethylene group, a 3-thiahexamethylene group, a $-CH_2-(5\text{-methoxycarbonyl-1,3-phenylene})-CH_2-$group, a 2,6-pyridylene group, a 4-azaheptamethylene group, or a 4-aza-4-methylheptamethylene group.

In Formula XVII, X is preferably an ethylene, trimethylene, 2-(2-pyridyl)trimethylene group or a 2-(N-methyl-2-pyridino)-trimethylene group, while Y is preferably a trimethylene group. The preferred anions are hexafluorophosphate and chloride.

The preferred substituents in Formula XVIIA are the same as those in Formula XVII.

It is believed that, for certain purposes, such as producing oxidation catalysts, it is advantageous to immobilize the compounds of Formulae XVII and XVIIA by grafting or otherwise chemically bonding the compounds to oligomer or polymer chains. This grafting or chemical bonding of the compounds of Formula XVII and XVIIA is conveniently accomplished by using a compound in which at least one of the groups $R_4$ is hydrogen and bonding the compound of Formula XVII or XVIIA to the oligomer or polymer at this point. Alternatively, one may employ polymers having pendant groups (e.g. pyridyl) which can function as a ligand Z, and use a compound of Formula XVII, thereby attaching the compound of Formula XVII to the polymer by permitting one of the pendant groups on the polymer to function as a ligand Z in the compound of Formula XVIIA.

The preferred compounds of Formula XVII can conveniently be divided into four groups as follows:

(a) The compounds in which two separate $R_3$ groups are present, but the two $R_6$ groups together form a carbon-carbon bridge. These are the compounds of Formula I in FIG. 1 of the accompanying drawings, in which M, $n^{30}$, $R_1$, $R_2$, $R_3$, $R_4$, X and Y are as defined above with reference to Formula XVII and R is a polymethylene group containing from 4 to about 12 carbon atoms, a polymethylene group containing from about 4 to about 12 carbon atoms and substituted by a methoxycarbonyl group, or a grouping of the formula:

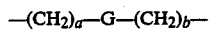

where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group, subject to the proviso that when G is a sulfur atom, a imino group or a methylimino group, the sum of a and b is at least 4.

(b) The compounds in which the two $R_3$ groups together form a carbon-carbon bridge, while two separate $R_6$ groups are present. These are the compounds of Formula III in FIG. 1 of the accompanying drawings, in which M, $n+$, $R_1$, $R_2$, $R_4$, X and Y are as defined above with reference to Formula XVII, each $R_6$ group independently is hydrogen or a methyl group and $R_5$ is a polymethylene group containing from about 7 to about 12 carbon atoms or a m- or p-xylylene group.

(c) The compounds in which the two $R_3$ groups together from a carbon-carbon bridge, and the two $R_6$ together form a nitrogen-nitrogen bridge. These are the compounds of Formula II in FIG. 1 of the accompanying drawings, wherein M, $N+$, $R_1$, $R_2$, $R_4$, X and Y are as defined above with reference to Formula XVII; R is a polymethylene group containing from 4 to about 12 carbon atoms, a polymethylene group containing from about 4 to about 12 carbon atoms and substituted by a methoxycarbonyl group, or a grouping of the formula:

where a and b are each independently 1,2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group, subject to the proviso that when G is a sulfur atom, a imino group or a methylimino group, the sum of a and b is at least 4; and $R_5$ is a polymethylene group containing from 7 to about 12 carbon atoms or a m or p-xylylene group.

(d) The compounds in which the two $NR_4R_6$ groups together form a bispiperazino bridge. These are the compounds of Formula XVIII in FIG. 1 of the accompanying drawings, wherein M, $n+$, $R_1$, $R_2$, $R_3$, X and Y are as defined above with reference to Formula XVII, the two $NR_4R_6$ groups together form a bispiperazino bridge and D is a 1,3-phenylene group, a 1,4-phenylene group, a 1,4-phenylene group substituted by one or more methyl groups, a 9,10-anthracene group or a 2,6-pyridylene group.

Formulae IA, IIIA, IIA, and XVIIIA in FIG. 1 of the accompanying drawings represent four sub-sets of compounds falling within Formula XVIIA; the definitions of the various substituents in Formulae IA, IIA, IIIA, and XVIIIA are exactly the same as those of the same substituents in Formulae I, II, III and XVIII respectively, while in each of the Formulae IA, IIA, IIIA and XVIIIA the ligand Z has the same meaning as defined above with reference to Formula XVIIA.

In the compounds of Formula I, the preferred metal ions and groups $R_1$, $R_2$, $R_4$, $R_6$ and the anion are the same as those in the compounds of Formula XVII, while the group R is preferably a polymethylene bridge of 4 to about 8 carbon atoms, an m- or p-xylylene group, a (5-methoxy)-m-xylylene group, a $-(CH_2)_3-(9,9$-flourylene)$-(CH_2)_3-$ group, a $-(CH_2)_4CH(COOCH_3)(CH_2)_4-$ group, a $-CH_2-(1,3$-cyclohexylene)$-CH_2-$ group, a $-(CH_2)_2C(CH_3)_2(CH_2)_2-$ group, a 3-thiapentamethylene group, a 3-thiahexamethylene group, a $-CH_2-(5$-methyoxycarbonyl-1,3-phenylene)$-CH_2-$group, a 2,6-pyridylene group, a 4-azaheptamethylene group, or a 4-aza-4-methylheptamethylene group. An especially preferred group of compounds of Formula I are those in which $M^{n+}$ is $Co^{2+}$, $Co^{3+}$, $Fe^{2+}$, $Fe^{3+}$, $Mn^{2+}$, $Mn^{3+}$ or $Cu^{2+}$, each $R_1$ is hydrogen, each $R_2$ is a methyl group, each $R_3$ is hydrogen, a methyl group, a t-butyl group, and n-heptyl group, a 4-methoxyphenyl group, a 4-chlorophenyl group, a 4-fluorophenyl group or a 3,5-dimethoxyphenyl group, $R_4$ is hydrogen or a methyl group, R is a polymethylene group containing 4 to 8 carbon atoms, a m or p-xylylene group and the anion is hexafluorophosphate or chloride.

In the compounds of Formula III, the preferred metal ions are $Co^{2+}$ and $Fe^{2+}$, X and Y are preferably each a dimethylene or trimethylene group, while $R_1$ is preferably hydrogen. The preferred $R_4$ groups are hydrogen, methyl, n-propyl and benzyl, while $R_5$ is preferably a polymethylene group containing from 7 to 9 carbon atoms and the anions is preferably hexafluorophosphate or chloride. An especially preferred sub-group of compounds of Formula III is that in which each of the substituents have the preferred values given above. In the salts of Formula II, X and Y are preferably each a trimethylene group, each $R_1$ group is preferably hydrogen, each $R_2$ is preferably a methyl group, each $R_4$ is preferably hydrogen, $R_5$ is preferably a polymethylene group containing from 7 to 10 carbon atoms and R is preferably a polymethylene group containing 6 or 7 carbon atoms or an m-xylylene group. The preferred anion is hexafluorophosphate. Again, a specifically preferred sub-group of salts of Formula II is that in which each of the substituents has the preferred value given above.

In the salts of Formula XVIII, the preferred metal ions are $Co^{2+}$, $Fe^{2+}$ or $Cu^{2+}$, while X is preferably a trimethylene group or a 2-(N-methyl-2-pyridino)-trimethylene group and Y is preferably a trimethylene group. Also in the salts of Formula XVIII, $R_1$ is preferably hydrogen, $R_2$ is preferably methyl and $R_3$ is preferably methyl or phenyl. The preferred groups D are 1,3-phenylene, 1,4-phenylene, tetramethyl-1,4-phenylene, 9,10-anthracene and 2,6-pyridylene. The preferred anions of hexafluorophosphate and chloride. Again, an especially preferred sub-group of salts of Formula XVIII is that in which each of the substituents has the preferred values given above.

Specific preferred compounds of Forumula I are:
[(2,3,8,9,11,17-hexam ethyl-3,8,12,16,19,23-hexaazabicyclo[8.7.7]tetracosa-1,9,11,16,18,23-hexaene-$\kappa^4N$)cobalt(II)] hexafluorophosphate;
[(2,3,9,10,12,18-hexamethyl-3,9,13,17,20,24-hexaazabicyclo[9.7.7]pentacosa-1,10,12,17,19,24-hexaene-$\kappa^4N$)cobalt(II)] hexafluorophosphate;
[(2,3,10,11,13,19-hexamethyl-3,10,14,18,21,25-hexaazabicyclo[10.7.7]hexacosa-1,11,13,18,20,25-hexaene-$\kappa^4N$)cobalt(II)] hexafluorophosphate;
[(3,8,11,17-tetramethyl-2,9-diphenyl-3,8,12,16,19,23-hexaazabicyclo[8.7.7]tetracosa-1,9,11,16,18,23-hexaene-$\kappa^4N$)cobalt(II)] hexafluorophosphate;

[(3,9,12,18-tetramethyl-2,10-diphenyl-3,9,13,17,20,24-hexaazabicyclo[9.7.7]pentacosa-1,10,12,17,19,24-hexaene-κ⁴N)cobalt(II)] hexafluorophosphate;

[(3,10,13,19-tetramethyl-2,11-diphenyl-3,10,14,18,21,25-hexaazabicyclo[10.7.7]hexacosa-1,11,13,18,20,25-hexaene-κ⁴N)cobalt(II)] hexafluorophosphate;

[(2,10,12,18-tetramethyl-3,9,13,17,20,24-hexaazabicyclo[9.7.7]pentacosa-1,10,12,17,19,24-hexaene-κ⁴N)cobalt(II)] hexafluorophosphate;

[(2,11,13,19-tetramethyl-3,10,14,18,21,25-hexaazabicyclo[10.7.7]hexacosa-1,11,13,18,20,25-hexaene-κ⁴N)cobalt(II)] hexafluorophosphate;

[(2,7,12,14,20-pentamethyl-3,7,11,15,19,22,26-heptaazabicyclo[11.7.7]heptacosa-1,12,14,19,21,26-hexaene-κ⁴N)cobalt(II)] hexafluorophosphate;

[(12,18-dimethyl-2,10-diphenyl-3,9,13,17,20,24-hexaazabicyclo[9.7.7]pentacosa-1,10,12,17,19,24-hexaene-κ⁴N)cobalt(II)] hexafluorophosphate;

[(13,19-dimethyl-2,11-diphenyl-3,10,14,18,21,25-hexaazabicyclo[10.7.7]hexacosa-1,11,13,18,20,25-hexaene-κ⁴N)cobalt(II)] hexafluorophosphate; and

[(2,3,10,11,13,19-hexamethyl-23-(2-pyridyl)-3,10,14,18,21,25-hexaazabicyclo[10.7.7]hexacosa-1,11,13,18,20,25-hexaene-κ⁴N)cobalt(II)] hexafluorophosphate.

A specific preferred compound of Formula III is:
[(12,18-dimethyl-2,10-bis-methylamino-13,17,20,24-tetraazabicyclo[9.7.7]pentacosa-1,10,12,17,19,24-hexaene-κ⁴N)cobalt(II)] hexafluorophosphate A specific preferred compound of Formula XVIII is:
[(2,9,10,17,19,25,33,34-octamethyl-3,6,13,16,20,24,27,31-octaazapentacyclo[16.7.7.2⁸,¹¹.2³,⁶.2¹³,¹⁶]octatriaconta-1,8,10,17,19,24,26,31,33-nonaene-κ⁴N)cobalt(II)] hexafluorophosphate.

In Formula IA, each $R_1$ is preferably hydrogen and each $R_2$ is preferably methyl. Each $R_3$ is preferably is hydrogen, a methyl group, a phenyl group, a t-butyl group, an n-heptyl group, a 4-methoxyphenyl group, a 4-chlorophenyl group, a 4-fluorophenyl group or a 3,5-dimethoxyphenyl group, while each $R_4$ is preferably hydrogen, a methyl group or a benzyl group. R is preferably a polymethylene bridge of 4 to about 12 carbon atoms, an m- or p-xylylene group or a —(CH₂)₃—(9,9-flourylene)—(CH₂)₃— group, and X and Y are preferably each a trimethylene group. The preferred ligands Z are chloride, cyanate, thiocyanate, azide, ethanol, acetonitrile, pyridine, 4-aminopyridine, imidazole or N-methylimidazole. The preferred anions are hexafluorophosphate and chloride. Again, a specifically preferred sub-group of compounds of Formula IA are those wherein each of the substituents has one of the preferred values given above.

The preferred sub-group of compounds of Formula IIIA are those in which the metal is cobalt or iron, n is 2, each $R_1$ is hydrogen, each $R_2$ and $R_4$ is hydrogen or a methyl group, each $R_3$ is hydrogen, a methyl group, an ethyl group, a n-propyl group or a benzyl group, X and Y are each a trimethylene group, $R_5$ is a polymethylene group containing 7 to 10 carbon atoms, Z is chloride, acetonitrile or water and the anion is hexafluorophosphate.

In the source of Formula XVIIIA, the metal ion is preferably $Co^{2+}$ or $Fe^{2+}$, X and Y are preferably each a trimethylene group and each $R_1$ is preferably hydrogen. Each $R_2$ and $R_3$ is preferably a methyl group, while D is preferably a 1,3-phenylene group, a 1,4-phenylene group, a tetramethyl-1,4-phenylene group or a 9,10-anthracine group. The preferred anion is hexafluorophosphate. Again, a preferred sub-group of compounds are of Formula XVIIIA of those in which each of the substituents has the preferred values given above.

Specific preferred salts of Formula IA are:
[chloro(2,3,11,12,14,20-hexamethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[chloro(2,12-di-n-heptyl-3,11,14,20-tetramethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[chloro(2,12-di-p-methoxyphenyl-3,11,14,20-tetramethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[chloro(2,12-di-p-chlorophenyl-3,11,14,20-tetramethyl-3,11,15,19,22,26-hexaazatricyclo[11.7.7.1⁵,⁹]octacosa-1,5,7,9(28),12,14,19,21,26-nonaene-κ⁴N)iron(II)] hexafluoro-phosphate;

[chloro(2,12-di-p-fluorophenyl-3,11,14,20-tetramethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[acetonitrile(14,20-dimethyl-2,12-diphenyl-3,11,15,19,22,26-hexaazatricyclo[11.7.7.1⁵,⁹]octacosa-1,5,7,9(28),12,14,19,21,26-nonaene-κ⁴N)cobalt(II)] hexafluorophosphate;

[acetonitrile(2,3,11,12,14,20-hexamethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[acetonitrile(3,11-dibenzyl-2,12,14,20-tetramethyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[acetonitrile(3,11,14,20-tetramethyl-2,12-diphenyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[acetonitrile(3,11-dibenzyl-14,20-dimethyl-2,12-diphenyl-3,11,15,19,22,26-hexaazatricyclo[11.7.7.1⁵,⁹]octacosa-1,5,7,9(28),12,14,19,21,26-nonaene-κ⁴N)iron(II)] hexafluorophosphate;

[acetonitrile(2,12,14,20-tetramethyl-3,11,15,19,22,26-hexaazabicyclo[11.7.7]heptacosa-1,12,14,19,21,26-hexaene-κ⁴N)cobalt(II)] hexafluorophosphate;

[acetonitrile(2,12,14,20-tetramethyl-3,11,15,19,22,26-hexaazatricyclo[11.7.7.1⁵,⁹]octacosa-1,5,7,9(28),12,14,19,21,26-nonaene-κ⁴N)cobalt(II)] hexafluorophosphate; and

[acetonitrile(3,10,13,19-tetramethyl-3,10,14,18,21,25-hexaazabicyclo[10.7.7]hexacosa-1,11,13,18,20,25-hexaene-κ⁴N)cobalt(II)] hexafluorophosphate.

Specific preferred salts of Formula IIIA are:
[chloro(2,10-bis-dimethylamino-12,18-dimethyl-13,17,20,24-tetraazabicyclo[9.7.7]pentacosa-1,10,12,17,19,24-hexaene-κ⁴N)iron(II)] hexafluorophosphate;

[chloro(2,11-bis-dimethylamino-13,19-dimethyl-14,18,21,25-tetraazabicyclo[10.7.7]hexacosa-1,11,13,18,20,25-hexaene-κ⁴N)iron(II)] hexafluorophosphate;

[acetonitrile(12,18-dimethyl-2,10-bis-propylamino-13,17,20,24-tetraazabicyclo[9.7.7]pentacosa-1,10,12,17,19,24-hexaene-κ⁴N)cobalt(II)] hexafluorophosphate; and

[acetonitrile(2,11-bis-dimethylamino-13,19-dimethyl-14,18,21,25-tetraazabicyclo[10.7.7]hexacosa-1,11,13,18,20,25-hexaene-$\kappa^4$N)cobalt(II)] hexafluorophosphate.

It should be noted that certain of the possible anions (e.g. chloride) in the salts of Formula XVII A can also function as the ligand Z in the same salts. Thus, as those skilled in the art will appreciate, when preparing for example a salt of Formula XVII A in which the anion is chloride but Z is not chloride, some replacement of the ligand Z with chloride may occur and it may be difficult to prepare the desired salt in a pure form, especially when the metal M is iron.

A somewhat similar problem exists with respect to the metal atom M. As described below, the salts of Formulae XVII and XVII A may be synthesized via a tetrachlorozincate salt of the corresponding nickel cation. However, if one attempts to prepare a salt of Formula XVII or XVII A having M=Co, the cobalt and zinc compete for the metal coordination site in the cation and it is often not possible to prepare pure cobalt salts in the presence of tetrachlorozincate anion. It is for this reason that it is preferred to convert the tetrachlorozincate salt to the corresponding hexafluorophosphate salt during the synthesis, as described below.

Figure 2:
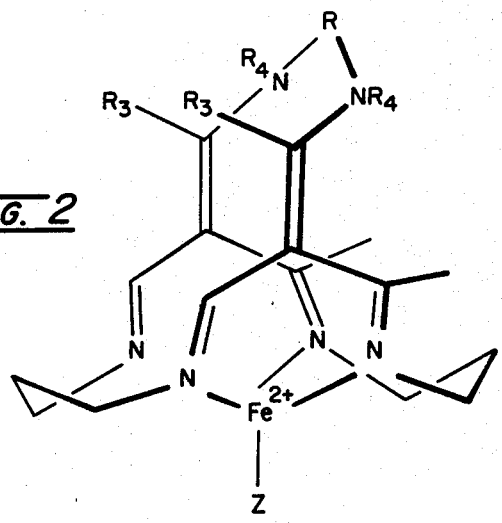
FIG. 2 shows Formula IV, a schematic stereochemical representation of one compound of the invention.
Figure 3A:
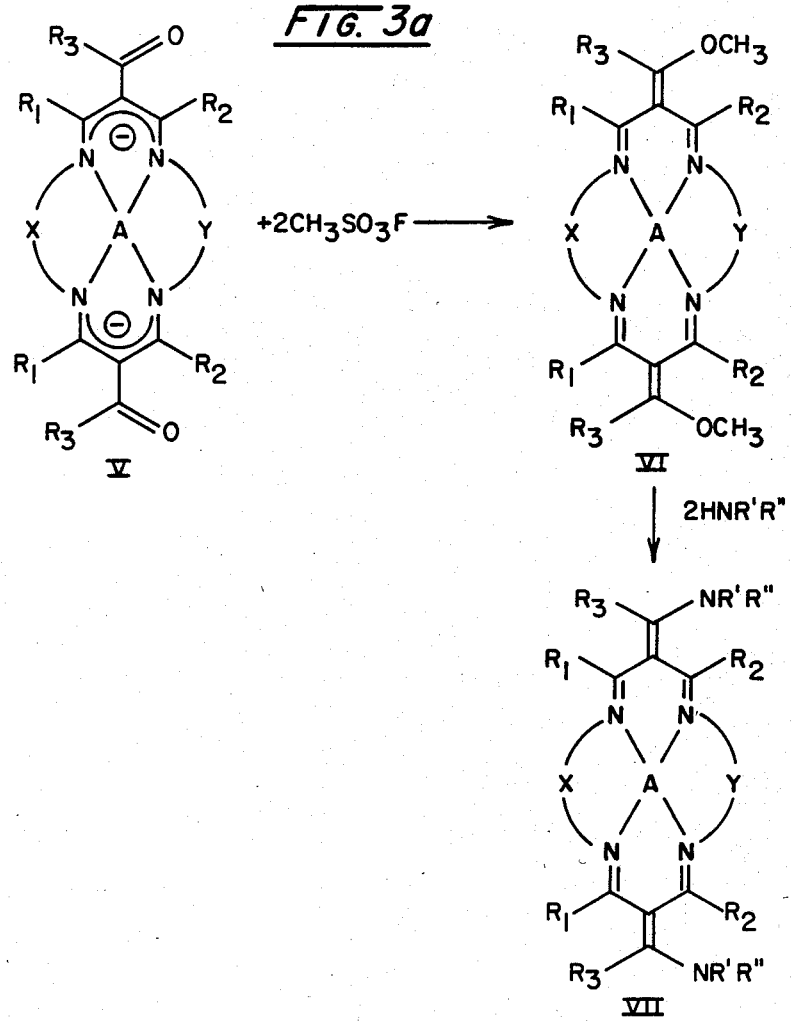
FIG. 3 shows various synthetic methods used to prepare compounds of the invention, together with the structure of the compound produced in Example VII below.
Figure 3A:
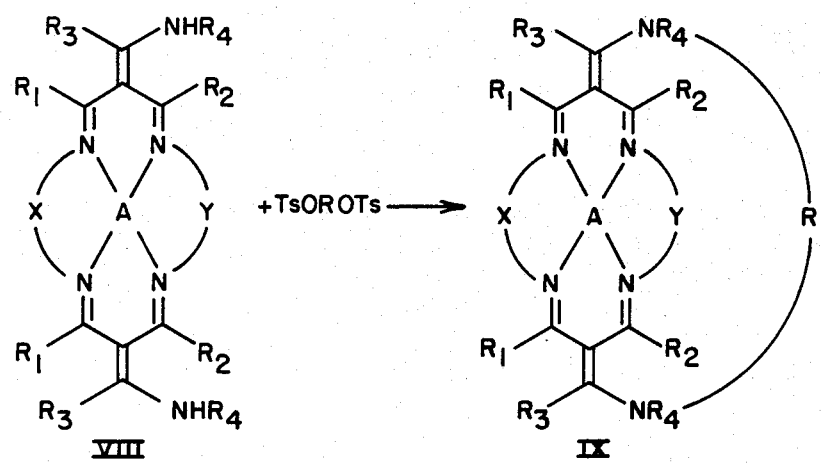
Figure 3B:
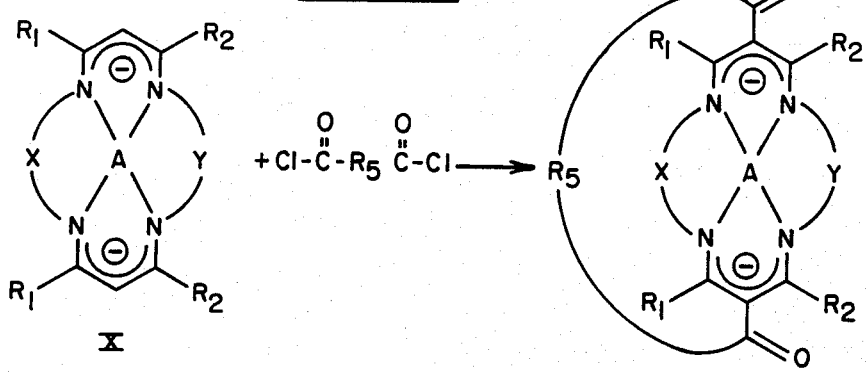
Figure 3B:
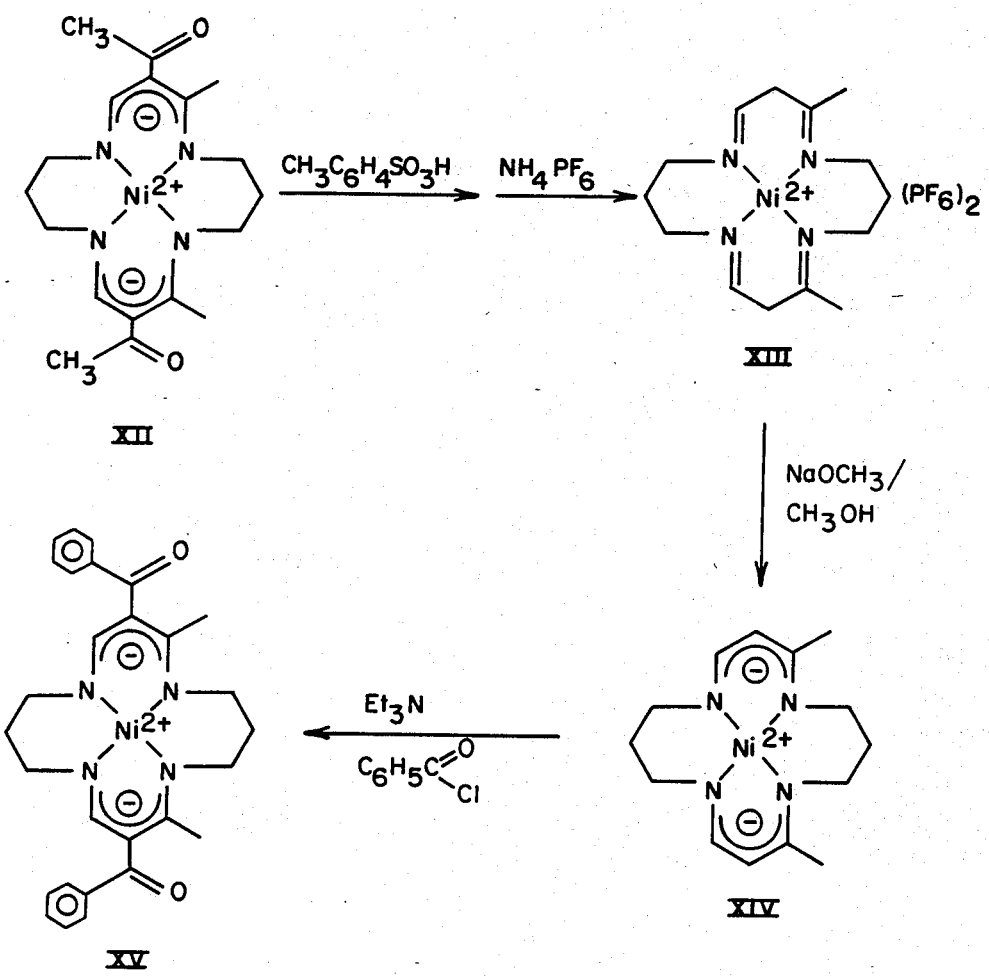
Figure 3C:
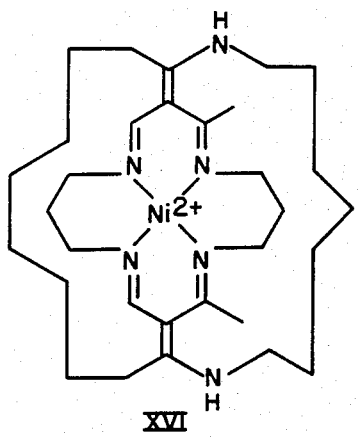

A most striking feature of the dry cave cation complexes in the salts of Formulae XVII and XVIIA is the configuration and conformation of the macrocycle and the bridge(s) which form(s) the interior walls and roof of the dry cave site. FIG. 2 of the accompanying drawings shows the stereochemistry of a compound of Formula I A, this being the cation of Formula I where in $M^{n+}=Fe^{2+}$, $R_1=H$, $R_2=CH_3$, and X=Y trimethylene. The bridge R (and all other $R_5$ or bis-piperazino bridges) effectively forms both the roof and back of the cave by its tilt, yet its displacement from over the center of the metal ion leaves a wide opening or mouth to the cave, the base of which is formed by the square planar arrangement of nitrogen atoms around the metal ion. Thus, small molecules, such as dioxygen and carbon monoxide, for example, can be accommodated in the dry cave and protected from the surrounding environment, especially when an axial ligand Z is coordinated to the metal from the side opposite the bridging group (the ligand Z is disposed directly below the metal ion M in Formula IV). The metal dry cave cation complexes, then, can combine with molecular oxygen (dioxygen or $O_2$) or promote reactions of the dioxygen molecule, or promote reactions of its derived intermediate reaction products including $O_2^-$, $HO_2$, $O_2^{2-}$, $H_2O_2$, etc. The oxygen adducts of the cation complexes can and do exist efficaciously in solution in various solvents, including water. Further, certain of the oxygen-adducts have shown remarkable thermal stability not only at room temperature but also at temperatures ranging upwards to 40°–50° C. Such thermal stability is quite unexpected, though certainly a propitious property possessed by the salts of the present invention.

All the utilities of the salts of Formulae XVII and XVIIA suggested herein are based upon the ability of the cation complexes of the salts to complex with oxygen and other small molecules such as carbon monoxide. Firstly, the salts of Formula XVII and XVIIA are useful for scavenging low levels of molecular oxygen from various atmospheres. For this purpose, it is desirable to chose a salt which has a high oxygen affinity (low half-saturation partial pressure of oxygen) in order that the salt will extract the greatest possible amount of oxygen from the atmosphere to be scavenged. In order to effect removal of oxygen from a gaseous mixture, and thus to scavenge the mixture, it is only necessary to expose a salt of Formula XVII or XVIIA (and some of the instant compounds are soluble and stable in solution) to the gaseous mixture to be scavenged. As those skilled in the art are well aware, to effect the maximum possible scavenging of oxygen from the gas, it is essential that intimate control between the gas and scavenging salt be achieved. Such intimate contact may be achieved, for example, by spraying a finely divided jet of a liquid solution of the salt through a stream of the gas to be scavenged, by bubbling the gas through the liquid solution or by allowing the liquid to flow down a tower packed with inert, granular material while the gas to be scavenged flows up the tower.

A closely-related utility of the salts of Formulae XVII and XVIIA is their use in determining the amount of molecular oxygen present in an oxygen-depleted atmosphere. The formation of an adduct between the cation of the salt and oxygen changes the spectrum of a solution of the salt. Therefore upon passing a beam of light or other electromagnetic radiation through the salt solution, the absorbance of which differs as between the free cation and the oxygen adduct, the proportion of the salt in the adduct form, and hence the equilibrium constant may be determined. The relationship between the equilibrium constant, partial pressure of molecular oxygen in the system and the color change, as measured spectrophotometrically, is indicated by the following equation:

$$(A - A_0)^{-1} = (K(E_{adduct} - E_{complex})[\text{Complex}] P_{O_2})^{-1} + \quad (1)$$

$$((E_{adduct} - E_{complex})[\text{Complex}])^{-1}$$

In equation 1, A-Ao represents the change in absorbance that occurs for a given total concentration of the dry cave complex cation, [Complex], and the partial pressure of molecular oxygen, ($P_{O_2}$). K is the equilibrium constant for $O_2$ adduct formation, E $_{adduct}$ and E $_{complex}$ are molar extinction coefficients for the $O_2$ adduct and for the dry cave complex, respectively. By way of example, for a cobalt dry cave complex, typical parameters are $E_{adduct}-E_{complex}=250$, $K_{O_2}=1$ torr$^{-1}$ and total concentration of [Complex]$=10^{-3}$M. For this case, and making the modest assumption that $\alpha$ A can be measured to within an accuracy of 0.02 units, $P_{O_2}$ can be measured directly over the range of from about 0.09 torr to about 12 torr. By choosing a system in which $K_{O_2}=5$ torr$^{-1}$ with the other parameters remaining about the same, the measurable range is from about 0.02 torr to 2.3 torr. Moving in the other direction, for $K_{O_2}=0.1$ torr$^{-1}$ and under otherwise equivalent conditions, the measurable range of $P_{O_2}$ is from 0.87 torr to 115 torr. Thus, it is readily apparent that the salts of the present invention have excellent flexibility in the determination of the molecular oxygen concentration present in oxygen-depleted atmospheres. Furthermore since the instant salts can be used in a liquid solution, they may be useful in situations where introduction of the oxygen-measuring instruments would be difficult or impossible. For example, a solution of an instant salt could be introduced into a location within an animal or human body where it is desirable to measure the oxygen concentration and the colorimetric measurement made by means of an optic fiber endoscope.

However, by far the most important utility of the salt of Formula XVII and XVIIA lies in their use in separating oxygen from air (or any other readily-available and cheap source of oxygen-containing gas). The essential requirement for a compound to be used for separating oxygen from air is that the compound must load and unload molecular oxygen reversibly at appropriate partial pressures of molecular oxygen; given the present cost of producing the salts of Formulae XVII and XVIIA (and indeed of all other oxygen-complexing compounds known) and the relatively low value per unit weight of the molecular oxygen which is the end product of the process, from an economic standpoint it is essential that an oxygen-complexing compound be able to undergo many oxygen complexing/decomplexing cycles without destruction, and it is an important advantage of the salts of Formulae XVII and XVIIA that they can undergo an extremely large number of such oxygen complexing/decomplexing cycles.

Contact between the salt of Formula XVII or XVII A and the oxygen-containing gas may be effected in a number of different ways. The salt may be used in the solid phase; for obvious reasons, if it is desired to use the salt in the solid phase, this solid phase is preferably in a finely divided form so as to expose a large surface area to the oxygen-containing gas and may, for example, be in the form of a thin coating upon an inert substrate such as finely-divided silica or some other similar material having a large surface area. Alternatively, the salt may be used in the liquid phase, either in the form of a true solution, a colloid or a dispersion; such a dispersion might be in the form of a slurry. Finally, the salt may be attached to a supporting solid; as already indicated, the salt may be in the form of a thin layer on an inert substrate but the salt may also be chemically bonded to the substrate. A convenient form of substrate to which the salt may be chemically bonded is a synthetic polymer provided with substituents susceptible to nucleophilic attack, for example a crosslinked polystyrene polymer containing benzyl chloride functional groups. One possible method for attaching the salts of Formula XVII or XVII A to such a polymer involves reaction of a salt in which the two groups $R_4$ are hydrogen atoms with the polymer containing the functional groups; it is believed (although the invention is in no way limited to this belief) that in most cases the two primary or secondary amine groups $NR_4R_6$ react with separate, spaced functional groups on the polymer thereby causing the four central nitrogen atoms coordinated to the metal atom to lie in a plane approximately parallel to the plane of the polymer surface and thereby creating a cavity between the metal atom and the polymer surface in which the oxygen or similar molecule can be accommodated. Alternatively, one may use a polymer having pendant group (e.g. pyridyl) capable of acting as an axial ligand Z and treating this polymer with a salt of Formula XVII, thereby allowing the pendant groups to coordinate with the metal atoms in the salts and binding the salts to the polymer.

It will of course be appreciated that, where it is desired to chemically bond a salt of Formula XVII A to a support, it may be more convenient to effect reaction between a salt of Formula XVII and the support, and then to pass a material appropriate to supply the desired ligand Z over the support. Furthermore, in many cases it may be more convenient to use the nickel or other relatively unreactive salt of Formula XVII, or a demetallated form of the salt of Formula XVII, in the reaction with the support, and then to carry out the insertion of the desired active metal (and, if desired, insertion of the ligand Z) thereby generating the desired salt of Formula XVII or XVII A in situ on the support.

As already mentioned, to be useful in separating oxygen from air in a practical process, the oxygen complexing compound must load and unload molecular oxygen at appropriate partial pressures thereof, and this ability can be evaluated on the basis of the equilibrium constant for the reaction:

$$\text{Complex} + O_2 \rightleftharpoons \text{Complex}(O_2) \quad (2)$$

where "Complex" represents the cationic metal complex of a salt of Formula XVII or XVIIA. In most practical processes for the separation of oxygen from air, the salt will be allowed to take up molecular oxygen in contact with air under approximately atmospheric pressure (in order to avoid the large energy consumption needed to compress the volumes of air involved), and the oxygen partial pressure in the atmosphere is approximately 160 torr. The oxygenated salt will normally give up its oxygen to a chamber at a pressure of about 10 to about 50 torr, and since the gas given off will be reasonably pure oxygen the oxygen partial pressure in the chamber will have substantially the same value. Obviously, in order to extract the maximum amount of oxygen per pass of a given quantity of salt through the process, it is desirable that the percentage saturation of the salt with oxygen show the maximum difference for the oxygen partial pressures used for loading and unloading oxygen in the process. Table 1 below shows the degrees of saturation for various values of the equilibrium constant for a loading oxygen partial pressure of 160 torr and off loading oxygen partial pressures of 50 and 10 torr, together with the percentage difference in saturation (shown below the symbol Δ) at 160 torr as compared with 50 and 10 torr respectively.

TABLE 1

| Equilibrium constant $K_{O, torr^{-1}}$ | Percent Saturation, oxygen partial pressure | | |
|---|---|---|---|
| | 160 torr | 50 torr(Δ) | 10 torr(Δ) |
| 0.3 | 98 | 94 (4) | 75 (23) |
| 0.1 | 94 | 83 (11) | 50 (44) |
| 0.03 | 83 | 60 (23) | 23 (60) |
| 0.01 | 62 | 33 (29) | 9 (53) |
| 0.003 | 32 | 13 (19) | 3 (29) |
| 0.001 | 14 | 5 (9) | 1 (13) |

It will be seen that a reasonable amount of oxygen separation can be achieved with salts having an equilibrium constant in the range of about 0.003 to about 0.1 torr, and that the optimum equilibrium constant is about 0.01 to about 0.03 torr. Naturally, the equilibrium constant varies considerably with temperature and thus in choosing an appropriate salt for any given process, it is important to take into account the temperature at which the process will be operated.

The foregoing discussion has assumed that the loading and unloading of oxygen from the salt solution is effected at the same temperature, i.e. that the oxygen separation process is effected isothermally, but of course the process may be operated so that off-loading of oxygen from the salt is effected at a higher temperature than loading of the oxygen. Since the equilibrium constant of the salts of Formulae XVII and XVIIA decreases relatively quickly with temperature, the amount of oxygen separated per pass of any given quantity of salt through an oxygen separation process can be increased by unloading the oxygen at a higher temperature than that at which the oxygen is loaded. For example, compound number 32 (see Tables 2 and 3 below) has an equilibrium constant of 0.3 torr at 0° C. and an equilibrium constant of 0.003 torr at +30° C., so loading with molecular oxygen at 0° C. gives 98% saturation at 160 torr oxygen partial pressure while off-loading at 30° C. and 50 torr leaves only 13% saturation, a difference of 85%. However, when using non-isothermal processes, account will of course have to be taken of the energy consumed in warming and cooling the salt solution during the process.

The oxygen affinity of the salts of Formulae XVII and XVIIA can be caused to vary over at least five orders of magnitude depending on the nature of the substituent groups attached to the complex and the solvent in which the complex is dissolved or dispersed. It is particularly important that this binding affinity can be tuned to values close to those that may be desired for specific applications. For example, the salt of Formula IA having $R_1=H$, $R_2=R_3=R_4=CH_3$, $R=$hexamethylene, $X=Y=$trimethylene, and $Z=N$-methylimidazole, in aqueous solution has $P_{\frac{1}{2}(O2)}=0.625$ torr at 20° C. This value of the half-saturation partial pressure is very close to that of human myoglobin at the same temperature ($P_{\frac{1}{2}(O2)}=0.667$ torr at pH 8). In contrast, at the same temperature but in acetonitrile solvent, the complex differing only in that X is an ethylene group, has a value of $P_{\frac{1}{2}(O2)}=2.13$ torr, which is quite close to the equilibrium constant of human hemoglobin ($P_{\frac{1}{2}}(O_2)=2.50$ torr at pH 8). Thus, the dry cave complexes can be useful when molecular oxygen must be made available at a precise partial pressure. Obviously, those salts of Formulae XVII and XVIIA having equilibrium constants close to those of mammalian hemoglobins can be used to load oxygen in the lungs of a mammal and to unload oxygen in the non-lung tissues of the mammal, i.e. the salts can be used as a synthetic blood. Naturally, when a salt is to be used for this purpose it is essential to select a salt which will not be toxic to the mammal in which the synthetic blood is to be employed and which can be broken down and excreted from the mammal's body without injury to its metabolic systems.

Figure 4:
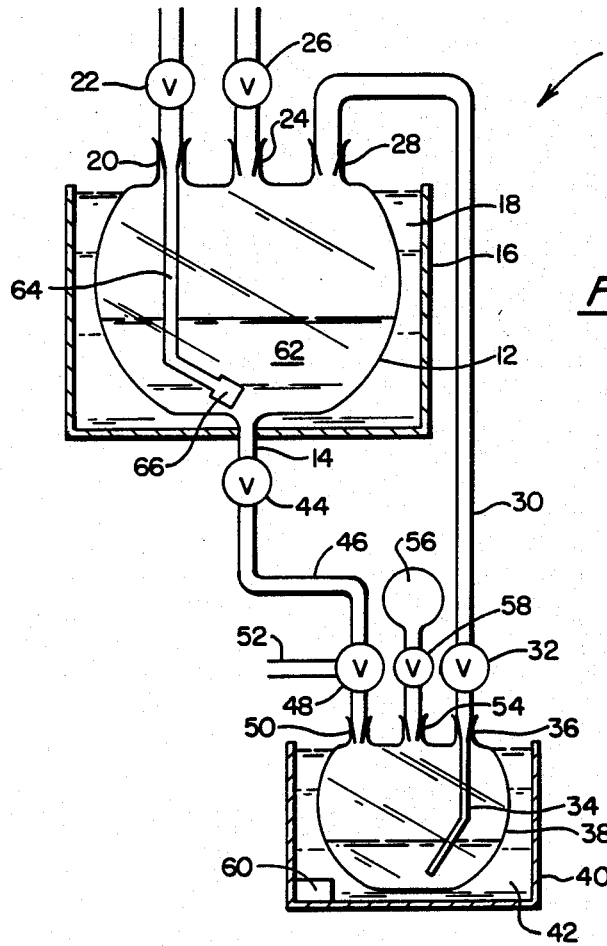
FIG. 4 shows a simple apparatus which can be used to separate oxygen from air using the compounds of the invention.

FIG. 4 of the accompanying drawings shows an experimental apparatus which can be used for separating oxygen from air on a small scale. This apparatus, generally designated 10, comprises an air inlet vessel 12 in the form of a three-necked, 500 ml. flask 12 which is equipped with an outlet tube 14 at its base. The flask 12 is surrounded by a liquid container 16 containing a liquid 18 which serves to maintain the flask 12 at constant temperature. The outlet tube 14 passes through the base of the container 16 in a fluid-tight manner.

One neck 20 of the flask 12 is connected via a stop-cock 22 to a source (not shown) of air under slight pressure. The central neck 24 of the flask 12 is similarly connected via a stop-cock 26 to an air outlet (which may be simply a tube open to the air, as shown in FIG. 4). The third neck 28 of the flask 12 is connected via a tube 30 and a stop-cock 32 to a tube 34, which extends from one neck 36 of an outlet flask 38 to a position near the base of this flask. The outlet flask 38 is a three-necked, 250 ml. flask disposed within a container 40 containing an appropriate liquid 42 which functions in the same manner as the liquid 18 surrounding the inlet flask 12, thereby holding the outlet flask 38 at a constant temperature.

The outlet tube 14 extends from the inlet flask 12 through a stop cock 44, a connecting stop 46 and a three-way valve 48 to a second neck 50 of the outlet flask 38. A side limb 52 attached to the three-way valve 48 is connected to a monometer and vacuum pump (neither of which is shown). The third neck 54 of the outlet flask 38 is closed by means of a sample tube 56 equipped with a stop-cock 58. Finally, an ultrasonic cleaning device, indicated schematically at 60, is disposed within the liquid 42 surrounding the outlet flask 38.

To use the apparatus shown in FIG. 4 to separate molecular oxygen from air, isopropanol at −40° C. is used as the liquid 18 surrounding the inlet flask 12, while water at 30° C. is used as the liquid 42 surrounding the outlet flask 38. After ensuring that the stop-cock 44 is closed, a solution 62 of a compound of the invention is placed within the inlet flask 12, the stop-cocks 22 and 26 are opened and the stop-cock 32 closed. Air is then blown through the stop-cock 22, the neck 20 and a gas inlet tube 64 extending from the neck 20 of the inlet flask 12 to adjacent the base of this flask, the lower end of this gas inlet tube 64 being provided with a gas dispersion frit 66. The passage of air through the tube 64 into the solution 62 is continued until the solution 62 becomes substantially saturated with oxygen; during this passage of air through the solution 62, the open stop-cock 26 serves as an outlet for excess air. While the air is thus being passed through the solution 62, the three-way valve 48 is disposed so as to allow communication between the side limb 52, the tube 46 and the outlet flask 38; the stop-cock 58 is held open so as to permit fluid communication between the sample tube 56 and the outlet flask 38. Thus, the vacuum pump attached to the side limb 52 evacuates the tube 46, the outlet flask 38 and the sample tube 56.

After the solution 62 has become saturated with oxygen, the valve 48 is adjusted so as to permit fluid communication between the tube 46 and the outlet flask 38, but to cut off both this tube and flask from the side limb 52. The stop-cock 44 is then opened, whereupon the low pressure in the flask 38 transfers the solution 62 from the inlet flask 12 via the tube 46 through the outlet flask 38. After about 95% of the solution 62 has been removed from the inlet flask 12, the stop-cock 44 and the valve 48 are closed completely. The ultrasonic cleaning device 60 is then operated to ensure good evolution of molecular oxygen from the solution 62 (which is now in the outer flask 38); the oxygen thus evolved enters the sample tube 56 and may also if desired may be removed by the side limb 52. After evolution of molecular oxygen has ceased, the stop-cock 22 is closed and the stop cock 26 connected to a vacuum pump thereby evacuating the inlet flask 12 and the tube 30 (it will be recalled that the stop-cocks 32 and 44 are closed). If it is desired to retain a sample of the gas evolved for mass spectrometric or gas chromatographic analysis, the stop-cock 58 is now closed, thereby isolating the gas sample in the sample tube 56. Next, the stop-cock 32 is open, whereupon the low pressure in the tube 30 and the inlet flask 12 causes the solution 62 to be recycled from the outlet flask 38 to the inlet flask 12; the stop-cock 32 should be reclosed before the level of the solution 62 in the outlet flask 38 falls below the lower end of the tube 34. The apparatus is now ready to carry out another cycle.

Although the apparatus just described is suitable for separating oxygen from air on a very small scale, for commercial purposes it will probably be found more satisfactory to employ an immobilized liquid membrane apparatus to effect such separaton; details of appropriate methods of forming such liquid membranes are described in the references already listed above.

The usefulness of such immobilized liquid membranes is however, not confined to separating molecular oxygen from air. Since such membranes are selectively permeable to molecular oxygen, they are useful in situations where it is desired to transport molecular oxygen into a container without allowing egress of other compounds from the container. For example, the limiting factor on the life of zinc/air batteries is often escape of water vapor from the battery through passages designed to allow entrance of oxygen into the battery, rather than exhaustion of anode material. By using an immobilized liquid membrane containing a salt of the invention, molecular oxygen can enter the battery without water vapor escaping therefrom, thus increasing the life of the battery.

Finally, certain salts of Formulae XVII and XVIIA, and in particular the cobalt salts, show promise as possible catalytic, possible stoichiometric promoters of oxidation reactions in which atmospheric oxygen serves as the oxidizing agent. For such use, the bridging groups may be viewed as possible substrates for such oxidations. Thus, the instant salts might be used in zinc/air batteries to increase the concentration of molecular oxygen in the electrolyte and therefore increase the flux of cathode material to facilitate higher discharge rates. When the salts are to be used catalytically, it may be especially advantageous to bond them chemically to a support. Further, the complexes may exhibit a buffer-like action in generating a desired partial pressure of molecular oxygen and may find wide use as an electrode coating where the complexes may facilitate the reduction of oxygen to water or the anodic formulation of molecular oxygen from water, e.g. on the cathodes of zinc/air batteries.

As already mentioned, the invention extends to the nickel salts of Formulae II, III, XVIII, IIA, IIIA, and XVIIIA. As described in more detail below, these nickel salts are useful as intermediates for the preparation of the corresponding complexes containing other metals.

Methods will now be described for synthesis of the salts of Formulae XVII and XVIIA. It will be appreciated that the exact synthetic techniques employed may vary somewhat with the exact substituents in the cationic metal complexes; for example, where one of the substituents contains a reactive group, it may be necessary to protect the reactive group during certain stages of the synthesis. Furthermore, the exact techniques needed for isolation and purification of the salts may vary considerably depending upon the exact salt employed. However, the necessary variations in synthetic techniques are believed to be apparent to those skilled in the art or easily discoverable by the routine empirical techniques employed by skilled chemists in preparing new compounds. As mentioned above, in the salts of Formula XVII and XVIIA, it does not appear to be possible to prepare pure cobalt salts having a tetrachlorozincate anion, while in the case of the salts of Formula XVIIA having iron as the metal ion, it appears that if chloride is present in the reaction mixture used to prepare the ion complex, the chloride tends to prefer to enter the cation as the ligand Z in preference to remaining as the anion. It will also be apparent to those skilled in the art that certain combinations of the groups $R_4$ and $R_6$ may cause electronic and steric hindrances during the preparative process which may make salts having these combinations of $R_4$ and $R_6$ difficult to prepare by certain synthetic routes. Finally, it is probable that those skilled in the art will be able to devise different syntheses of the salts of Formulae XVII and XVIIA and it should be noted that the invention is not limited to any particular method for the synthesis of such salts.

The preferred synthesis of the salts of the present invention proceeds from the "Jäger" complexes prepared as described by Jäger in *Z. Anorg. Allg. Chem.*, 346, 76 (1966) and *Z. Chem.*, 8, 30, 392 (1968). Additional published definitive syntheses of the Jäger complexes can be found in the following publications: Dennis E. Riley and Daryle H. Busch, Inorganic Synthesis, 18, 36 (1978) and Jerome Streeky, Thesis, The Ohio State University, Columbus, Ohio (1979). The Jäger complexes may be represented by Formula V shown in FIG. 3 of the accompanying drawings.

The first step in the synthesis of the instant salts involves conversion of the acyl groups of the Jäger complex to methyl vinyl ether groups as reported by P. W. R. Corfield, J. D. Mokren, C. J. Hipp, and D. H. Busch, *Journal of the American Chemical Society*, 95, 4465 (1973); the products of this reaction are of Formula VI shown in FIG. 3 of the accompanying drawings. Reagents useful in this reaction include not only the $CH_3SO_3F$ shown in FIG. 3 but also for example trialkyloxonium cations ($R_3O^+$). As reported by Corfield et al vide supra, primary and secondary amines HNR'R'' readily displace the methoxy group from the methyl vinyl ether grouping in the compounds of Formula VI to produce the compounds of Formula VII, which contain the macrocyclic ligand of the salts of the present invention. This ligand has a serendipitous arrangement of atoms and electrons such that good metaldioxygen carriers are formed.

The second major aspect of the synthesis of the salts of the present invention involves bridging of the compound of Formula VII to form a bicyclic compound of Formula I or a tricyclic compound of Formula II. At this stage compounds of Formula III can already have their carbon-carbon bridge from a variant synthesis of the Jäger complex which will be described in detail below. A salt of Formula I can be formed most easily by one of two routes. The first synthesis route involves the reaction of the methyl vinyl ether intermediate of Formula VI with an appropriate $\alpha,\omega$-diamine containing R. This reaction parallels the reaction detailed above for synthesizing the ligand of Formula VII from the methyl vinyl ether intermediate of Formula VI and is a very general reaction which can be applied to almost any diamine. Additional information on this reaction route can be found in the following publication: Wayne Schammel, Thesis, The Ohio State University, Columbus, Ohio (1976). This reaction route will also be illustrated in the examples which follow.

The second route for synthesizing the metal dry cave complex of Formula I is often more useful since it does not require the existence of a diamine, but rather a diol or dihalide is adequate. For this route, a compound of Formula VIII is prepared in which at least one substituent on each nitrogen atom is hydrogen. The reaction of this compound with the ditosylate of a diol or with a dibromide, or similar reagent, readily yields the desired bridged compound of Formula IX, as shown in FIG. 3. Additional useful reagents for this reaction include brosylates, nosylates, mesylates, oxonium ions, alkyl perchlorates, alkyl fluorosulfonates, and the fluorinated compounds, triflates, nonaflates, tresylates, and the like.

The synthesis of a compound of Formula III differs from the two reaction routes outlined above for the formation of a compound of Formula I in that formation of a bicyclic structure precedes conversion of the Jäger macrocycle of Formula V into the neutral ligand of Formula VII. A variant of the Jäger complex having a bicyclic structure serves as the starting material in this synthesis route. For preparation of the starting material, reference is made to the following publication: J. Eilmes and E. Sledziewska, *Bulletin De L'Academie Polonaise Des Sciences, Serie Du Sciences Chemique XXVI*, No. 6, 441 (1978). The reaction procedure for synthesis of compound of Formula III can be varied at an intermediate step in the procedure for synthesizing either a compound of Formula III or a doublebridged compound of Formula II. The reaction procedure commences with a compound of Formula X, a neutralized, deacylated species of the Jäger macrocycle (see Example IV for further details on synthesis of this species). As shown in FIG. 3 this compound of Formula X is reacted with a dicarbonyl halide or the like to introduce the $R_5$ bridge group, thereby producing a compound of Formula XI. This compound of Formula XI can have its carbonyl group converted to a methyl vinyl ether group in a manner described above for preparation of a compound of Formula VI and the methyl vinyl ether group then replaced by an amine group in the manner described above for preparation of a compound of Formula VII, thus synthesizing a compound of Formula III. Alternatively, a diamine can be added to the methyl vinyl ether functional complex to introduce an R bridge and thus synthesize a compound of Formula II.

The original Jäger complexes described in the papers mentioned above are substituted such that the compounds of Formula XVII produced therefrom have the groups $R_1$ hydrogen atoms and the groups $R_2$ methyl groups. Compounds in which both such groups are hydrogen atoms may be prepared by the methods described in Hiller, Dimroth and Pfitzner, Liebigs Ann. Chem. 717, 137 (1968); this paper also describes starting materials suitable for preparing compounds of Formula XVII in which X and Y are o-phenylene groups. Starting materials suitable for producing compounds of Formula XVII in which R and $R_2$ are both methyl groups are described in Tang et al, Inorganic Chemistry, 12, 2589-95 (1973); this paper also discusses techniques for varying the length of the carbon chain in the groups X and Y in Formula XVII.

In all of the foregoing illustrative syntheses, the use of any particular substituent is strictly for purposes of illustrating the present invention and is not a limitation of the present invention. Also an oxidation state (valence) of two for metal A has been arbitrarily selected herein for illustration and instructional purposes and is not intended to be a limitation of the present invention. The organic part of the cations of the instant salts generally are synthesized on a relatively unreactive metal ion such as nickel or zinc, nickel being the preferred metal for this purpose. Some copper compounds of Formulae XVII can be synthesized with the copper already in place. Once the ligand structure has been correctly synthesized with a relatively unreactive metal ion, that metal ion is removed and the ligand is coordinated to a more reactive metal ion. The relatively unreactive metal ion can be removed by the addition of dry HCl to an acetonitrile solution of the compound first prepared. The addition of $ZnCl_2$ then results in separation of the solid tetrachlorozincate salt. Before reaction with the desired reactive metal ion, the ligand tetrachlorozincate salt preferably is converted to the hexafluorophosphate salt, by reaction with a soluble hexafluorophosphate e.g.

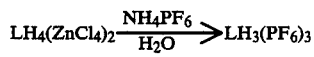

Alternatively, the hexafluorophosphate salt can be isolated directly, after separation of the ligand from the relatively unreactive metal ion by HCl, upon addition of $NH_4PF_6$, as illustrated below.

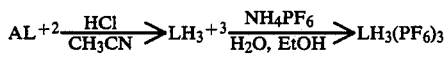

(Although the formula of the demetallated hexafluorophosphates has been written above as $LH_3(PF_6)_3$, our latest experiments indicate that, in at least some cases, a chloride anion may be present along with the hexafluorophosphates so that the formula may be more correctly given as $LH_4Cl(PF_6)_3$. However, it will be appreciated that this uncertainty as to the formula of the demetallated intermediate makes no difference in the practice of the preparative method, and does not extend to the formula of the instant metallated salts produced as described below.) As already mentioned, it has not been possible to prepare pure chlorozincate salts of Formula XVII where the metal is cobalt. Thus, for example, in preparing cobalt(II) complexes, the ligand hexafluorophosphate salts, $LH_3(PF_6)_3$, slurried in methanol may have added thereto a solution of sodium acetate and cobalt(II) acetate tetrahydrate in methanol:

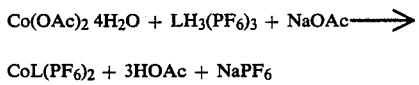

The compounds must be prepared in the absence of oxygen. The four coordinate complexes separate from solution. Alternatively, additional ligand salts and solvents which can be used in removing the unreactive metal ion and replacing it with a desired reactive metal ion include the perchlorate, hexafluoroarsenate, fluoroborate, trifluoromethylsulfonate, or halide salts; and as solvents, nitriles, alcohols, nitroalkanes, or water.

The salts of Formula XVIIA, which tend to have a stronger oxygen affinity than the corresponding salts of Formula XVII, may be prepared from the corresponding compounds of Formula XVII. Usually, it is only necessary to dissolve the salt of Formula XVII in a solution containing the desired axial ligand Z to form the corresponding compound of Formula XVIIA. Suitable solvents for carrying out such reactions include methanol, acetone and other ketones, acetonitrile and other nitriles, dimethylformamide and other amides, sulfoxides, sulfones, and the like and mixtures thereof. This reaction is illustrated below.

Since the compounds of Formula XVIIA differ from the compounds of Formula XVII only in the presence of the ligand Z, interconversion of the two groups of compounds can occur readily in solution, and there is some reason to believe than in many cases in which a compound of Formula XVII is used in solution, the species present may in fact be a compound of Formula XVIIA having a molecule of the solvent as the axial ligand. For example, it is likely that many of the compounds of Formula XVII exist in aqueous solution in the form of the corresponding compound of Formula XVIIA with a molecule of water as the ligand Z, even though crystalization of the salt from aqueous solution may take place in the form of the water-free salt of Formula XVII. Accordingly, the oxygen affinities measured for the salts of Formula XVII and XVIIA will often vary with the solvent used, since the choice of solvent may affect the ligand Z in the cation.

Oxygen-Binding Polymers Having Attached Thereto Bridging Groups of Formulae XIX or XIX A, or Molecules of Formula XIX B As mentioned above, the groups of Formula XVII and XVIIA may be used chemically bonded to a substrate such as a synthetic polymer. Rather surprisingly, I have found that groups of Formula XIX and XIX A, which are unbridged analogs of the compounds of Formulae XVII and XVIIA respectively, also complex molecular oxygen reversibly when chemically bonded to a support although the free forms (wherein hydrogen atoms are attached to the $NR'_6$ groups) of the corresponding complexes bond molecular oxygen largely irreversibly. I believe (although the invention is in no way limited by this belief) that the reason for this difference is that the irreversible decomposition of the free complex proceeds via a mechanism which requires close conjugation of two free complexes in a particular spatial arrangement, and that the chemical bonding of the complex to a substrate prevents two molecules of the complex coming together in the arrangement needed for the irreversible decomposition.

The synthesis of the unbridged compounds needed for synthesis of the oxygen-binding polymers of the invention will be apparent to those skilled in the art from the foregoing description. The nickel analogs of the free unbridged complexes are the compounds of Formula VII in which at least one of R' and R" is hydrogen, and the preparation of such nickel analogs has already been described above. The nickel analogs of Formula VII may be reacted with the polymer and the nickel then replaced with a more active metal in the manner already described. Alternatively, the compound of Formula VII may have the nickel replaced with a more active metal, and the resultant compound thereafter reacted with the nickel. Methods for the attachment of the compounds to the polymers are described in Examples 213–14 below. The unbridged compound is deprotonated with a base, such as methoxide, and a solution of a deprotonated compound allowed to flow through the resin, whereupon the deprotonated compound reacts with the polymer to form the bridging groups of Formula XIX or XIX A. Obviously, if it is desired to produce a polymer containing bridges of the Formula XIX A, insertion of the ligand Z may be affected as already described either before or after reaction of the free complex with the substrate.

In the polymers of the invention incorporating molecules of Formula XIX B, electron-donating groups on the polymer coordinate with the metal atom so that the electron-donating group in effect functions as a fifth ligand in a manner similr to the ligand Z in the compounds of Formulae I A-XVIII A. However, since the electron-donating group is fixedly attached to the polymer, the effect of its coordination to the metal atom is to attach the molecule of Formula XIX B to the polymer. Appropriate electron-donating groups include, for example, pyridyl and amino groups.

The polymers containing molecules of Formula XIX B may be prepared, as illustrated in Example 214, simply by passing a solution of the appropriate salt through the polymer.

Compounds of Formula XX

The effectiveness of the bridges in providing oxygen-complexing properties in the compounds of Formulae XVII and XVIIA, coupled with the fact that it is known that oxygen-complexing ability in such compounds is due to the provision of a hydrophobic cavity in which the oxygen molecule can rest, led to the discovery that, by adding similar bridges to other known types of macrocyclic compounds, such compounds can also be endowed with oxygen-complexing properties. These new oxygen-complexing compounds comprise the compounds of Formulae XX to XVI. Although some of Formulae XX to XVI are shown in the accompanying drawings in their demetallated forms, in all cases the invention extends to the complexes of such demetallated forms with nickel, cobalt, iron, copper or manganese ions in the +2 or +3 oxidation states and (except for the pentadentate compounds of Formula XXV) to such metal compounds possessing a fifth, axial ligand, which may be any of the ligands Z defined above with reference to Formula XVIIA.

The compounds of Formula XX may be prepared from 2,4-pentanedione, the appropriate alpha, omega-dihalide incorporating the group $R_7$, and the appropriate alpha, omega-diamine, $H_2NR_8NH_2$. The 2,4-pentanedione is treated with alkali metal to produce the 3-metallo derivative. Reaction of this metallo derivative with the alpha, omega-dihalide, Hal-$R_7$-HAL, produces the tetraketone shown in FIG. 7, which is then condensed with the alpha, omega-diamine, in for example ethanol, to produce the compound of Formula XX. This synthesis is similar to the synthesis of prior art compounds having much shorter bridges but which do not reversibly complex oxygen, as described in the following papers:

Crumbliss et al, Science, 164, 1168 (1969), and J.A.C.S., 92, 55 (1970)

Pignatello et al, J.A.C.S., 101, 5929 (1970)

Wallace et al, J. Biol. Chem., 257, 4966 (1982)

Hoffman et al, J.A.C.S., 92, 61 (1970) and 97, 673 (1975).

Compounds of Formula XXI

The compounds of Formula XXI are bridged derivatives of the well known anhydrotetramer of o-aminobenzaldehyde (TAAB). It has previously been shown that TAAB will add nucleophiles across two imine linkages to form bridged compounds, so that to produce the compounds of Formula XXI it is only necessary to react the appropriate dinucleophile with TAAB. The dinucleophile may be, for example, the dianion of a diol, dithiol or diamine or a carbon dinucleophile such as a dialkali metal alkyl or an enamine. If desired, the nucleophile used may contain additional functional groups to give structures able to undergo additional reactions. For example the nucleophile 1-(N-pyrrolidine)-1-phenylethylene may be used.

Details of the synthesis of TAAB and the manner of adding nucleophiles thereto, together with procedures for inserting metal atoms therein, are described in the following publications:

Goedken et al, J. Coord. Chem., 7, 89 (1977)
Taylor et al, J.A.C.S., 91, 1072 (1969)
Katovic et al, Inorg. Chem., 10, 458 (1971), and J.A.C.S., 91, 2122 (1969)
Kamenar et al, Inorg. Chem., 18, 815 (1979)
Madden, I. L., Ph.D. Thesis, The Ohio State University, (1975).

Compounds of Formulae XXIIA-XXIIE

These compounds are derivatives of the saturated tetraazamacrocycles cyclam, cyclen and their congeners. The bridging groups $R_{10}$ may be inserted by reacting the unbridged macrocycle (in which each nitrogen carries a single proton) with an appropriate alpha, omega-dihalide or dipseudohalide, such as a ditosylate. As with the other groups of compounds discussed above, insertion of the metal atom (and if desired the axial ligand) is effected in the same way as of compounds Formulae XVII and XXI; basically, it is only necessary to mix solutions of the compound of Formula XXII and an appropriate metal salt and then, if desired, to add the appropriate ligand Z.

Further details of appropriate conditions for carrying out the bridging reaction to produce compounds of Formula XXII are given in the following papers:

Barefield and Wagner, Inorg. Chem., 12, 2435 (1973) and 15, 408 (1976)
Ramasubbu et al, J. Chem., Soc., Chem. Commun., 1982, 277
Wainwright, J. Chem. Soc., Dalton Trans., 1980, 2117.

Compounds of Formula XXIII

The compounds of Formula XXIII are produced by a reaction which is generally similar to that described above for producing the compounds of Formula XXI and involves the addition of an alpha, omega dinucleophile to the azomethine groups in the known starting material shown in FIG. 7. Appropriate methods for carrying out reactions of this type are described in:

Taylor et al, J. Am. Chem. Soc., 91, 1072 (1969)
Keypour and Stotter, Inorg. Chim. Acta. 33, L149 (1979)

Insertion of the metal atoms and, if desired, the ligand Z may be effected in the manner already described above in relation to compounds of Formula XXI.

Compound of Formula XXIV

The insertion of the bridges, metal atoms and (optionally) the ligands Z may be effected in ways precisely analogous to those already described above for compounds of Formula XXII. Further discussion of appropriate reaction conditions may be found in the three papers cited above with reference to the compounds of Formula XXII.

Compounds of Formula XXV

The compounds of Formula XXV may be regarded as derivatives of the well-known "salen" ligand (1, 6-bis(2-hydroxyphenyl)-2,4-diazahexa-1,5-diene). As shown in FIG. 7, the compounds of Formula XXV are prepared by Schiff base condensation of a diamine with the appropriate triamino-dialdehyde. The preparation of the dialdehyde may be carried out by slight modifications of the synthesis described in the following papers:

Green et al, J. Chem. Soc. Chem. Commun. 1968, 518 and Inorg. Chim. Acta, 5, 17 (1971)
Black and Lane, Aust. J. Chem., 23, 2039 (1970)
Lindoy and Busch, Inorg. Nucl. Chem. Lett., 5, 525 (1969)
Fleischer et al, Inorg. Nuc. Chem. Lett., 9, 10610 (1973).

The preparation of the diamine starting material may be carried out by the method described in Martin et al, J. Chem. Soc., Dalton Trans., 1979, 1497 and 1503.

Insertion of the metal atoms into the compounds of Formula XXV may be made in the manners already described above with reference to other compounds of the invention. It should be noted, that unlike the other compounds of the invention already described, the compounds of Formula XXV are pentadentate; the four central nitrogen atoms complex the metal ion in the usual square planar arrangement, while the $NR_{13}$ group complexes the metal ion axially. Accordingly, the compounds of Formula XXV will not simultaneously complex both an oxygen molecule and a ligand Z.

Compounds of Formula XXVI

The compounds of Formula XXVI are closely related to the well known cobalt (II) complexes of dimethylglyoxime, and the compound in which $R_{15}$ is a $(CH_2)_{12}$ groups is described in papers in Helv. Chim. Acta, 54, 2747 and 2753 (1971). The other compounds of Formula XXVI may be prepared in manners exactly analogous to the synthetic procedure described in the first of these two papers.

As already mentioned, the compounds of Formulae XX to XXVI complex oxygen and may thus be used in any of the ways already described in relation to compounds of Formula XVII and XVIIA.

Numerous examples of compounds of the invention and intermediates useful in preparing such compounds will now be given, though by way of illustration only, and such examples should not be construed as limiting. All units are in the metric system unless otherwise expressly indicated and all references cited herein are incorporated herein by reference.

In view of the complexity of the chemical nomenclature necessary to describe the instant salts and the intermediates used to prepare them, for brevity there are set out in Table 2 below the formal names of all compounds prepared in the following examples, together with numbers by which the compounds are identified in later tables. It should be noted that the nomenclature used in Table 2 differs in certain respects from that used in the examples of my aforementioned parent application, Ser. No. 114,670. In particular, in the aforementioned parent application the attachment of the four nitrogen atoms to the metal ion was indicated by the nomenclature ". . . $N_4$)cobalt (II) . . . ", and similarly for other metals; in Table II, and elsewhere in the following examples, the more correct nomenclature ( . . . $\kappa^4 N$)cobalt(II) . . . " is employed instead. Rather more importantly, some of the examples in my aforementioned parent application use a slightly erroneous numbering system which has been corrected in the nomenclature used in Table 2; where such incorrect nomenclature was previously employed, the name originally given for the compound in the example is included in parentheses following "formerly designated".

Table 3 below sets out the various substituents in those compound listed in Table 2 which fall within Formulae I and IA; obviously, where no substituent value is given in the column for the ligand Z, the compound is of Formula I, while when a value is given for Z the compound is of Formula IA. In those cases where Z is stated in Table 3 to be carbon monoxide followed by another ligand, the compound actually prepared is the carbon monoxide adduct of the salt of Formula IA, so that the carbon monoxide is actually within the dry cave of the cation metal complex and the other ligand mentioned occupies the Z position. Similarly, where two identical ligands Z are stated in the present (as in compound No. 22, where Z is stated to be (NCS)$_2$), one of these ligands resides within the dry cave and the other occupies the normal Z position. In Table 3, "Py" denotes pyridine and "IM" designates imidazole. To improve legibility, the usual minus signs are omitted from the anions, and thus it should be noted that in Table 3 (and in Tables 4, 5 and 6) "Cl" denotes a chloride ion, not a free chlorine atom. In a few cases, demetallated compounds are produced; these compounds are indicated in Table 3 by a dash in the $M^{n+}$ column.

Table 4 lists the identities of the variable groups and substituents of the various compounds listed in Table 2 which fall within Formula II, Table 5 similarly lists the corresponding values of the compounds listed in Table 2 which fall within Formula III and IIIA, while Table 6 similarly lists the corresponding values of the compounds listed in Table 2 which fall within Formulae XVIII and XVIIIA. Table 7 gives analytical data for most of the compounds mentioned in Tables 2-6.

In the following Tables, compounds marked (c) after the compound No. are "control" compounds i.e. compounds similar to those of the invention but possessing different values of the variable substituents. These control compounds are provided to show that the properties of the instant compounds become less advantageous when the substituent values fall outside the ranges given.

TABLE 2

| Compound No. | |
|---|---|
| 1(c) | [(2,3,7,8,10,16-hexamethyl-3,7,11,15,18,22-hexaazabicyclo[7.7.7]tricosa-1,8,10,15,17,22-hexaene-κ$^4$N)nickel(II)] hexafluorophosphate |
| 2(c) | [acetonitrile(2,3,7,8,10,16-hexamethyl-3,7,11,15,18,22-hexaazabicyclo[7.7.7]tricosa-1,8,10,15,17,22-hexaene-κN)cobalt(II)] hexafluorophosphate |
| 3(c) | [chloro(2,3,7,8,10,16-hexamethyl-3,7,11,15,22-hexaazabicyclo[7.7.7]tricosa-1,8,10,15,17,22-hexaene-κ$^4$N)iron(II)] hexafluorophosphate |
| 4 | [2,9,11,17-tetramethyl-3,8,12,16,19,23-hexaazabicyclo[8.7.7]tetracosa-1,9,11,16,18,23-hexaene-κ$^4$N)nickel(II)] hexafluorophosphate |
| 5 | [chloro(2,9,11,17-tetramethyl-3,8,12,16,19,23-hexaazabicyclo[8.7.7]tetracosa-1,9,11,16,18,23-hexaene-κ$^4$N(iron(II)] hexafluorophosphate |
| 6 | [(2,3,8,9,11,17-hexamethyl-3,8,12,16,19,23-hexaazabicyclo[8.7.7]tetracosa-1,9,11,16,18,23-hexaene-κ$^4$N)nickel(II)] hexafluorophosphate |
| 7 | [(2,3,8,9,11,17-hexamethyl-3,8,12,16,19,23-hexaazabicyclo[8.7.7]tetra-88 $^4$N)cobalt(II)] hexafluorophosphate |
| 8 | [chloro(2,3,8,9,11,17-hexamethyl-3,8,12,16,19,23-hexaazabiclo[8.7.7]tetracosa-1,9,11,16,18,23-hexaene-κ$^4$N)iron(II)] hexafluorophosphate |
| 9 | [(11,17-dimethyl-2,9-diphenyl-3,8,12,16,19,23,-hexaazabicyclo[8.7.7]tetracosa-1,9,11,16,18,23-hexaene-κ$^4$N)nickel(II)] hexafluorophosphate |
| 10 | [acetonitrile(11,17-dimethyl-2,9-diphenyl,3,8,12,16,19,23-hexaazabicyclo[8.7.7]tetracosa-1,9,11,16,18,23-hexaene-κ$^4$N)cobalt(II)] hexafluorophosphate |
| 11 | [(3,8,11,17-tetramethyl-2-,9-diphenyl-3,8,12,16,19,23-hexaazabicyclo[8.7.7]tetracosa-1,9,11,16,18,23-hexaene-κ$^4$N)nickel(II)] hexafluorophosphate |
| 12 | [(3,8,11,17-tetramethyl-2,9-diphenyl-3,8,12,16,19,23-hexaazabicyclo[8.7.7]tetracosa-1,9,11,16,18,23-hexaene-κ$^4$N)cobalt(II)] hexafluorophosphate |
| 13 | [chloro(3,8,11,17-tetramethyl-2,9-diphenyl-3,8,12,16,19,23-hexaazabicyclo[8.7.7]tetracosa-1,9,11,16,18,23-hexaene-κ$^4$)iron(II)] hexafluorophosphate |
| 14 | [chloro(2,3,8,9,11,17-hexamethyl-3,8,12,16,19,23-hexaazabicyclo[8.7.7]tetracosa-1,9,11,16,18,23-hexaene-κ$^4$N)copper(II)]hexafluorophosphate |
| 15 | [2,9-di-t-butyl-11,17 dimethyl-3,8,12,16,19,23-hexaazabicyclo[8.7.7]tetracosa-1,9,11,16,18,23-hexaene-κ$^4$N)nickel(II)] hexafluorophosphate |
| 16 | [(2,10,12,18-tetramethyl-3,9,13,17,20,24-hexaazabicyclo[9.7.7]pentacosa-1,10,12,17,19,24-hexaene-κ$^4$N)nickel(II)] hexafluorophosphate |
| 17 | [(2,10,12,18-tetramethyl-3,9,13,17,20,24-hexaazabicyclo[9.7.7]pentacosa-1,10,12,17,19,24-hexaene-κ$^4$N)cobalt(II)]hexafluorophosphate |
| 18 | [chloro(2,10,12,18-tetramethyl-3,9,13,17,20,24-hexaazabicyclo[9.7.7]pentacosa-1,10,12,17,19,24-hexaene-κ$^4$N)iron(II)] chloride |
| 19 | trans-[(carbonyl)(pyridine)(2,10,12,18-tetramethyl-3,9,13,17,20,24-hexaazabicyclo[9.7.7]pentacosa-1,10,12,17,19,24-hexaene-κ$^4$N)iron(II)] hexafluorophosphate |
| 20 | [(2,3,9,10,12,18-hexamethyl-3,9,13,17,20,24-hexaazabicyclo[9.7.7]pentacosa-1,10,12,17,19,24-hexaene-κ$^4$N)nickel(II)] hexafluorophosphate |
| 21 | [(2,3,9,10,12,18-hexamethyl-3,9,13,17,20,24-hexaazabicyclo[9.7.7]pentacosa-1,10,12,17,19,24-hexaene-κ$^4$N)cobalt(II)] hexafluorophosphate |
| 22 | [chloro(2,3,9,10,12,18-hexamethyl-3,9,13,17,20,24-hexaazabicyclo[9.7.7]pentacosa-1,10,12,17,19,24-hexaene-κ$^4$N)iron(II)] hexafluorophosphate |
| 23 | trans-[bis-thiocyanato(2,3,9,10,12,18-hexamethyl-3,9,13,17,20,24-hexaazabicyclo[9.7.7]pentacosa-1,10,12,17,19,24-hexaene-κ$^4$N)cobalt(III)]hexafluorophosphate |

TABLE 2-continued

| Compound No. | |
|---|---|
| 24 | [(12,18-dimethyl-2,10-diphenyl-3,9,13,17,20,24-hexaazabicyclo[ 9.7.7] pentacosa-1,10,12,17,19,24-hexane-κ⁴N)nickel(II)]hexafluorophosphate |
| 25 | [(12,18-dimethyl-2,10-diphenyl-3,9,13,17,20,24-hexaazabicyclo[9.7.7] pentacosa-1,10,12,17,19,24-hexaene-κ⁴N)cobalt(II)] hexafluorophosphate |
| 26 | [(3,9,12,18-tetramethyl-2,10-diphenyl-3,9,13,17,20,24-hexaazabicyclo [9.7.7]pentacosa-1,10,12,17,19,24-hexaene-κ⁴N)nickel(II)] hexafluorophosphate |
| 27 | [(3,9,12,18-tetramethyl-2,10-diphenyl-3,9,13,17,20,24-hexaazabicyclo [9.7.7]pentacosa-1,10,12,17,19,24-hexaene-κ⁴N)cobalt(II)] hexafluorophosphate |
| 28 | [chloro(3,9,12,18-tetramethyl-2,10-diphenyl-3,9,13,17,20,24-hexaazabicyclo [9.7.7]pentacosa-1,10,12,17,19,24-hexane-κ⁴N)iron(II)] hexafluorophosphate |
| 29 | [(2,10-di-t-butyl-12,18-dimethyl-3,9,13,17,20,24-hexaazabicyclo[9.7.7] pentacosa-1,10,12,17,19,24-hexaene-κ⁴N)nickel(II)] hexafluorophosphate |
| 30 | [acetonitrile(2,10-di-t-butyl-12,18-dimethyl-3,9,13,17,20,24-hexaazabicyclo[9.7.7]pentacosa-1,10,12,17,24-hexaene-κ⁴N)cobalt(II)] hexafluorophosphate |
| 31 | [(2,11,13,19-tetramethyl-3,10,14,18,21,25-hexaazabicyclo[10.7.7] hexacosa-1,11,13,18,20,25-hexaene-κ⁴N)nickel(II)] hexafluorophosphate |
| 32 | [(2,11,13,19-tetramethyl-3,10,14,18,21,25-hexaazabicyclo[10.7.7] hexacosa-1,11,13,18,20,25-hexaene-κ⁴N)cobalt(II)] hexafluorophosphate |
| 33 | [chloro(2,11,13,19-tetramethyl-3,10,14,18,21,25-hexaazabicyclo[10.7.7] hexacosa-1,11,13,18,20,25-hexaene-κ⁴N)iron(II)] hexafluorophosphate |
| 34 | trans-[(carbonyl)(pyridine)(2,11,13,19-tetramethyl-3,10,14,18,21,25-hexaazabicyclo[10.7.7]hexacosa-1,11,13,18,20,25-hexaene-κ⁴N)iron(II)] hexafluorophosphate |
| 35 | [ethanol(2,11,13,19-tetramethyl-3,10,14,18,21,25-hexaazabicyclo[10.7.7] hexacosa-1,11,13,18,20,25-hexaene-κ⁴N)copper(II)] hexafluorophosphate |
| 36 | [(2,3,10,11,13,19-hexamethyl-3,10,14,18,21,25-hexaazabicyclo[10.7.7] hexacosa-1,11,13,18,20,25-hexaene-κ⁴N)nickel(II)]hexafluorophosphate |
| 37 | [(2,3,10,11,13,19-hexamethyl-3,10,14,18,21,25-hexaazabicyclo[10.7.7] hexacosa-1,11,13,18,20,25-hexaene-κ⁴N)nickel(II)]chloride |
| 38 | [(2,3,10,11,13,19-hexamethyl-3,10,14,18,21,25-hexaazabicyclo[10.7.7] hexacosa-1,11,13,18,20,25-hexaene-κ⁴N)cobalt(II)]hexafluorophosphate |
| 39 | [1-methylimidazole(2,3,10,11,13,19-hexamethyl-3,10,14,18,21,25-hexaazabicyclo[10.7.7]hexacosa-1,11,13,18,20,25-hexaene-κ⁴N)cobalt(II)] hexafluorophosphate |
| 40 | [imidazole(2,3,10,11,13,19-hexamethyl-3,10,14,18,21,25-hexaazabicyclo-[10.7.7]hexacosa-1,11,13,18,20,25-κ⁴N)cobalt(II)] hexafluorophosphate |
| 41 | [pyridine(2,3,10,11,13,19-hexamethyl-3,10,14,18,21,25-hexaazabicyclo-[10.7.7]hexacosa-1,11,13,18,20,25-hexaene-κ⁴N)cobalt(II)] hexafluorophosphate |
| 42 | [thiocyanato(2,3,10,11,13,19-hexamethyl-3,10,14,18,21,25-hexaazabicyclo-[10.7.7]hexacosa-1,11,13,20,25-hexaene-κ⁴N)cobalt(II)] hexafluorophosphate |
| 43 | trans-[bis-thiocyanato(2,3,10,11,13,19-hexamethyl-3,10,14,18,21,25-hexaazabicyclo[10.7.7]hexacosa-1,11,13,18,20,25-hexaene-κ⁴N)cobalt (III)] hexafluorophosphate |
| 44 | trans[bis-cyanato(2,3,10,11,13,19-hexamethyl-3,10,14,18,21,25-hexaazabicyclo]10.7.7]hexacosa-1,11,13,18,20,25-hexaene-κ⁴N)cobalt (III)] hexafluorophosphate |
| 44 | trans-[bis-cyanato(2,3,10,11,13,19-hexamethyl-3,10,14,18,21,25-hexaazabicyclo[10.7.7]hexacosa-1,11,13,18,20,25-hexaene-κ⁴N)cobalt (III)] hexafluorophosphate |
| 45 | trans-[bis-azido(2,3,10,11,13,19-hexamethyl-3,10,14,18,21,25-hexaazabicyclo[10.7.7]hexacosa-1,11,13,18,20,25-hexaene-κ⁴N)cobalt(III)] hexafluorophosphate |
| 46 | [chloro(2,3,10,11,13,19-hexamethyl-3,10,14,18,21,25-hexaazabicyclo-[10.7.7]hexacosa-1,11,13,18,20,25-hexaene-κ⁴N)iron(II)] hexafluorophosphate |
| 47 | trans-[(carbonyl)(acetonitrile)(2,3,10,11,13,19-hexamethyl-3,10,14,18,21,25-hexaazabicyclo[10.7.7]hexacosa-1,11,13,18,20,25-hexaene-κ⁴N)iron(II)] hexafluorophosphate |
| 48 | trans-[(carbonyl)(pyridine)(2,3,10,11,13,19-hexamethyl-3,10,14,18,21,25-hexaazabicyclo[10.7.7]hexacosa-1,11,13,18,20,25-hexaene-κ⁴N)iron(II)] hexafluorophosphate |
| 49 | trans-[(carbonyl)(1-methylimidazole)(2,3,10,11,13,19-hexamethyl-3,10, 14,18,21,25-hexaazabicyclo[10.7.7]hexacosa-1,11,13,18,20,25-hexaene-κ⁴N)iron(II)] hexafluorophosphate |
| 50 | [chloro(2,3,10,11,13,19-hexamethyl-3,10,14,18,21,25-hexaazabicyclo[10.7.7] hexacosa-1,11,13,18,20,15-hexaene-κ⁴N)iron(III)] hexafluorophosphate |
| 51 | [chloro(2,3,10,11,13,19-hexamethyl-3,10,14,18,21,25-hexaazabicyclo[10.7.7] hexacosa-1,11,13,18,20,25-hexaene-κ⁴N)manganese(II)] hexafluorophosphate |
| 52 | [chloro(2,3,10,11,13,19-hexamethyl-3,10,14,18,21,25-hexaazabicyclo[10.7.7] hexacosa-1,11,13,18,20,25-hexaene-κ⁴N)manganese(III)] hexafluorophosphate |
| 53 | [(2,3,10,11,13,19-hexamethyl-3,10,14,18,21,25-hexaazabicyclo[10.7.7] hexacosa-1,11,13,18,20,25-hexaene-κ⁴N)copper(II)] hexafluorophosphate |
| 54 | [13,19,dimethyl-2,11-diphenyl-3,10,14,18,21,25-hexaazabicyclo[10.7.7] hexacosa-1,11,13,18,20,25-hexaene-κ⁴N)nickel(II)] hexafluorophosphate |

TABLE 2-continued

| Compound No. | |
|---|---|
| 55 | [13,19-dimethyl-2,11,diphenyl-3,10,14,18,21,25-hexaazabicyclo[10.7.7] hexacosa-1,11,13,18,20,25-hexaene-$\kappa^4$N)cobalt(II)] hexafluorophosphate |
| 56 | [(3,10,13,19-tetramethyl-2,11-diphenyl-3,10,14,18,21,25-hexaazabicyclo [10.7.7]hexacosa-1,11,13,18,20,25-hexaene-$\kappa^4$N)nickel(II)] hexafluorophosphate |
| 57 | [(3,10,13,19-tetramethyl-2,11-diphenyl-3,10,14,18,21,25-hexaazabicyclo [10.7.7]hexacosa-1,11,13,18,20,25-hexaene-$\kappa^4$N)cobalt(II)] hexafluorophosphate |
| 58 | [chloro(3,10,13,19-tetramethyl-2,11-diphenyl-3,10,14,18,21,25-hexaazabicyclo[10.7.7]hexacosa-1,11,13,18,20,25-hexaene-$\kappa^4$N)iron(II)] hexafluorophosphate |
| 59 | [chloro(3,10-dibenzyl-13,19-dimethyl-2,11-diphenyl-3,10,14,18,21,25-hexaazabicyclo[10.7.7]hexacosa-1,11,13,18,20,25-hexaene-$\kappa^4$N)iron(II)] hexafluorophosphate |
| 60 | [(2,11-di-t-butyl-13,19-dimethyl-3,10,14,18,21,25-hexaazabicyclo[10.7.7] hexacosa-1,11,13,18,20,25-hexaene-$\kappa^4$N)nickel(II)] hexafluorophosphate |
| 61 | [(2,11-di-t-butyl-13,19-dimethyl-3,10,14,18,21,25-hexaazabicyclo[10.7.7] hexacosa-1,11,13,18,20,25-hexaene-$\kappa^4$N)cobalt(II)] hexafluorophosphate |
| 62 | [(2,11,-di-n-heptyl-13,19-dimethyl-3,10,14,18,21,25-hexaazabicyclo[10.7.7] hexacosa-1,11,13,18,20,25-hexaene-$\kappa^4$N)nickel(II)] hexafluorophosphate |
| 63 | [(3,10,13,19-tetramethyl-3,10,14,18,21,25-hexaazabicyclo[10.7.7]hexacosa-1,11,13,18,20,25-hexaene-$\kappa^4$N)nickel(II)] hexafluorophosphate |
| 64 | [acetonitrile(3,10,13,19-tetramethyl-3,10,14,18,21,25-hexaazabicyclo [10.7.7]hexacosa-1,11,13,18,20,25-hexaene-$\kappa^4$N)cobalt(II)] hexafluorophosphate |
| 65(c) | [(13,19-dimethyl-3,10,14,18,21,25-hexaazatricyclo[10.7.7.6$^{2,11}$]dotriaconta-1,11,13,18,20,25-hexaene-$\kappa^4$N)nickel(II)] hexafluorophosphate |
| 66 | [(13,19-dimethyl-3,10,14,18,21,25-hexaazatricyclo[10.7.7.7$^{2,11}$]tritriaconta-1,11,13,18,20,25-hexaene-$\kappa^4$N)nickel(II)] hexafluorophosphate |
| 67 | [(13,19-dimethyl-3,10,14,18,21,25-hexaazatricyclo[10.8$^{2,11}$.7.7]tetratriaconta-1,11,13,18,20,25-hexaene-$\kappa^4$N)nickel(II)] Hexafluorophosphate |
| 68 | [(2,12,14,20-tetramethyl-3,11,15,19,22,26-hexaazabicyclo)11.7.7]-heptacosa-1,12,14,19,21,26-hexaene-$\kappa^4$N)nickel(II)] hexafluorophosphate |
| 69 | [acetonitrile(2,12,14,20-tetramethyl-3,11,15,19,22,26-hexaazabicyclo [11.7.7]heptacosa-1,12,14,19,21,26-hexaene-$\kappa^4$N)cobalt(II)] hexafluorophosphate |
| 70 | [(2,3,11,12,14,20-hexamethyl-3,11,15,19,22,26-hexaazabicyclo[11.7.7] heptacosa-1,12,14,19,21,26-hexaene-$\kappa^4$N)nickel(II)] hexafluorophosphate |
| 71 | [(2,3,11,12,14,20-hexamethyl-3,11,15,19,22,26-hexaazabicyclo[11.7.7] heptacosa-1,12,14,19,21,26-hexaene-$\kappa^4$N)cobalt(II)] hexafluoro phosphate |
| 72 | [bis-thiocyanato(2,3,11,12,14,20-hexamethyl-3,11,15,19,22,26-hexaazabicyclo[11.7.7]heptacosa-1,12,14,19,21,26-hexaene-$\kappa^4$N)cobalt(III)] hexafluorophosphate |
| 73 | [(14,20-dimethyl-2,12-diphenyl-3,11,15,19,22,26-hexaazabicyclo[11.7.7] heptacosa-1,12,14,19,21,26-hexaene-$\kappa^4$N)nickel(II)] hexafluoro phosphate |
| 74 | [(14,20-dimethyl-2,12-diphenyl-3,11,15,19,22,26-hexaazabicyclo[11.7.7] heptacosa-1,12,14,19,21,26-hexaene-$\kappa^4$N)cobalt(II)] hexafluoro phosphate |
| 75 | [(3,11,14,20-tetramethyl-2,12-diphenyl-3,11,15,19,22,26-hexaazabicyclo-[11.7.7]heptacosa-1,12,14,19,21,26-hexaene-$\kappa^4$N)nickel(II)] hexafluorophosphate |
| 76 | [(3,11,14,20-tetramethyl-2,12-diphenyl-3,11,15,19,22,26-hexaazabicyclo-[11.7.7]heptacosa-1,12,14,19,21,26-hexaene-$\kappa^4$N)cobalt(II)] hexafluorophosphate |
| 77 | [(2,12-di-t-butyl-14,20-dimethyl-3,11,15,19,22,26-hexaazabicyclo[11.7.7] heptacosa-1,12,14,19,21,26-hexaene-$\kappa^4$N)nickel(II)] hexafluoro phosphate |
| 78 | [(2,12-di-t-butyl-14,20-dimethyl-3,11,15,19,22,26-hexaazabicyclo[ 11.7.7] heptacosa-1,12,14,19,21,26-hexaene-$\kappa^4$N)cobalt(II)] hexafluoro phosphate |
| 79 | [(14,20-dimethyl-3,11,15,19,22,26-hexaazatricyclo[11.8$^{2,12}$.7.7]pentatriaconta-1,12,14,19,21,26-hexaene-$\kappa^4$N)nickel(II)] hexafluorophosphate |
| 80 | [(2,13,15,21-tetramethyl-3,12,16,20,23,27-hexaazabicyclo[12.7.7]octacosa-1,13,15,20,22,27-hexaene-$\kappa^4$N)nickel(II)] hexafluorophosphate |
| 81 | [(2,13,15,21-tetramethyl-3,12,16,20,23,27-hexaazabicyclo[12.7.7]octacosa-1,13,15,20,22,27-hexaene-$\kappa^4$N)cobalt(II)] hexafluorophosphate |
| 82 | [(2,3,12,13,15,21-hexamethyl-3,12,16,20,23,27-hexaazabicyclo[12.7.7] octacosa-1,13,15,20,22,17-hexaene-$\kappa^4$N)nickel(II)] hexafluorophosphate |
| 83 | [acetonitrile(2,3,12,13,15,21-hexamethyl-3,12,16,20,23,27-hexaazabicyclo-[12.7.7] octacosa-1,13,15,20,22,27-hexaene-$\kappa^4$N)cobalt(II)] hexafluoro phosphate |
| 84 | [(15,21-dimethyl-2,13-diphenyl-3,12,16,20,23,27-hexaazabicyclo-[12.7.7] octacosa-1,13,15,20,22,27-hexane-$\kappa$-$^4$N)nickel(II)] hexafluoro phosphate |
| 85 | [acetonitrile(3,12,15,21-tetramethyl-2,13-diphenyl-3,12,16,20,23,27- |

TABLE 2-continued

| Compound No. | |
|---|---|
| | hexaazabicyclo[12.7.7]octacosa-1,13,15,20,22,27-hexane-$\kappa^4$N)cobalt(II)] hexafluorophosphate |
| 86 | [(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)nickel(II)] hexafluorophosphate |
| 87 | [acetonitrile(2,12,14,20-tetramethyl-3,11,15,19,22,26-hexaazatricyclo-[11.7.7.1$^{5,9}$] octacosa-1,5,7,9(28),12,14,19,21,26-nonaene-$\kappa^4$N)cobalt(II)] hexafluorophosphate |
| 88 | [chloro(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] hexafluorophosphate |
| 89 | trans-[(carbonyl)(pyridine)(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] hexafluorophosphate |
| 90 | trans-[(carbonyl)(1-methylimidazole)(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] hexafluorophosphate |
| 91 | trans-[(carbonyl)(imidazole)(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] hexafluorophosphate |
| 92 | trans-[(carbonyl)(4-aminopyridine)(2,12,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate |
| 93 | [(2,3,11,12,14,20-hexamethyl-3,11,15,19,22,26-hexaazatricyclo-[11.7.7.1$^{5,9}$] octacosa-1,5,7,9(28),12,14,19,21,26-nonaene-$\kappa^4$N)nickel(II)] hexafluorophosphate |
| 94 | [aquo(2,3,11,12,14,20-hexamethyl-3,11,15,19,22,26-hexaazatricyclo-[11.7.7.1$^{5,9}$] octacosa-1,5,7,9(28),12,14,19,21,26-nonaene-$\kappa^4$N)cobalt(II)] hexafluorophosphate |
| 95 | [chloro(2,3,11,12,14,20-hexamethyl-3,11,15,19,22,26-hexaazatricyclo-[11.7.7.1$^{5,9}$] octacosa-1,5,7,9(28),12,14,19,21,26-nonaene-$\kappa^4$N(iron(II)] hexafluorophosphate |
| 96 | trans-[(carbonyl)(1-methylimidazole)(2,3,11,12,14,20-hexamethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate |
| 97 | trans-[(carbonyl)(acetonitrile)(2,3,11,12,14,20-hexamethyl-3,11,15,19,22,26-hexaazatricyclo[11.7.7.1$^{5,9}$] octacosa-1,5,7,9(28),12,14,19,21,26-nonaene-$\kappa^4$N)iron(II)]hexafluorophosphate |
| 98 | trans-[(carbonyl)(imidazole)(2,3,11,12,14,20-hexamethyl-3,11,15,19 22,26-hexaazatricyclo[11.7.7.1$^{5,9}$] octacosa-1,5,7,9(28),12,14,19,21,26-nonaene-$\kappa^4$N)iron(II)] hexafluorophosphate |
| 99 | trans-[(carbonyl)(4-aminopyridine)(2,3,11,12,14,20-hexamethyl-3,11,15,19 22,26-hexaazatricyclo[11.7.7.1$^{5,9}$]octacosa-1,5,7,9(28),12,14,19,21,26-nonaene-$\kappa^4$N)iron(II)] hexafluorophosphate |
| 100 | [chloro(2,3,11,12,14,20-hexamethyl-3,11,15,19,22,26-hexaazatricyclo-[11.7.7.1$^{5,9}$]octacosa-1,5,7,9(28),12,14,19,21,26-nonaene-$\kappa^4$N)iron(II)] hexafluorophosphate |
| 101 | [(2,3,11,12,14,20-hexamethyl-3,11,15,19,22,26-hexaazatricyclo[11.7.7.1$^{5,9}$] octacosa-1,5,7,9(28),12,14,19,21,26-nonaene-$\kappa^4$N)manganese(II)] hexafluorophosphate |
| 102 | [chloro(2,3,11,12,14,20-hexamethyl-3,11,15,19,22,26-hexaazatricyclo-[11.7.7.1$^{5,9}$]octacosa-1,5,7,9(28),12,14,19,21,26-nonaene-$\kappa^4$N)manganese(II)] hexafluorophosphate |
| 103 | [acetonitrile(2,3,11,12,14,20-hexamethyl-3,11,15,19,22,26-hexaazatricyclo-[11.7.7.1$^{5,9}$]octacosa-1,5,7,9(28),12,14,19,21,26-nonaene-$\kappa^4$N)copper(II)] hexafluorophosphate |
| 104 | [(3,11-di-n-butyl-2,12,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)nickel(II)] hexafluorophosphate |
| 105 | [(2,12,14,20-tetramethyl-3,11-di-propylnitrile-3,11,15,19,22,26-hexaazatricyclo[11.7.7.1$^{5,9}$]octacosa-1,5,7,9(28),12,14,19,21,26-nonaene-$\kappa^4$N) nickel(II)] hexafluorophosphate |
| 106 | [(3,11-dibenzyl-2,12,14,20-tetramethyl-3,11,15,19,22,26-hexaazatricyclo [11.7.7.1$^{5,9}$]octacosa-1,5,7,9(28),12,14,19,21,26-nonaene-$\kappa^4$N)nickel (II)] hexafluorophosphate |
| 107 | [acetonitrile(3,11-dibenzyl-2,12,14,20-tetramethyl-3,11,15,19,22,26-hexaazatricyclo[11.7.7.1$^{5,9}$]octacosa-1,5,7,9(280,12,14,19,21,26-nonaene-$\kappa^4$N)iron(II)] hexafluorophosphate |
| 108 | [3,11,14,20-tetramethyl-3,11,15,19,22,26-hexaazatricyclo[ 11.7.7.1$^{5,9}$] octacosa-1,5,7,9(28),12,14,19,21,26-nonaene-$\kappa^4$N)nickel(II)] hexafluorophosphate |
| 109 | [(2,12-di-n-heptyl-14,20-dimethyl-3,11,15,19,22,26-hexaazatricyclo-[11.7.7.1$^{5,9}$]octacosa-1,5,7,9(28),12,14,19,21,26-nonaene-$\kappa^4$N)nickel(II)] hexafluorophosphate |
| 110 | [(2,12-di-n-heptyl-3,11,14,20-tetramethyl-3,11,15,19,22,26-hexaaza tricyclo-[11.7.7.1$^{5,9}$]octacosa-1,5,7,9(28),12,14,19,21,26-nonaene-$\kappa^4$N) nickel(II)] hexafluorophosphate |
| 111 | [chloro(2,12-di-n-heptyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N) iron(II)] hexafluorophosphate |

TABLE 2-continued

| Compound No. | |
|---|---|
| 112 | [(14,20-dimethyl-2,12-diphenyl-3,11,15,19,22,26-hexaazatricyclo-[11.7.7.1$^{5,9}$]octacosa-1,5,7,9(28),12,14,19,21,26-nonaene-$\kappa^4$N)nickel(II)] hexafluorophosphate |
| 113 | [acetonitrile(14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)cobalt(II)] hexafluorophosphate |
| 114 | [(3,11,14,20-tetramethyl-2,12-diphenyl-3,11,15,19,22,26-hexaazatricyclo-[11.7.7.1$^{5,9}$]octacosa-1,5,7,9(28),12,14,19,21,26-nonaene-$\kappa^4$N)nickel(II)] hexafluorophosphate |
| 115 | [(3,11,14,20-tetramethyl-2,12,-diphenyl-3,11,15,19,22,26-hexaazatricyclo-[11.7.7.1$^{5,9}$]octacosa-1,5,7,9(28),12,14,19,21,26-nonaene-$\kappa^4$N)cobalt(II)] hexafluorophosphate |
| 116 | [acetonitrile(3,11,14,20-tetramethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate |
| 117 | [(3,11-dibenzyl-14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)nickel(II)] hexafluorophosphate |
| 118 | [acetonitrile(3,11-dibenzyl-14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate |
| 119 | [chloro(2,12-di-p-methoxyphenyl-3,11,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)iron(II)] hexafluorophosphate |
| 120 | [chloro(2,12-di-p-chlorophenyl-3,11,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)iron(II)] hexafluorophosphate |
| 121 | [chloro(2,12-di-p-fluorophenyl-3,11,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)iron(II)] hexafluorophosphate |
| 122 | [chloro(2,12-di(3,5-dimethoxyphenyl)-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate |
| 123 | [(14,20-dimethyl-3,11,15,19,22,26-hexaazatetracyclo[11.8$^{2,12}$.7.7.1$^{5,9}$]hexatriaconta-1,5,7,9(36),12,14,19,21,26-nonaene-$\kappa^4$N)nickel(II)] hexafluorophosphate |
| 124 | [(14,20-dimethyl-3,11,15,19,22,26-hexaazatetracyclo[11.7.7.7$^{2,12}$.1$^{5,9}$]pentatriaconta-1,5,7,9(35),12,14,19,21,26-nonaene-$\kappa^4$N)nickel(II)] hexafluorophosphate |
| 125 | [(2,11,13,19-tetramethyl-3,10,14,18,21,25-hexaazatricyclo[10.7.7.2$^{5,8}$]octacosa-1,5,7,11,13,18,20,25,27-nonaene-$\kappa^4$N)nickel(II)] hexafluorophosphate |
| 126 | [chloro(2,11,13,19-tetramethyl-3,10,14,18,21,25-hexaazatricyclo[10.7.7.2$^{5,8}$]octacosa-1,5,7,11,13,18,20,25,27-nonaene-$\kappa^4$N)iron(II)] hexafluoro phosphate |
| 127 | trans-[(carbonyl)(aectonitrile)(2,11,13,19-tetramethyl-3,10,14,18,21,25-hexaazatricyclo[10.7.7.2$^{5,8}$]octacosa-1,5,7,11,13,18,20,25,27-nonaene-$\kappa^4$N)iron(II)] hexafluorophosphate |
| 128 | trans-[(carbonyl)(pyridine)(2,11,13,19-tetramethyl-3,10,14,18,21,25-hexaazatricyclo[10.7.7.2$^{5,8}$]octacosa-1,5,7,11,13,18,20,25,27-nonaene-$\kappa^4$N)iron(II)] hexafluorophosphate |
| 129 | trans-[(carbonyl)(1-methylimidazole)(2,11,13,19-tetramethyl-3,10,14,18,21,25-hexaazatricyclo[10.7.7.2$^{5,8}$]octacosa-1,5,7,11,13,18,20,25,27-nonaene-$\kappa^4$N)iron(II)] hexafluorophosphate |
| 130 | [(2,3,10,11,13,19-hexamethyl-3,10,14,18,21,25-hexaazatricyclo[10.7.7.2$^{5,8}$]octacosa-1,5,7,11,13,18,20,25,27-nonaene-$\kappa^4$N)nickel(II)] hexafluoro phosphate |
| 131 | [2,12,14,20-tetramethyl-3,11,15,19,22,26-hexaazapentacyclo[11.7.7.4$^{7,7}$.4$^{28,29}$.4$^{30,31}$] nonatriconta-1,12,14,19,21,26,28(20),30(31),32,34,36,38-dodecaene-$\kappa^4$N)nickel(II)] hexafluorophosphate |
| 132 | [chloro(2,12,14,20-tetramethyl-3,11,15,19,22,26-hexaazapentacyclo[11.7.7.4$^{7,7}$.4$^{28,29}$.4$^{30,31}$] nonatriconta-1,12,14,19,21,28(29),30(31),32,34,36,38-dodecaene-$\kappa^4$N)iron(II)] chloride |
| 133 | trans-[(carbonyl)(pyridine)(2,12,14,20-tetramethyl-3,11,15,19,22,26-hexaazapentacyclo[11.7.7.4$^{7,7}$.4$^{28,29}$.4$^{30,31}$] nonatriconta-1,12,14,19,21,26,28(29),30(31),32,34,36,38-dodecaene-$\kappa^4$N)iron(II)] hexafluoro phosphate |
| 134 | trans-[(carbonyl)(1-methylimidazole)(2,12,14,20-tetramethyl-3,11,15,19,22,26-hexaazapentacyclo[11.7.7.4$^{7,7}$.4$^{28,29}$.4$^{30,31}$] nonatriconta-1,12,14,19,21,26,28(29),30(31),32,34,36,38-dodecaene-$\kappa^4$N)iron(II)] hexafluorophosphate |
| 135 | [(4-methoxycarbonyl-2,10,12,18-tetramethyl-3,9,13,17,20,24-hexaazabicyclo[9.7.7]pentacosa-1,10,12,17,19,24-hexaene-$\kappa^4$N)nickel(II)] hexafluorophosphate |
| 136 | [2,12,14,20-tetramethyl-3,11,15,19,22,26-hexaazatricyclo[11.7.7.1$^{5,9}$]octacosa-1,12,14,19,21,26-hexaene-$\kappa^4$N)nickel(II)]hexafluorophosphate |
| 137 | [(3,6,6,9,12,18-hexamethyl-2,10-diphenyl-3,9,13,17,20,24-hexaazabicyclo-[9.7.7]pentacosa-1,10,12,17,19,24-hexaene-$\kappa^4$N)nickel(II)] hexafluoro phosphate |
| 138 | [(7-methoxy-2,3,11,12,14,20-hexamethyl-3,11,15,19,22,26-hexaazatricyclo- |

TABLE 2-continued

| Compound No. | |
|---|---|
| | [11.7.7.1$^{5,9}$]octacosa-1,5,7,9(28),12,14,19,21,26-nonaene-κ$^4$N)nickel(II)] hexafluorophosphate |
| 139 | [(2,10,12,18-tetramethyl-6-thia-3,9,13,17,20,24-hexaazabicyclo[9.7.7] pentacosa-1,10,12,17,19,24-hexaene-κ$^4$N)nickel(II)] hexafluoro phosphate |
| 140 | [(2,11,13,19-tetramethyl-6-thia-3,10,14,18,21,25-hexaazabicyclo[10.7.7] hexacosa-1,11,13,18,20,25-hexaene-κ$^4$N)nickel(II)] hexafluoro-phosphate |
| 141 | [(7-methoxycarbonyl-2,3,11,12,14,20-hexamethyl-3,11,15,19,22,26-hexaazatricyclo[11.7.7.1$^{5,9}$]octacosa-1,5,7,9(28),12,14,19,21,26-nonaene-κ$^4$N)nickel(II)] hexafluorophosphate |
| 142 | [(2,3,11,12,14,20-hexamethyl-3,11,15,19,22,26,28-heptaazatricyclo [11.7.7.1$^{5,9}$]octacosa-1,5,7,9(28),12,14,19,21,26-nonaene-κ$^4$N)nickel (II)] hexafluorophosphate |
| 143 | [(2,12,14,20-tetramethyl-3,7,11,15,19,22,26-heptaazabicyclo[11.7.7] heptacosa-1,12,14,19,21,26-hexaene-κ$^4$N)nickel(II)] hexafluoro phosphate |
| 144 | [(2,7,12,14,20-pentamethyl-3,7,11,15,19,22,26-heptaazabicyclo[11.7.7] heptacosa-1,12,14,19,21,26-hexaene-κ$^4$N)nickel(II)] hexafluoro phosphate |
| 145 | [(2,7,12,14,20-pentamethyl-3,7,11,15,19,22,26-heptaazabicyclo[11.7.7] heptacosa-1,12,14,19,21,26-hexaene-κ$^4$N)cobalt(II)] hexafluoro phosphate |
| 146(c) | [(2,8,-bis-dimethylamino-10,16-dimethyl-11,15,18,22-tetrabicyclo-[7.7.7]tricosa-1,8,10,17,22-hexaene-κ $^4$N)nickel(II)] hexafluoro phosphate |
| 147(c) | [acetonitrile(2,8-bis-dimethylamino-10,16-dimethyl-11,15,18,22-tetraaza-bicyclo[7.7.7]tricosa-1,8,10,15,17,22-hexaene-κ$^4$N)cobalt(II)] hexafluoro-phosphate |
| 148(c) | [(11,17-dimethyl-2,9-bis-methylamino-12,16,19,23-tetraazabicyclo[8.7.7] tetracosa-1,9,11,16,18,23-hexaene-κ$^4$N)(II)] hexafluorophosphate |
| 149(c) | [(2,9-bis(dimethylamino)-11,17-dimethyl-12,16,19,23-tetraaza-bicyclo[8.7.7]tetracosa-1,9,11,16,18,23-hexaene-κ$^4$N)nickel(II)] hexafluoro-phosphate |
| 150(c) | [acetonitrile(2,9-bis(dimethylamino)-11,17-dimethyl-12,16,19,23-tetraaza-bicyclo[8.7.7]tetracosa-1,9,11,16,18,23-hexaene-κ$^4$N)cobalt(II)] hexafluoro-phosphate |
| 151 | [(12,18-dimethy-2,10-bis-methylamino-13,17,20,24-tetraazabicyclo[9.7.7] pentacosa-1,10,12,17,19,24-hexaene-κ$^4$N)nickel(II)] hexafluoro phosphate |
| 152 | [(12,18-dimethyl-2,10-bis-methylamino-13,17,20,24-tetraazabicyclo[9.7.7] pentacosa-1,10,12,17,19,24-hexaene-κ$^4$N)cobalt(II)] hexafluoro phosphate |
| 153 | [chloro(12,18-dimethyl-2,10-bis-methylamino-13,17,20,24-tetraazabicyclo-[9.7.7]pentacosa-1,10,12,17,19,24-hexaene-κ$^4$N)iron(II)] hexafluoro phosphate |
| 154 | [(12,18-dimethyl-2,10-bis-propylamino-13,17,20,24-tetraazabicyclo[9.7.7] pentacosa-1,10,12,17,19,24-hexaene-κ$^4$N)nickel(II)] hexafluoro phosphate |
| 155 | [acetonitril(12,18-dimethyl-2,10-bis-propylamino-13,17,20,24-tetraaza-bicyclo[9.7.7]pentacosa-1,10,12,17,19,24-hexaene-κ$^4$N)cobalt(II)] hexafluorophosphate |
| 156 | [(2,10-bis-benzylamino-12,18-dimethyl-13,17,20,24-tetrabicyclo-[9.7.7]pentacosa-1,10,12,17,19,24-hexaene-κ$^4$N)(II)] hexafluoro-phosphate |
| 157 | [(2,10-bis-dimethylamino-12,18-dimethyl-12,17,20,24-tetraazabicyclo-[9.7.7]pentacosa-1,10,12,17,19,24-hexaene-κ $^4$N)nickel(II)] hexafluoro-phosphate |
| 158 | [aquo(2,10-bis-dimethalamino-12,18-dimethyl-12,17,20,24-tetraazabicyclo-[9.9.7]pentacosa-1,10,12,17,19,24-hexaene-κ$^4$N)cobalt(II)] hexafluoro-phosphate |
| 159 | [chloro(2,10-bis-dimethylamino-12,18-dimethyl-13,17,20,24-tetraazabicyclo-[9.7.7]pentacosa-1,10,12,17,19,24-hexaene-κ$^4$N)iron(II)] hexafluoro phosphate |
| 160 | [(13,19-dimethyl-2,11-bis-methylamino-14,18,21,25-tetraazabicyclo[10.7.7]-hexacosa-1,11,13,18,20,25-hexaene-κ$^4$N)nickel(II)] hexafluorophosphate |
| 161 | [(2,11-bis-dimethylamino-13,19-dimethyl-14,18,21,25-tetraazabicyclo[10.7.7]-hexacosa-1,11,13,18,20,25-hexaene-κ$^4$N)nickel(II)] hexafluorophosphate |
| 162 | [acetonitrile(2,11-bis-dimethylamino-13,19-dimethyl-14,18,21,25-tetraazabicyclo[10.7.7]hexacosa-1,11,13,18,20,25-hexaene-κ$^4$N)cobalt(II)] hexafluorophosphate |
| 163 | [chloro(2,11-bis-dimethylamino-13,19-dimethyl-14,18,21,25-tetraaza-bicyclo[10.7.7]hexacosa-1,11,13,18,20,25-hexaene-κ$^4$N)iron(II)] hexafluoro-phosphate |
| 164 | [(2,2,9,10,12,18-hexamethyl-22-(1-methyl-2-pyridinio)-3,9,13,17,20,24-hexaazabicyclo[9.7.7]pentacosa-1,10,12,17,19,24-hexaene-κ$^4$N)nickel(II)] hexafluorophosphate |
| 165 | [(2,3,10,11,13,19-hexamethyl-23-(1-methyl-2-pyridinio)-3,10,14,18,21,25-hexaazabicyclo[10.7.7]hexacosa-1,11,13,18,20,25-hexaene-κ$^4$N)nickel(II)] hexafluorophosphate |

TABLE 2-continued

| Compound No. | |
|---|---|
| 166 | [(2,3,10,11,13,19-hexamethyl-23-(1-methyl-2-pyridinio)-3,10,14,18,21,25-hexaazabicyclo[10.7.7]hexacosa-1,11,13,18,20,25-κ$^4$N)cobalt(II)] hexafluorophosphate |
| 167 | [(2,2,11,12,14,20-hexamethyl-24-(1-methyl-2-pyridinio)-3,11,15,19,22,26-hexaazatricyclo[11.7.7.1$^{5,9}$]octacosa-1,5,7,9(28),12,14,19,21,16-nonaene-κ$^4$N)nickel(II)] hexafluorophosphate |
| 168 | [(2,3,10,11,13,19-hexamethyl-23-(2-pyridyl)-3,10,14,18,21,25-hexaazabicyclo[10.7.7]hexacosa-1,11,13,18,20,25-hexaene-κ$^4$N)cobalt(II)]-hexafluorophosphate |
| 169 | [(2,3,10,11,12,19-hexamethyl-3,10,14,18,21,24-hexaazabicyclo[10.7.6]pentacosa 1,11,13,18,20,24-hexaene-κ$^4$N)nickel(II)] hexafluorophosphate |
| 170 | [(2,3,8,9,11,17-hexamethyl-3,8,12,16,19,23-hexaazabicyclo[8.7.7]tetracosa-1.9,11,16,18,23-hexaene-κ$^4$N)] hexafluorophosphate |
| 171 | [chloro(2,12,14,20-tetramethyl-3,11,15,19,22,26-hexaazatricyclo[11.7.7.1$^{5,9}$]octocosa-1,5,7,9(28),12,14,19,21,26-nonaene-κ$^4$N)iron(II)] chloride dimethanolate |
| 172 | [(2,12,14,20-tetramethyl-3,11,15,19,22,26-hexaazapentacyclo[11.7.7.4$^{7,7}$.4$^{28,29}$.4$^{30,31}$]nonatriaconta-1,12,14,19,21,26,28(29),30(31),32,34,36,38-dodecaene-κ$^4$N)zinc(II)]chloride |
| 173 | [(2,18,20,26-tetramethyl-3,6,14,17,21,25,28,32-octaazapentacyclo-[17.7.7.2$^{3,6}$.2$^{14,17}$.1$^{8,12}$]octatriaconta-1,8,12,12(38),18,20,25,27,32-nonaene-κ$^4$N)nickel(II)] hexafluorophosphate |
| 174 | [(2,18,20,26-tetramethyl-3,6,14,17,21,25,28,32-octaazapentacyclo-[17.7.7.2$^{3,6}$.2$^{14,17}$.1$^{8,12}$]octatriconta-1,8,10,12(38),18,20,25,27,32-nonaene-κ$^4$N)nickel(II) chloride |
| 175 | [methanol(2,18,20,26-tetramethyl-3,6,14,17,21,25,28,32-octaazapentacyclo-[17.7.7.2$^{3,6}$.2$^{14,17}$.1$^{8,12}$]octatriaconta-1,8,10,12(38),18,20,25,27,32-nonaene-κ$^4$N)cobalt(II)] hexafluorophosphate |
| 176 | [(2,17,19,25-tetramethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)nickel(II)] hexafluorophosphate |
| 177 | [(2,17,19,25-tetramethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)cobalt(II)] hexafluorophosphate |
| 178 | [(2,9,10,17,19,25,33,34-octamethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)nickel(II)] hexafluorophosphate |
| 179 | [(2,9,10,17,19,25,33,34-octamethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)nickel(II)] chloride |
| 180 | [(2,9,10,17,19,25,33,34-octamethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)cobalt(II)] hexafluorophosphate |
| 181 | [chloro(2,9,10,17,19,25,33,34-octamethyl-3,6,13,16,20,24,27,31-octaazapentacyclo[16.7.7.2$^{8,11}$.2$^{3,6}$.2$^{13,16}$]octatriaconta-1,8,10,17,19,24,26,31,33-nonaene-κ$^4$N)iron(II)] hexafluorophosphate |
| 182 | [aquo(2,9,10,17,19,25,33,34-octamethyl-3,6,13,16,20,24,27,31-octaazapentacylco[16.7.7.2$^{8,11}$.2$^{3,6}$.2$^{13,16}$]octatriaconta-1,8,10,17,19,24,26,31,33-nonaene-κ$^4$N)iron(II)] hexafluorophosphate |
| 183 | [(2,9,10,17,19,25,33,34-octamethyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)copper(II)] hexafluorophosphate |
| 184 | [(9,10,19,25,33,34-hexamethyl-2,17-diphenyl-3,6,13,16,20,24,27,31-octaazapentacyclo-[16.7.7.2$^{8,11}$.2$^{3,6}$.2$^{13,16}$]octatriaconta-1,8,10,17,19,24,26,31,33-nonaene-κ$^4$N)nickel(II)] hexafluorophosphate |
| 185 | [(2,21,23,29-tetramethyl-3,6,17,20,24,28,31,35-octaazaheptacyclo-[20.7.7.6$^{8,15}$.2$^{3,6}$.2$^{17,20}$.0$^{9,14}$.0$^{37,42}$]hexatetraconta-1,8(37),9,11,13 15(42),21,23,28,30,35,38,40-tridecaene-κ$^4$N)nickel(II)] hexafluoro phosphate |
| 186 | [(2,21,23,29-tetramethyl-3,6,17,20,24,28,31,35-octaazaheptacyclo-[20.7.7.6$^{8,15}$.2$^{3,6}$.2$^{17,20}$.0$^{9,14}$.0$^{37,42}$]hexatetraconta-1,8(37),9,11,13, 15(42),21,23,28,30,35,38,40-tridecaene-κ$^4$N)nickel(II)] chloride |
| 187 | [methanol(2,21,23,29-tetramethyl-3,6,17,20,24,28,31,35-octaazaheptacyclo-[20.7.7.6$^{8,15}$.2$^{3,6}$.2$^{17,20}$.0$^{9,14}$.0$^{37,42}$]hexatetraconta-1,8(37),9,11,13, 15(42),21,23,28,30,35,38,40-tridecaene-κ$^4$N)cobalt(II)] hexafluoro phosphate |
| 188 | [chloro(2,21,23,29-tetramethyl-3,6,17,20,24,28,31,35-octaazaheptacyclo-[20.7.7.6$^{8,15}$.2$^{3,6}$.2$^{17,20}$.0$^{9,14}$.0$^{37,42}$]hexatetraconta-1,8(37),9,11,13, 15(42),21,23,28,30,35,38,40-tridecaene-κ$^4$N)iron(II)] hexafluoro phosphate |
| 189 | [(23,29-dimethyl-2,21-diphenyl-3,6,17,20,24,28,31,35-octaazaheptacyclo-[20.7.7.6$^{8,15}$.2$^{3,6}$.2$^{17,20}$.0$^{9,14}$.0$^{37,42}$]hexatetraconta-1,8(37),9,11,13, 15(42),21,23,28,30,35,38,40-tridecaene-κ$^4$N)nickel(II)] hexafluoro phosphate |
| 190 | [(2,18,20,26-tetramethyl-3,6,14,17,21,25,28,32,38-nonaazapentacyclo-[17.7.7.2$^{3,6}$.2$^{14,17}$.1$^{8,12}$]octatriaconta-1,8,10,12(38),18,20,25,27,32-nonaene-κ$^4$N)nickel(II)] hexafluorophosphate |
| 191 | [(2,18,20,26-tetramethyl-3,6,14,17,21,25,28,32,38-nonaazapentacyclo-[17.7.7.2$^{3,6}$.2$^{14,17}$.1$^{8,12}$]octatriaconta-1,8,10,12(38),18,20,25,27,32-nonaene-κ$^4$N)cobalt(II)] hexafluorophosphate |

TABLE 2-continued

| Compound No. | |
|---|---|
| 192 | [(2,9,10,17,19,25,33,34-octamethyl-29-(1-methyl-2-pyridinio)-3,6,13,16,20 24,27,31-octaazapentacyclo[16.7.7.2$^{8,11}$.2$^{3,6}$.2$^{13,16}$]octatriaconta-1,8,10,17,19,24,26,31,33-nonaene-$\kappa^4$N)nickel(II)] hexafluorophosphate |
| 193 | [(2,21,23,29-tetramethyl-33-(1-methyl-2-pyridinio)-3,6,17,20,24,28,31,35-octaazaheptacyclo[20.7.7.6 $^{8,15}$.2$^{3,6}$.2$^{17,20}$.0$^{9,14}$.0$^{37,42}$]hexatetraconta-1,8(37),9,11,13,15(42),21,23,28,30,35,38,40-tridecaene-$\kappa^4$N)nickel(II)] hexafluorophosphate |
| 194 | [(3,11,14,20,24,24-hexamethyl-2,12-diphenyl-3,11,15,19,22,26-hexa-azatricyclo[11.7.7.1$^{5.9}$]octacosa-1,5,7,9(28),12,14,19,21,26-nonaene-$\kappa^4$N) nickel(II)] hexafluorophosphate. |
| 195 | [(3,11,14,20,24,24-hexamethyl-2,12-diphenyl-3,11,15,29,22,26-hexa-azatricyclo[11.7.7.1$^{5.9}$]octacosa-1,5,7,9(28),12,14,19,21,26-nonaene-)] hexafluorophosphate. |
| 196 | [(3,11,14,20,24,24-hexamethyl-2,12-diphenyl-3,11,15,19,22,26-hexa-azatricyclo[11.7.7.1$^{5.9}$]-octacose-1,5,7,9(28),12,14,19,21,26-nonaene-$\kappa^4$N)iron(II)] hexafluorophosphate. |
| 197 | 2,17-di(n-heptadecyl)-9,10,19,25,33,34-hexamethyl-3,6,13,16,20,24,27,31-octaazapentacyclo[16.7.7.2$^{8,11}$.2$^{3,6}$.2$^{13,16}$]octatriaconta-1,8,10,17,19,24, 26,31,33-nonaene-$\kappa^4$N)nickel(II)] hexafluorophosphate |
| 198 | [(9,10,19,25,41,42-hexamethyl-3,6,13,16,20,24,27,31-octaazahexa-cyclo[16.8$^{2,17}$.7.7.2$^{8,11}$.2$^{3,6}$.2$^{13,16}$]hexatetraconta-1,8,10,17,19 24,26,31,41-nonaene-$\kappa^4$N)nickel(II)] hexafluorophosphate |
| 199 | [(2,3,14,15,17,23-hexamethyl-3,14,18,22,25,29-hexaaazabicyclo [14.7.7]triaconta-1,15,17,22,24,29-hexaene-$\kappa^4$N)nickel(II)] hexafluorophosphate |
| 200 | [(2,3,14,15,17,23-hexamethyl-3,14,18,22,25,29-hexaazabicyclo [14.7.7]triaconta-1,15,17,22,24,29-hexaene-$\kappa^4$N)cobalt(II)] hexafluorophosphate |

TABLE 3
FORMULAE I AND IA

| Compd. No. | $M^{n+}$ | X | Y | $R_1$ | $R_2$ | $R_3$ | $R_4$ | R | Anion | Z |
|---|---|---|---|---|---|---|---|---|---|---|
| 1 | $Ni^{2+}$ | $(CH_2)_3$ | $(CH_2)_3$ | H | $CH_3$ | $CH_3$ | $CH_3$ | $(CH_2)_3$ | $PF_6$ | — |
| 2 | $Co^{2+}$ | $(CH_2)_3$ | $(CH_2)_3$ | H | $CH_3$ | $CH_3$ | $CH_3$ | $(CH_2)_3$ | $PF_6$ | $CH_3CN$ |
| 3 | $Fe^{2+}$ | $(CH_2)_3$ | $(CH_2)_3$ | H | $CH_3$ | $CH_3$ | $CH_3$ | $(CH_2)_3$ | $PF_6$ | Cl |
| 4 | $Ni^{2+}$ | $(CH_2)_3$ | $(CH_2)_3$ | H | $CH_3$ | $CH_3$ | $CH_3$ | $(CH_2)_4$ | $PF_6$ | — |
| 5 | $Fe^{2+}$ | $(CH_2)_3$ | $(CH_2)_3$ | H | $CH_3$ | $CH_3$ | H | $(CH_2)_4$ | $PF_6$ | Cl |
| 6 | $Ni^{2+}$ | $(CH_2)_3$ | $(CH_2)_3$ | H | $CH_3$ | $CH_3$ | H | $(CH_2)_4$ | $PF_6$ | — |
| 7 | $Co^{2+}$ | $(CH_2)_3$ | $(CH_2)_3$ | H | $CH_3$ | $CH_3$ | $CH_3$ | $(CH_2)_4$ | $PF_6$ | — |
| 8 | $Fe^{2+}$ | $(CH_2)_3$ | $(CH_2)_3$ | H | $CH_3$ | $CH_3$ | $CH_3$ | $(CH_2)_4$ | $PF_6$ | Cl |
| 9 | $Ni^{2+}$ | $(CH_2)_3$ | $(CH_2)_3$ | H | $CH_3$ | $\phi$ | H | $(CH_2)_4$ | $PF_6$ | — |
| 10 | $Co^{2+}$ | $(CH_2)_3$ | $(CH_2)_3$ | H | $CH_3$ | $\phi$ | H | $(CH_2)_4$ | $PF_6$ | $CH_3CN$ |
| 11 | $Ni^{2+}$ | $(CH_2)_3$ | $(CH_2)_3$ | H | $CH_3$ | $\phi$ | $CH_3$ | $(CH_2)_4$ | $PF_6$ | — |
| 12 | $Co^{2+}$ | $(CH_2)_3$ | $(CH_2)_3$ | H | $CH_3$ | $\phi$ | $CH_3$ | $(CH_2)_4$ | $PF_6$ | — |
| 13 | $Fe^{2+}$ | $(CH_2)_3$ | $(CH_2)_3$ | H | $CH_3$ | $CH_3$ | $CH_3$ | $(CH_2)_4$ | $PF_6$ | Cl |
| 14 | $Cu^{2+}$ | $(CH_2)_3$ | $(CH_2)_3$ | H | $CH_3$ | $C(CH_3)_3$ | $CH_3$ | $(CH_2)_4$ | $PF_6$ | — |
| 15 | $Ni^{2+}$ | $(CH_2)_3$ | $(CH_2)_3$ | H | $CH_3$ | $CH_3$ | H | $(CH_2)_5$ | $PF_6$ | — |
| 16 | $Co^{2+}$ | $(CH_2)_3$ | $(CH_2)_3$ | H | $CH_3$ | $CH_3$ | H | $(CH_2)_5$ | $PF_6$ | — |
| 17 | $Ni^{2+}$ | $(CH_2)_3$ | $(CH_2)_3$ | H | $CH_3$ | $CH_3$ | $CH_3$ | $(CH_2)_5$ | $PF_6$ | — |
| 18 | $Fe^{2+}$ | $(CH_2)_3$ | $(CH_2)_3$ | H | $CH_3$ | $CH_3$ | H | $(CH_2)_5$ | Cl | Cl |
| 19 | $Fe^{2+}$ | $(CH_2)_3$ | $(CH_2)_3$ | H | $CH_3$ | $CH_3$ | $CH_3$ | $(CH_2)_5$ | $PF_6$ | CO/Py |
| 20 | $Ni^{2+}$ | $(CH_2)_3$ | $(CH_2)_3$ | H | $CH_3$ | $CH_3$ | H | $(CH_2)_5$ | $PF_6$ | — |
| 21 | $Co^{2+}$ | $(CH_2)_3$ | $(CH_2)_3$ | H | $CH_3$ | $CH_3$ | H | $(CH_2)_5$ | $PF_6$ | — |
| 22 | $Fe^{2+}$ | $(CH_2)_3$ | $(CH_2)_3$ | H | $CH_3$ | $CH_3$ | H | $(CH_2)_5$ | $PF_6$ | Cl |
| 23 | $Co^{3+}$ | $(CH_2)_3$ | $(CH_2)_3$ | H | $CH_3$ | $CH_3$ | H | $(CH_2)_5$ | $PF_6$ | $(NCS)_2$ |
| 24 | $Ni^{2+}$ | $(CH_2)_3$ | $(CH_2)_3$ | H | $CH_3$ | $\phi$ | H | $(CH_2)_5$ | $PF_6$ | — |
| 25 | $Co^{2+}$ | $(CH_2)_3$ | $(CH_2)_3$ | H | $CH_3$ | $\phi$ | H | $(CH_2)_5$ | $PF_6$ | — |
| 26 | $Ni^{2+}$ | $(CH_2)_3$ | $(CH_2)_3$ | H | $CH_3$ | $\phi$ | $CH_3$ | $(CH_2)_5$ | $PF_6$ | — |
| 27 | $Fe^{2+}$ | $(CH_2)_3$ | $(CH_2)_3$ | H | $CH_3$ | $\phi$ | $CH_3$ | $(CH_2)_5$ | $PF_6$ | Cl |
| 28 | $Ni^{2+}$ | $(CH_2)_3$ | $(CH_2)_3$ | H | $CH_3$ | $C(CH_3)_3$ | $CH_3$ | $(CH_2)_5$ | $PF_6$ | — |
| 29 | $Co^{2+}$ | $(CH_2)_3$ | $(CH_2)_3$ | H | $CH_3$ | $C(CH_3)_3$ | $CH_3$ | $(CH_2)_5$ | $PF_6$ | $CH_3CN$ |
| 30 | $Ni^{2+}$ | $(CH_2)_3$ | $(CH_2)_3$ | H | $CH_3$ | $CH_3$ | $CH_3$ | $(CH_2)_6$ | $PF_6$ | — |
| 31 | $Co^{2+}$ | $(CH_2)_3$ | $(CH_2)_3$ | H | $CH_3$ | $CH_3$ | $CH_3$ | $(CH_2)_6$ | $PF_6$ | — |
| 32 | $Fe^{2+}$ | $(CH_2)_3$ | $(CH_2)_3$ | H | $CH_3$ | $CH_3$ | $CH_3$ | $(CH_2)_6$ | $PF_6$ | Cl |
| 33 | $Fe^{2+}$ | $(CH_2)_3$ | $(CH_2)_3$ | H | $CH_3$ | $CH_3$ | H | $(CH_2)_6$ | $PF_6$ | CO/Py |
| 34 | $Cu^{2+}$ | $(CH_2)_3$ | $(CH_2)_3$ | H | $CH_3$ | $CH_3$ | H | $(CH_2)_6$ | $PF_6$ | $CH_3CH_2OH$ |
| 35 | $Ni^{2+}$ | $(CH_2)_3$ | $(CH_2)_3$ | H | $CH_3$ | $CH_3$ | H | $(CH_2)_6$ | $PF_6$ | — |
| 36 | $Co^{2+}$ | $(CH_2)_3$ | $(CH_2)_3$ | H | $CH_3$ | $CH_3$ | H | $(CH_2)_6$ | $PF_6$ | — |
| 37 | $Ni^{2+}$ | $(CH_2)_3$ | $(CH_2)_3$ | H | $CH_3$ | $CH_3$ | H | $(CH_2)_6$ | Cl | — |
| 38 | $Co^{2+}$ | $(CH_2)_3$ | $(CH_2)_3$ | H | $CH_3$ | $CH_3$ | $CH_3$ | $(CH_2)_6$ | $PF_6$ | — |
| 39 | $Co^{2+}$ | $(CH_2)_3$ | $(CH_2)_3$ | H | $CH_3$ | $CH_3$ | $CH_3$ | $(CH_2)_6$ | $PF_6$ | $1-CH_3-Im$ |
| 40 | $Co^{3+}$ | $(CH_2)_3$ | $(CH_2)_3$ | H | $CH_3$ | $CH_3$ | H | $(CH_2)_6$ | $PF_6$ | Im |
| 41 | $Co^{3+}$ | $(CH_2)_3$ | $(CH_2)_3$ | H | $CH_3$ | $CH_3$ | H | $(CH_2)_6$ | $PF_6$ | Py |
| 42 | $Co^{3+}$ | $(CH_2)_3$ | $(CH_2)_3$ | H | $CH_3$ | $CH_3$ | H | $(CH_2)_6$ | $PF_6$ | NCS |
| 43 | $Co^{3+}$ | $(CH_2)_3$ | $(CH_2)_3$ | H | $CH_3$ | $CH_3$ | H | $(CH_2)_6$ | $PF_6$ | $(NCS)_2$ |
| 44 | $Co^{3+}$ | $(CH_2)_3$ | $(CH_2)_3$ | H | $CH_3$ | $CH_3$ | $CH_3$ | $(CH_2)_6$ | $PF_6$ | $(NCO)_2$ |
| 45 | $Co^{3+}$ | $(CH_2)_3$ | $(CH_2)_3$ | H | $CH_3$ | $CH_3$ | $CH_3$ | $(CH_2)_6$ | $PF_6$ | $(N_3)_2$ |
| 46 | $Fe^{2+}$ | $(CH_2)_3$ | $(CH_2)_3$ | H | $CH_3$ | $CH_3$ | $CH_3$ | $(CH_2)_6$ | Cl | Cl |
| 47 | $Fe^{2+}$ | $(CH_2)_3$ | $(CH_2)_3$ | H | $CH_3$ | $CH_3$ | $CH_3$ | $(CH_2)_6$ | $PF_6$ | $CO/CH_3CN$ |
| 48 | $Fe^{2+}$ | $(CH_2)_3$ | $(CH_2)_3$ | H | $CH_3$ | $CH_3$ | $CH_3$ | $(CH_2)_6$ | $PF_6$ | CO/Py |
| 49 | $Fe^{2+}$ | $(CH_2)_3$ | $(CH_2)_3$ | H | $CH_3$ | $CH_3$ | $CH_3$ | $(CH_2)_6$ | $PF_6$ | $CO/1-CH_3-Im$ |
| 50 | $Fe^{3+}$ | $(CH_2)_3$ | $(CH_2)_3$ | H | $CH_3$ | $CH_3$ | $CH_3$ | $(CH_2)_6$ | $PF_6$ | Cl |

TABLE 3-continued
FORMULAE I AND IA

| Compd. No. | $M^{n+}$ | X | Y | $R_1$ | $R_2$ | $R_3$ | $R_4$ | R | Anion | Z |
|---|---|---|---|---|---|---|---|---|---|---|
| 51 | $Mn^{2+}$ | $(CH_2)_3$ | $(CH_2)_3$ | H | $CH_3$ | $CH_3$ | $CH_3$ | $(CH_2)_6$ | $PF_6$ | Cl |
| 52 | $Mn^{3+}$ | $(CH_2)_3$ | $(CH_2)_3$ | H | $CH_3$ | $CH_3$ | $CH_3$ | $(CH_2)_6$ | $PF_6$ | Cl |
| 53 | $Cu^{2+}$ | $(CH_2)_3$ | $(CH_2)_3$ | H | $CH_3$ | $CH_3$ | $CH_3$ | $(CH_2)_6$ | $PF_6$ | Cl |
| 54 | $Ni^{2+}$ | $(CH_2)_3$ | $(CH_2)_3$ | H | $CH_3$ | $\phi$ | H | $(CH_2)_6$ | $PF_6$ | — |
| 55 | $Co^{2+}$ | $(CH_2)_3$ | $(CH_2)_3$ | H | $CH_3$ | $\phi$ | H | $(CH_2)_6$ | $PF_6$ | — |
| 56 | $Ni^{2+}$ | $(CH_2)_3$ | $(CH_2)_3$ | H | $CH_3$ | $\phi$ | $CH_3$ | $(CH_2)_6$ | $PF_6$ | — |
| 57 | $Co^{2+}$ | $(CH_2)_3$ | $(CH_2)_3$ | H | $CH_3$ | $\phi$ | $CH_3$ | $(CH_2)_6$ | $PF_6$ | — |
| 58 | $Fe^{2+}$ | $(CH_2)_3$ | $(CH_2)_3$ | H | $CH_3$ | $\phi$ | $CH_3$ | $(CH_2)_6$ | $PF_6$ | Cl |
| 59 | $Fe^{2+}$ | $(CH_2)_3$ | $(CH_2)_3$ | H | $CH_3$ | $\phi$ | $CH_2\phi$ | $(CH_2)_6$ | $PF_6$ | Cl |
| 60 | $Ni^{2+}$ | $(CH_2)_3$ | $(CH_2)_3$ | H | $CH_3$ | $C(CH_3)_3$ | H | $(CH_2)_6$ | $PF_6$ | — |
| 61 | $Co^{2+}$ | $(CH_2)_3$ | $(CH_2)_3$ | H | $CH_3$ | $C(CH_3)_3$ | H | $(CH_2)_6$ | $PF_6$ | — |
| 62 | $Ni^{2+}$ | $(CH_2)_3$ | $(CH_2)_3$ | H | $CH_3$ | $(CH_2)_6CH_3$ | H | $(CH_2)_6$ | $PF_6$ | — |
| 63 | $Ni^{2+}$ | $(CH_2)_3$ | $(CH_2)_3$ | H | $CH_3$ | H | $CH_3$ | $(CH_2)_6$ | $PF_6$ | $CH_3CN$ |
| 64 | $Co^{2+}$ | $(CH_2)_3$ | $(CH_2)_3$ | H | $CH_3$ | H | $CH_3$ | $(CH_2)_6$ | $PF_6$ | $CH_3CN$ |
| 68 | $Ni^{2+}$ | $(CH_2)_3$ | $(CH_2)_3$ | H | $CH_3$ | $CH_3$ | H | $(CH_2)_7$ | $PF_6$ | — |
| 69 | $Co^{2+}$ | $(CH_2)_3$ | $(CH_2)_3$ | H | $CH_3$ | $CH_3$ | H | $(CH_2)_7$ | $PF_6$ | — |
| 70 | $Ni^{2+}$ | $(CH_2)_3$ | $(CH_2)_3$ | H | $CH_3$ | $CH_3$ | $CH_3$ | $(CH_2)_7$ | $PF_6$ | $CH_3CN$ |
| 71 | $Co^{2+}$ | $(CH_2)_3$ | $(CH_2)_3$ | H | $CH_3$ | $CH_3$ | $CH_3$ | $(CH_2)_7$ | $PF_6$ | $CH_3CN$ |
| 72 | $Co^{3+}$ | $(CH_2)_3$ | $(CH_2)_3$ | H | $CH_3$ | $CH_3$ | $CH_3$ | $(CH_2)_7$ | $PF_6$ | $(NCS)_2$ |
| 73 | $Ni^{2+}$ | $(CH_2)_3$ | $(CH_2)_3$ | H | $CH_3$ | $\phi$ | H | $(CH_2)_7$ | $PF_6$ | — |
| 74 | $Co^{2+}$ | $(CH_2)_3$ | $(CH_2)_3$ | H | $CH_3$ | $\phi$ | H | $(CH_2)_7$ | $PF_6$ | — |
| 75 | $Ni^{2+}$ | $(CH_2)_3$ | $(CH_2)_3$ | H | $CH_3$ | $\phi$ | $CH_3$ | $(CH_2)_7$ | $PF_6$ | — |
| 76 | $Co^{2+}$ | $(CH_2)_3$ | $(CH_2)_3$ | H | $CH_3$ | $\phi$ | $CH_3$ | $(CH_2)_7$ | $PF_6$ | — |
| 77 | $Ni^{2+}$ | $(CH_2)_3$ | $(CH_2)_3$ | H | $CH_3$ | $C(CH_3)_3$ | H | $(CH_2)_7$ | $PF_6$ | — |
| 78 | $Co^{2+}$ | $(CH_2)_3$ | $(CH_2)_3$ | H | $CH_3$ | $C(CH_3)_3$ | H | $(CH_2)_7$ | $PF_6$ | — |
| 80 | $Ni^{2+}$ | $(CH_2)_3$ | $(CH_2)_3$ | H | $CH_3$ | $CH_3$ | H | $(CH_2)_8$ | $PF_6$ | — |
| 81 | $Co^{2+}$ | $(CH_2)_3$ | $(CH_2)_3$ | H | $CH_3$ | $CH_3$ | H | $(CH_2)_8$ | $PF_6$ | — |
| 82 | $Ni^{2+}$ | $(CH_2)_3$ | $(CH_2)_3$ | H | $CH_3$ | $CH_3$ | $CH_3$ | $(CH_2)_8$ | $PF_6$ | $CH_3CN$ |
| 83 | $Co^{2+}$ | $(CH_2)_3$ | $(CH_2)_3$ | H | $CH_3$ | $CH_3$ | $CH_3$ | $(CH_2)_8$ | $PF_6$ | $CH_3CN$ |
| 84 | $Ni^{2+}$ | $(CH_2)_3$ | $(CH_2)_3$ | H | $CH_3$ | $\phi$ | H | $(CH_2)_8$ | $PF_6$ | — |
| 85 | $Co^{2+}$ | $(CH_2)_3$ | $(CH_2)_3$ | H | $CH_3$ | $CH_3$ | H | m-xylylene | $PF_6$ | $CH_3CN$ |
| 86 | $Ni^{2+}$ | $(CH_2)_3$ | $(CH_2)_3$ | H | $CH_3$ | $CH_3$ | $CH_3$ | m-xylylene | $PF_6$ | $CH_3CN$ |
| 87 | $Co^{2+}$ | $(CH_2)_3$ | $(CH_2)_3$ | H | $CH_3$ | $CH_3$ | $CH_3$ | m-xylylene | $PF_6$ | Cl |
| 88 | $Fe^{2+}$ | $(CH_2)_3$ | $(CH_2)_3$ | H | $CH_3$ | $CH_3$ | H | m-xylylene | $PF_6$ | $CO/Py$ |
| 89 | $Fe^{2+}$ | $(CH_2)_3$ | $(CH_2)_3$ | H | $CH_3$ | $CH_3$ | H | m-xylylene | $PF_6$ | $CO/1\text{-}CH_3\text{-}Im$ |
| 90 | $Fe^{2+}$ | $(CH_2)_3$ | $(CH_2)_3$ | H | $CH_3$ | $CH_3$ | H | m-xylylene | $PF_6$ | $CO/CH_3CN$ |
| 91 | $Fe^{2+}$ | $(CH_2)_3$ | $(CH_2)_3$ | H | $CH_3$ | $CH_3$ | H | m-xylylene | $PF_6$ | $CO/Im$ |
| 92 | $Fe^{2+}$ | $(CH_2)_3$ | $(CH_2)_3$ | H | $CH_3$ | $CH_3$ | H | m-xylylene | $PF_6$ | $CO/4\text{-}NH_2\text{-}Py$ |
| 93 | $Ni^{2+}$ | $(CH_2)_3$ | $(CH_2)_3$ | H | $CH_3$ | $CH_3$ | $CH_3$ | m-xylylene | $PF_6$ | $H_2O$ |
| 94 | $Co^{2+}$ | $(CH_2)_3$ | $(CH_2)_3$ | H | $CH_3$ | $CH_3$ | $CH_3$ | m-xylylene | $PF_6$ | Cl |
| 95 | $Fe^{2+}$ | $(CH_2)_3$ | $(CH_2)_3$ | H | $CH_3$ | $CH_3$ | $CH_3$ | m-xylylene | $PF_6$ | $CO/1\text{-}CH_3\text{-}Im$ |
| 96 | $Fe^{2+}$ | $(CH_2)_3$ | $(CH_2)_3$ | H | $CH_3$ | $CH_3$ | $CH_3$ | m-xylylene | $PF_6$ | $CO/CH_3CN$ |
| 97 | $Fe^{2+}$ | $(CH_2)_3$ | $(CH_2)_3$ | H | $CH_3$ | $CH_3$ | $CH_3$ | m-xylylene | $PF_6$ | $CO/Im$ |
| 98 | $Fe^{2+}$ | $(CH_2)_3$ | $(CH_2)_3$ | H | $CH_3$ | $CH_3$ | $CH_3$ | m-xylylene | $PF_6$ | $CO/4\text{-}NH_2\text{-}Py$ |
| 99 | $Fe^{2+}$ | $(CH_2)_3$ | $(CH_2)_3$ | H | $CH_3$ | $CH_3$ | $CH_3$ | m-xylylene | $PF_6$ | Cl |
| 100 | $Mn^{2+}$ | $(CH_2)_3$ | $(CH_2)_3$ | H | $CH_3$ | $CH_3$ | $CH_3$ | m-xylylene | $PF_6$ | Cl |
| 101 | $Mn^{3+}$ | $(CH_2)_3$ | $(CH_2)_3$ | H | $CH_3$ | $CH_3$ | $CH_3$ | m-xylylene | $PF_6$ | Cl |
| 102 | $Cu^{2+}$ | $(CH_2)_3$ | $(CH_2)_3$ | H | $CH_3$ | $CH_3$ | $CH_3$ | m-xylylene | $PF_6$ | $CH_3CN$ |
| 103 | $Ni^{2+}$ | $(CH_2)_3$ | $(CH_2)_3$ | H | $CH_3$ | $CH_3$ | $(CH_2)_3CH_3$ | m-xylylene | $PF_6$ | — |

TABLE 3-continued

FORMULAE I AND IA

| Compd. No. | $M^{n+}$ | X | Y | $R_1$ | $R_2$ | $R_3$ | $R_4$ | R | Anion | Z |
|---|---|---|---|---|---|---|---|---|---|---|
| 105 | $Ni^{2+}$ | $(CH_2)_3$ | $(CH_2)_3$ | H | $CH_3$ | $CH_3$ | $CH_2CH_2CN$ | m-xylylene | $PF_6$ | — |
| 106 | $Ni^{2+}$ | $(CH_2)_3$ | $(CH_2)_3$ | H | $CH_3$ | $CH_3$ | $CH_2\phi$ | m-xylylene | $PF_6$ | — |
| 107 | $Fe^{2+}$ | $(CH_2)_3$ | $(CH_2)_3$ | H | $CH_3$ | $CH_3$ | $CH_2\phi$ | m-xylylene | $PF_6$ | $CH_3CN$ |
| 108 | $Ni^{2+}$ | $(CH_2)_3$ | $(CH_2)_3$ | H | $CH_3$ | $CH_3$ | $CH_3$ | m-xylylene | $PF_6$ | — |
| 109 | $Ni^{2+}$ | $(CH_2)_3$ | $(CH_2)_3$ | H | $CH_3$ | H | H | m-xylylene | $PF_6$ | — |
| 110 | $Fe^{2+}$ | $(CH_2)_3$ | $(CH_2)_3$ | H | $CH_3$ | $(CH_2)_6CH_3$ | $CH_3$ | m-xylylene | $PF_6$ | — |
| 111 | $Ni^{2+}$ | $(CH_2)_3$ | $(CH_2)_3$ | H | $CH_3$ | $(CH_2)_6CH_3$ | H | m-xylylene | $PF_6$ | — |
| 112 | $Fe^{2+}$ | $(CH_2)_3$ | $(CH_2)_3$ | H | $CH_3$ | $(CH_2)_6CH_3$ | $CH_3$ | m-xylylene | $PF_6$ | Cl |
| 113 | $Ni^{2+}$ | $(CH_2)_3$ | $(CH_2)_3$ | H | $CH_3$ | $\phi$ | H | m-xylylene | $PF_6$ | — |
| 114 | $Co^{2+}$ | $(CH_2)_3$ | $(CH_2)_3$ | H | $CH_3$ | $\phi$ | H | m-xylylene | $PF_6$ | $CH_3CN$ |
| 115 | $Ni^{2+}$ | $(CH_2)_3$ | $(CH_2)_3$ | H | $CH_3$ | $\phi$ | $CH_3$ | m-xylylene | $PF_6$ | — |
| 116 | $Co^{2+}$ | $(CH_2)_3$ | $(CH_2)_3$ | H | $CH_3$ | $\phi$ | $CH_3$ | m-xylylene | $PF_6$ | $CH_3CN$ |
| 117 | $Fe^{2+}$ | $(CH_2)_3$ | $(CH_2)_3$ | H | $CH_3$ | $\phi$ | $CH_3$ | m-xylylene | $PF_6$ | — |
| 118 | $Ni^{2+}$ | $(CH_2)_3$ | $(CH_2)_3$ | H | $CH_3$ | $\phi$ | $CH_2\phi$ | m-xylylene | $PF_6$ | $CH_3CN$ |
| 119 | $Fe^{2+}$ | $(CH_2)_3$ | $(CH_2)_3$ | H | $CH_3$ | $\phi$ | $CH_2\phi$ | m-xylylene | $PF_6$ | Cl |
| 120 | $Fe^{2+}$ | $(CH_2)_3$ | $(CH_2)_3$ | H | $CH_3$ | p-MeO$\phi$ | $CH_3$ | m-xylylene | $PF_6$ | Cl |
| 121 | $Fe^{2+}$ | $(CH_2)_3$ | $(CH_2)_3$ | H | $CH_3$ | p-Cl$\phi$ | $CH_3$ | m-xylylene | $PF_6$ | Cl |
| 122 | $Fe^{2+}$ | $(CH_2)_3$ | $(CH_2)_3$ | H | $CH_3$ | p-F$\phi$ | $CH_3$ | m-xylylene | $PF_6$ | Cl |
| 125 | $Ni^{2+}$ | $(CH_2)_3$ | $(CH_2)_3$ | H | $CH_3$ | 3,5-diMeO$\phi$ | $CH_3$ | m-xylylene | $PF_6$ | — |
| 126 | $Fe^{2+}$ | $(CH_2)_3$ | $(CH_2)_3$ | H | $CH_3$ | $CH_3$ | $CH_3$ | p-xylylene | $PF_6$ | Cl |
| 127 | $Fe^{2+}$ | $(CH_2)_3$ | $(CH_2)_3$ | H | $CH_3$ | $CH_3$ | H | p-xylylene | $PF_6$ | $CO/CH_3CN$ |
| 128 | $Fe^{2+}$ | $(CH_2)_3$ | $(CH_2)_3$ | H | $CH_3$ | $CH_3$ | H | p-xylylene | $PF_6$ | CO/Py |
| 129 | $Fe^{2+}$ | $(CH_2)_3$ | $(CH_2)_3$ | H | $CH_3$ | $CH_3$ | H | p-xylylene | $PF_6$ | $CO/1$-$CH_3$—Im |
| 130 | $Ni^{2+}$ | $(CH_2)_3$ | $(CH_2)_3$ | H | $CH_3$ | $CH_3$ | $CH_3$ | p-xylylene | $PF_6$ | — |
| 131 | $Ni^{2+}$ | $(CH_2)_3$ | $(CH_2)_3$ | H | $CH_3$ | $CH_3$ | H | $(CH_2)_3$—(9,9-flourylene)—$(CH_2)_3$ | $PF_6$ | — |
| 132 | $Fe^{2+}$ | $(CH_2)_3$ | $(CH_2)_3$ | H | $CH_3$ | $CH_3$ | H | $(CH_2)_3$—(9,9-flourylene)—$(CH_2)_3$ | Cl | Cl |
| 133 | $Fe^{2+}$ | $(CH_2)_3$ | $(CH_2)_3$ | H | $CH_3$ | $CH_3$ | H | $(CH_2)_3$—(9,9-flourylene)—$(CH_2)_3$ | $PF_6$ | CO/Py |
| 134 | $Fe^{2+}$ | $(CH_2)_3$ | $(CH_2)_3$ | H | $CH_3$ | $CH_3$ | H | $(CH_2)_3$—(9,9-flourylene)—$(CH_2)_3$ | $PF_6$ | $CO/1$-$CH_3$—Im |
| 135 | $Ni^{2+}$ | $(CH_2)_3$ | $(CH_2)_3$ | H | $CH_3$ | $CH_3$ | H | $CH(COOCH_3)(CH_2)_4$ | $PF_6$ | — |
| 136 | $Ni^{2+}$ | $(CH_2)_3$ | $(CH_2)_3$ | H | $CH_3$ | $CH_3$ | H | $CH_2$—(1,3-cyclohexylene)—$CH_2$ | $PF_6$ | — |
| 137 | $Ni^{2+}$ | $(CH_2)_3$ | $(CH_2)_3$ | H | $CH_3$ | $\phi$ | $CH_3$ | $(CH_2)_2C(CH_3)_2(CH_2)_2$ | $PF_6$ | — |
| 138 | $Ni^{2+}$ | $(CH_2)_3$ | $(CH_2)_3$ | H | $CH_3$ | $CH_3$ | $CH_3$ | (5-methoxy-m-xylylene) | $PF_6$ | — |
| 139 | $Ni^{2+}$ | $(CH_2)_3$ | $(CH_2)_3$ | H | $CH_3$ | $CH_3$ | H | $(CH_2)_2S(CH_2)_2$ | $PF_6$ | — |
| 140 | $Ni^{2+}$ | $(CH_2)_3$ | $(CH_2)_3$ | H | $CH_3$ | $CH_3$ | H | $(CH_2)_2S(CH_2)_3$ | $PF_6$ | — |
| 141 | $Ni^{2+}$ | $(CH_2)_3$ | $(CH_2)_3$ | H | $CH_3$ | $CH_3$ | $CH_3$ | 5-(COOCH_3)-m-xylylene | $PF_6$ | — |

TABLE 3-continued
FORMULAE I AND IA

| Compd. No. | $M^{n+}$ | X | Y | $R_1$ | $R_2$ | $R_3$ | $R_4$ | R | Anion | Z |
|---|---|---|---|---|---|---|---|---|---|---|
| 142 | $Ni^{2+}$ | $(CH_2)_3$ | $(CH_2)_3$ | H | $CH_3$ | $CH_3$ | $CH_3$ | 2,6-bis(CH₂)-pyridine | $PF_6$ | — |
| 143 | $Ni^{2+}$ | $(CH_2)_3$ | $(CH_2)_3$ | H | $CH_3$ | $CH_3$ | H | $(CH_2)_3NH(CH_3)_3$ | $PF_6$ | — |
| 144 | $Ni^{2+}$ | $(CH_2)_3$ | $(CH_2)_3$ | H | $CH_3$ | $CH_3$ | H | $(CH_2)_3NCH_3(CH_3)_3$ | $PF_6$ | — |
| 145 | $Co^{2+}$ | $(CH_2)_3$ | $(CH_2)_3$ | H | $CH_3$ | $CH_3$ | H | $(CH_2)_3NCH_3(CH_3)_3$ | $PF_6$ | — |
| 164 | $Ni^{2+}$ | CH₂–CH–CH₂–(N⁺-methylpyridinium) | $(CH_2)_3$ | H | $CH_3$ | $CH_3$ | $CH_3$ | $(CH_2)_5$ | $PF_6$ | — |
| 165 | $Ni^{2+}$ | " | $(CH_2)_3$ | H | $CH_3$ | $CH_3$ | $CH_3$ | $(CH_2)_6$ | $PF_6$ | — |
| 166 | $Co^{2+}$ | " | $(CH_2)_3$ | H | $CH_3$ | $CH_3$ | $CH_3$ | $(CH_2)_6$ | $PF_6$ | — |
| 167 | $Ni^{2+}$ | " | $(CH_2)_3$ | H | $CH_3$ | $CH_3$ | $CH_3$ | m-xylylene | $PF_6$ | — |
| 168 | $Co^{2+}$ | CH₂–CH–CH₂–pyridine | $(CH_2)_3$ | H | $CH_3$ | $CH_3$ | $CH_3$ | $(CH_2)_6$ | $PF_6$ | — |
| 169 | $Ni^{2+}$ | $(CH_2)_2$ | $(CH_2)_3$ | H | $CH_3$ | $CH_3$ | $CH_3$ | $(CH_2)_6$ | $PF_6$ | — |
| 170 | — | $(CH_2)_3$ | $(CH_2)_3$ | H | $CH_3$ | $CH_3$ | $CH_3$ | $(CH_2)_4$ | $PF_6$ | — |
| 171 | $Fe^{2+}$ | $(CH_2)_3$ | $(CH_2)_3$ | H | $CH_3$ | $CH_3$ | H | m-xylylene | Cl | Cl |
| 172 | $Zn^{2+}$ | $(CH_2)_3$ | $(CH_2)_3$ | H | $CH_3$ | $CH_3$ | H | $(CH_2)_3$–(9,9-flourylene)–$(CH_2)_3$ | Cl | — |
| 194 | $Ni^{2+}$ | $CH_2C(CH_3)_2CH_2$ | $(CH_2)_3$ | H | $CH_3$ | φ | $CH_3$ | m-xylylene | $PF_6$ | — |
| 195 | — | " | " | " | " | " | " | " | " | — |
| 196 | $Fe^{2+}$ | " | " | " | " | " | " | " | " | — |
| 199 | $Ni^{2+}$ | $(CH_2)_3$ | $(CH_2)_3$ | H | $CH_3$ | $CH_3$ | $CH_3$ | $(CH_2)_{10}$ | $PF_6$ | — |
| 200 | $Co^{2+}$ | " | " | " | " | " | " | " | $PF_6$ | — |

TABLE 4
FORMULA II

| Cmpd. No. | $M^{n+}$ | X | Y | $R_1$ | $R_2$ | $R_4$ | $R_5$ | R | Anion | Z |
|---|---|---|---|---|---|---|---|---|---|---|
| 65(c) | $Ni^{2+}$ | $(CH_2)_3$ | $(CH_2)_3$ | H | $CH_3$ | H | $(CH_2)_6$ | $(CH_2)_6$ | $PF_6$ | — |
| 66 | $Ni^{2+}$ | $(CH_2)_3$ | $(CH_2)_3$ | H | $CH_3$ | H | $(CH_2)_7$ | $(CH_2)_6$ | $PF_6$ | — |
| 67 | $Ni^{2+}$ | $(CH_2)_3$ | $(CH_2)_3$ | H | $CH_3$ | H | $(CH_2)_8$ | $(CH_2)_6$ | $PF_6$ | — |
| 79 | $Ni^{2+}$ | $(CH_2)_3$ | $(CH_2)_3$ | H | $CH_3$ | H | $(CH_2)_8$ | $(CH_2)_7$ | $PF_6$ | — |
| 123 | $Ni^{2+}$ | $(CH_2)_3$ | $(CH_2)_3$ | H | $CH_3$ | H | $(CH_2)_8$ | m-xylene | $PF_6$ | — |
| 124 | $Ni^{2+}$ | $(CH_2)_3$ | $(CH_2)_3$ | H | $CH_3$ | H | $(CH_2)_7$ | m-xylene | $PF_6$ | — |

TABLE 5
FORMULAE III AND IIIA

| Cmpd. No. | $M^{n+}$ | X | Y | $R_1$ | $R_2$ | $R_4$ | $R_6$ | $R_5$ | Anion | Z |
|---|---|---|---|---|---|---|---|---|---|---|
| 146(c) | $Ni^{2+}$ | $(CH_2)_3$ | $(CH_2)_3$ | H | $CH_3$ | $CH_3$ | $CH_3$ | $(CH_2)_5$ | $PF_6$ | — |
| 147(c) | $Co^{2+}$ | $(CH_2)_3$ | $(CH_2)_3$ | H | $CH_3$ | $CH_3$ | $CH_3$ | $(CH_2)_5$ | $PF_6$ | $CH_3CN$ |
| 148(c) | $Ni^{2+}$ | $(CH_2)_3$ | $(CH_2)_3$ | H | $CH_3$ | $CH_3$ | H | $(CH_2)_6$ | $PF_6$ | — |
| 149(c) | $Ni^{2+}$ | $(CH_2)_3$ | $(CH_2)_3$ | H | $CH_3$ | $CH_3$ | $CH_3$ | $(CH_2)_6$ | $PF_6$ | — |
| 150(c) | $Co^{2+}$ | $(CH_2)_3$ | $(CH_2)_3$ | H | $CH_3$ | $CH_3$ | $CH_3$ | $(CH_2)_6$ | $PF_6$ | $CH_3CN$ |
| 151 | $Ni^{2+}$ | $(CH_2)_3$ | $(CH_2)_3$ | H | $CH_3$ | H | $CH_3$ | $(CH_2)_7$ | $PF_6$ | — |
| 152 | $Co^{2+}$ | $(CH_2)_3$ | $(CH_2)_3$ | H | $CH_3$ | H | $CH_3$ | $(CH_2)_7$ | $PF_6$ | — |
| 153 | $Fe^{2+}$ | $(CH_2)_3$ | $(CH_2)_3$ | H | $CH_3$ | H | $CH_3$ | $(CH_2)_7$ | $PF_6$ | Cl |
| 154 | $Ni^{2+}$ | $(CH_2)_3$ | $(CH_2)_3$ | H | $CH_3$ | $(CH_2)_2CH_3$ | H | $(CH_2)_7$ | $PF_6$ | — |
| 155 | $Co^{2+}$ | $(CH_2)_3$ | $(CH_2)_3$ | H | $CH_3$ | $(CH_2)_2CH_3$ | H | $(CH_2)_7$ | $PF_6$ | $CH_3CN$ |
| 156 | $Ni^{2+}$ | $(CH_2)_3$ | $(CH_2)_3$ | H | $CH_3$ | $CH_2\phi$ | H | $(CH_2)_7$ | $PF_6$ | — |
| 157 | $Ni^{2+}$ | $(CH_2)_3$ | $(CH_2)_3$ | H | $CH_3$ | $CH_3$ | $CH_3$ | $(CH_2)_7$ | $PF_6$ | — |
| 158 | $Co^{2+}$ | $(CH_2)_3$ | $(CH_2)_3$ | H | $CH_3$ | $CH_3$ | $CH_3$ | $(CH_2)_7$ | $PF_6$ | $H_2O$ |
| 159 | $Fe^{2+}$ | $(CH_2)_3$ | $(CH_2)_3$ | H | $CH_3$ | $CH_3$ | $CH_3$ | $(CH_2)_7$ | $PF_6$ | Cl |
| 160 | $Ni^{2+}$ | $(CH_2)_3$ | $(CH_2)_3$ | H | $CH_3$ | $CH_3$ | H | $(CH_2)_8$ | $PF_6$ | — |
| 161 | $Ni^{2+}$ | $(CH_2)_3$ | $(CH_2)_3$ | H | $CH_3$ | $CH_3$ | $CH_3$ | $(CH_2)_8$ | $PF_6$ | — |
| 162 | $Co^{2+}$ | $(CH_2)_3$ | $(CH_2)_3$ | H | $CH_3$ | $CH_3$ | $CH_3$ | $(CH_2)_8$ | $PF_6$ | Cl |

TABLE 6
FORMULAE XVIII AND XVIIIA

| Cmpd. No. | $M^{n+}$ | X | Y | $R_1$ | $R_2$ | $R_3$ | D | Anion | Z |
|---|---|---|---|---|---|---|---|---|---|
| 173 | $Ni^{2+}$ | $(CH_2)_3$ | $(CH_2)_3$ | H | $CH_3$ | $CH_3$ | 1,3-phenylene | $PF_6$ | — |
| 174 | $Ni^{2+}$ | $(CH_2)_3$ | $(CH_2)_3$ | H | $CH_3$ | $CH_3$ | 1,3-phenylene | Cl | — |
| 175 | $Co^{2+}$ | $(CH_2)_3$ | $(CH_2)_3$ | H | $CH_3$ | $CH_3$ | 1,3-phenylene | $PF_6$ | $CH_3OH$ |
| 176 | $Ni^{2+}$ | $(CH_2)_3$ | $(CH_2)_3$ | H | $CH_3$ | $CH_3$ | 1,4-phenylene | $PF_6$ | — |
| 177 | $Co^{2+}$ | $(CH_2)_3$ | $(CH_2)_3$ | H | $CH_3$ | $CH_3$ | 1,4-phenylene | $PF_6$ | — |
| 178 | $Ni^{2+}$ | $(CH_2)_3$ | $(CH_2)_3$ | H | $CH_3$ | $CH_3$ | 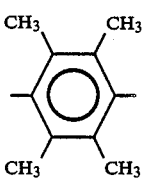 | $PF_6$ | — |
| 179 | $Ni^{2+}$ | $(CH_2)_3$ | $(CH_2)_3$ | H | $CH_3$ | $CH_3$ | " | Cl | — |
| 180 | $Co^{2+}$ | $(CH_2)_3$ | $(CH_2)_3$ | H | $CH_3$ | $CH_3$ | " | $PF_6$ | — |
| 181 | $Fe^{2+}$ | $(CH_2)_3$ | $(CH_2)_3$ | H | $CH_3$ | $CH_3$ | " | $PF_6$ | Cl |
| 182 | $Fe^{2+}$ | $(CH_2)_3$ | $(CH_2)_3$ | H | $CH_3$ | $CH_3$ | " | $PF_6$ | $H_2O$ |
| 183 | $Cu^{2+}$ | $(CH_2)_3$ | $(CH_2)_3$ | H | $CH_3$ | $CH_3$ | " | $PF_6$ | — |
| 184 | $Ni^{2+}$ | $(CH_2)_3$ | $(CH_2)_3$ | H | $CH_3$ | $\phi$ | " | $PF_6$ | — |
| 185 | $Ni^{2+}$ | $(CH_2)_3$ | $(CH_2)_3$ | H | $CH_3$ | $CH_3$ | 9,10-anthracene | $PF_6$ | — |
| 186 | $Ni^{2+}$ | $(CH_2)_3$ | $(CH_2)_3$ | H | $CH_3$ | $CH_3$ | " | Cl | — |
| 187 | $Co^{2+}$ | $(CH_2)_3$ | $(CH_2)_3$ | H | $CH_3$ | $CH_3$ | " | $PF_6$ | $CH_3OH$ |
| 188 | $Fe^{2+}$ | $(CH_2)_3$ | $(CH_2)_3$ | H | $CH_3$ | $CH_3$ | " | $PF_6$ | Cl |
| 189 | $Ni^{2+}$ | $(CH_2)_3$ | $(CH_2)_3$ | H | $CH_3$ | $\phi$ | " | $PF_6$ | — |
| 190 | $Ni^{2+}$ | $(CH_2)_3$ | $(CH_2)_3$ | H | $CH_3$ | $CH_3$ | 2,6-pyridylene | $PF_6$ | — |
| 191 | $Co^{2+}$ | $(CH_2)_3$ | $(CH_2)_3$ | H | $CH_3$ | $CH_3$ | " | $PF_6$ | — |
| 192 | $Ni^{2+}$ | 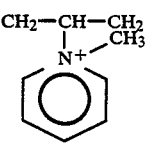 | $(CH_2)_3$ | H | $CH_3$ | $CH_3$ | 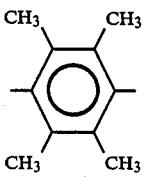 | $PF_6$ | — |
| 193 | $Ni^{2+}$ | " | $(CH_2)_3$ | H | $CH_3$ | $CH_3$ | 9,10-anthracene | $PF_6$ | — |

TABLE 6-continued

FORMULAE XVIII AND XVIIIA

| Cmpd. No. | $M^{n+}$ | X | Y | $R_1$ | $R_2$ | $R_3$ | D | Anion | Z |
|---|---|---|---|---|---|---|---|---|---|
| 197 | $Ni^{2+}$ | $(CH_2)_3$ | $(CH_2)_3$ | H | $CH_3$ | n-$C_{17}H_{35}$ | 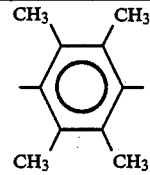 | $PF_6$ | — |
| 198 | $Ni^{2+}$ | $(CH_2)_3$ | $(CH_2)_3$ | H | $CH_3$ | $(CH_2)_8$ bridge | 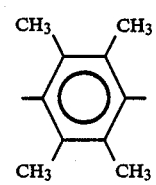 | $PF_6$ | — |

EXAMPLE I

[(2,11,13,19-Tetramethyl-3,10,14,18,21,25-hexaazabicyclo-[10.7.7]-hexacosa-1,11,13,18,20,25-hexaene-$\kappa^4$N)nickel(II)] Hexafluorophosphate formerly designated (2,11,20,26-Tetramethyl-3,10,14,18,21,25-hexaazabicyclo[10.7.7]hexacosa-1,11,13,18,20,25-hexaene N$_4$)nickel(II) Hexafluorophosphate)

This is compound 31 in Tables 2 and 3.

To a solution of 20 g of (2,12-dimethyl-3,11-bis[1-methoxyethylidene]-1, 5, 9, 13-tetraazacyclohexadeca-1, 4, 9, 12-tetraene N$_4$)nickel(II) hexafluorophosphate (28 mmole) in 1 L of acetonitrile was added, dropwise with stirring, to a solution of 3.3 g (28 mmole) of 1,6-hexanediamine in 1 L of acetonitrile. The resultant red solution was taken to dryness on a rotary evaporator and the residue redissolved in 25 ml of acetonitrile. This solution was chromatographed on a column of Woelm neutral alumina (2.5 cm by 20 cm), eluting with acetonitrile. The yellow band was collected and the solvent was removed by rotary evaporation. The residue was slurried with ethanol and the product was isolated by suction filtration, washed with ether and dried in vacuo. Yield: 19 g (90%).

EXAMPLE II

[(2,12,14,20-Tetramethyl-3,11,15,19,22,26-hexaazapentacyclo[11.7.7.4$^{7,7}$.4$^{28,29}$.4$^{30,31}$] nonatriconta-1,12,14,19,21,26,28(29),30(31),32,34,36,38-dodecaene-$\kappa^4$N)nickel(II)] Hexafluorophosphate formerly designated (2,12,21,27-Tetramethyl-3,11,15,19,22,26-hexaazapentacyclo[11.7.7.4$^{7,7}$.4$^{28,29}$.4$^{30,31}$] nonatriaconta-1,12,14,19,21,26,28(29),30(31),32,34,36,38-dodecaene N$_4$) nickel(II)Hexafluorophosphate)

This is compound 131 in Tables 2 and 3.

A solution of 1.98 g (7.1 mmoles) of 9,9-bis(3-aminopropyl)fluorene in 500 ml of acetonitrile was added dropwise to 5.03 g (7.1 mmoles) of (2,12-dimethyl-3, 11-bis[1-methoxyethylidene]-1, 5, 9, 13-tetraazacyclohexadeca-1, 4, 9, 12-tetraene N$_4$) nickel(II) hexafluorophosphate in 500 ml of acetonitrile. The color changed from yellow-green to orange upon addition of the diamine. The solution was reduced in volume to 30 ml and then passed through a column (1½" diameter, 6" length) of alumina with acetonitrile. The solvent was evaporated, methanol (200 ml) was added and the solution was filtered to obtain a yellow powder. Yield 3.92 g (60%).

EXAMPLE III

[(2,3,11,12,14,20-Hexamethyl-3,11,15,19,22,26-hexaazatricyclo-[11.7.7.1$^{5,9}$] octacosa-1,5,7,9(28),12,14,19,21,26-nonaene-$\kappa^4$N)nickel(II)] Hexafluorophosphate formerly designated (2, 3, 11, 12, 21, 27-Hexamethyl-3, 11, 15, 19, 22, 26-hexaazatricyclo[11.7.7.1$^{5,9}$] octacosa-1, 5, 7, 9(28), 12, 14, 19, 21, 26-nonaene N$_4$)nickel(II) Hexafluorophosphate)

This is compound 93 in Tables 2 and 3.

To 4.41 g (6.24 mmole) of (2,12-dimethyl-3, 11-bis[1-methylaminoethylidene]-1, 5, 9, 13-tetraazacyclohexadeca-1, 4, 9, 12-tetraene N$_4$)nickel(II) hexafluorophosphate in 400 ml of acetonitrile was added 0.30 g (13.7 mmole) of sodium metal in 25 ml of methanol. This solution was brought to reflux under an atmosphere of nitrogen and a solution of $\alpha$, $\alpha'$-dibromo-m-xylene, 1.80 g (6.24 mmole), in 125 ml of acetonitrile was slowly added dropwise with stirring. The solution turned from red-purple to light orange during the addition and a white precipitate of sodium bromide formed. The solution was refluxed for 2 hrs, then cooled and filtered. The filtrate was concentrated to about 50 ml on a rotary evaporator and methanol was added to the cloud point. Upon standing, the yellow microcrystalline product precipitated and was collected by suction filtration, washed with ether and dried in vacuo at 50° C. Yield: 3.41 g (68%).

EXAMPLE IV

[(13,19-Dimethyl-2,11-diphenyl-3,10,14,18,21,25-hexaazabicyclo[10.7.7] hexacosa-1,11,13,18,20,25-hexaene-$\kappa^4$N)nickel(II)] Hexafluorophosphate formerly designated (2,11-Diphenyl-20,26-dimethyl-3,10,14,18,21,25-hexaazabicyclo[10.7.7]hexacosa-1,11,13,18,20,25-hexaene N$_4$)nickel(II) Hexafluorophosphate)

This is compound 54 in Tables 2 and 3 and this Example illustrates the several steps which are necessary to replace a methyl group R$_3$ in a compound of Formula V shown in FIG. 3 with a phenyl group in order to prepare a compound of Formula I having $R_3$=phenyl.

As shown in FIG. 3, this synthesis begins with the anion of Formula XII, which is actually a species of Formula V in which $R_1$=H, $R_2$=$R_3$=$CH_3$. The anion of Formula XII is first deacetylated with p-toluene sulfonic acid, then treated with ammonium hexafluorophosphate to produce the compound of Formula XIII. A sample (19.4 g, 0.05 mole) of (3,11-diacetyl-2,12-dimethyl-1,5,9,13-tetraazacyclohexadeca-1,3,9,11-tetraenato $N_4$)nickel(II) (Formula XII) and 19.0 g of p-toluene sulfonic acid monohydrate (0.1 mole) were refluxed in 200 ml of methanol for 5 minutes. The heat was removed and a solution of 8 g of $NH_4PF_6$ (0.11 mole) in 50 ml of $H_2O$ was added to the reaction mixture. The flask was kept in a freezer for crystallization. After five hours, 27.5 g of yellow crystals were isolated by filtration, washed with methanol and dried in vacuo over $P_4O_{10}$. Yield: 93%.

The cationic complex of the compound of Formula XIII was then deprotonated with sodium methoxide. For this purpose, a sample of (2,12-dimethyl-1,5,9,13-tetraazacyclohexadeca-1,4,9,12-tetraene $N_4$)nickel(II) hexafluorophosphate (Formula XIII)(11.92 g, 0.02 mole) was slurried in a solution containing 0.045 mole of sodium methoxide (from 1 g of sodium) in 50 ml of methanol. The mixture was slurried for 5 minutes and left in the freezer for crystallization. After 1 hour the very dark crystalline product was filtered and washed with a small amount of cold methanol. Yield: 5.5 g (90%). of the compound of Formula XIV.

Reaction of this intermediate with benzoyl chloride yielded the di-benzoyl-Jäger complex of Formula XV. This reaction was effected in the following manner. Benzoyl chloride (0.022 mole) was added to a stirred mixture of 3.05 g (0.01 mole) of (2,12-dimethyl-3,11-dibenzoyl-1,5,9,13-tetraazacyclohexadeca-1,3,9,11-tetraenato $N_4$)nickel(II) (Formula XIV) and 3.31 ml (0.024 mole) of triethylamine in 300 ml of ethyl ether. The deep red color changed immediately to orange and the precipitation of the orange product and $Et_3NHCl$ occurred. After 30 minutes, the solids were filtered and washed with water. The ether filtrate was evaporated to dryness and the residue was combined with the solid product. The combined solids were dissolved in chloroform and chromatographed on alumina. The red-orange eluent solution (chloroform solvent) was evaporated and the residue recrystallized from a dichloromethane-ethyl ether mixture. Yield: 80%.

The salt of Formula I containing the substituted methyl vinyl ether functional group was prepared by reaction with $CH_3SO_3F$ as described above. Ring closure proceeded as follows. A solution of 0.002 mole of the methyl vinyl ether complex in 200 ml of $CH_3CN$ and 0.0022 mole of 1,6-diaminohexane in 200 ml of acetonitrile were simultaneously added at a slow rate to a third vigorously stirred 200 ml volume of acetonitrile, using a peristaltic pump. The volume of the solution was then reduced to about 30 ml by rotary evaporation at about 30° C. The resulting solution was chromatographed on an alumina column (2.5 cm by 20 cm) using acetonitrile. A yellow band was collected and its volume reduced to about 30 ml. The addition of ethanol followed by further evaporation led to precipitation of the product. Yield: 82%.

EXAMPLE V

[(2,3,9,10,12,18-Hexamethyl-3,9,13,17,20,24-hexaazabicyclo[9.7.7]-pentacosa-1,10,12,17,19,24-hexaene-$\kappa^4$N)nickel(II)] Hexafluorophosphate formerly designated (2,3,9,10,19,25-Hexamethyl-3,9,13,17,20,24-hexaazabicyclo[9.7.7]pentacosa-1,10,12,17,19,24-hexaene $N_4$)nickel(II) Hexafluorophosphate)

This is compound 20 in Tables 2 and 3.

10.9 Gram of (2,12-dimethyl-3,11-bis[1-methylaminoethylidene]-1,5,9,13-tetraazacyclohexadeca-1,4,9,12-tetraene $N_4$)nickel(II) hexafluorophosphate (15.4 mmole) was dissolved in 500 ml of acetonitrile under nitrogen in a 2 L, 3-necked, round-bottomed flask equipped with a condenser, stirbar, and a 1 L dropping funnel. A solution of 6.37 g of 1,5-bis(para-toluene-sulfonato)pentane (15.4 mmole) dissolved in 500 ml of acetonitrile was placed in the dropping funnel. A solution of 0.71 g of sodium metal (30.8 mmole) in 25 ml of methanol was added to the solution of the nickel complex, whereupon the color turned deep red. The solution was brought to reflux under nitrogen and the solution of the ditosylate was slowly added over a 4 hr period, after which time the solution turned dark yellow-red and a white crystalline precipitate of sodium para-toluenesulfonate had formed. The solution was concentrated on a rotary evaporator to about 100 ml and filtered through celite. Two hundred and fifty ml of methanol, saturated with ammonium hexafluorophosphate, was slowly added and the solution was rotary evaporated to give the yellow microcrystalline product. Yield: 9.1 g (76%). Sometimes the product was dark brown and was chromatographed on alumina, eluting with acetonitrile.

EXAMPLE VI

[(2,3,10,11,13,19-hexamethyl-3,10,14,18,21,24-hexaazabicyclo[10.7.6]pentacosa-1,11,13,18,20,24-hexaene-$\kappa^4$N)nickel(II)] Hexafluorophosphate formerly designated (2,3,10,11,19,25-Hexamethyl-3,10,14,17,20,24-hexaazabicyclo[10.7.6]pentacosa-1,11,13,17,19,24-hexaene$N_4$)nickel(II) Hexafluorophosphate)

This is compound 169 in Tables 2 and 3 having X=$(CH_2)_2$.

This 15-membered macrocyclic dry cave complex was prepared by dissolving 5.0 g (7.19 mmole) of (2,11-dimethyl-3,11-bis[1-methoxyethylidene]-1,5,8,12-tetraazacyclopentadeca-1,4,8,11-tetraene $N_4$)nickel(II) hexafluorophosphate in 500 ml of acetonitrile and slowly adding a solution of 1.04 g (7.19 mmole) of N,N'-dimethyl-1,6-hexanediamine in 500 ml of acetonitrile. The solution turned a dark brown-red and was rotary evaporated to give a viscous dark red oil which was dissolved in a minimum amount of acetone and chromatographed on an alumina column (3" wide by 12–15 inches long) eluting slowly with a 1:1 mixture of acetone and dichloromethane. The light yellow band was collected, leaving numerous dark bands at the top of the column, rotary evaporated to dryness and slurried with absolute ethanol. The product was isolated by suction filtration, washed with ether, and then dried in vacuo. Yield: 1.0 g (18%).

EXAMPLE VII

[(14,20-Dimethyl-3,11,15,19,22,26-hexaazatricyclo[11.8$^{2,12}$.7.7]pentatriaconta-1,12,14,19,21,26-hexaene-κ$^4$N)nickel(II)] Hexafluorophosphate formerly designated (14,20-Dimethyl-3,11,15,19,22,26-hexaazatricyclo[11.7.7.8$^{2,11}$]pentatriaconta (1,11,14,19,21,26-hexaeneN$_4$)nickel(II)Hexafluorophosphate)

This is the doubly-bridged compound 79 in Tables 2 and 4 and has the Formula XVI shown in FIG. 3. A solution of 3.05 g (0.01 mol) of the neutralized cationic complex of Example IV (Formula XIV) and 3.30 ml (0.024 mole) of triethylamine in 300 ml of ether was slowly mixed (3 hrs) with a solution of 2.3 ml (0.01 mole) of sebacoyl chloride in 300 ml of ether, using a peristalsic pump. Both solutions are added to a third portion of 300 ml of ether which is stirred vigorously in a round bottomed, 3-necked flask. The reaction was carried out under nitrogen and the product was isolated and purified like the usual Jäger complexes of nickel(II). Yield: 3.0 g (70%).

This compound was converted into the corresponding methoxy compound in the usual way; i.e., reaction with $CH_3SO_3F$, followed by crystallization as the $PF_6$ salt. The product was soluble in methanol but precipitated upon addition of ethanol.

Formation of the second bridge proceeded upon addition of 0.002 mole of the product described immediately above in 200 ml of $CH_3CN$ and 0.0022 mole of 1,7-heptanediamine in 200 ml of acetonitrile, slowly and simultaneously (4 hrs) into a vigorously stirred 200 ml volume of acetonitrile by means of a peristaltic pump. The volume of the resulting solution was reduced to about 30 ml on a rotary evaporator. The concentrated solution was loaded onto an alumina column (2.5 cm×20 cm) packed under acetonitrile, and eluted with acetonitrile. A yellow band was collected. After reducing the volume to 30 ml, the product was precipitated by the addition of methanol followed by evaporation of the acetonitrile. Yield: 48%.

EXAMPLE VIII (2,3,8,9,11,17-hexamethyl-3,8,12,16,19,23-hexaazabicyclo[8.7.7]tetracosa-1,9,11,16,18,23-hexaena-κ$^4$N) Hexafluorophosphate formerly designated (2,3,8,9,11,17-Hexamethyl-3,8,12,16,19,23-hexaazabicyclo[8.7.7] tetracosa-(1,9,11,16,18,23-hexaeneN$_4$) Hexafluorophosphate.)

This is compound 170 in Tables 2 and 3.

This ligand salt was prepared by bubbling a stream of hydrogen chloride gas through a solution of 2.62 g (3.44 mmole) of the corresponding nickel(II) hexafluorophosphate complex of the titled ligand hexafluorophosphate in 50 ml of acetonitrile. The solution turned blue within several minutes. The ligand was precipitated by slow addition of a solution of tetrachlorozincate ions which were prepared as follows: 4.37 g (68.8 mmole) of granular zinc was added to 100 ml of acetonitrile and digested with hydrogen chloride gas until no more zinc remained. The flocculent white precipitate was filtered, washed with acetonitrile and ether, and dried in vacuo. The crude ligand tetrachlorozincate salt was dissolved in 25 ml of $H_2O$. Slow addition of aqueous ammonium hexafluorophosphate resulted in the formation of the white granular product which was suction filtered, washed with ether, and dried in vacuo. Yield: 4.12 g (71%).

EXAMPLE IX (2,11,13,19-Tetramethyl-3,10,14,18,21,25-hexaazabicyclo[10.7.7] hexacosa-1,11,13,18,20,25-hexaene-κ$^4$N) Hexafluorophosphate formerly designated (2,11,20,26-Tetramethyl-3,10,14,18,21,25-hexaazabicyclo[10.7.7] hexacosa-1,11,13,18,20,25-hexaene N$_4$) Hexafluorophosphate)

This is the metal-free salt derived from the nickel salt prepared in Example 1 above.

A solution of 5.0 g (6.6 mmole) of the nickel salt of Example I in 100 ml of acetonitrile was bubbled with hydrogen chloride gas for several minutes until the solution was deep blue. The solvent was stripped off by rotary evaporation and the residue dissolved in 100 ml of $H_2O$. Ten milliliters of absolute ethanol was added to the solution, followed by slow addition of a solution of 10.7 g of ammonium hexafluorophosphate in 50 ml of water. The off-white granular solid which formed was isolated by suction filtration, washed with ethyl ether, and dried in vacuo. Yield: 4.48 g (80%).

EXAMPLE X

[(2,3,8,9,11,17-Hexamethyl-3,8,12,16,19,23-hexaazabicyclo[8.7.7] tetracosa-1,9,11,16,18,23-hexaene-κ$^4$N)cobalt(II)] Hexafluorophosphate formerly designated (2,3,8,9,18,24-Hexamethyl-3,8,12,16,19,23-hexaazabicyclo[8.7.7] tetracosa-1,9,11,16,18,23-hexaene N$_4$)cobalt(II) Hexafluorophosphate)

This is compound 7 in Tables 2 and 3. The preparation of this compound, and of the other cobalt and iron complexes in Examples XI–XV below, must be conducted under a nitrogen atmosphere.

This cobalt(II) complex was prepared by slurrying 2.0 g of (2,3,8,9,18,24-hexamethyl-3,8,12,16,19,23-hexaazabicyclo[8.7.7] tetracosa-1,9,11,16,18,23-hexaene N$_4$) hexafluorophosphate (2.35 mmole) in 10 ml of methanol. This mixture was stirred and warmed on a hot plate. A solution was prepared by dissolving 0.59 g (2.35 mmole) of cobalt acetate tetrahydrate and 0.33 g (2.35 mmole) of sodium acetate trihydrate in 25 ml of hot methanol. The two solutions were mixed and the resulting solution turned orange. The orange microcrystalline product began to precipitate immediately. The solution was cooled, the product collected by suction filtration and washed with methanol and ether and dried under vacuum. Yield: 1.54 g (86%).

EXAMPLE XI

[1-Methylimidazole(2,3,10,11,13,19-hexamethyl-3,10,14,18,21,25-hexaazabicyclo[10.7.7] hexacosa-1,11,13,18,20,25-hexaene-κ$^4$N)cobalt(II)] Hexafluorophosphate formerly designated (2,3,10,11,20,26-Hexamethyl-3,10,14,18,21,25-hexaazabicyclo[10.7.7] hexacosa-1,11,13,18,20,25-hexaene N$_4$)(N-methylimidazole)cobalt(II) Hexafluorophosphate)

This compound, number 39 in Tables 2 and 3 above, was prepared by slurrying 226 mg of (2,3,10,11,13,19-hexamethyl-3,10,14,18,21,25-hexaazabicyclo[10.7.7] hexacosa-1,11,13,18,20,25-hexaene-κ$^4$N)cobalt(II) hexafluorophosphate (0.286 mmole) (this is compound 37 prepared as described in the Additional Examples below) in 5 ml of methanol. One hundred milligrams (1.22 mmole) of N-methylimidazole was added and the solution darkened considerably. The solution was heated for about 15 minutes and allowed to cool. The dark orange microcrystals were collected, washed with ether, and dried in vacuo. Yield: 178 mg (71%).

EXAMPLE XII

[Chloro(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] Chloride dimethanolate formerly designated Chloro(2,12,21,27-tetramethyl-3,11,15,19,22,26-hexaazatricyclo-[11.7.7.1$^{5,9}$]-(octacosa-1,5,7,9(28),12,14,19,21,26-nonaeneN$_4$)iron(II)Chloride dimethanol)

This is compound 171 in Tables 2 and 3.

To a solution of 1.0 g (1.2 mmole) of (2,12,14,20-tetramethyl-3,11,15,19,22,26-hexaazatricyclo[11.7.7.1$^{5,9}$] octacosa-1,5,7,9(28),12,14,19,21,26-nonaeneN$_4$)hexafluorophosphate (prepared by demetallation of the corresponding nickel compound (compound 86, the synthesis of which is indicated in Table 7 below) by the method of Example VIII above) dissolved in 50 ml of acetonitrile was added to 0.24 g (1.2 mmole) of bis-(acetonitrile)iron(II) chloride and 0.35 g (3.5 mmole) of triethylamine to yield a deep red solution which was filtered through celite. The solution was stirred overnight during which time an orange precipitate formed which was collected and dried in vacuo. Yield 0.5 g (78%). Anal: Calc. for FeC$_{26}$H$_{36}$N$_6$Cl$_2$: C, 55.83; H, 6.49; N, 15.02. Found: C, 55.73; H, 6.53; N, 15.16. This product was recrystallized from methanol to yield large crystals of dimethanol solvate.

EXAMPLE XIII

[Chloro(2,12,14,20-tetramethyl-3,11,15,19,22,26-hexaazatricyclo[11.7.7.1$^{5,9}$] octacosa-1,5,7,9(28),12,14,19,21,26-nonaene-$\kappa^4$N)iron(II)] Hexafluorophosphate formerly designated Chloro(2,12,21,27-tetramethyl-3,11,15,19,22,26-hexaazatricyclo-[11.7.7.1$^{5,9}$] octacosa-1,5,7,9(28),12,14,19,21,26-nonaeneN$_4$)iron(II) Hexafluorophosphate)

This compound, compound 88 in Tables 2 and 3, is a different salt of the iron(II) complex of Example XII. To a solution of 0.5 g (0.89 mmole) of the iron(II) salt of Example XII dissolved in 75 ml of methanol was added an excess of ammonium hexafluorophosphate dissolved in methanol to yield a red-orange microcrystalline precipitate which was collected and dried in vacuo. Yield: 0.5 g (85%).

EXAMPLE XIV

[Chloro(2,3,11,12,14,20-hexamethyl-3,11,15,19,22,26-hexaazatricyclo-[11.7.7.1$^{5,9}$-] octacosa-1,5,7,9(28),12,14,19,21,26-nonaene-$\kappa^4$N)iron(II)] Hexafluorophosphate formerly designated Chloro(2,3,11,12,21,27-hexamethyl-3,11,15,19,22,26-hexaazatricyclo-[11.7.7.1$^{5,9}$] octacosa-1,5,7,9(28),12,14,19,21,26-nonaeneN$_4$)iron(II) Hexafluorophosphate)

This is compound 95 in Tables 2 and 3.

To a suspension of 2.0 g (2.3 mmole) of (2,3,11,12,14,20-hexamethyl-3,11,15,19,22,26-hexaazatricyclo[11.7.7.1$^{5,9}$] octacosa-1,5,7,9(28),12,14,19,21,26-nonaeneN$_4$) tetrachlorozincate in 50 ml of methanol was added 0.48 g (2.3 mmole) of bis-acetonitrile iron(II) chloride and 0.92 g (9.1 mmole) of triethylamine. The solution was refluxed for 10 minutes then filtered through celite. After addition of 3.0 g (18.4 mmole) of ammonium hexafluorophosphate dissolved in a minimum volume of methanol the solution was allowed to stand overnight. The large red crystals which formed were collected and dried in vacuo. Yield: 1.15 g (72%).

EXAMPLE XV

[Chloro(2,3,10,11,13,19-hexamethyl-3,10,14,18,21,25-hexaazabicyclo[10.7.7] hexacosa-1,11,13,18,20,25-hexaene-$\kappa^4$N)iron(III)] Hexafluorophosphate formerly designated Chloro(2,3,10,11,20,26-hexamethyl-3,10,14,18,21,25-hexaazabicyclo[10.7.7] hexacosa-1,11,13,18,20,25-hexaeneN$_4$)iron(III) Hexafluorophosphate)

This is compound 50 in Tables 2 and 3 and is the iron(III) salt of Formula IA corresponding to the cobalt(II) salt of Example XI.

Under an atmosphere of nitrogen, 1.0 g (1.5 mmoles) of the iron(II) salt, chloro(2,3,10,11,13,19-hexamethyl-3,10,14,18,21,25-hexaazabicyclo[10.7.7] hexacosa-1,11,13,18,20,25-hexaene-$\kappa^4$N)iron(II) hexafluorophosphate, was dissolved in 25 ml of acetonitrile. 0.26 g (1.5 mmoles) of solid NOPF$_6$ were added to the stirred solution and the flask immediately connected to the vacuum line to trap evolved NO gas. The solution rapidly changed color from red-brown to deep-blue with the evolution of a colorless gas under partial vacuum. Evaporation of the solvent to dryness left a blue-green oily powder which can be carefully recrystallized, under N$_2$, from hot acetonitrile to give deep-blue blocks of crystalline material. Recrystallized yield: 0.49 g (41%).

EXAMPLE XVI

[(2,12,14,20-Tetramethyl-3,11,15,19,22,26-hexaazapentacyclo[11.7.7.4$^{7,7}$.4$^{28,29}$.4$^{30,31}$] nonatriaconta-1,12,14,19,21,26,28(29),30(31),32,34,36,38-dodecaene-$\kappa^4$N)zinc(II) Chloride formerly designated (2,12,21,27-Tetramethyl-3,11,15,19,22,26-hexaazapentacyclo[11.7.7.4$^{7,7}$.4$^{28,29}$.4$^{30,31}$] nonatriaconta-1,12,14,19,21,26,28(29),30(31),32,34,36,38-dodecaeneN$_4$)zinc(II) Chloride.)

This is compound 172 in Tables 2 and 3.

The tetrachlorozincate salt of the ligand obtained from the nickel(II) salt synthesized in Example II was dissolved in boiling acetonitrile (50–75 ml). The solution was filtered while hot and 1.0 g of triethylamine was added. A yellow solution was obtained which yielded a solid product on standing overnight. Anal. Calcd: for the zinc complex: C, 62.31; H, 6.78; N, 11.78. Found: C, 61.65; H, 7.10; N, 11.59.

EXAMPLE XVII

[(2,3,10,11,13,19-Hexamethyl-3,10,14,18,21,25-hexaazabicyclo[10.7.7]
hexacosa-1,11,13,18,20,25-hexaene-$\kappa^4$N)copper(II)]
Hexafluorophosphate formerly designated (2,3,10,11,20,26-Hexamethyl-3,10,14,18,21,25-hexaazabicyclo[10.7.7]
hexacosa-1,11,13,18,20,25-hexaeneN$_4$)copper(II)
Hexafluorophosphate)

This is compound 53 in Tables 2 and 3 and is the copper (II) salt corresponding to the cobalt(II) salt synthesized in Example XI.

One gram (1.1 mmole) of (2,3,10,11,13,19-hexamethyl-3,10,14,18,21,25-hexaazabicyclo[10.7.7] hexacosa-1,11,13,18,20,25-hexaene-$\kappa^4$N) hexafluorophosphate was slurried in 20 ml of refluxing methanol. To this solution was added a solution of 0.25 g (1.3 mmole) of copper(II) acetate hydrate and 0.46 g (3.4 mmole) of sodium acetate trihydrate dissolved in 15 ml of hot methanol. The solution turned brown immediately with the formation of a red crystalline product. The product was recrystallized from an acetonitrile/ethanol solution to yield large red crystals. Yield 0.74 g (85%).

EXAMPLE XVIII

[Acetonitrile(2,3,11,12,14,20-hexamethyl-3,11,15,19,22,26-hexaazatricyclo-[11.7.7.1$^{5,9}$]
octacosa-1,5,7,9(28),12,14,19,21,26-nonaene-$\kappa^4$N)copper(II)] Hexafluorophosphate formerly designated (2,3,11,12,21,27-Hexamethyl-3,11,15,19,22,26-hexaazatricyclo[11.7.7.1$^{5,9}$]
octacosa-1,5,7,9(28),12,14,19,21,26-nonaeneN$_4$)copper(II) Hexafluorophosphate, acetonitrile This is compound 103 in Tables 2 and 3 and is the copper(II) salt corresponding to the iron(II) salt synthesized in Example XIV. This copper complex was synthesized using exactly the same procedure described in Example XVII.

EXAMPLE XIX

[Chloro(2,3,10,11,13,19-hexamethyl-3,10,14,18,21,25-hexaazabicyclo[10.7.7]
hexacosa-1,11,13,18,20,25-hexaene-$\kappa^4$N)manganese(III)] Hexafluorophosphate formerly designated Chloro(2,3,10,11,20,26-Hexamethyl-3,10,14,18,21,25-Hexaazabicyclo[10.7.7]
hexacosa-1,11,13,18,20,25-hexaeneN$_4$)manganese(III) Hexafluorophosphate)

This is compound 52 in Tables 2 and 3 and is the manganese (III) salt corresponding to the cobalt (II) salt prepared in Example XI.

Under an atmosphere of nitrogen, 3.00 g (3.3 mmoles) of (2,3,10,11,13,19-hexamethyl-3,10,14,18,21,25-hexaazabicyclo[10.7.7] hexacosa-1,11,13,18,20,25-hexaene-$\kappa^4$N) hexafluorophosphate hydrogen chloride was dissolved in 25 ml of acetonitrile. To this solution was added a solution containing 1.20 g (3.4 mmoles) of tris-2,4-pentanedionato-manganese(III) (Mn(acac)$_3$) in 10 ml of acetonitrile. The resultant yellow-brown solution was warmed and stirred for 1 hour after which the volume was reduced until a dark-brown crystalline precipitate began to appear. Addition of 5 ml ethanol produced copious amounts of powdery brown material which was filtered and washed with toluene to remove any unreacted Mn(acac)$_3$. The brown material may be recrystallized from acetonitrile/ethanol to give dark-brown microcrystals which may be recrystallized from acetonitrile by slow evaporation to give large rectangular blocks. Recrystallized yield: 1.02 g (32%). The instant Mn(III) salts as in this example appear to be readily synthesized. The Mn(II) salts are most readily prepared from the Mn(III) salts by reduction.

ADDITIONAL EXAMPLES

For the sake of brevity, the remaining examples will be presented in tabular form. Table 7 below shows the synthetic methods (Methods A–S) used to prepare all the compounds listed in Table 2 above; in the case of those compounds which are prepared in Examples I–XIX above, Table 7 refers to both one of the lettered synthetic methods described below and to the appropriate one of Examples I–XIX, though it should be noted that the two methods are not always the same. Table 7 also shows the theoretical and empirically-determined analyses of each of the compounds for carbon, hydrogen, nitrogen and (in some cases) metal. The various synthetic methods referred to in Table 7 are as follows:

METHOD A

This is an example of the bridging of a compound of Formula VI with an $\alpha$, $\Omega$-diamine, as shown in FIG. 3 of the accompanying drawings.

0.01 mole of a [2,12-di-R$_2$-4,10-di-R$_1$-3,11-bis(1-methoxy-R$^3$-idene)-1,5,9,13-tetraazacyclohexadeca-1,4,9,12-tetraene-N$^1$,N$^5$,N$^9$,N$^{13}$] nickel(II) hexafluorophosphate and 0.01 mole of appropriate diamine R$^4$NHRNHR$^4$ are each dissolved in 250 mls of acetonitrile. The two solutions are slowly (over 1 hour) dripped simultaneously into a round-bottom flask containing 250 mls of refluxing stirred acetonitrile, using a peristaltic pump. The solution is stirred at reflux for an additional 3 hours before concentrating it on a rotary evaporator to about ~30 mls. This solution is chromatographed on neutral alumina with acetonitrile eluent and the fastest moving yellow or orange band collected. Evaporation to dryness and recrystallization from acetonitrile/ethanol results in the desired bridged complex as the hexafluorophosphate salt.

This method is described in Busch et al, J.A.C.S., 103, 1472(1981).

METHOD B

This is essentially a variant of Method A and again involves the use of a diamine to bridge a compound of Formula VI.

Method A is followed using the appropriate primary diamine but after the product has been separated by the chromatography on alumina, the product must be separated from contaminant oligomers. This is done by converting the hexafluorophosphate anion to chloride by dissolving the salt in dry acetone and adding acetone saturated with tetrabutylammonium chloride. The chloride salt, which precipitates immediately, is collected by filtration and washed with acetone, then dissolved in a minimum volume of water and loaded onto a chromotography column of CM- or SP-Sephadex ion exchange resin. Elution of the desired monomer is accomplished using 0.2M Na$_2$SO$_4$ in water. The yellow band is collected and upon addition of excess NH$_4$PF$_6$ in water an immediate precipitate of the desired complex forms as the hexafluorophosphate salt. This product is collected by filtration and recrystallized from CH$_3$CN/ethanol.

This method is described in Busch et al, Inorg. Chem., 20, 2384(1981).

METHOD C

This is an example of the reaction of a compound of Formula VIII with a ditosylate to form a compound of Formula IX, as shown in FIG. 3 of the accompanying drawings. The method can also be carried out using the corresponding dichloride or dibromide.

0.01 moles of a [2,12-di-$R_2$-4,10-di-$R_1$-3,11-bis(1-($R^4$amino)-$R^3$-idene)-1,5,9,13-tetraazacyclohexadeca-1,4,9,12-tetraene-$N^1,N^5,N^9,N^{13}$] nickel-(II) hexafluorophosphate (Formula VIII) is dissolved in 250 mls $CH_3CN$ and 0.02 moles of metallic sodium dissolved in 25 mls of methanol are added. This solution and one containing 0.01 moles of an appropriate difunctional bridge material X—R—X (X×tosylate, Cl or Br) are simultaneously dripped into 250 mls of stirred refluxing acetonitrile using a peristaltic pump over a period of 1 hour. The solution is stirred at reflux for at least 3 more hours before filtering to remove NaX by-product. The resultant solution is worked up exactly as described in method A.

This method is described in the paper in J.A.C.S., 103, 1472(1981) referred to in Method A above.

Method D

This method, like several of the other methods described below, begins with the appropriate ligand salt from which the metal has been removed. As described above, this ligand salt can be prepared by demetalling a nickel or other compound of Formula VIII with hydrochloric acid and acetonitrile, followed by addition of zinc chloride to precipitate the ligand tetrachlorozincate salt. Since in most cases the compounds listed in Table 2 are hexafluorophosphate salts, it is advantageous to convert the tetrachlorozincate salt to the hexafluorophosphate salt by addition of ammonium hexafluorophosphate, as described above.

The entire procedure described in the following paragraph must be carried out under nitrogen.

0.001 mole of cobalt (II) acetate tetrahydrate and 0.004 moles of sodium acetate trihydrate are dissolved in 25 ml of hot methanol. This solution is added to one containing 0.001 mole of the appropriate ligand salt in 25 mls of hot methanol. An immediate color change to deep yellow orange occurs and, often, orange products beings to precipitate. If the product does not volunteer from solution, addition of methanol or ethanol saturated with $NH_4PF_6$ will induce precipitation. The product is collected by filtration, washed with ethanol and ether and vacuum dried. The orange powder may if necessary be recrystallized from acetonitrile/ethanol.

This procedure is described in a Ph.D. dissertation by J. C. Stevens (Ohio State University, 1979) and by a post-doctoral report by M. Kojima (Ohio State University, 1980). In certain cases, the salt prepared by this process may include ethanol or acetonitrile either as the ligand Z or as solvent of crystallization.

METHOD E

This method must also be carried out under nitrogen.

0.001 mole of the appropriate ligand salt is dissolved in 25 mls of $CH_3CN$ and 0.002 mole of (bis-pyridine)iron(II) chloride is added as a green solid. The slurry is stirred and 0.006 mole of triethylamine is slowly dripped in, resulting in a color change from green to deep red. The solution is stirred at reflux for 10 minutes before filtration and evaporation to dryness leaving a red gum. Addition of methanol or ethanol causes the gum to dissolve and, frequently, precipitation of the desired complex follows almost immediately. If not, the product may be induced to precipitate by addition of a methanol or ethanol solution saturated with $NH_4PF_6$. The products is collected by filtration and may be recrystallized from $CH_3CN$/ethanol.

This method is described in a PhD. dissertion by L. L. Zimmer (Ohio State University, 1979).

METHOD F

This method is identical to Method E except that the (bis-pyridine)iron(II) chloride is replaced by the corresponding bis-acetonitrile salt; again, the entire procedure is carried out under nitrogen.

METHOD G

This method is generally similar to Method D, except that a copper salt is prepared instead of a cobalt salt.

0.001 mole of the appropriate ligand salt is slurried in 20 ml of refluxing methanol to which is then added a solution of 0.0012 mole of copper (II) acetate hydrate or copper(II) chloride hydrate and 0.003 mole of sodium acetate trihydrate in 15 ml of hot methanol. The solution turns brown immediately and a red crystalline product precipitates. The product may be recrystallized from acetonitrile/ethanol.

This method is also described in the Zimmer dissertation referred to under Method E above.

METHOD H

The following procedure must be carried out under nitrogen.

0.001 moles of the appropriate cobalt (II) complex (prepared by method D above) is dissolved in 50 mls of acetonitrile. 0.015 moles of NaX (where X is the desired axial ligand $NCS^-$, $N_3^-$, $NCO^-$) in 25 mls of water is added. 0.001 mole of $(NH_4)_2Ce(NO_3)_6$ in 10 ml of methanol is slowly dripped into the resultant mixture. The solution becomes dark and is removed from the $N_2$ atmosphere, filtered, and allowed to stand for 1 week whereupon the crystals which had formed were collected by filtration. If crystals do not volunteer then water saturated with $NH_4PF_6$ may be slowly added to induce precipitation.

This method is described in the Stevens' dissertation referred to under Method D above and also in a PhD. dissertation by P. J. Jackson (Ohio State University, 1981).

METHOD I

The following procedure must be carried out under nitrogen.

0.001 mole of the appropriate four-coordinate cobalt-(II) complex (prepared by method D above) is slurried in 20 mls methanol. 0.01 moles of the desired axial ligand B as either the neat ligand (for imidazole, N-methylimidazole or pyridine) or as the sodium salt (for ligand $NCS^-$) is added and the solution refluxed for 15 minutes. Upon cooling, orange crystals form and are collected by filtration.

This method is described in the Stevens' dissertation referred to under Method D above.

METHOD J

The following procedure must be carried out under nitrogen.

0.001 moles of the appropriate iron(II) complex (prepared by method E or F above) are dissolved in 10 mls of $CH_3CN$ and a solution of 0.001 moles $(NH_4)_2Ce(NO_3)_6$ in 5 mls methanol is slowly added dropwise with stirring.

This method is described in the Zimmer dissertation referred to under Method E above.

METHOD K

The following procedure must be carried out under nitrogen.

0.001 mole of the appropriate ligand salt is dissolved in 10 mls $CH_3CN$ and 0.0014 mole of (tris-2,4-petanedionato)manganese(III) is added. The mixture is refluxed for 40 minutes whereupon brown micro-crystals begin to fall from solution. Addition of ethanol saturated with $NH_4PF_6$ induces further crystallization. The product may be collected by filtration, washed with ethanol, toluene and either and recrystallized from $CH_3CN$/ethanol.

METHOD L

The following procedure must be carried out under nitrogen.

0.001 mole of the appropriate manganese(III) complex (prepared by method K above) is dissolved in acetonitrile containing 0.1M $N(CH_3)_4PF_6$. The solution is stirred and electrolyzed with a platinum gauze at $-0.2V$ vs $Ag°/Ag^+$ until a steady coulomb count is reached. The solution brightens from deep red-brown to deep orange during the process of reduction. The solution is pumped to dryness and extensive, repeated recrystallizations from acetonitrile/ethanol yield large red crystals of the desired product.

METHOD M

This is an example of the conversion of a dianion of Formula X to a compound of Formula XI using a diacid chloride, as shown in FIG. 3 of the accompanying drawings.

0.01 moles of the appropriate [2,12-di-$R_2$-4,10-di-$R_1$-1,5,9,13-tetraazacyclohexadeca-1,3,9,11-tetraenato] nickel (the protonated form of a compound of Formula X) in 300 ml dry ether is stirred under nitrogen. 0.024 mole of triethylamine is added followed by the slow dropwise addition of 0.01 mole of the appropriate diacid chloride ClOC—$R_5$—COCl dissolved in 300 mls ether over a period of 3 hours. The red solution and orange product are evaporated to dryness, washed with water to remove $NHEt_3Cl$ and dried in vacuo. After chromatography on neutral alumina using chloroform eluent, the red solution is evaporated to dryness yielding red crystals of the bridged diketone. Methylation on the ketone oxygen atoms is carried out using published procedures as for the simple unbridged Jägermolecules .0.005 moles of the methylated complex in 25 mls of $CH_3CN$ is exposed to 0.01 moles of the appropriate amine $HNRR_4$ in acetonitrile resulting in an immediate color change from green to deep orange-yellow. Evaporation to dryness followed by recrystallization from acetonitrile/ethanol results in the desired retro-bridged material.

This method is described in the Kojima post-doctoral report referred to under method D above and in a post-doctoral report by B. K. Daszkiewicz (Ohio State University, 1978).

METHOD N

The following procedure must be carried out under nitrogen.

0.001 mole of the appropriate iron(II) complex (prepared by method E or F above) and 0.010 moles of axial ligand Z are dissolved in 10 ml of $CH_3CN$ and 60 ml of ethanol. The solution is filtered into a Schlenk flask and removed from the nitrogen atmosphere. The flask is connected to a cylinder of high-grade CO and evacuated under high vacuum. CO is introduced at a pressure slightly above atmospheric, causing the solution color to change from deep red to a less intense orange. The flask is re-sealed and returned to the nitrogen atmosphere whereupon 0.5 g of $NH_4PF_6$ in a minimum volume of ethanol is added. This procedure yields a red-orange, generally crystalline precipitate which is collected and washed with ethanol and ether.

This method is described in the Zimmer dissertation referred to under method E above.

METHOD P

Double bridged complexes of Formula II or IIA are prepared by a combination of methods B and M. The appropriate retro-bridged methylated complex is prepared as described in method M and is reacted with 1 equivalent of the necessary diamine $H_2N$—R—$NH_2$ in acetonitrile as described in method B. The resultant double bridged compound is worked up as described in method B on sephadex ion exchanger to remove any unwated oligomers.

This method is described in the Kojima post-doctoral report referred to under Method D above and in the Dasckiewicz post-doctoral report referred to in method M above.

METHOD Q

This method is used for the synthesis of the bis(-piperazino)-bridged complexes of Formulae XVIII and XVIIIA.

0.005 moles of the same starting material of Formula VI used in method A above are dissolved in 100 ml of acetonitrile and slowly added to a solution of 0.1 mole of piperazine in 100 ml of methanol. The orange solution is reduced in volume and methanol added. This latter process is repeated until orange microcrystals begin to fall from solution. This product is recrystallized from acetonitrile/methanol (1:2 v/v). 0.0012 moles of this material are dissolved in 100 ml of acetonitrile; 0.0013 moles of the desired difunctional bridge material X—R—X (X×Cl or Br) are dissolved in 100 ml. acetonitrile and both solutions are simultaneously dripped into 50 ml of refluxing acetonitrile (2 hours addition time). The solution is stirred for an additional hour whereupon the volume is reduced to 10 ml and 0.003 moles of triethylamine are added. The mixture is chromatographed on neutral alumina using acetonitrile eluent and the fastest moving band is collected. The volume of the collected solution is reduced to 10 ml and ethanol is added to induce crystallization of the desired product.

This method (together with methods R and S below) is described in a Ph.D. dissertation by K. J. Takeuchi (Ohio State University, 1981).

METHOD R

This method is used for converting the hexafluorophosphate salts of Formulae XVIII prepared by method Q to the corresponding chloride salts.

0.001 moles of the appropriate nickel (II) bis hexafluorophosphate salt prepared by method Q above are dissolved in a minimum volume of dry acetone. To this solution is slowly added acetone saturated with tetrabutylammonium chloride to induce immediately a voluminous yellow precipitate which is recovered and dried in vacuo. The product may be recrystallized by dissolution in a minimum volume of dry acetonitrile followed by slow addition of dry acetone. The resultant dichloride salts are usually very hygroscropic and are best stored in a vacuum desiccator.

METHOD S

This method must be carried out under nitrogen.

The nickel hexafluorophosphate salts in Formula XVIII prepared by Method Q above are demetallated in the manner already described using hydrochloric acid in acetonitrile, and the free-ligand salts thus produced are converted to the corresponding iron(II) salts using either method E or method F above, except that in either case precipitation of the iron(II) complex salts is induced by addition of tetrabutylammonium tetrafluoroborate in ethanol.

METHOD T 3,4-diacetyl-2,12-dihydroxy-7,7-dimethyl-5,9-diazatrideca-2,4,9,11-tetraene was synthesized by the method described in Riley et al, Inorganic Synthesis, 18, 36 (1978) and Riley, D. P., Ph.D. Thesis, The Ohio State University, Columbus, Ohio (1975), from 2,2-dimethyl-1,3-propanediamine. The product crystallized in the freezer after several hours in a yield of 75% based upon the diamine. The product was then converted to (3,11-diacetyl-1,12-dihydroxy-7,7-dimethyl-5,9-diazatrideca-2,4,9,11-tetraenato)nickel(II) in 90% yield by the method described in the same two references. Ring closure of the product was then effected by placing 46 grams (0.12 mole) of the product in 130 ml. of 1,3-propanediamine, freshly distilled from potassium hydroxide. The result slurry was brought to reflux whereupon, after approximately 10 to 15 minutes, an orange solid precipitated. The solution was cooled, 50 ml. of water were added and the precipitate was collected by filtration. The orange solid was washed with copious amounts of water and dried in vacuo at room temperature to yield (3,11-diacetyl-2,7,7,12-tetramethyl-1,5,9,13-tetratriazacyclohexadeca-2,4,9,11-tetraenato)-nickel (II) in a yield of 78% based upon the starting complex. The product was deacetylated by the procedure described in the aforementioned Riley et al paper in Inorganic Synthesis 18, 36 (1978) to produce (2,7,7,12-tetramethyl-1,5,9,13-tetraazacyclohexadeca-2,4,9,11-tetraenato)nickel (II). Next, benzoyl groups were added by dissolving 6.7 g. of the deacetylated compound in 300 ml of ether, then adding 5.8 ml. (0.4 mole) of triethylamine, followed by dropwise addition of a mixture of 4.7 ml. (0.4 mole) of benzoyl chloride and 100 ml. of ether to the rapidly stirred solution. An orange precipitate resulted and this precipitate was filtered, washed with water and dried and the resultant solid taken up in a small amount of chloroform and passed through a column of alumina. The orange band was collected, the solvent evaporated and ethanol added to cause the oil to solidify, giving 8 g. of (3,11-dibenzoyl-2,7,7,12-tetramethyl-1,5,9,13-tetraazacyclohexadeca-2,4,9,11-tetraenato) nickel(II). (A yield of 73% based upon the deacetylated starting material.)

The carbonyl groups of this compound were methylated in the manner described in Schammel et al, Inorg. Chem., 19, 3159 (1980) to produce (2,7,7,12-tetramethyl-3,11-bis($\alpha$-methoxybenzylidine)-1,5,9,13-tetraazacyclohexadeca-1,4,9,12-tetraene)nickel(II), the compound of Formula VI in which $R_1$ is hydrogen, $R_2$ is methyl and $R_3$ is phenyl.

Next, the methoxyl groups of the product were replaced by methylamino groups in the manner described in the aforementioned Schammel paper and also described above, thereby producing the corresponding compound of Formula VII in which $R'$ is hydrogen and $R''$ is methyl, namely (2,7,7,12-tetramethyl-3,11-bis($\alpha$-methylaminobenzylidine)-1,5,9,13-tetraazacyclohexadeca-1,4,9,12-tetraene)nickel(II) hexafluorophosphate. This compound was then reacted with acetonitrile and sodium methoxide in methanol and then with the appropriate dibromide to introduce an m-xylene bridge R, as described in Busch et al, J.A.C.S. 103, 1472 (1981), thereby producing the final product, compound 194.

METHOD U

Example IV above was repeated except that stearoyl chloride was substituted for benzoyl chloride, thereby producing a compound analogous to the compound of Formula XV but having n-heptadecyl groups in place of the phenyl groups. 4 g. (3.5 mmole) of the resultant compound was dissolved in 100 ml. of acetonitrile and slowly dripped into a solution of 3.0 g. (35 mmole) of piperazine in 100 ml. of methanol. The resultant solution was concentrated to an oil on a rotary evaporator, ethanol was added and the solution was placed in a freezer overnight. The solution was then filtered to remove an oily precipitate and the filtrate returned to the freezer. Yellow microcrystals precipitated and were collected, washed with a small amount of ethanol, and air dried to produce 0.85 g. of product (19.4% based upon the heptadecyl compound). Alternatively, the product could be isolated by removing the solvent from the reaction mixture on a rotary evaporator, adding ethanol to the residue and very slowly evaporating the solvent without heat. 1 g. (0.79 mmole) of the yellow product was dissolved in 125 ml. of acetonitrile and 0.20 g. (0.87 mmole) of 3,6-bis(chloromethyl)durene was dissolved separately in 125 ml. of acetonitrile. The two solutions were dripped simultaneously into a reservoir of 100 ml. of refluxing acetonitrile and the resulting solution was gently refluxed overnight. Heating was discontinued, 0.5 ml. (3.6 mmole) of triethylamine was added and the solution was concentrated to 10 ml. on a rotary evaporator. The liquid residue was applied to an alumina and eluted with acetonitrile, the fastest moving yellow band being collected and then concentrated to an oil on a rotary evaporator. Ethanol was added to yield an orange powder which was recrystallized from acetonitrile/ethanol to yield orange plate-like crystals of the final product, 2,17-di(n-heptadecyl)-9,10,19,25,33,34-hexamethyl-3,6,13,16,20,24,27,31-octaazapentacyclo[16.7.7.2$^{8,11}$,2$^{3,6}$,2$^{13,16}$]octatriaconta-1,8,10,17,19,24,26,31,33-nonaene-$\kappa^4$N)nickel(II)] hexafluorophosphate.

METHOD V

This is essentially a variant of Method U above. To produce a octamethylene group $R_3$, sebacoyl chloride was substituted for stearoyl and the intermediate piperazine product was isolated by reducing the reaction mixture to dryness and slurrying the residue twice with ethanol and once with water to remove the excess piperazine. The remaining solid was filtered, air-dried and used for the subsequent bridging reaction to insert the bis(piperazino) bridge. The second reaction was carried out exactly as in Method U. The structure of the product (compound 198) was confirmed by a complete X-ray structure determination.

TABLE 7

| Cmpd. No. | Synthetic Method | Analysis (Calculated) | | | | Analysis (Found) | | | | Formula |
|---|---|---|---|---|---|---|---|---|---|---|
| | | % C | % H | % N | % M | % C | % H | % N | % M | |
| 1(c) | A | 36.97 | 5.13 | 11.25 | 7.86 | 36.84 | 5.21 | 11.14 | 7.98 | $[NiC_{23}H_{38}N_6](PF_6)_2$ |
| 2(c) | D | 38.08 | 5.24 | 12.43 | 7.47 | 37.99 | 5.13 | 12.34 | 7.48 | $[CoC_{25}H_{41}N_7](PF_6)_2$ |
| 3(c) | E | 44.23 | 6.10 | 14.23 | 8.38 | 44.03 | 6.20 | 14.31 | 8.25 | $[FeC_{23}H_{38}N_6Cl]PF_6$ |
| 4 | B | 36.04 | 4.95 | 11.46 | — | 36.09 | 5.18 | 11.41 | — | $[NiC_{22}H_{36}N_6](PF_6)_2$ |
| 5 | E | 42.56 | 5.85 | 13.54 | 8.99 | 42.61 | 5.87 | 13.65 | 8.76 | $[FeC_{22}H_{36}N_6Cl]PF_6$ |
| 6 | A | 37.87 | 5.30 | 11.04 | 7.71 | 38.11 | 5.41 | 11.02 | 7.55 | $[NiC_{24}H_{40}N_6](PF_6)_2$ |
| 7 | D/Ex. X | 37.86 | 5.30 | 11.04 | — | 38.16 | 5.47 | 11.17 | — | $[CoC_{24}H_{40}N_6](PF_6)_2$ |
| 8 | E | 44.41 | 6.17 | 12.95 | 8.64 | 44.30 | 6.09 | 12.90 | 8.72 | $[FeC_{24}H_{40}N_6Cl]PF_6$ |
| 9 | A | 44.83 | 4.70 | 9.80 | 6.85 | 44.95 | 4.83 | 9.93 | 6.56 | $[NiC_{32}H_{40}N_6](PF_6)_2$ |
| 10 | D | 45.77 | 5.23 | 10.38 | 6.24 | 45.63 | 5.37 | 10.28 | 6.09 | $[CoC_{36}H_{49}N_7O](PF_6)_2$ |
| 11 | A | 46.12 | 5.01 | 9.49 | 6.63 | 46.07 | 5.20 | 9.60 | 6.47 | $[NiC_{26}H_{44}N_6](PF_6)_2$ |
| 12 | D | 46.11 | 5.01 | 9.50 | 6.68 | 46.11 | 5.19 | 9.63 | 6.45 | $[CoC_{34}H_{44}N_6](PF_6)_2$ |
| 13 | E | 52.83 | 5.47 | 10.87 | 7.22 | 52.60 | 5.74 | 10.68 | 7.32 | $[FeC_{34}H_{44}N_6Cl]PF_6$ |
| 14 | G | 42.66 | 6.32 | 12.44 | 9.41 | 42.62 | 6.81 | 12.15 | 8.98 | $[CuC_{24}H_{40}N_6Cl]PF_6$ |
| 15 | A | 41.15 | 5.92 | 10.28 | — | 41.14 | 6.14 | 10.36 | — | $[NiC_{28}H_{48}N_6](PF_6)_2$ |
| 16 | B | 36.97 | 5.13 | 11.25 | — | 37.35 | 5.34 | 11.46 | — | $[NiC_{23}H_{38}N_6](PF_6)_2$ |
| 17 | D | 36.96 | 5.12 | 11.24 | 7.88 | 36.79 | 5.13 | 11.21 | 7.62 | $[CoC_{23}H_{38}N_6](PF_6)_2$ |
| 18 | E | 51.25 | 7.11 | 15.59 | — | 51.27 | 7.13 | 15.65 | — | $[FeC_{23}H_{38}N_6Cl]Cl$ |
| 19 | N | 40.78 | 5.36 | 11.10 | — | 40.82 | 5.45 | 11.10 | — | $[FeC_{29}H_{43}N_7O](PF_6)_2$ |
| 20 | C/Ex. V | 38.73 | 5.46 | 10.84 | — | 38.51 | 5.71 | 10.74 | — | $[NiC_{25}H_{42}N_6](PF_6)_2$ |
| 21 | D | 38.72 | 5.46 | 10.84 | 7.60 | 38.67 | 5.66 | 10.64 | 7.49 | $[CoC_{25}H_{42}N_6](PF_6)_2$ |
| 22 | E | 45.28 | 6.34 | 12.68 | 8.45 | 45.56 | 6.51 | 12.90 | 8.22 | $[FeC_{25}H_{42}N_6Cl]PF_6$ |
| 23 | H | 43.43 | 5.67 | 15.01 | — | 43.39 | 5.70 | 14.96 | — | $[CoC_{27}H_{42}N_8S_2]PF_6$ |
| 24 | B | 45.49 | 4.86 | 9.64 | — | 45.79 | 5.06 | 9.59 | — | $[NiC_{33}H_{42}N_6](PF_6)_2$ |
| 25 | D | 45.48 | 4.86 | 9.64 | 6.76 | 45.20 | 5.06 | 9.87 | 6.58 | $[CoC_{33}H_{42}N_6](PF_6)_2$ |
| 26 | C | 45.14 | 5.07 | 9.32 | — | 45.14 | 5.07 | 9.27 | — | $[NiC_{35}H_{46}N_6](PF_6)_2$ |
| 27 | D | 44.77 | 5.00 | 9.29 | 6.27 | 44.78 | 5.56 | 8.92 | 6.04 | $[CoC_{35}H_{46}N_6](PF_6)_2$ |
| 28 | E | 53.41 | 5.89 | 10.68 | 7.10 | 53.36 | 5.89 | 10.78 | 7.33 | $[FeC_{35}H_{46}N_6Cl]PF_6$ |
| 29 | B | 41.90 | 6.06 | 10.11 | — | 42.28 | 6.21 | 10.18 | — | $[NiC_{29}H_{50}N_6](PF_6)_2$ |
| 30 | D | 43.14 | 6.49 | 10.67 | 6.41 | 43.44 | 6.50 | 10.96 | 6.45 | $[CoC_{33}H_{59}N_7O](PF_6)_2$ |
| 31 | A/Ex. I | 38.68 | 5.74 | 10.41 | — | 38.64 | 5.72 | 10.53 | — | $[NiC_{24}H_{40}N_6](PF_6)_2$ (contains one $C_2H_5OH$ |
| 32 | D | 37.86 | 5.30 | 11.04 | — | 37.77 | 5.32 | 11.48 | — | $[CoC_{24}H_{40}N_6](PF_6)_2$ |
| 33 | E | 44.42 | 6.21 | 12.95 | 8.61 | 44.38 | 5.93 | 12.66 | 8.89 | $[FeC_{24}H_{40}N_6Cl]PF_6$ |
| 34 | N | 41.48 | 5.50 | 10.92 | — | 41.59 | 5.66 | 10.87 | — | $[FeC_{30}H_{45}N_7O](PF_6)_2$ |
| 35 | G | 38.45 | 5.71 | 10.35 | 7.82 | 38.38 | 5.89 | 10.40 | 7.61 | $[CuC_{26}H_{46}N_6O](PF_6)_2$ |
| 36 | A | 39.56 | 5.62 | 10.65 | — | 39.46 | 5.53 | 10.60 | — | $[NiC_{26}H_{44}N_6](PF_6)_2$ |
| 37 | R | 53.08 | 7.88 | 14.29 | — | 53.10 | 8.14 | 14.38 | — | $[NiC_{26}H_{44}N_6]Cl_2$ |
| 38 | D | 39.55 | 5.62 | 10.64 | 7.46 | 39.53 | 5.70 | 10.76 | 7.43 | $[CoC_{26}H_{44}N_6](PF_6)_2$ |
| 39 | I/Ex. XI | 41.34 | 5.78 | 12.86 | — | 41.44 | 6.08 | 12.91 | — | $[CoC_{30}H_{50}N_8](PF_6)_2$ |
| 40 | I | 40.61 | 5.64 | 13.07 | — | 40.87 | 5.83 | 13.06 | — | $[CoC_{29}H_{48}N_8](PF_6)_2$ |
| 41 | I | 42.86 | 5.69 | 11.29 | — | 42.99 | 5.60 | 11.40 | — | $[CoC_{31}H_{49}N_7](PF_6)_2$ |
| 42 | I | 46.15 | 6.31 | 13.95 | — | 45.90 | 6.44 | 13.64 | — | $[CoC_{27}H_{44}N_7S]PF_6$ |
| 43 | H | 44.20 | 5.82 | 14.71 | 7.75 | 44.35 | 5.90 | 14.80 | 7.61 | $[CoC_{28}H_{44}N_8S_2]PF_6$ |
| 44 | H | 46.16 | 6.09 | 15.38 | — | 45.88 | 6.01 | 15.02 | — | $[CoC_{28}H_{44}N_8O_2]PF_6$ |
| 45 | H | 42.86 | 6.09 | 23.07 | — | 42.51 | 6.39 | 22.50 | — | $[CoC_{26}H_{44}N_{12}]PF_6$ |
| 46 | E | 46.13 | 6.55 | 12.41 | — | 45.93 | 6.77 | 12.24 | — | $[FeC_{26}H_{44}N_6Cl]PF_6$ |
| 47 | N | 41.20 | 5.59 | 12.08 | — | 40.97 | 5.66 | 12.25 | — | $[FeC_{29}H_{47}N_7O](PF_6)_2$ |
| 48 | N | 43.01 | 5.53 | 10.97 | 6.25 | 41.91 | 5.73 | 11.29 | 5.90 | $[FeC_{32}H_{49}N_7O](PF_6)_2$ |
| 49 | N | 41.53 | 5.62 | 12.50 | 6.23 | 41.80 | 5.68 | 12.98 | 5.78 | $[FeC_{31}H_{50}N_8O](PF_6)_2$ |
| 50 | J/Ex. XV | 37.99 | 5.40 | 10.23 | 6.80 | 37.99 | 5.11 | 10.24 | 7.03 | $[FeC_{26}H_{44}N_6Cl](PF_6)_2$ |
| 51 | L | 45.80 | 6.83 | 11.87 | — | 45.55 | 6.63 | 12.12 | — | $[MnC_{26}H_{44}N_6Cl]PF_6$ |
| 52 | K/Ex. XIX | 38.00 | 5.36 | 10.23 | 6.69 | 38.21 | 5.51 | 10.21 | 6.50 | $[MnC_{26}H_{44}N_6Cl](PF_6)_2$ |
| 53 | G/Ex. XVII | 39.32 | 5.58 | 10.58 | 8.00 | 39.42 | 5.49 | 10.49 | 7.95 | $[CuC_{26}H_{44}N_6](PF_6)_2$ |
| 54 | A/Ex. IV | 46.12 | 5.01 | 9.49 | 6.63 | 45.97 | 5.14 | 9.36 | 6.37 | $[NiC_{34}H_{44}N_6](PF_6)_2$ |
| 55 | D | 46.11 | 5.01 | 9.49 | 6.65 | 45.83 | 5.20 | 9.26 | 6.52 | $[CoC_{34}H_{44}N_6](PF_6)_2$ |
| 56 | A | 47.34 | 5.30 | 9.20 | — | 47.38 | 5.35 | 9.11 | — | $[NiC_{36}H_{48}N_6](PF_6)_2$ |
| 57 | D | 47.33 | 5.30 | 9.20 | 6.45 | 47.29 | 5.40 | 9.01 | 6.28 | $[CoC_{36}H_{48}N_6](PF_6)_2$ |
| 58 | E | 53.00 | 6.43 | 9.87 | 6.56 | 52.70 | 6.21 | 10.10 | 6.71 | $[FeC_{36}H_{48}N_6Cl]PF_6$ |
| 59 | E | 60.48 | 5.92 | 8.82 | 5.86 | 60.56 | 6.02 | 8.84 | 6.12 | $[FeC_{48}H_{56}N_6Cl]PF_6$ |
| 60 | A | 42.62 | 6.20 | 9.94 | 6.94 | 42.79 | 6.40 | 10.00 | 6.73 | $[NiC_{30}H_{52}N_6](PF_6)_2$ |
| 61 | D | 42.61 | 6.20 | 9.94 | 6.97 | 42.67 | 6.34 | 9.98 | 6.84 | $[CoC_{30}H_{52}N_6](PF_6)_2$ |
| 62 | A | 46.52 | 6.94 | 9.04 | 6.25 | 46.60 | 7.09 | 9.15 | 6.17 | $[NiC_{36}H_{60}N_6](PF_6)_2$ |
| 63 | A | 38.92 | 5.40 | 12.22 | — | 38.73 | 5.58 | 12.00 | — | $[NiC_{26}H_{43}N_7](PF_6)_2$ |
| 64 | D | 38.91 | 5.40 | 12.22 | 7.34 | 39.00 | 5.72 | 11.94 | 7.40 | $[CoC_{26}H_{43}N_7](PF_6)_2$ |
| 65(c) | P | 41.25 | 5.69 | 10.31 | — | 41.23 | 6.19 | 10.41 | — | $[NiC_{28}H_{46}N_6](PF_6)_2$ |
| 66 | P | 42.00 | 5.83 | 10.13 | — | 41.91 | 5.86 | 10.09 | — | $[NiC_{29}H_{48}N_6](PF_6)_2$ |
| 67 | P | 42.72 | 5.98 | 9.96 | — | 42.99 | 6.00 | 9.91 | — | $[NiC_{30}H_{50}N_6](PF_6)_2$ |
| 68 | B | 39.24 | 5.51 | 11.44 | — | 38.97 | 5.62 | 11.50 | — | $[NiC_{26}H_{43.5}N_{6.5}](PF_6)_2$ |
| 69 | D | 40.62 | 5.64 | 13.07 | 6.87 | 40.61 | 5.79 | 13.01 | 7.25 | $[CoC_{29}H_{48}N_8](PF_6)_2$ |
| 70 | C | 40.37 | 5.77 | 10.46 | — | 40.07 | 6.10 | 10.52 | — | $[NiC_{27}H_{46}N_6](PF_6)_2$ |

TABLE 7-continued

| Cmpd. No. | Synthetic Method | Analysis (Calculated) | | | | Analysis (Found) | | | | Formula |
|---|---|---|---|---|---|---|---|---|---|---|
| | | % C | % H | % N | % M | % C | % H | % N | % M | |
| 71 | D | 40.36 | 5.77 | 10.46 | 7.33 | 40.53 | 5.96 | 10.60 | 7.11 | $[CoC_{27}H_{46}N_6](PF_6)_2$ |
| 72 | H | 44.90 | 6.00 | 14.48 | — | 44.50 | 5.92 | 13.50 | — | $[CoC_{29}H_{46}N_8S_2]PF_6$ |
| 73 | B | 46.74 | 5.16 | 9.34 | 6.53 | 46.78 | 5.38 | 9.41 | 6.27 | $[NiC_{35}H_{46}N_6](PF_6)_2$ |
| 74 | D | 46.73 | 5.15 | 9.34 | 6.55 | 46.54 | 5.19 | 9.25 | 6.55 | $[CoC_{35}H_{46}N_6](PF_6)_2$ |
| 75 | C | 47.92 | 5.43 | 9.06 | — | 47.75 | 5.58 | 8.91 | — | $[NiC_{37}H_{50}N_6](PF_6)_2$ |
| 76 | D | 47.90 | 5.43 | 9.06 | 6.35 | 47.51 | 5.53 | 9.23 | 6.04 | $[CoC_{37}H_{50}N_6](PF_6)_2$ |
| 77 | B | 43.68 | 6.36 | 10.35 | — | 43.73 | 6.50 | 10.17 | — | $[NiC_{31}H_{54}N_6](PF_6)_2$ |
| 78 | D | 43.31 | 6.33 | 9.78 | 6.85 | 43.53 | 6.42 | 10.03 | 6.54 | $[CoC_{31}H_{54}N_6](PF_6)_2$ |
| 79 | P/Ex. VII | 43.42 | 6.11 | 9.80 | 6.84 | 43.62 | 6.24 | 9.86 | 6.62 | $[NiC_{31}H_{52}N_6](PF_6)_2$ |
| 80 | B | 40.04 | 5.66 | 11.24 | — | 40.31 | 5.97 | 11.05 | — | $[NiC_{26}H_{44}N_6](PF_6)_2$ |
| 81 | D | 39.55 | 5.62 | 10.64 | 7.46 | 39.81 | 5.69 | 10.59 | 7.56 | $[CoC_{26}H_{44}N_6](PF_6)_2$ |
| 82 | C | 41.15 | 5.92 | 10.28 | — | 41.08 | 5.98 | 10.16 | — | $[NiC_{28}H_{48}N_6](PF_6)_2$ |
| 83 | D | 41.00 | 6.17 | 9.89 | 6.94 | 40.69 | 6.11 | 9.87 | 6.94 | $[CoC_{29}H_{52}N_6](PF_6)_2$ |
| 84 | B | 47.34 | 5.30 | 9.20 | — | 47.12 | 5.45 | 9.08 | — | $[NiC_{36}H_{48}N_6](PF_6)_2$ |
| 85 | D | 48.47 | 5.57 | 8.92 | 6.26 | 48.36 | 5.47 | 8.73 | 6.07 | $[CoC_{38}H_{52}N_6](PF_6)_2$ |
| 86 | B | 39.97 | 4.64 | 10.76 | — | 40.29 | 4.84 | 10.84 | — | $[NiC_{26}H_{36}N_6](PF_6)_2$ |
| 87 | D | 40.89 | 4.78 | 11.92 | 7.16 | 41.17 | 5.00 | 11.96 | 7.24 | $[CoC_{28}H_{39}N_7](PF_6)_2$ |
| 88 | F/Ex. XIII | 46.69 | 5.43 | 12.56 | — | 46.53 | 5.48 | 12.57 | — | $[FeC_{26}H_{36}N_6Cl]PF_6$ |
| 89 | N | 43.41 | 4.67 | 11.07 | 6.31 | 42.83 | 4.93 | 10.72 | 5.80 | $[FeC_{32}H_{41}N_7O](PF_6)_2$ |
| 90 | N | 41.91 | 4.76 | 12.61 | 6.29 | 40.99 | 4.85 | 12.64 | 5.61 | $[FeC_{31}H_{42}N_8O](PF_6)_2$ |
| 91 | N | 41.21 | 4.61 | 12.81 | — | 41.33 | 4.84 | 12.36 | — | $[FeC_{30}H_{40}N_8O](PF_6)_2$ |
| 92 | N | 42.68 | 4.70 | 12.44 | 6.20 | 42.57 | 4.70 | 12.57 | 6.14 | $[FeC_{32}H_{42}N_8O](PF_6)_2$ |
| 93 | C/Ex. III | 41.55 | 4.98 | 10.38 | — | 41.48 | 5.02 | 10.40 | — | $[NiC_{28}H_{40}N_6](PF_6)_2$ |
| 94 | D | 40.64 | 5.11 | 10.15 | 7.12 | 40.97 | 5.40 | 9.91 | 6.93 | $[CoC_{28}H_{42}N_6O](PF_6)_2$ |
| 95 | F/Ex. XIV | 48.26 | 5.78 | 12.06 | — | 48.22 | 5.93 | 12.00 | — | $[FeC_{28}H_{40}N_6Cl]PF_6$ |
| 96 | N | 43.24 | 5.06 | 112.23 | — | 43.76 | 5.01 | 12.92 | — | $[FeC_{33}H_{46}N_8O](PF_6)_2$ |
| 97 | N | 42.53 | 4.95 | 11.20 | — | 43.20 | 5.33 | 12.24 | — | $[FeC_{31}H_{43}N_7O](PF_6)_2$ |
| 98 | N | 42.59 | 4.91 | 12.42 | 6.19 | 41.37 | 5.08 | 12.37 | 5.90 | $[FeC_{32}H_{44}N_8O](PF_6)_2$ |
| 99 | N | 43.98 | 4.99 | 12.07 | 6.01 | 43.51 | 5.27 | 12.70 | 5.89 | $[FeC_{34}H_{46}N_8O](PF_6)_2$ |
| 100 | J | 39.95 | 4.79 | 9.98 | 6.63 | 39.99 | 4.91 | 10.03 | 6.95 | $[FeC_{28}H_{40}N_6Cl](PF_6)_2$ |
| 101 | L | 41.75 | 5.01 | 10.43 | 6.82 | 41.96 | 5.32 | 10.67 | 6.63 | $[MnC_{28}H_{40}N_6](PF_6)_2$ |
| 102 | K | 39.99 | 4.80 | 9.99 | 6.52 | 39.99 | 4.97 | 10.12 | 6.26 | $[MnC_{28}H_{40}N_6Cl](PF_6)_2$ |
| 103 | G/Ex. XVIII | 42.13 | 5.07 | 11.47 | 7.43 | 42.10 | 5.10 | 11.22 | 7.37 | $[CuC_{30}H_{43}N_7](PF_6)_2$ |
| 104 | C | 45.71 | 5.87 | 9.41 | — | 45.05 | 5.97 | 9.22 | — | $[NiC_{34}H_{52}N_6](PF_6)_2$ |
| 105 | C | 36.71 | 4.62 | 14.27 | 7.48 | 36.79 | 4.85 | 14.21 | 7.29 | $[NiC_{32}H_{48}N_8](PF_6)_2$ |
| 106 | C | 49.97 | 5.03 | 8.74 | — | 49.63 | 5.29 | 8.71 | — | $[NiC_{40}H_{48}N_6](PF_6)_2$ |
| 107 | E | 50.46 | 5.14 | 9.81 | 5.59 | 50.44 | 5.16 | 9.39 | 5.72 | $[FeC_{42}H_{51}N_7](PF_6)_2$ |
| 108 | A | 40.60 | 4.50 | 11.40 | — | 40.56 | 4.90 | 11.40 | — | $[NiC_{26}H_{34}N_6](PF_6)_2$ |
| 109 | B | 48.07 | 6.37 | 8.85 | 6.19 | 48.14 | 6.56 | 8.91 | 6.32 | $[NiC_{38}H_{58}N_6](PF_6)_2$ |
| 110 | C | 49.14 | 6.55 | 8.60 | — | 49.40 | 6.88 | 8.59 | — | $[NiC_{40}H_{62}N_6](PF_6)_2$ |
| 111 | E | 53.96 | 7.31 | 9.44 | — | 53.81 | 7.38 | 9.69 | — | $[FeC_{40}H_{62}N_6Cl](PF_6) \cdot 1.5H_2O$ |
| 112 | B | 47.76 | 4.45 | 9.28 | 6.48 | 47.65 | 4.59 | 9.28 | 6.29 | $[NiC_{36}H_{40}N_6](PF_6)_2$ |
| 113 | D | 48.21 | 4.58 | 10.36 | 6.22 | 48.24 | 4.60 | 10.26 | 6.18 | $[CoC_{38}H_{43}N_7](PF_6)_2$ |
| 114 | C | 48.90 | 4.75 | 9.00 | — | 48.58 | 4.86 | 9.21 | — | $[NiC_{38}H_{44}N_6](PF_6)_2$ |
| 115 | D | 48.88 | 4.75 | 9.00 | 6.31 | 48.59 | 4.80 | 8.99 | 6.28 | $[CoC_{38}H_{44}N_6](PF_6)_2$ |
| 116 | E | 49.52 | 5.10 | 9.82 | 5.59 | 49.27 | 4.95 | 9.62 | 5.60 | $[FeC_{40}H_{47}N_2](PF_6)_2 \cdot 0.5C_2H_5OH$ |
| 117 | C | 55.32 | 4.83 | 7.74 | 5.41 | 55.47 | 4.89 | 7.58 | 5.37 | $[NiC_{50}H_{52}N_6](PF_6)_2$ |
| 118 | E | 54.41 | 5.43 | 8.16 | 4.65 | 54.28 | 5.17 | 8.26 | 4.54 | $[FeC_{52}H_{55}N_7](PF_6)_2 \cdot 2.5CH_3OH$ |
| 119 | E | 54.52 | 5.49 | 9.54 | 6.34 | 53.81 | 5.58 | 9.38 | 6.19 | $[FeC_{40}H_{48}N_6ClO_2]PF_6$ |
| 120 | E | 50.76 | 4.99 | 9.11 | — | 50.20 | 5.14 | 8.95 | — | $[FeC_{38}H_{42}N_6Cl_3]PF_6 \cdot CH_3OH$ |
| 121 | E | 49.64 | 4.88 | 8.91 | 8.28 | 49.95 | 5.06 | 9.02 | 7.82 | $[FeC_{38}H_{42}N_6ClF_2]PF_6$ |
| 122 | C | 47.88 | 4.97 | 7.98 | — | 47.90 | 5.28 | 7.81 | — | $[NiC_{42}H_{52}N_6O_4](PF_6)_2$ |
| 123 | P | 44.90 | 5.76 | 9.24 | — | 45.31 | 5.87 | 9.60 | — | $[NiC_{32}H_{46}N_6](PF_6)_2$ |
| 124 | P | 43.84 | 5.22 | 9.89 | — | 44.19 | 4.78 | 9.99 | — | $[NiC_{31}H_{44}N_6](PF_6)_2$ |
| 125 | B | 39.97 | 4.64 | 10.76 | — | 40.15 | 4.50 | 10.96 | — | $[NiC_{26}H_{36}N_6](PF_6)_2$ |
| 126 | F | 46.69 | 5.43 | 12.56 | — | 46.59 | 5.77 | 11.93 | — | $[FeC_{26}H_{36}N_6Cl]PF_6$ |
| 127 | N | 41.10 | 4.64 | 11.57 | — | 40.05 | 4.97 | 11.01 | — | $[FeC_{29}H_{39}N_7O](PF_6)_2$ |
| 128 | N | 43.41 | 4.67 | 11.07 | — | 43.07 | 4.76 | 11.09 | — | $[FeC_{32}H_{41}N_7O](PF_6)_2$ |
| 129 | N | 41.91 | 4.76 | 12.61 | — | 41.50 | 5.12 | 12.57 | — | $[FeC_{31}H_{42}N_8O](PF_6)_2$ |
| 130 | C | 41.56 | 4.98 | 10.38 | — | 41.90 | 5.37 | 10.18 | — | $[NiC_{28}H_{40}N_6](PF_6)_2$ |
| 131 | B/Ex. II | 48.02 | 5.32 | 9.08 | — | 48.36 | 5.36 | 9.14 | — | $[NiC_{37}H_{48}N_6](PF_6)_2$ |
| 132 | F | 63.16 | 6.88 | 11.94 | 7.94 | 62.90 | 6.87 | 12.16 | 7.64 | $[FeC_3H_{48}N_6Cl]Cl$ |
| 133 | N | 49.77 | 5.41 | 9.23 | 5.26 | 49.72 | 5.43 | 9.65 | 5.11 | $[FeC_{43}H_{53}N_7O](PF_6)_2$ |
| 134 | N | 48.50 | 5.49 | 10.52 | 5.25 | 48.61 | 5.48 | 10.59 | 5.14 | $[FeC_{42}H_{54}N_8O](PF_6)_2$ |
| 135 | B | 37.28 | 4.97 | 10.44 | — | 37.39 | 5.04 | 10.37 | — | $[NiC_{25}H_{40}N_6O_2](PF_6)_2$ |
| 136 | B | 39.18 | 5.32 | 10.57 | — | 39.64 | 5.34 | 10.69 | — | $[NiC_{26}H_{42}N_6](PF_6)_2$ |
| 137 | C | 47.92 | 5.40 | 9.07 | — | 47.89 | 5.40 | 9.06 | — | $[NiC_{37}H_{50}N_6](PF_6)_2$ |
| 138 | C | 41.50 | 5.04 | 10.01 | 6.99 | 41.28 | 5.19 | 9.98 | 6.73 | $[NiC_{29}H_{42}N_6O](PF_6)_2$ |
| 139 | B | 32.98 | 5.03 | 10.49 | 7.33 | 33.13 | 5.01 | 10.55 | 7.43 | $[NiC_{22}H_{36}N_6S](PF_6)_2$ |
| 140 | B | 34.65 | 5.06 | 10.54 | 7.36 | 34.72 | 5.23 | 10.53 | 7.22 | $[NiC_{23}H_{38}N_6S](PF_6)_2$ |
| 141 | C | 41.54 | 4.88 | 9.69 | — | 41.05 | 4.51 | 9.62 | — | $[NiC_{30}H_{44}N_6O_2](PF_6)_2$ |
| 142 | C | 38.19 | 5.00 | 12.47 | 7.47 | 38.38 | 4.98 | 12.22 | 7.20 | $[NiC_{27}H_{41}N_7](PF_6)_2$ |
| 143 | A | 37.13 | 5.32 | 12.63 | — | 37.29 | 5.45 | 12.46 | — | $[NiC_{24}H_{41}N_7](PF_6)_2$ |
| 144 | A | 37.99 | 5.48 | 12.41 | — | 38.09 | 5.65 | 12.20 | — | $[NiC_{25}H_{43}N_7](PF_6)_2$ |
| 145 | D | 37.98 | 5.48 | 12.40 | — | 37.50 | 5.40 | 12.65 | — | $[CoC_{25}H_{43}N_7](PF_6)_2$ |
| 146(c) | M | 38.73 | 5.46 | 10.84 | — | 38.68 | 5.63 | 10.93 | — | $[NiC_{25}H_{42}N_6](PF_6)_2$ |

TABLE 7-continued

| Cmpd. No. | Synthetic Method | Analysis (Calculated) % C | % H | % N | % M | Analysis (Found) % C | % H | % N | % M | Formula |
|---|---|---|---|---|---|---|---|---|---|---|
| 147(c) | D | 39.71 | 5.55 | 12.01 | 7.22 | 39.81 | 5.65 | 12.07 | 7.10 | $[CoC_{27}H_{45}N_7](PF_6)_2$ |
| 148(c) | M | 38.92 | 5.40 | 12.22 | — | 39.18 | 5.53 | 12.20 | — | $[NiC_{24}H_{40}N_6](PF_6)_2$ |
| 149(c) | M | 40.50 | 5.70 | 11.18 | — | 40.49 | 5.93 | 11.86 | — | $[NiC_{26}H_{44}N_6](PF_6)_2$ |
| 150(c) | D | 40.49 | 5.70 | 11.80 | 7.09 | 40.26 | 5.69 | 11.47 | 7.18 | $[CoC_{28}H_{47}N_7](PF_6)_2$ |
| 151 | M | 38.71 | 5.46 | 10.84 | — | 38.79 | 5.50 | 10.82 | — | $[NiC_{25}H_{42}N_6](PF_6)_2$ |
| 152 | D | 40.01 | 5.60 | 10.37 | 7.27 | 39.81 | 5.34 | 10.77 | 7.24 | $[CoC_{25}H_{42}N_6](PF_6)_2$ |
| 153 | E | 45.29 | 6.39 | 12.68 | 8.42 | 45.14 | 6.12 | 12.69 | 8.28 | $[FeC_{25}H_{42}N_6Cl]PF_6$ |
| 154 | M | 41.90 | 6.06 | 10.11 | — | 41.86 | 6.05 | 10.16 | — | $[NiC_{29}H_{50}N_6](PF_6)_2$ |
| 155 | D | 42.67 | 6.12 | 11.24 | 6.75 | 42.58 | 5.85 | 11.16 | 6.64 | $[CoC_{31}H_{53}N_7](PF_6)_2$ |
| 156 | M | 47.92 | 5.43 | 9.06 | — | 47.71 | 5.56 | 9.10 | — | $[NiC_{37}H_{50}N_6](PF_6)_2$ |
| 157 | M | 40.37 | 5.77 | 10.46 | — | 40.21 | 5.82 | 10.37 | — | $[NiC_{27}H_{46}N_6](PF_6)_2$ |
| 158 | D | 39.47 | 5.89 | 10.23 | 7.17 | 39.40 | 6.04 | 9.97 | 6.87 | $[CoC_{27}H_{48}N_6O](PF_6)_2$ |
| 159 | E | 46.93 | 6.71 | 12.16 | 8.08 | 47.02 | 6.79 | 12.08 | 8.23 | $[FeC_{27}H_{48}N_6Cl]PF_6$ |
| 160 | M | 39.56 | 5.62 | 10.65 | — | 39.44 | 5.70 | 10.57 | — | $[NiC_{26}H_{44}N_6](PF_6)_2$ |
| 161 | M | 41.15 | 5.92 | 10.28 | — | 41.08 | 5.98 | 10.19 | — | $[NiC_{28}H_{48}N_6](PF_6)_2$ |
| 162 | D | 41.96 | 5.99 | 11.42 | 6.86 | 42.09 | 6.04 | 11.45 | 6.80 | $[CoC_{30}H_{512}N_7](PF_6)_2$ |
| 163 | E | 47.70 | 6.86 | 11.92 | 7.92 | 46.50 | 6.90 | 11.52 | 8.15 | $[FeC_{28}H_{48}N_6Cl]PF_6$ |
| 164 | C | 36.78 | 4.68 | 9.69 | — | 36.60 | 5.00 | 9.64 | — | $[NiC_{31}H_{48}N_7](PF_6)_3$ |
| 165 | A | 37.44 | 4.91 | 9.55 | — | 37.30 | 4.83 | 9.53 | — | $[NiC_{32}H_{50}N_7](PF_6)_3$ |
| 166 | D | 37.44 | 4.91 | 9.55 | 5.74 | 34.40 | 4.86 | 9.68 | 5.61 | $[CoC_{32}H_{50}N_7](PF_6)_3$ |
| 167 | C | 39.03 | 4.43 | 9.37 | — | 39.11 | 4.59 | 9.43 | — | $[NiC_{34}H_{46}N_7](PF_6)_3$ |
| 168 | D | 42.96 | 5.46 | 11.31 | 6.80 | 42.94 | 5.46 | 11.31 | 6.73 | $[CoC_{31}H_{47}N_7](PF_6)_2$ |
| 169 | Ex. VI | — | — | — | — | — | — | — | — | — |
| 170 | Ex. VIII | — | — | — | — | — | — | — | — | — |
| 171 | Ex XII | 53.94 | 7.11 | 13.48 | 8.96 | 53.99 | 6.94 | 13.77 | 8.75 | $[FeC_{28}H_{44}N_6O_2]Cl_2$ |
| 172 | Ex. XVI | 62.31 | 6.78 | 11.78 | — | 61.65 | 7.11 | 11.59 | — | $[ZnC_{37}H_{46}N_6]Cl_2$ |
| 173 | Q | 43.96 | 5.94 | 11.39 | — | 43.78 | 5.85 | 11.53 | — | $[NiC_{34}H_{50}N_8](PF_6)_2$ .2CH$_3$OH |
| 174 | R | 56.84 | 7.30 | 15.60 | — | 56.74 | 7.30 | 15.57 | — | $[NiC_{34}H_{50}N_8]Cl.H_2O$ |
| 175 | D | 43.75 | 6.15 | 11.03 | 5.80 | 43.70 | 6.28 | 11.10 | 5.79 | $[CoC_{35}H_{54}N_8O](PF_6)_2$ .2CH$_3$OH |
| 176 | Q | 44.41 | 5.48 | 12.19 | — | 44.23 | 5.69 | 12.05 | — | $[NiC_{34}H_{50}N_8](PF_6)_2$ |
| 177 | D | 44.40 | 5.48 | 12.18 | 6.41 | 44.28 | 5.66 | 12.02 | 6.32 | $[CoC_{34}H_{50}N_8](PF_6)_2$ |
| 178 | Q | 46.78 | 5.99 | 11.49 | 6.02 | 46.67 | 6.10 | 11.37 | 6.03 | $[NiC_{38}H_{58}N_8](PF_6)_2$ |
| 179 | R | 53.34 | 8.13 | 13.10 | — | 53.03 | 8.01 | 12.84 | — | $[NiC_{38}H_{58}N_8]Cl_2$ .5.5H$_2$O |
| 180 | D | 46.77 | 5.99 | 11.48 | 6.04 | 46.60 | 6.28 | 11.22 | 5.88 | $[CoC_{38}H_{58}N_8](PF_6)_2$ |
| 181 | F | 51.27 | 6.91 | 12.59 | 6.27 | 51.17 | 6.97 | 12.18 | 6.55 | $[FeC_{38}H_{58}N_8Cl]PF_6$ .1.5H$_2$O |
| 182 | S | 52.19 | 6.92 | 12.81 | 6.39 | 52.44 | 7.57 | 12.55 | 6.04 | $[FeC_{38}H_{60}N_8O](PF_6)_2$ |
| 183 | G | 35.87 | 4.75 | 8.81 | 4.99 | 35.78 | 4.88 | 8.73 | 4.98 | $[CuC_{38}H_{58}N_8](PF_6)_2$ |
| 184 | Q | 52.42 | 5.91 | 9.88 | 5.18 | 52.67 | 6.21 | 10.12 | 5.26 | $[NiC_{48}H_{62}N_8](PF_6)_2$ 0.7C$_2$H$_5$OH |
| 185 | Q | 49.51 | 5.53 | 10.93 | — | 49.48 | 5.34 | 10.99 | — | $[NiC_{42}H_{59}N_8](PF_6)_2$ |
| 186 | R | 56.64 | 7.24 | 12.58 | — | 56.85 | 7.16 | 12.17 | — | $[NiC_{42}H_{54}N_8]Cl_2$ .5H$_2$O |
| 187 | D | 49.10 | 5.56 | 10.65 | 5.60 | 48.97 | 5.38 | 10.45 | 5.96 | $[CoC_{43}H_{58}N_8O](PF_6)_2$ |
| 188 | F | 52.48 | 6.29 | 11.66 | 5.81 | 52.28 | 6.12 | 11.48 | 5.73 | $[FeC_{42}H_{54}N_8Cl]PF_6$ .3H$_2$O |
| 189 | Q | 54.62 | 5.31 | 10.02 | 4.91 | 54.25 | 5.67 | 9.98 | 4.94 | $[NiC_{56}H_{58}N_8](PF_6)_2$ .0.5CH$_3$CN.0.5C$_2$H$_5$OH |
| 190 | Q | 41.83 | 5.53 | 13.31 | — | 41.92 | 5.67 | 13.16 | — | $[NiC_{33}H_{52}N_9](PF_6)_2$ .1.5H$_2$O |
| 191 | D | 38.33 | 4.91 | 12.19 | 5.70 | 38.67 | 5.11 | 11.81 | 5.59 | $[CoC_{33}H_{52}N_9](PF_6)_2$ .1.4HBr |
| 192 | Q | 43.58 | 5.32 | 10.39 | — | 43.48 | 5.51 | 10.34 | — | $[NiC_{44}H_{64}N_9](PF_6)_3$ |
| 193 | Q | 45.88 | 4.81 | 10.03 | — | 45.76 | 5.01 | 10.03 | — | $[NiC_{40}H_{60}N_9](PF_6)_3$ |
| 194 | T | 49.97 | 5.03 | 8.74 | — | 50.21 | 5.36 | 8.65 | — | $[NiC_{40}H_{48}N_6](PF_6)_2$ |
| 195 | T + Ex. VIII | — | — | — | — | — | — | — | — | $[C_{40}H_{48}N_6](PF_6)_2$ |
| 196 | T + Ex. VIII + E | — | — | — | — | — | — | — | — | $[FeC_{40}H_{48}N_6](PF_6)_2$ |
| 197 | U | 59.20 | 8.61 | 8.24 | 4.06 | 59.27 | 8.47 | 8.19 | 4.04 | $[NiC_{70}H_{122}N_8](PF_6)_2$ ½ CH$_3$CN |
| 198 | V | — | — | — | — | — | — | — | — | $[NiC_{44}H_{68}N_8](PF_6)_2$ |
| 199 | C | — | — | — | — | — | — | — | — | $[NiC_{30}H_{52}N_6](PF_6)_2$ |
| 200 | D | 42.61 | 6.19 | 9.94 | 6.94 | 42.71 | 6.28 | 9.88 | 6.99 | $[CoC_{30}H_{52}N_6](PF_6)_2$ |

OXYGEN-COMPLEXING TESTS

A large number of the compounds listed in Table 2 above were subjected to standard thermodynamic tests (which will be familiar to those skilled in the art) to determine their oxygen affinity at various temperatures, together with the changes in enthalpy and entropy associated with the reaction for the complexing of the cationic metal complex with molecular oxygen. It should be noted that, in most cases, these tests were carried out in the presence of ligands capable of acting as the ligand Z in Formula XVIIA; thus, although the compound may be named in Table 2, and its substituents listed in Table 3, 4, 5 or 6, as a compound of Formula XVII, for the reasons described above in solution the compound will exist as a compound of Formula XVIIA with the ligand present in the solution entering the position Z so that the oxygen affinity being measured in in fact of the related salt of Formula XVIIA having the ligand available in solution as the ligand Z.

The results of the oxygen affinity tests are shown in Table 8 below, in which 1-Mim. indicates N-methylimidazole, An indicates acetonitrile, py indicates pyridine, Ace indicated acetone and 311APW indicates 3:1:1 acetone:pyridine:water.

TABLE 8

| Cmpd. No. | Solvent | $K_{O_2}$, torr$^{-1}$ | Degrees C. | $\Delta H$ Kcal/M | $\Delta S$ eu. |
|---|---|---|---|---|---|
| 2(c) | 1.5 M 1-Mim/An | $<10^{-4}$ | −40 | — | — |
| 7 | 1.5 M 1-Mim/An | 0.0020 ± 0.0002 | −40.1 | — | — |
| 10 | 1.5 M 1-Mim/An | 0.0018 ± 0.0001 | −19.3 | — | — |
|  |  | 0.0011 ± 0.0002 | −10.2 | — | — |
| 12 | 1.5 M 1-Mim/An | 0.005 | −40 | — | — |
| 17 | 1.5 M 1-Mim/An | 0.210 ± 0.003 | −30 | −15.2 ± 0.6 | −65 ± 2 |
|  |  | 0.0499 ± 0.0005 | −20 |  |  |
|  |  | 0.0252 ± 0.0003 | −12 |  |  |
|  |  | 0.0191 ± 0.0004 | −10.1 |  |  |
|  |  | 0.0066 ± 0.0002 | −0.6 |  |  |
| 21 | 1.5 M 1-Mim/An | 0.66 ± 0.02 | −20 | −16.2 ± 0.6 | −65 ± 2 |
|  |  | 0.215 ± 0.005 | −10.1 |  |  |
|  |  | 0.058 ± 0.003 | +1.0 |  |  |
|  |  | 0.0186 ± 0.005 | +20.0 |  |  |
|  |  | 0.0094 ± 0.0005 | +20.0 |  |  |
| 21 | 2.5 M 1-Mim/H$_2$O | 0.167 ± 0.003 | +4.8 | −16.7 ± 1.0 | −63 ± 3 |
|  |  | 0.112 ± 0.002 | +10 |  |  |
|  |  | 0.055 ± 0.002 | +15.3 |  |  |
|  |  | 0.0265 ± 0.0008 | +25 |  |  |
|  |  | 0.0131 ± 0.0002 | +29.8 |  |  |
|  |  | 0.009 ± 0.001 | +37 |  |  |
| 25 | 1.5 M 1-Mim/An | 0.017 ± 0.001 | −10.2 | −14.3 ± 0.6 | −62 ± 2 |
|  |  | 0.0079 ± 0.0003 | −1.5 |  |  |
|  |  | 0.0026 ± 0.0002 | +8.6 |  |  |
|  |  | 0.0012 ± 0.0002 | +18.6 |  |  |
| 27 | 1.5 M 1-Mim/An | 0.09 | −10 | −16.3 ± 0.6 | −67 ± 3 |
|  |  | 0.025 | 0 |  |  |
|  |  | 0.0097 | +10 |  |  |
|  |  | 0.0031 | +20 |  |  |
|  |  | 0.0015 | +30 |  |  |
| 28 | Acetone | 0.03 | −19 | — | — |
| 28 | 311APW | >100 | −31 | — | — |
| 28 | Pyridine | ~0.01 | (0) | — | — |
| 32 | 1.5 M 1-Mim/An | 1.66 ± 0.05 | −20.0 | −16.6 ± 0.3 | −64 ± 1 |
|  |  | 0.97 ± 0.03 | −15.0 |  |  |
|  |  | 0.492 ± 0.008 | −10.1 |  |  |
|  |  | 0.138 ± 0.002 | +1.0 |  |  |
|  |  | 0.122 ± 0.004 | +2.1 |  |  |
| 32 | 2.5 M 1-Mim/H$_2$O | 1.6 ± 0.1 | +19.7 | — | — |
| 38 | 1.5 M 1-Mim/An | 4.6 ± 0.1 | −10.1 | −17.2 ± 0.4 | −62 ± 1 |
|  |  | 1.32 ± 0.04 | +1.0 |  |  |
|  |  | 0.98 ± 0.02 | +2.1 |  |  |
|  |  | 0.295 ± 0.008 | +15.3 |  |  |
|  |  | 0.155 ± 0.004 | +20.1 |  |  |
| 38 | 2.5 M 1-Mim/DMF | 2.76 ± 0.06 | +1.0 | — | — |
|  |  | 1.06 ± 0.02 | +10.0 |  |  |
| 38 | 2.5 M 1-Mim/H$_2$O | 4.5 ± 0.4 | +10 |  |  |
|  |  | 1.6 ± 0.1 | +19.7 |  |  |
| 38 | Acetonitrile | 0.026 | −20 | — | — |
|  |  | 0.006 | −10 |  |  |
| 38 | Ace/1M py | 0.68 | −20 | — | — |
|  |  | 0.19 | −10 |  |  |
| 46 | Acetone | >200 | −40 | — | — |
| 55 | 1.5 M 1-Mim/An | 1.27 ± 0.04 | −10 | −17.2 ± 0.6 | −65 ± 2 |
|  |  | 0.64 ± 0.01 | −5 |  |  |
|  |  | 0.41 ± 0.01 | +1 |  |  |
|  |  | 0.24 ± 0.02 | +5 |  |  |
|  |  | 0.116 ± 0.004 | +10 |  |  |
|  |  | 0.071 ± 0.002 | +15 |  |  |
|  |  | 0.025 ± 0.002 | +20 |  |  |
| 57 | 1.5 M 1-Mim/An | 0.85 ± 0.02 | 0 | −17.5 ± 0.4 | −64 ± 2 |
|  |  | 0.51 ± 0.02 | +5 |  |  |
|  |  | 0.31 ± 0.01 | +10 |  |  |
|  |  | 0.170 ± 0.006 | +15.1 |  |  |
|  |  | 0.101 ± 0.005 | +20 |  |  |
|  |  | 0.065 ± 0.002 | +25 |  |  |
|  |  | 0.032 ± 0.001 | +30 |  |  |
| 61 | 1.5 M 1-Mim/An | ~170 ± 7 | −0.4 | — | — |
| 64 | 1.5 M 1-Mim/An | 0.164 ± 0.008 | −25 | −14.8 ± 0.8 | −63 ± 3 |
|  |  | 0.083 ± 0.003 | −20 |  |  |
|  |  | 0.042 ± 0.002 | −15.4 |  |  |
|  |  | 0.026 ± 0.001 | −10 |  |  |
|  |  | 0.0104 ± 0.0007 | 0 |  |  |
| 69 | 1.5 M 1-Mim/An | 2.46 ± 0.04 | −10 | −17.3 ± 0.5 | −64 ± 2 |
|  |  | 0.80 ± 0.04 | 0 |  |  |

TABLE 8-continued

| Cmpd. No. | Solvent | $K_{O_2}$, torr$^{-1}$ | Degrees C. | ΔH Kcal/M | ΔS eu. |
|---|---|---|---|---|---|
| | | 0.41 ± 0.01 | +5 | | |
| | | 0.23 ± 0.01 | +10 | | |
| | | 0.15 ± 0.01 | +15 | | |
| 71 | 1.5 M 1-Mim/An | 4.5 ± 0.1 | 0 | −18.6 ± 0.9 | −65 ± 3 |
| | | 1.4 ± 0.1 | +10 | | |
| | | 0.93 ± 0.04 | +14.9 | | |
| | | 0.62 ± 0.04 | +19.4 | | |
| | | 0.26 ± 0.01 | +25 | | |
| | | 0.160 ± 0.004 | +30 | | |
| 76 | 1.5 M 1-Mim/An | 2.3 | +5 | −18.0 ± 0.9 | −65 ± 3 |
| | | 0.94 | +10 | | |
| | | 0.51 | +15 | | |
| | | 0.27 | +20 | | |
| | | 0.16 | +25 | | |
| 78 | 1.5 M 1-Mim/An | >200 | 0 | — | — |
| 81 | 1.5 M 1-Mim/An | 1.7 ± 0.1 | 0 | — | — |
| 83 | 1.5 M 1-Mim/An | 5.92 ± 0.04 | 0 | −17.2 ± 0.3 | −60 ± 1 |
| | | 3.34 ± 0.04 | +4.9 | | |
| | | 1.95 ± 0.04 | +10 | | |
| | | 1.13 ± 0.02 | +15 | | |
| | | 0.65 ± 0.02 | +20 | | |
| | | 0.45 ± 0.02 | +25 | | |
| | | 0.25 ± 0.01 | +29.8 | | |
| 87 | 1.5 M 1-Mim/An | 0.0085 ± 0.0007 | −40 | — | — |
| 94 | 311 Ace/Mim/H$_2$O | 0.0019 ± 0.0001 | −39 | — | — |
| 95 | 311 APW | 0.16 ± 0.01 | −41.5 | — | — |
| | | 0.019 ± 0.001 | −20.2 | | |
| | | 0.003 ± 0.0005 | 0 | | |
| 95 | 4/1 Ace/py | 0.08 ± 0.01 | −41.5 | — | — |
| 97 | 4/1 Ace/Mim | 1.7 ± 0.2 | −41.5 | — | — |
| 97 | 4/1 Ace/py | 0.015 ± 0.003 | −41.5 | — | — |
| 107 | 311 APW | 0.016 ± 0.002 | −34.7 | −16.1 ± 1 | 76 ± 3 |
| | | 0.0133 ± 0.002 | −34 | | |
| | | 0.0074 ± 0.0009 | −26.5 | | |
| | | 0.0043 ± 0.0009 | −19.5 | | |
| | | 0.001 ± 0.0006 | 0 | | |
| 111 | 311 APW | 0.12 ± 0.004 | −20 | | |
| 113 | 1.5 M 1-Mim/An | 0.01 | −30 | — | — |
| | | 0.0023 | −18.5 | | |
| | | 0.0020 | −16.4 | | |
| 115 | 1.5 M 1-Mim/An | 0.0012 | −30 | — | — |
| 116 | 311 APW | 0.125 ± 0.004 | −40.5 | −14.2 ± 0.5 | −65 ± 2 |
| | | 0.119 ± 0.004 | −39.2 | | |
| | | 0.032 ± 0.002 | −30 | | |
| | | 0.025 ± 0.002 | −29.1 | | |
| | | 0.0112 ± 0.0008 | −20 | | |
| | | 0.0045 ± 0.0003 | −12 | | |
| 118 | 311 APW | 0.55 ± 0.07 | −37.7 | −17.5 ± 0.4 | −76 ± 2 |
| | | 0.20 ± 0.01 | −32.3 | | |
| | | 0.050 ± 0.001 | −21.3 | | |
| | | 0.0091 ± 0.002 | −10.1 | | |
| | | 0.0095 ± 0.003 | −10.2 | | |
| | | 0.0025 ± 0.0004 | 0 | | |
| 118 | 1.5 M 1-Mim/Tol | 0.022 ± 0.001 | 0 | — | — |
| 118 | 1.5 M 1-Mim/An | 0.0155 ± 0.0009 | 0 | — | — |
| 118 | 1.5 M 1-Mim/H$_2$O | 0.031 ± 0.002 | 0 | — | — |
| 118 | 1.5 M 1-Mim/MeOH | 0.0041 ± 0.0003 | 0 | — | — |
| 118 | 1.5 M 1-Mim/Ace | 0.0086 ± 0.0007 | 0 | — | — |
| 118 | 1-Mim | 0.021 ± 0.001 | 0 | — | — |
| | | 0.0012 ± 0.0003 | +20 | | |
| 119 | 311 APW | 0.0325 ± 0.0009 | −41.1 | −15.9 ± 0.6 | −75 ± 3 |
| | | 0.013 ± 0.0005 | −34.2 | | |
| | | 0.0065 ± 0.0003 | −29.5 | | |
| | | 0.0046 ± 0.0004 | −29 | | |
| | | 0.00295 ± 0.0001 | −23.8 | | |
| | | 0.00135 ± 0.00006 | −15.7 | | |
| | | 0.00089 ± 0.00007 | −9.8 | | |
| 120 | 311 APW | 0.076 ± 0.004 | −34.5 | −17.6 ± 0.6 | −76 ± 3 |
| | | 0.034 ± 0.002 | −29.8 | | |
| | | 0.0073 ± 0.0005 | −19.1 | | |
| | | 0.0022 ± 0.0001 | −9.4 | | |
| 121 | 311 APW | 0.026 ± 0.002 | −29.8 | −16.8 ± 0.4 | −76 ± 2 |
| | | 0.0101 ± 0.0003 | −23 | | |
| | | 0.0037 ± 0.0001 | −15.4 | | |
| | | 0.0025 ± 0.0001 | −6.6 | | |
| 145 | 1.5 M 1-Mim/An | 0.114 ± 0.004 | −20 | −14 ± 1 | −60 ± 4 |
| | | 0.053 ± 0.001 | −15 | | |
| | | 0.0027 ± 0.001 | −10 | | |
| | | 0.016 ± 0.001 | −5 | | |
| | | 0.0099 ± 0.0006 | 0 | | |

TABLE 8-continued

| Cmpd. No. | Solvent | $K_{O_2}$, torr$^{-1}$ | Degrees C. | ΔH Kcal/M | ΔS eu. |
|---|---|---|---|---|---|
| | | 0.0064 ± 0.0009 | +10 | | |
| 145 | An | 0.054 ± 0.007 | −20 | — | — |
| | | 0.0051 ± 0.0006 | −15 | | |
| 145 | An/1 equiv p-toluic acid | 0.011 ± 0.001 | −20 | — | — |
| | | 0.0017 ± 0.0002 | −15 | | |
| 152 | 1.5 M 1-Mim/An | 0.015 ± 0.001 | −20.2 | −13.8 ± 0.6 | −63 ± 2 |
| | | 0.0081 ± 0.0005 | −14.4 | | |
| | | 0.0047 ± 0.0003 | −10 | | |
| | | 0.0020 ± 0.0001 | 0 | | |
| 155 | 1.5 M 1-Mim/An | 0.014 ± 0.001 | −14.8 | — | — |
| 158 | 1.5 M 1-Mim/An | >10$^{-4}$ | −20 | — | — |
| 159 | Acetone | 0.0055 ± 0.0001 | −38.8 | — | — |
| 162 | 1.5 M 1-Mim/An | 0.020 ± 0.001 | −37.6 | — | — |
| | | 0.0099 ± 0.0003 | −33.2 | | |
| | | 0.0037 ± 0.0002 | −25.0 | | |
| 163 | Acetone | 0.223 ± 0.006 | −41 | −14.2 ± 0.2 | −64 ± 2 |
| | | 0.212 ± 0.008 | −40.6 | | |
| | | 0.1181 ± 0.009 | −34.9 | | |
| | | 0.048 ± 0.004 | −29.7 | | |
| | | 0.044 ± 0.004 | −29.3 | | |
| | | 0.0315 ± 0.002 | −25.0 | | |
| | | 0.019 ± 0.002 | −20.5 | | |
| 168 | Acetonitrile | 0.004 | −20 | — | — |
| | | 0.001 | −10 | | |
| 168 | Acetone | 0.004 | −20 | — | — |
| | | 0.001 | −10 | | |
| 168 | H$_2$O | 0.003 | +2 | — | — |
| 180 | Acetonitrile | 0.075 ± 0.013 | −16.3 | — | — |
| | | 0.053 ± 0.003 | −7.9 | | |
| | | 0.020 ± 0.002 | −6.2 | | |
| | | 0.021 ± 0.002 | +0.9 | | |
| | | 0.024 ± 0.001 | +6.6 | | |
| | | 0.036 ± 0.002 | +8.5 | | |
| | | 0.051 ± 0.008 | +10.5 | | |
| 180 | 1.5 M 1-Mim/An | 31 ± 7 | +1 | — | — |

As mentioned above, for practical use in separating oxygen from the atmosphere, it is desirable that the value of the equilibrium constant be in the range of 0.003 to 0.1 torr$^{-1}$, with the range of 0.01–0.03 being especially valuable. Accordingly, based upon the results in Table 8 above, the following salts, solvents and temperature ranges are recommended for use in separating oxygen from air. It will be seen that compounds 21, 27, 55, 57, 118 and 145 are likely to be especially useful since their equilibrium constants are within the desired range at about ambient temperature.

TABLE 9

| Cmpd. No. | Solvent | Temp. Range, °C. | $K_{O_2}$, range, torr$^{-1}$ |
|---|---|---|---|
| 7 | 1.5 M 1-Mim/An | −40 | 0.002 |
| 10 | 1.5 M 1-Mim/An | −30 | 0.003 |
| 12 | 1.5 M 1-Mim/An | −40 | 0.005 |
| 17 | 1.5 M 1-Mim/An | −25 to 0 | 0.1 to 0.005 |
| 21 | 1.5 M 1-Mim/An | −5 to +25 | 0.1 to 0.005 |
| 21 | 2.5 M 1-Mim/H$_2$O | +10 to +40 | 0.1 to 0.005 |
| 25 | 1.5 M 1-Mim/An | −10 to +8 | 0.02 to 0.003 |
| 27 | 1.5 M 1-Mim/An | −10 to +20 | 0.1 to 0.003 |
| 28 | acetone | −20 | 0.03 |
| 28 | pyridene | 0 | 0.01 |
| 32 | 1.5 M 1-Mim/An | −20 to +2 | 1.66 to 0.12 |
| 38 | acetonitrile | −20 to −10 | 0.03 to 0.005 |
| 38 | acetone/1M py | −5 | 0.1 |
| 55 | 1.5 M 1-Mim/An | +10 to +30 | 0.1 to 0.005 |
| 57 | 1.5 M 1-Mim/An | +20 to +40 | 0.1 to 0.008 |
| 64 | 1.5 M 1-Mim/An | −22 to +10 | 0.1 to 0.003 |
| 69 | 1.5 M 1-Mim/An | +20 | 0.1 |
| 87 | 1.5 M 1-Mim/An | −40 | 0.009 |
| 95 | 3/1/1 ace/py/H$_2$O | −40 to 0 | 0.15 to 0.003 |
| 95 | 4/1 acetone/py | −40 | 0.08 |
| 97 | 4/1 acetone/py | −40 | 0.02 |
| 107 | 3/1/1 ace/py/H$_2$O | −35 to −20 | 0.17 to 0.004 |
| 111 | 3/1/1 ace/py/H$_2$O | −20 | 0.12 |
| 113 | 1.5 M 1-Mim/An | −30 to −20 | 0.01 to 0.003 |
| 116 | 3/1/1 ace/py/H$_2$O | −39 to −12 | 0.1 to 0.004 |
| 118 | 3/1/1 ace/py/H$_2$O | −25 to 0 | 0.1 to 0.003 |
| 118 | 1.5 M 1-Mim/toluene | 0 | 0.02 |
| 118 | 1.5 M 1-Mim/An | 0 | 0.02 |
| 118 | 1.5 M 1-Mim/H$_2$O | 0 | 0.03 |
| 118 | 1.5 M 1-Mim/MeOH | 0 | 0.004 |
| 118 | 1.5 M 1-Mim/acetone | 0 | 0.009 |
| 118 | Mim | 0 to +20 | 0.02 to 0.001 |
| 119 | 3/1/1 ace/py/H$_2$O | −40 to −24 | 0.03 to 0.003 |
| 120 | 3/1/1 ace/pyH$_2$O | −35 to −10 | 0.08 to 0.002 |
| 121 | 3/1/1 ace/pyH$_2$O | −30 to −15 | 0.03 to 0.003 |
| 145 | 1.5 M 1-Mim/An | −20 to +15 | 0.1 to 0.003 |
| 145 | acetonitrile | −20 | 0.05 |
| 152 | 1.5 M 1-Mim/An | −20 to −8 | 0.02 to 0.003 |
| 155 | 1.5 M 1-Mim/An | −15 | 0.01 |
| 159 | acetone | −40 | 0.006 |
| 162 | 1.5 M 1-Mim/An | −40 to −25 | 0.02 to 0.003 |
| 163 | acetone | −35 to −10 | 0.1 to 0.003 |
| 168 | acetonitrile | −20 | 0.004 |
| 168 | acetone | −20 | 0.004 |
| 168 | H$_2$O | 2 | 0.003 |

Figure 5:
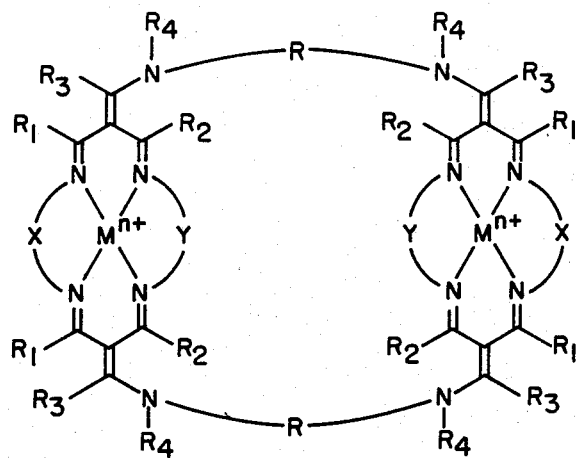
FIG. 5 shows the formula of a dimeric complex which may be produced as an impurity during the preparation of a compound of Formula I.
Figure 6:
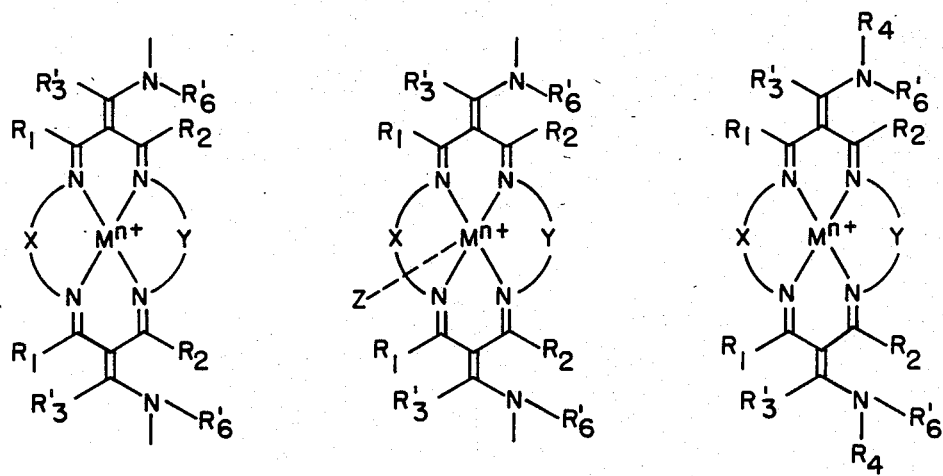
FIG. 6 shows the Formulae XIX and XIX A of the radicals used in the oxygen-binding polymers of the invention.
Figure 7A:
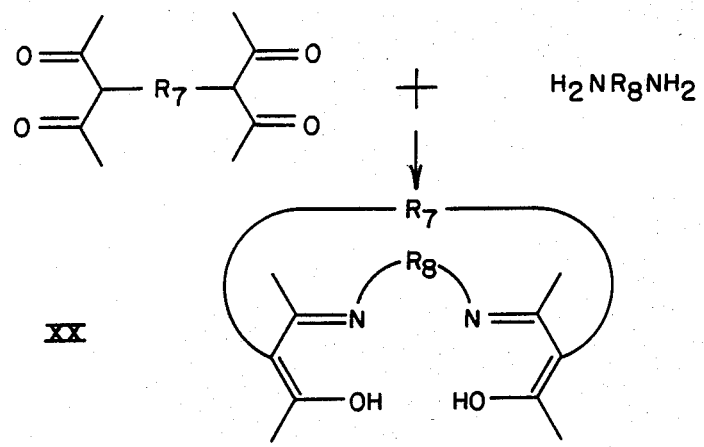
FIG. 7 shows Formulae XX-XXVI of the compounds of the invention which do not fall within Formulae XVII or XVII A, together with the methods used for synthesizing these compounds.
Figure 7A:
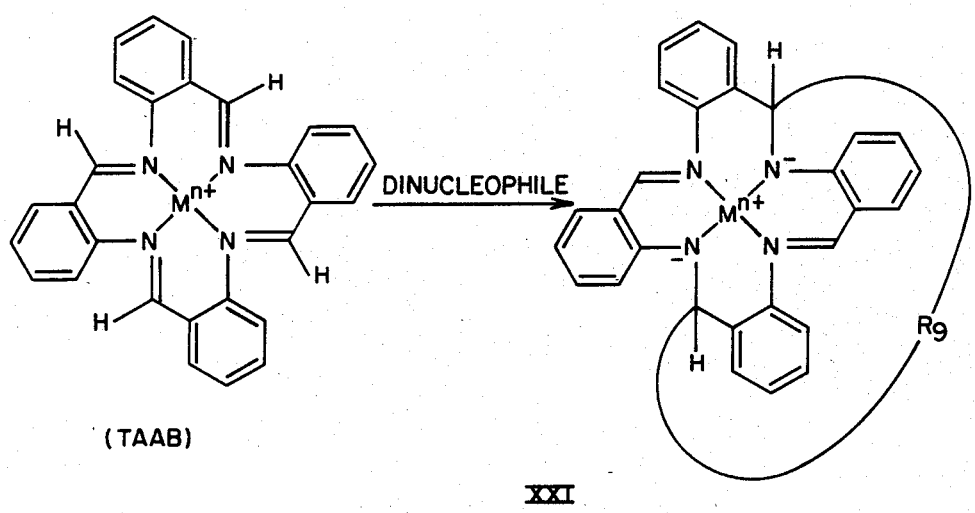
Figure 7A:
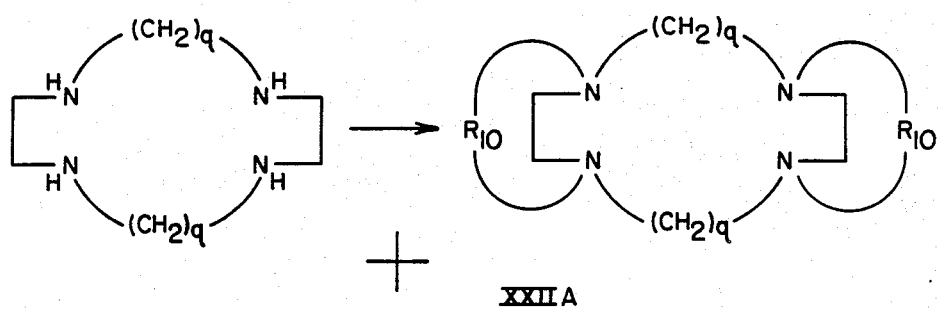
Figure 7B:
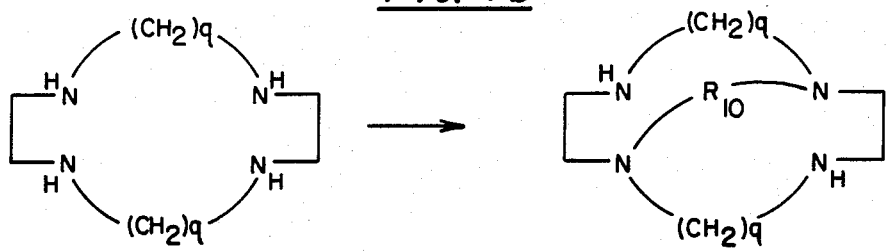
Figure 7B:
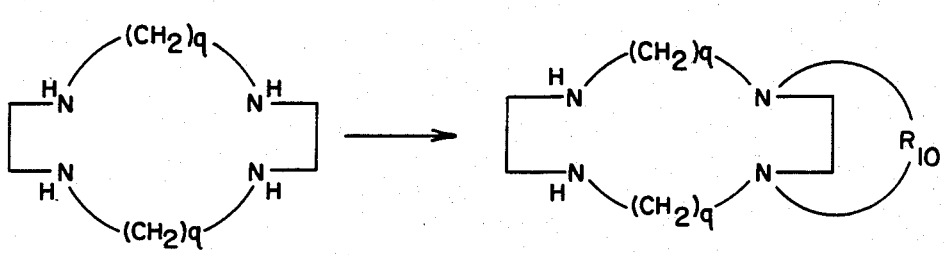
Figure 7B:
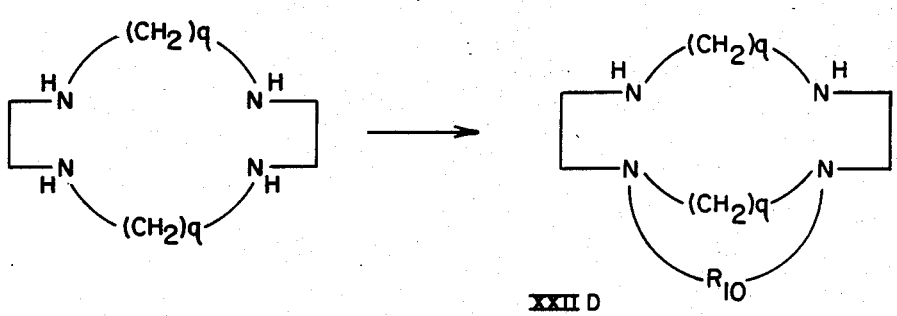
Figure 7B:
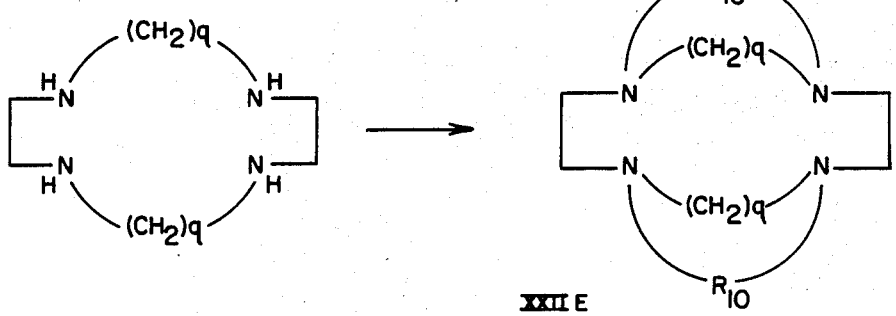
Figure 7C:
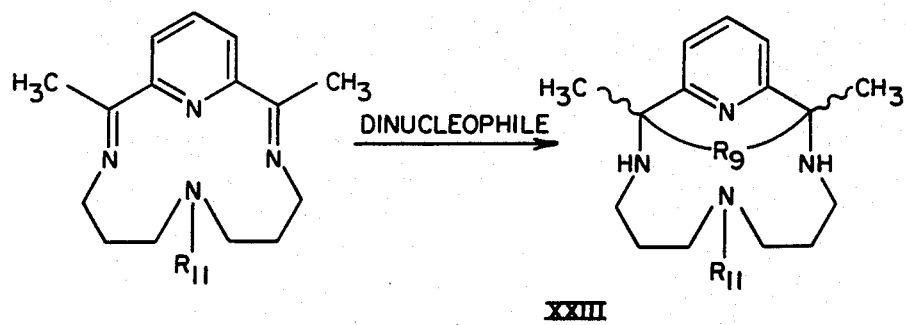
Figure 7C:
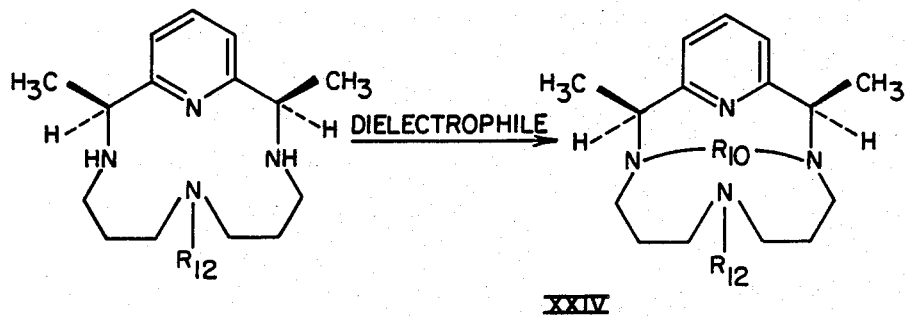
Figure 7C:
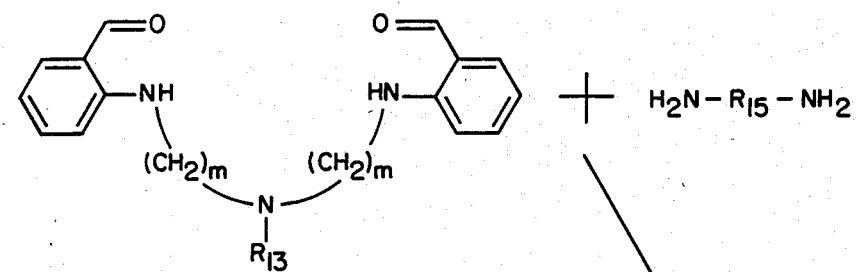
Figure 7C:
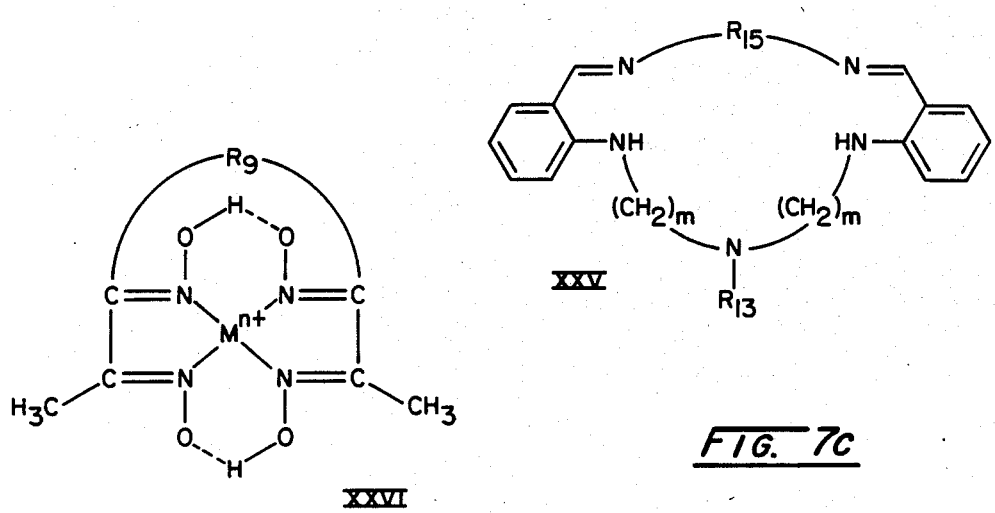

It should be noted that, in some cases, synthesis of a nitrogen-nitrogen bridged salt of Formula I produces as a by-product a corresponding salt having a dimeric cation of the Formula XIX shown in FIG. 5 of the accompanying drawings. As indicated in method B above, the resultant mixture of monomeric compound of Formula I and dimeric compound of Formula XIX can be separated by chromatography upon a ion exchange resin; the monomeric compound is eluted by a 0.2M aqueous solution of sodium sulphate, while the dimeric compound is not, being eluted only with a 0.4M aqueous sodium sulphate solution. The monomeric and dimeric complexes can readily be distinguished; as already indicated, the two compounds differ in the concentration of aqueous sodium sulfate solution necessary to elute them from an ion exchange resin. A second method of distinguishing the two compounds is to deprotonate the cations with a powerful base such as an alkoxide, whereupon the cationic monomer and dimer are converted into neutral molecules suitable for molecular weight determinations. The dimer and monomer can then be distinguished by molecular weight determinations using, for example, vapor pressure osmometry or (in many cases where the neutral species are sufficiently volatile) by mass spectrometry. Thirdly, in many cases the monomeric and dimeric cations can be distinguished by proton nuclear resonance spectrometry. Further details as to distinguishing between the monomeric and dimeric salts are given in the paper entitled "Synthesis and Characterization of a Novel Family of Dimeric Nickel (II) Complexes-Bi-metallic Species Separated by a Persistent Void" by Busch et al in J.A.C.S., 103, 5107 (1981).

EXAMPLES 201-212

These examples illustrate the preparation of compounds of Formula I in which the bridging groups X and Y are not identical. Also, these examples illustrates the formation of a compound of Formula I in which the bridging group R is a dodecamethylene group.

Figure 8:
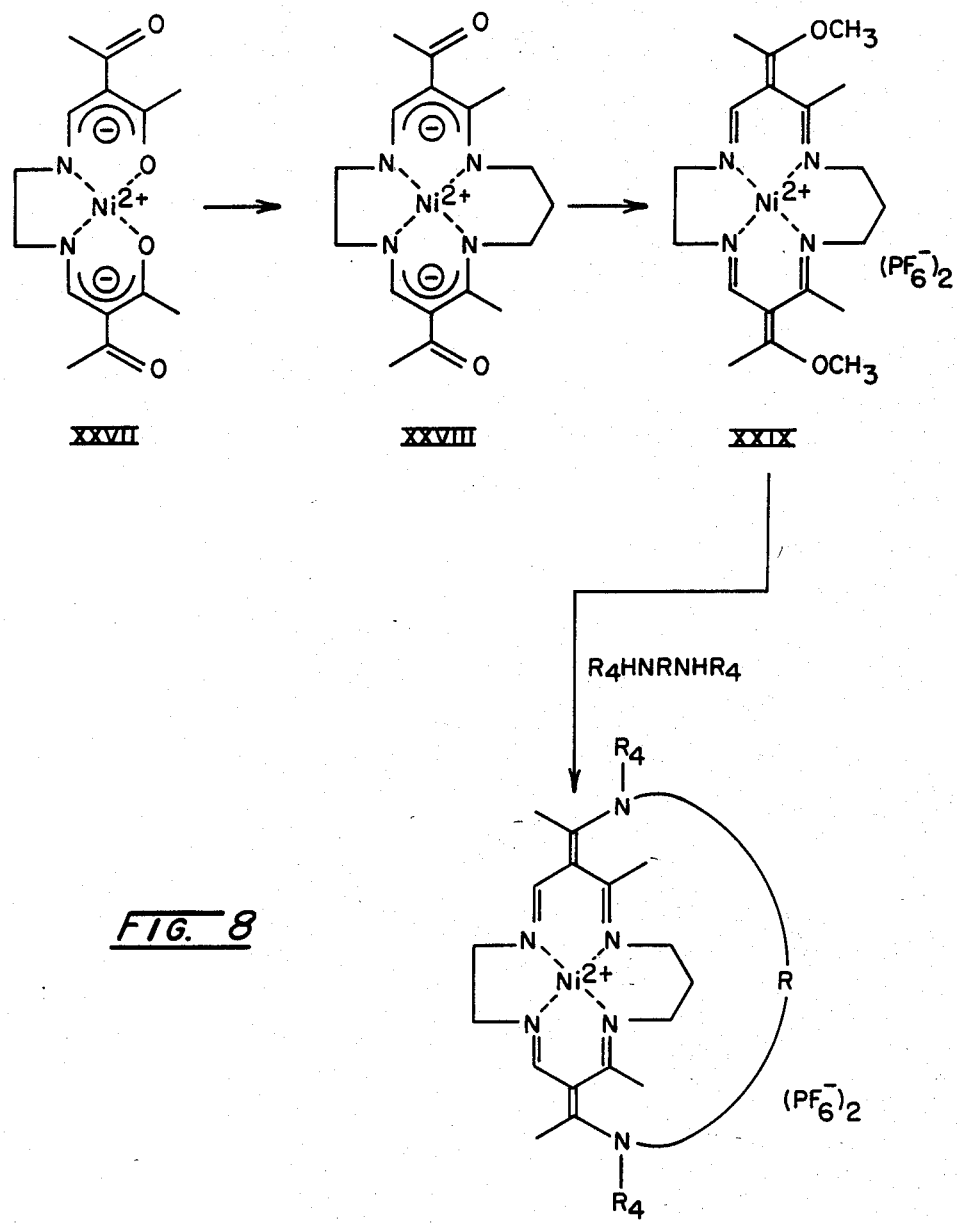
FIG. 8 is a reaction scheme showing the synthesis used in Examples 201-212 below.

The synthetic route employed is shown in FIG. 8 of the accompanying drawings. The starting material of Formula XXVII was prepared by the procedure described in Riley, D. P., PhD. thesis, The Ohio State University, Columbus, Ohio (1975) and in Riley et al, Inorganic Synthesis, 18, 36(1978). The compound of Formula XXVII was a bright orange powder and was obtained in a yield of 79%. Formation of a trimethylene group Y to produce the compound of Formula XXVIII was effected by refluxing 50 g. of the compound of Formula XXVII in approximately 300 ml. of 1,3-diaminopropane (freshly distilled from potassium hydroxide) for 15 minutes. The very dark, hot solution was then poured into 1.5 l. of vigorously stirred water to precipitate a light pink product in a yield of 84%. The product was thoroughly dried and chromatographed on alumina, eluting with chloroform. This solvent was removed, the resulting solid ground to a dark pink powder and this powder dried in a vacuum of about 60° C.

The resultant compound of Formula XXVIII was methylated to produce the compound of Formula XXIX by dissolving 10 g. of the compound of Formula XXIX in approximately 30 ml. of methylene chloride, freshly distilled from phosphorous pentoxide. 5 ml. of $CH_3OSO_2F$ was added and the solution stirred overnight at room temperature. The resultant solution contains some suspended material, but this was redissolved by addition of 20 ml. of methanol to yield a light yellow/brown solution which was then reduced to dryness on a rotary evaporator to yield a brown oil. A filtered solution of 10 g. of ammonium hexafluorophosphate in 20 ml. of methanol was added to this oil and the solution vigorously swirled until a precipitate appeared (in some cases difficulty is experienced in initiating precipitation, but precipitation could always be begun by adding approximately 1-2 ml. of acetonitrile). Crystallization was allowed to continue for several hours at room temperature and the solution was filtered to yield a bright green/yellow solid in a yield of 50 to 80%. This material darkened on standing for several weeks in air and if stored for substantial periods before being used in the following step of the process needed to be recrystallized from acetonitrile/methanol.

As shown in FIG. 8, introduction of the nitrogen-nitrogen bridge into the compound of Formula XXIX to produce a compound of Formula XXX (which is, of course, also a compound of Formula I having M=Ni, n=2, $R_1$=hydrogen, $R_2$=methyl, X=ethylene and Y=trimethylene) was effected by reaction with the appropriate alpha, omega-diamine. 10 g. (0.027 mole) of the compound of Formula XXIX and 0.027 mole of the diamine were separately dissolved in 300 ml. aliquots of acetonitrile and were injected into 200 ml. of stirred, refluxing acetonitrile over a period of 5 to 6 hours using a peristaltic pump. A very dark solution invariably resulted and carrying out the reaction under nitrogen did not improve the color. The volume of the solution was then reduced to about 20 ml. on a rotary evaporator and the resultant liquid chromatrographed on alumina eluting with acetonitrile. This chromatographic separation produced a yellow or red, fast-moving band followed by, but not completely resolved from a dark material. The red or yellow band was separated as far as possible from the dark material, reconcentrated and rechromatographed on fresh alumina, this time eluting with methylene chloride or methylene/chloride acetone. The red or yellow material was collected, evaporated to dryness on a rotary evaporator and dissolved in approximately 100 ml. of acetone. Water was added to the acetone solution until a precipitate formed which was then just redissolved by the addition of further acetone to give approximately 300 ml. of solution, which was passed through a 30 ml. frit half filled with CM Sephadex resin under suction. The light yellow filtrate was further diluted with approximately 200 ml. of water and again passed through fresh CM Sephadex resin to yield a substantially clear filtrate.

The Sephadex resin containing the compound was loaded onto a 4×20 cm. column of the same resin by pouring it into a column of water above the resin column so that a distinct layer of compound-containing resin was obtained. The column was then topped off with a layer of sand. Elution with 0.2M sodium sulfate produced a red band followed by, but separated from, dark material. The red band was collected and the product of Formula XXX precipitated by addition of ammonium hexofluorophosphate; if a $^{13}C$ NMR spectrum showed that the compound was still impure, it was rechromatographed on Sephadex resin.

The compounds prepared in this manner and the yields obtained were as follows:

| Compound No. | R | $R_4$ | Yield |
|---|---|---|---|
| 201 | $(CH_2)_5$ | $CH_3$ | 8% |
| 202 | $(CH_2)_6$ | $CH_3$ | 33% |
| 203 | $(CH_2)_7$ | $CH_3$ | 20% |
| 204 | $(CH_2)_8$ | $CH_3$ | 7% |
| 205 | $(CH_2)_{12}$ | $CH_3$ | 4% |
| 206 | m-xylylene | H | 10% |
| 207 | $(CH_2)_5$ | H | 6% |
| 208 | m-xylylene | $CH_3$ | 15% |

Compounds 201-204 were converted to the corresponding cobalt complexes by demetallating by the method of Example VIII above, then inserting cobalt by a variant of Method D above, again carried out under a nitrogen atmosphere, in which 0.1 g. of the ligand salt is stirred overnight with 0.05 g. of cobalt acetate tetrahydrate and 0.1 g. of sodium acetate trihydrate at room temperature in 20 ml. of methanol. Analytical data for the cobalt complexes thus prepared were as follows: (in all three cases, $R_4$ is a methyl group and the anion is hexfluorophosphate; compound 209 only crystallizes with 1 molecule of water of crystallization):

Compound 209, $R=(CH_2)_6$: Calculated: C, 37.84%; H, 5.59%; N, 10.59%. Found: C 37.12%; H, 5.56%; N, 10.30%.

Compound 210, $R=(CH_2)_7$): Calculated: C 39.55%, H, 5.61%; N, 10.64%. Found: C 39.48%; H, 5.62%; N, 10.62%.

Compound 211, $R=(CH_2)_8$. Calculated: C, 40.35%, H, 5.77%, N, 10.45%. Found: C 41.32%; H, 6.03%; N, 10.72%.

Compound 208 was also converted to the corresponding Fe(II) complex by demetallating by the method of Example VIII above, followed by insertion of $Fe^{2+}$ by Method E above. The resultant iron complex, compound 212, gave the following elemental analysis:

$C_{27}$; $H_{38}$; $N_6$; Fe; Cl; $PF_6.H_2O$: Calculated: C, 46.28%; H, 11.99%; N, 5.71%; Fe, 7.97%. Found: C, 46.41% H, 12.12%; N, 5.59%; Fe, 7.95%.

Oxygen Affinity Tests

Solutions of the cobalt complexes, compounds 209–211 above were made in 1.5 Molar N-methylimidazole in acetonitrile so that an absorption of 1.5–2.6 was obtained at about 380 mn. The spectral differences were measured at 420, 440 and 460 nm. at 20° C. Good isosbestic points were obtained at 390 and 530 mn. The nickel complex, 205, having $R=(CH_2)_{12}$ was also converted to the corresponding cobalt complex in very low yield in the same manner as the other complexes and this dodecamethylene-bridged cobalt complex exhibited a very high oxygen affinity; some decomposition occured when pure oxygen was bubbled for a long time through the solution, but the spectrum remained isosbestic for oxygen pressures up to 38 torr at 20° C.

The measured oxygen affinities for compound 209–211 were as follows:

| Compound No. | $K_{O_2}$, Torr$^{-1}$ |
|---|---|
| 209 | 0.52 |
| 210 | 1.32 |
| 211 | 5.2 |

These oxygen affinities are all measured at 20° C., and in all cases are much lower than the oxygen affinities of the corresponding compounds in which both X and Y are trimethylene bridges. It is believed (although the invention is in no way limited by this belief) that the substitution of an ethylene group for a trimethylene group as the group X tends to produce a flatter macrocycle, thus producing a smaller cave for oxygen to enter and reducing oxygen affinity.

EXAMPLE 213

This example illustrates the attachment of various compounds of Formula XVII to polymeric supports.

(A) Compound No. 32

Compound No. 32 was deprotonated with sodium methoxide, thereby removing the two protons $R_4$. The deprotonated compound was then run through a 6% crosslinked polystyrene polymer containing 3 meq/g of benzyl chloride groups, thereby attaching compound No. 32 to the polymer via covalent bonds between the two nitrogens in the bridge and separate benzyl groups.

Upon exposure to molecular oxygen at a pressure of 1 atmosphere, the polymer-supported compound slowly absorbed molecular oxygen, as shown by the electron paramagnetic resonance spectrum. The resultant molecular oxygen complex was stable for weeks, deoxygenated slowly on standing in the absence of oxygen and could be re-oxygenated, although minor irreversibility was demonstrated in the EPR spectrum, apparently due to irreversible decomposition of the oxygen complex.

Compound No. 32 was also attached to a similar polymer having only 1% crosslinking; the loading of compound No. 32 was 0.06 meq/g. of polymer. Again, upon exposure to oxygen at a pressure of 1 atmosphere the EPR spectrum showed the formation of an oxygen complex stable for at least one week at room temperature.

(B) Compound No. 38

Compound No. 38 was added to Porapak S, a commercially-available polyvinylpyridine polymer. The compound became attached to the polymer by coordination of the cobalt ion to the pyridine groups on the polymer, the pyridine functioning as the axial ligand, in effect transforming compound 38 into the corresponding compound of Formula XVII A having a pyridine ligand Z. Upon exposure to molecular oxygen, the polymer-supported compound formed a molecular oxygen adduct, as demonstrated in the change in the EPR spectrum, and this adduct was stable as a dry solid for several days at room temperature. Vacuum pumping removed only part of the molecular oxygen from the oxygen adduct and after prolonged standing at room temperature organic radical species were visible as shown by the EPR spectrum of the adduct.

Compound No. 38 was also attached to control pore glass aminopropyl polymer in the same manner; in this case, attachment of the polymer to the compound took place via coordination of an aminopropyl group on the polymer to the cobalt ion of compound No. 38. Upon exposure to molecular oxygen, an oxygen adduct was formed, as indicated by the EPR spectrum. This adduct was stable for several days at room temperature in a sealed tube.

(C) Compound No. 25

Compound No. 25 was attached to Porapak S in the same way as described in part (B) of this Example above. The properties of the polymer-supported compound were generally similar to those of compound No. 38 on the same polymer except that, on standing in a sealed tube, the molecular oxygen adduct regenerated the unoxygenated form of Compound No. 25 in addition to a radical species. The regenerated cobalt complex would be reoxygenated and the cycle repeated.

EXAMPLE 214

This example illustrates the attachment of a compound of Formula XIX A to a polymer.

The compound of Formula XIX A having $M^{n+}=Co^{2+}$, $X=Y=(CH_2)_3$, $R_1=$hydrogen, $R_2=R'_3=R_4=R'_6=CH_3$ was attached to Porapak S in the same manner as described in Example 213 (B) above. Again, on exposure to molecular oxygen, the polymer-supported compound produced an oxygen adduct which, upon standing in a sealed tube at room temperature for an extended period regenerated the unoxygenated form of the polymer-supported compound; this unoxygenated form could be reoxygenated. The EPR spectrum gave no evidence for the formation of the radical species generated upon standing, so that the oxygen adduct formation reaction appears to be substantially completely reversible.

EXAMPLE 215

This example illustrates the preparation of a compound of Formula XX and the formation of an oxygen adduct thereof.

(A) 1,1,12,12-Tetraacteyldodecane 60 g (0.6 mole) of 2,4-pentanedione were added to a solution of 15.6 g. (0.4 mole) of potassium metal in 450 ml. of t-butyl alcohol contained in a one liter three-necked flask fitted with a water condensor. The resulting milky white solution was refluxed for 30 minutes and then 60 g. (0.2 mole) of 1,10-dibromodecane were added over a five minute period via a pressure-equalizing dropping funnel. The resultant mixture was refluxed for another hour and then 8 g. of potassium iodide were added, after which the mixture was refluxed for a further 48 hours.

Three-quarters of the alcohol solvent was distilled off and the remaining mixture washed with 200 ml. of water, then extracted with 200 ml. of benzene. After separation of the benzene from the reaction mixture, the benzene was dried over anhydrous sodium sulfate for 24 hours and then the benzene removed in a rotary evaporator until an oil was obtained. Storage of this oil under pentane in a refrigerator produced gradual solidification of the desired tetraacetylododecane after prolonged standing. The yield was 55% based upon the pentanedione and the product had the expected NMR and IR spectra: $^{13}C$ N MR: 204.3, 68.9, 30.6, 29.3, 28.9, 28.8, 27.9 and 27.2 ppm. IR: 3400 (w, hydroxyl), 1720 (vs,b, carbonyl) and 1580 (m,sh, enol-chelate) cm$^{-1}$.

(B) Condensation with ethylenediamine 2 g. (0.006 mmole) of the 1,1,12,12-tetraacetyldodecane prepared as thus described was dissolved in 1 liter of dry ethanol. 0.36 g. (0.006 mole) of ethylenediamine was dissolved separately in 1 liter of dry ethanol. The two ethanolic solutions were then allowed to drip via separate pressure-equalizing dropping funnels into a 3-liter, three-necked flask containing 500 ml. of boiling ethanol, the total addition of the two solutions taking 6 hours. Condensation of the tetraacetyldodecane with the ethylenediamine thus took place under extremely high dilution conditions, thereby reducing as far as possible any tendency for polymerization. After the addition of the two ethanolic solutions to the flask have been completed, the resultant solution was refluxed for a further 24 hours and the solvent removed by rotary evaporation until the volume of the reaction mixture had been reduced to about 50 ml. The produced was precipitated by addition of about 100 ml. of dry ethyl ether to the solution followed by filtration and purified by recrystallization from ether. The yield of the product (the compound of Formula XX in which $R_7$ is $(CH_2)_{10}$ and $R_8$ is $(CH_2)_2$ was 1.9 g. (88%).

To confirm that the desired product was obtained, a $^{13}C$ N MR spectrum was run. This spectrum showed peaks at 195.4, 162.0, 105.0, 43.7, 31.4, 29.7, 29.4, 27.5 and 14.4, ppm. This spectrum was very different from that of the tetraketone starting material, but closely similar to that of the previously known "acacen" ligand (a compound similar to the compounds of Formula XX having $R_8=(CH_2)_2$, but with the bridging group $R_7$ replaced by two hydrogen atoms); the acacen ligand has a $^{13}C$ MMR spectrum with peaks at 195.4, 162.7, 96.1, 43.5, 28.8 and 18.5 ppm. Furthermore, a molecular weight determination on the compound in chloroform solution indicated that it was indeed monomeric.

(C) Preparation of Nickel (II) Complex 0.2 g. (0.00055 mole) of the compound of Formula XX prepared in part (b) of this Example was dissolved in 60 ml. of dry, hot ethanol and added to a solution of 0.1 g. (0.0004 mole) of nickel (II) of acetate tetrahydrate in 60 ml. of hot dry, hot ethanol. The mixture turned deep brown in color and a fine flocculant precipitate formed, which was removed by filtration. The brown filtrate was reduced in volume and dry diethyl ether added thereto to precipitate the nickel complex as a brown amorphous solid in a yield of 54%.

The nickel complex was found to be monomeric by molecular weight determination in chloroform solution. Furthermore, the structure was confirmed by a $^{13}C$ N MR spectrum which was closely similar to that of the nickel (II) complex of acacen; the $^{13}C$ spectrum of the nickel complex of the invention showed peaks at 173.8, 165.0, 106.9, 53.9, 31.2, 30.4, 29.6, 29.5, 24.2 and 17.9 ppm, closely analogous to the corresponding spectrum of the acacen complex which shows peaks at 176.6, 164.4, 99.4, 52.0, 24.2 and 17.9 ppm—the only bands in the spectrum of the instant complex not closely analogous to the acacen complex are attributable to the methylene bridge.

(D) Preparation of Cobalt (II) Complex 0.15 g. (0.000414 mole) of the compound of Formula XX produced in part B of this Example was dissolved in 10 ml. of dry, boiling methanol and added to a solution of 0.1 g. (0.000414 mole) of cobalt (II) acetate tetrahydrate and 0.11 g. (0.0005 mole) of sodium acetate trihydrate in 20 ml. of boiling methanol. The purple solution of the cobalt acetate immediately turned orange upon addition of the compound of Formula XX and a fine flocculant precipitate appeared. The mixture was then stirred for an additional three hours at room temperature and the solvent removed under vacuum. The solid residue obtained was extracted with 10 ml. of dry toluene.

The entire preparation of the cobalt complex was carried out in an inert atmosphere glove box. The yellow solid isolated produced no resolvable EPR spectrum in toluene at liquid nitrogen temperature or above, but this was not unexpected since it has been observed for the corresponding acacen complex and appears to be a common phenomenon; see for example, Hoffman et al, J.A.C.S., 92, 61 (1970).

Addition of pyridine to a toluene solution of the cobalt complex readily produced the corresponding complex having a pyridine axial ligand, and this pyridino complex yielded, in frozen toluene solution, a EPR spectrum indicating near axial symmetry about the cobalt ion but with the perpendicular region split by a rhombic distortion. All eight $^{59}Co$ hyperfine lines (I=7/2 for $^{59}Co$) were observable for the high field parallel component, and several of these lines were split into triplets of equal intensity by the single nitrogen of the single coordinated pyridine molecule.

When molecular oxygen was admitted to a sample tube containing a solution of the pyridino cobalt complex at −40° C., an EPR spectrum characteristic of a cobalt (II)/molecular oxygen adduct was obtained. The spectrum showed clear evidence of interaction of molecular oxygen with only a single cobalt atom and the expected eight line hyperfine coupling due to $^{59}Co$ was observed in both the parallel and perpendicular components.

It will be apparent to those skilled in the art that numerous changes and modifications can be made in the compounds and processes of the invention without departing from the scope thereof. In particular, I consider that it should be possible to prepare compounds having properties similar to those already described but having different values of the substituents in Formulae XVII, XVIIA, I, IA, II, IIA, III, IIIA, XVIII, and XVIIIA having properties similar to those of the compounds already described. In particular, I have very recently obtained very preliminary results which indicate that it is possible (using the methods described above for the synthesis of compounds of Formulae XVIII and XVIIIA) to prepare similar compounds in which the linkage between the two piperazine rings, —CH$_2$—D—CH$_2$— in Formulae XVIII and XVIIIA is replaced by a different linkage. My aforementioned preliminary results indicate that this linkage could be a methylene or ethylene linkage. For obvious reasons, it should be possible to prepare similar compounds with other polymethylene linkages or with linkages of the formula —CO—polymethylene—CO—. It is probably also possible to prepare similar compounds in which this linkage is a phenylene or other aromatic nucleus.

More generally, I would suggest that the metal M could be rhodium, ruthenium or platinum and that the oxidation state n+ could differ from those already given. Each group $R_1$, $R_2$, $R_3$, $R_4$ could be any of a wide variety of organic groups or heterocyclic groups, for example alkyl groups, aryl groups, fluorinated alkyl groups or (as mentioned briefly above) various types of polymeric groups; preferably the alkyl groups and fluorinated alkyl groups would not contain more than about 22 carbon atoms. The aryl groups could include phenyl, benzyl, tolyl and the like although substituted, fused rings and various other groups might be used. $R_3$ and $R_4$ could each be virtually any aliphatic, cycloaliphatic, aliphatic-aromatic or aromatic groups, optionally containing linkages via nitrogen or sulphur atoms and substituted by alkyl, aryl, carboxyl, cycloalkyl or fused aromatic rings and the like. I also consider that X and Y could be ethylene, trimethylene or o-phenylene groups substituted by alkyl groups, aryl groups, carboxyl groups or cycloalkyl groups or the like, or indeed X and Y could also be fused ring groups related to o-phenylene.

I also consider that the bridges R and $R_5$ can be any of a wide variety of organic groups, heterocyclic groups or metalloorganic chelates comprising two organic groups coordinated to a metal atom, For example, R and $R_5$ could each be a cyclohexylene or cycloheptylene groups, optionally substituted with, for example, alkyl, amino or other similar substituents all containing nitrogen or sulfur atoms within the ring or side-chains. Also, R and $R_5$ could be, for example, a m- or p-phenylene group or a group comprising multiple fused aromatic rings derived from such a m- or p-phenylene group. Further possibilities for the bridges R and $R_5$ include aliphatic and aromatic groups containing hetero atoms and substituted derivatives thereof.

In view of the possibility of the aforementioned modifications, the entire foregoing description is to be construed in an illustrative and not in a limitative manner, the scope of the invention being defined solely by the appended claims.

I claim:

1. A salt of a cationic metal complex of the formula:

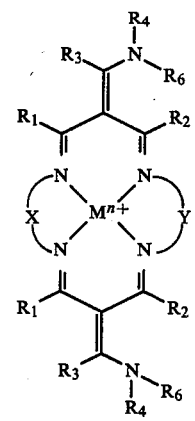

XVII wherein:
M is Co, Fe, Cu, or Mn;
n+ is a positive oxidation state of M, n being not greater than 3;
X and Y are each independently an o-phenylene, ethylene, trimethylene, 2-(2-pyridyl)-trimethylene, 2-methyl substituted trimethylene or 2-(N-methyl-2-pyridino)-trimethylene group;
each $R_1$ independently is hydrogen or a methyl group;
each $R_2$ independently is hydrogen or a methyl group;
each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;
each $R_4$ independently is hydrogen, an alkyl group containing not more than about 4 carbon atoms, a cyanoalkyl group containing not more than about four carbon atoms, a phenyl group or a benzyl group;
each $R_6$ independently is hydrogen or a methyl group; or the two $R_6$ groups together form a nitrogen-nitrogen bridge, said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula:

where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group, subject to the proviso that when G is a sulfur atom, a imino group or a methylimino group, the sum of a and b is at least 4;

or the two NR4R6 groups together form a bis-piperazino bridge of the formula

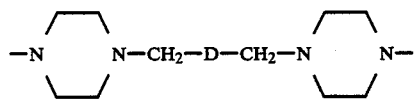

where D is a 1,3-phenylene group, a 1,4-phenylene group, a 1,4-phenylene group substituted by one or more methyl groups, a 9,10-anthracene group or a 2,6-pyridylene group, subject to the proviso that when the two $R_3$ groups do not form a carbon-carbon bridge, either the two $R_6$ groups must form a nitrogen-nitrogen bridge or the two NR4R6 groups must form a bis-piperazino bridge.

2. A salt according to claim 1 wherein the anion is selected from the group comprising hexafluorophosphate, tetrachlorozincate, perchlorate, hexafluoroarsenate, fluoroborate, trifluoromethylsulfonate and the halides.

3. A salt according to claim 1 wherein $M^{n+}$ is $Co^{2+}$, $Co^{3+}$, $Fe^{2+}$, $Fe^{3+}$, $Cu^{2+}$, $Mn^{2+}$ or $Mn^{3+}$.

4. A salt according to claim 1 wherein each $R_1$ is hydrogen.

5. A salt according to claim 1 wherein each $R_2$ is a methyl group.

6. A salt according to claim 1 wherein each $R_3$ is hydrogen, a methyl group, a phenyl group, a t-butyl group, an n-heptyl group, an n-heptadecyl group, a 4-methoxyphenyl group, a 4-chlorophenyl group, a 4-fluorophenyl group or a 3,5-dimethoxyphenyl group, or the two $R_3$ groups together form a polymethylene group containing 7 to 12 carbon atoms or a m-xylylene group.

7. A salt according to claim 1 wherein each $R_4$ is hydrogen, a methyl group, an n-propyl or n-butyl group, a 2-cyanoethyl group or a benzyl group.

8. A salt according to claim 1 wherein two $R_6$ groups together form a nitrogen-nitrogen bridge, said nitrogen bridge comprising a polymethylene bridge of 4 to about 8 carbon atoms, an m- or p-xylylene group, a (5-methoxy)-m-xylylene group, a —(CH2)3—(9,9-fluorylene)—(CH2)3— group, a —(CH2)4CH(COOCH3)(CH2)4— group, a —CH2—(1,3-cyclohexylene)—CH2— group, a —(CH2)2C(CH3)2(CH2)2— group, a 3-thiapentamethylene group, a 3-thiahexamethylene group, a —CH2—(5-methoxycarbonyl-1,3-phenylene)—CH2— group, a 2,6-pyridylene group, a 4-azaheptamethylene group, or a 4-aza-4-methylheptamethylene group.

9. A salt according to claim 2 wherein said anion is hexafluorophosphate or chloride.

10. A salt according to claim 1 wherein X is an ethylene group, a trimethylene group, a 2-(2-pyridyl)-trimethylene group, or a 2-(N-methyl-2-pyridino)-trimethylene group and Y is a trimethylene group.

11. A salt according to claim 1 wherein said cationic metal complex is of the formula

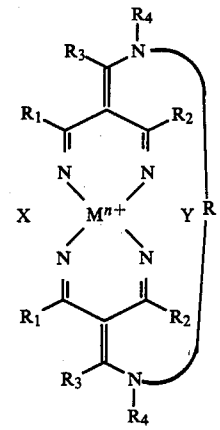

wherein:

M, n+, $R_1$, $R_2$, $R_3$, $R_4$, X and Y are as defined in claim 1;

each $R_3$ independently is hydrogen, an alkyl group containing not more than about 17 carbon atoms, a benzyl group, a phenyl group, or a phenyl group substituted by a halogen atom or by one or two methoxy groups; and R is a polymethylene group containing from 4 to about 12 carbon atoms, a polymethylene group containing from 4 to about 12 carbon atoms and substituted by a methoxycarbonyl group, or a grouping of the formula —(CH2)$_a$—G—(CH2)$_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4.

12. A salt according to claim 11 wherein the anion is hexafluorophosphate, tetrachlorozincate, perchlorate, hexafluoroarsenate, fluoroborate, trifluoromethylsulfonate and the halides.

13. A salt according to claim 11 where $M^{n+}$, is $Co^{2+}$, $Co^{3+}$, $Fe^{2+}$, $Fe^{3+}$, $Cu^{2+}$, $Mn^{2+}$ or $Mn^{3+}$.

14. A salt according to claim 11 wherein X is an ethylene group, a trimethylene group, a 2,2-dimethyltrimethylene group, a 2-(2-pyridyl)-trimethylene group or a 2-(N-methyl-2-pyridino)-trimethylene group and Y is a trimethylene group.

15. A salt according to claim 14 wherein X and Y are each a trimethylene group.

16. A salt according to claim 11 wherein each $R_1$ is hydrogen and each $R_2$ is a methyl group.

17. A salt according to claim 11 where each $R_3$ is hydrogen, a methyl group, a phenyl group, a t-butyl group, an n-heptyl group, an n-heptadecyl group, a 4-methoxyphenyl group, a 4-chlorophenyl group, a 4-fluorophenyl group or a 3,5-dimethoxyphenyl group.

18. A salt according to claim 11 where each $R_4$ is hydrogen, a methyl group, an n-propyl or n-butyl group, a 2-cyanoethyl group or a benzyl group.

19. A salt according to claim 11 wherein R is a polymethylene bridge of 4 to about 8 carbon atoms, an m- or p-xylylene group, a (5-methoxy)-m-xylylene group, a —(CH2)3—(9,9-fluorylene)—(CH2)3— group, a —(CH$_2$)$_4$CH(COOCH$_3$)CH$_2$)$_4$— group, a —(CH$_2$—(1,3-cyclohexylene)—CH$_2$— group, a —(CH$_2$)$_2$C(CH$_3$)$_2$(CH)$_2$— group, a 3-thiapentamethylene group, a 3-thiahexamethylene group, a —CH$_2$—(5-methoxycarbonyl-1,3-phenylene)—CH$_2$— group, a 2,6-pyridylene group, a 4-azaheptamethylene group, or a 4-aza-4-methylheptamethylene group.

20. A salt according to claim 12 wherein said anion is hexafluorophosphate or chloride.

21. A salt according to claim 20 wherein M$^{n+}$ is Co$^{2+}$, Co$^{3+}$, Fe$^{2+}$, Fe$^{3+}$, Mn$^{2+}$, Mn$^{3+}$ or Cu$^{2+}$, X is an ethylene group, a trimethylene group, a 2,2-dimethyltrimethylene group, a 2-(2-pyridyl)-trimethylene group or a 2-(N-methyl-2-pyridino)-trimethylene group, Y is a trimethylene group, each R$_1$ is hydrogen, each R$_2$ is a methyl group, each R$_3$ is hydrogen, a methyl group, a t-butyl group, an n-heptyl group a 4-methoxyphenyl group, a 4-chlorophenyl group, a 4-fluorophenyl group, or a 3,5-dimethoxyphenyl group, R$_4$ is hydrogen or a methyl group and R is a polymethylene group containing 4 to 8 carbon atoms, an m-xylylene group or a p-xylylene group.

22. A salt according to claim 21 where M is cobalt or iron.

23. A salt according to claim 21 wherein M is copper or manganese.

24. A salt according to claim 1 wherein said cationic metal complex is of the formula

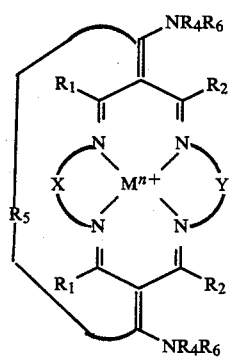

III wherein:
M, n+, R$_1$, R$_2$, X and Y are as defined in claim 1;
each R$_4$ independently is hydrogen, an alkyl group containing not more than about 4 carbon atoms or a benzyl group;
each R$_6$ independently is hydrogen or a methyl group; and
R$_5$ is a polymethylene group containing from 7 to about 12 carbon atoms or a m- or p-xylylene group.

25. A salt according to claim 24 wherein the anion is selected from the group comprising hexafluorophosphate, tetrachlorozincate, perchlorate, hexafluoroarsenate, fluoroborate, trifluoromethylsulfonate and the halides.

26. A salt according to claim 24 wherein M$^{n+}$ is Co$^{2+}$ or Fe$^{2+}$.

27. A salt according to claim 24 wherein X and Y are each a trimethylene group.

28. A salt according to claim 24 wherein each R$_1$ is hydrogen.

29. A salt according to claim 24 wherein each R$_2$ is a methyl group.

30. A salt according to claim 24 wherein each R$_4$ is hydrogen, a methyl group, an n-propyl group or a benzyl group.

31. A salt according to claim 24 wherein R$_5$ is a polymethylene group containing from 7 to 10 carbon atoms.

32. A salt according to claim 25 wherein said anion is hexafluorophosphate or chloride.

33. A salt according to claim 32 wherein X and Y are each a trimethylene group, M$^{n+}$ is Co$^{2+}$ or Fe$^{2+}$ each R$_1$ is hydrogen, each R$_2$ is a methyl group, each R$_4$ is hydrogen, a methyl group, an n-propyl group or a benzyl group and R$_5$ is a polymethylene group containing from 7 to 10 carbon atoms.

34. A salt according to claim 1 wherein said cationic metal complex is of the formula:

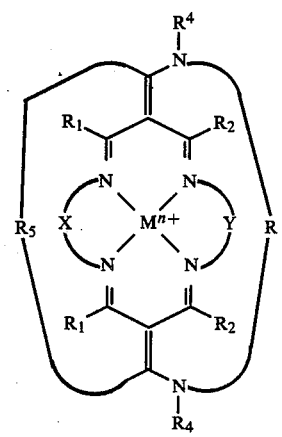

II wherein:
M, n+, R$_1$, R$_2$, R$_4$, X and Y are as defined in claim 1;
R is a polymethylene group containing from 4 to about 12 carbon atoms, a polymethylene group containing from 4 to about 12 carbon atoms and substituted by a methyoxycarbonyl group, or a grouping of the formula —(CH$_2$)$_a$—G—(CH$_2$)$_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4; and
R$_5$ is a polymethylene group containing from 7 to about 12 carbon atoms or an m- or p-xylylene group.

35. A salt according to claim 34 wherein the anion is selected from the group comprising hexafluorophosphate, tetrachlorozincate, perchlorate, hexafluoroarsenate, fluoroborate, trifluoromethylsulfonate and the halides.

36. A salt according to claim 34 wherein X and Y are each a trimethylene group.

37. A salt according to claim 34 wherein each R$_1$ is hydrogen.

38. A salt according to claim 34 wherein each R$_2$ is a methyl group.

39. A salt according to claim 34 wherein each R$_4$ is hydrogen.

40. A salt according to claim 34 wherein R$_5$ is a polymethylene group containing from 7 to 10 carbon atoms.

41. A salt according to claim 34 wherein R is a polymethylene group containing 6 to 7 carbon atoms or an m-xylylene group.

42. A salt according to claim 35 wherein said anion is hexafluorophosphate.

43. A salt according to claim 42 wherein X and Y are each a trimethylene group, each $R_1$ is hydrogen, each $R_2$ is a methyl group, each $R_4$ is hydrogen, $R_5$ is a polymethylene group containing from 7 to 10 carbon atoms and R is a polymethylene group containing 6 to 7 carbon atoms or an m-xylylene group.

44. A salt according to claim 1 wherein said cationic metal complex is of the formula:

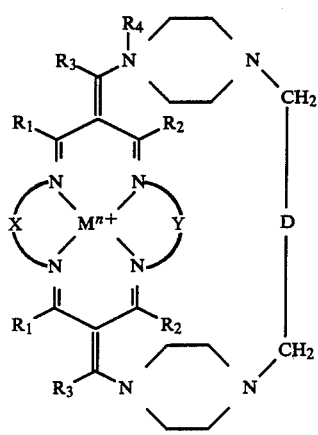

XVIII wherein:
M, n+, $R_1$, $R_2$, $R_3$, X and Y are as defined in claim 1; and
D is a 1,3-phenylene group, a 1,4-phenylene group, a 1,4-phenylene group substituted by one or more methyl groups, a 9,10-anthracene group or a 2,6-pyridylene group.

45. A salt according to claim 44 wherein the anion is hexafluorophosphate, tetrachlorozincate, perchlorate, hexafluoroarsenate, fluoroborate, trifluoromethylsulfonate and the halides.

46. A salt according to claim 44 wherein $M^{n+}$ is $Co^{2+}$, $Fe^{2+}$ or $Cu^{2+}$.

47. A salt according to claim 44 wherein X is a trimethylene group or a 2-(N-methyl-2-pyridino) group.

48. A salt according to claim 44 wherein Y is a trimethylene group.

49. A salt according to claim 44 wherein each $R_1$ is hydrogen.

50. A salt according to claim 44 wherein each $R_2$ is a methyl group.

51. A salt according to claim 44 wherein each $R_2$ is a methyl group or a phenyl group.

52. A salt according to claim 44 wherein D is a 1,3-phenylene group, a 1,4-phenylene group, a tetramethylphenylene group, a 9,10-anthracene group or a 2,6-pyridylene group.

53. A salt according to claim 45 wherein the anion is hexafluorophosphate or chloride.

54. A salt according to claim 53 wherein $M^{n+}$ is $Co^{2+}$, $Fe^{2+}$, or $Cu^{2+}$, X is a trimethylene group or a 2-(N-methyl-2-pyridino) group, Y is a trimethylene group, each $R_1$ is hydrogen, each $R_2$ is a methyl group, each $R_3$ is a methyl group or a phenyl group and D is a 1,3-phenylene group, a 1,4-phenylene group, a tetramethyphenylene group, a 9,10-anthracene group or a 2,6-pyridylene group.

55. The salts according to claim 20 wherein M is cobalt, n is 2, X and Y are each a trimethylene group, each $R_1$ is hydrogen, each $R_2$, $R_3$ and $R_4$ is a methyl group, R is a polymethylene group containing 4 to 6 carbon atoms and the anion is hexafluorophosphate, namely:
[(2,3,8,9,11,17-hexamethyl-3,8,12,16,19,23-hexaazabicyclo[8.7.7]tetracosa-1,9,11,16,18,23-hexaene-κ⁴N)cobalt(II)] hexafluorophosphate;
[(2,3,9,10,12,18-hexamethyl-3,9,13,17,20,24-hexaazabicyclo[9.7.7]pentacosa-1,10,12,17,19,24-hexaene-κ⁴N)cobalt(II)]hexafluorophosphate; and
[(2,3,10,11,13,19-hexamethyl-3,10,14,18,21,25-hexaazabicyclo[10.7.7]hexacosa-1,11,13,18,20,25-hexaene-κ⁴N)cobalt(II)] hexafluorophosphate.

56. The salts according to claim 20 wherein M is cobalt, n is 2, X and Y are each a trimethylene group, each $R_1$ is hydrogen, each $R_2$ and $R_4$ is a methyl group, each $R_3$ is a phenyl group, R is a polymethylene bridge containing 4 to 6 carbon atoms and the anion is hexafluorophosphate, namely:
[(3,8,11,17-tetramethyl-2,9-diphenyl-3,8,12,16,19,23-hexaazabicyclo[8.7.7]tetracosa-1,9,11,16,18,23-hexaene-κ⁴N)cobalt(II)] hexafluorophosphate;
[(3,9,12,18-tetramethyl-2,10-diphenyl-3,9,13,17,20,24-hexaazabicyclo[9.7.7]pentacosa-1,12,17,19,24-hexaene-κ⁴N)cobalt(II)] hexafluorophosphate; and
[(3,10,13,19-tetramethyl-2,11-diphenyl-3,10,14,18,21,25-hexaazabicyclo[10.7.7]hexacosa-1,13,18,20,25-hexaene-κ⁴N)cobalt(II)]hexafluorophosphate.

57. The salts according to claim 20 wherein M is cobalt n is 2, X and Y are each a trimethylene group, each $R_1$ and $R_4$ is hydrogen, each $R_2$ and $R_3$ is a methyl group, R is a pentamethylene, hexamethylene, or 4-azamethylhexamethylene group and the anion is hexafluorophosphate, namely:
[(2,10,12,18-tetramethyl-3,9,13,17,20,24-hexaazabicyclo[9.7.7]pentacosa-1,10,12,17,19,24-hexaene-κ⁴N)cobalt(II)] hexafluorophosphate;
[(2,11,13,19-tetramethyl-3,10,14,18,21,25-hexaazabicyclo[10.7.7]hexacosa-1,11,13,18,20,25-hexaene-κ⁴N)cobalt(II)] hexafluorophosphate; and
[(2,7,12,14,20-pentamethyl-3,7,11,15,19,22,26-heptaazabicyclo[11.7.7]heptacosa-1,12,14,19,21,26-hexaene-κ⁴N)cobalt(II)] hexafluorophosphate.

58. The salts according to claim 20 wherein M is cobalt, n is 2, X and Y are each a trimethylene group, each $R_1$ and $R_4$ is hydrogen, each $R_2$ is a methyl group, each $R_3$ is a phenyl group, R is pentamethylene or hexamethylene and the anion is hexafluorophosphate, namely:
[(12,18-dimethyl-2,10-diphenyl-3,9,13,17,20,24-hexaazabicyclo[9.7.7]pentacosa-1,10,12,17,19,24-hexaene-κ⁴N)cobalt(II)] hexafluorophosphate; and
[(13,19-dimethyl-2,11-diphenyl-3,10,14,18,21,25-hexaazabicyclo[10.7.7]hexacosa-1,11,13,18,20,25-hexaene-κ⁴N)cobalt(II)] hexafluorophosphate.

59. The salt according to claim 20 wherein M is cobalt, n is 2, X is a 2-(N-methyl-2-pyridino)-trimethylene group, Y is a trimethylene group, each $R_1$ is hydrogen, each $R_2$, $R_3$ and $R_4$ is a methyl group, R is a hexamethylene group and the anion is hexafluorophosphate, namely:
[(2,3,10,11,13,19-hexamethyl-23-(2-pyridyl)-3,10,14,18,21,25-hexaazabicyclo[10.7.7]hexacosa- 1,11,13,18,20,25-hexaene-κ⁴N)cobalt(II)] hexafluorophosphate.

60. The salt according to claim 32 wherein M is cobalt, n is 2, X and Y are each a trimethylene group, each $R_1$ and $R_4$ is hydrogen, each $R_2$ and $R_6$ is a methyl group, $R_5$ is a heptamethylene group and the anion is hexafluorophosphate, namely:
[(12,18-dimethyl-2,10bis-methylamino-13,17,20,24-tetraazabicyclo[9.7.7]pentacosa-1,10,12,17,19,24-hexaene-κ⁴N)cobalt(II)] hexafluorophosphate.

61. The salt according to claim 53 wherein M is cobalt, n is 2, X and Y are each a trimethylene group, each $R_1$ is hydrogen, each $R_2$ and $R_3$ is a methyl group, D is a tetramethyl-1,4-phenylene group and the anion is hexafluorophosphate, namely:
[(2,9,10,17,19,25,33,34-octamethyl-3,6,13,16,20,24,27,31-octaazapentacyclo[16.7.7.2⁸,¹¹.2³,⁶.2¹³,¹⁶]octatriaconta-1,8,10,17,19,24,26,31,33-nonaene-κ⁴N)cobalt(II)] hexafluorophosphate.

62. A salt according to claim 1 dispersed in an aqueous solvent or an organic solvent which does not destroy the complex.

63. An adduct of salt according to claim 1 and molecular oxygen or carbon monoxide.

64. A salt comprising a cationic metal complex of the formula:

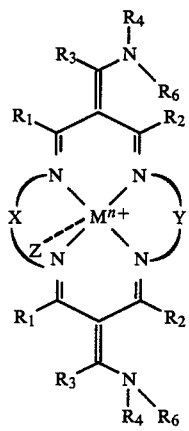

XVIIA wherein:
M is Co, Fe, Cu or Mn;
n+ is a positive oxidation state of M, n being not greater than 3;
X and Y are each independently an o-phenylene, ethylene, trimethylene, 2-(2-pyridyl)-trimethylene, 2-methyl substituted trimethylene or 2-(N-methyl-2-pyridino)-trimethylene group;
each $R_1$ independently is hydrogen or a methyl group;
each $R_2$ independently is hydrogen or a methyl group;
each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;
each $R_4$ independently is hydrogen, an alkyl group containing not more than about 4 carbon atoms, a cyanoalkyl group containing not more than about four carbon atoms, a phenyl group or a benzyl group;
each $R_6$ independently is hydrogen or a methyl group; or the two $R_6$ groups together form a nitrogen-nitrogen bridge said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula —$(CH_2)_a$—G—$(CH_2)_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4;
or the two $NR_4R_6$ groups together form a bis-piperazino bridge of the formula:

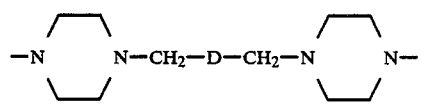

where D is a 1,3-phenylene group, a 1,4-phenylene group, a 1,4-phenylene group substituted by one or more methyl groups, a 9,10-anthracene group or a 2,6-pyridylene group,
subject to the proviso that when the two $R_3$ groups do not form a carbon-carbon bridge, either the two $R_6$ groups must form a nitrogen-nitrogen bridge or the two $NR_4R_6$ groups must form a bis-piperazino bridge; and
Z is an electron donor selected from the group consisting of the halide ions, cyanate, thiocyanate, azide, acetonitrile, water, an alkanol containing not more than about five carbon atoms, pyridine, 4-aminopyridine, imidazole and N-methylimidazole.

65. A salt according to claim 64 wherein the anion is selected from the group comprising hexafluorophosphate, tetrachlorozincate, perchlorate, hexafluoroarsenate, fluoroborate, trifluoromethylsulfonate and the halides.

66. A salt according to claim 64 wherein $M^{n+}$ is $Co^{2+}$, $Co^{3+}$, $Fe^{2+}$, $Fe^{3+}$, $Cu^{2+}$, $Mn^{2+}$, or $Mn^{3+}$.

67. A salt according to claim 64 wherein X and Y are each a trimethylene group.

68. A salt according to claim 64 wherein each $R_1$ is hydrogen.

69. A salt according to claim 64 wherein each $R_2$ is a methyl group.

70. A salt according to claim 64 wherein $R_3$ is hydrogen, a methyl group, a phenyl group, a t-butyl group, an n-heptyl group, an n-heptadecyl group a 4-methoxyphenyl group, a 4-chlorophenyl group, a 4-fluorophenyl group or a 3,5-dimethoxyphenyl group, or the two $R_3$ groups together form a polymethylene group containing 7 to 12 carbon atoms or a m-xylylene group.

71. A salt according to claim 64 wherein $R_4$ is hydrogen, a methyl group, an n-propyl group or a benzyl group.

72. A salt according to claim 64 wherein the two $R_6$ groups together form a nitrogen-nitrogen bridge, said nitrogen bridge comprising a polymethylene bridge of 4 to about 8 carbon atoms, an m- or p-xylylene group or a —$(CH_2)_3$—(9,9-flourylene)—$(CH_2)_3$— group.

73. A salt according to claim 65 wherein said anion is hexafluorophosphate or chloride.

74. A salt according to claim 64 wherein said cationic metal complex is of the formula:

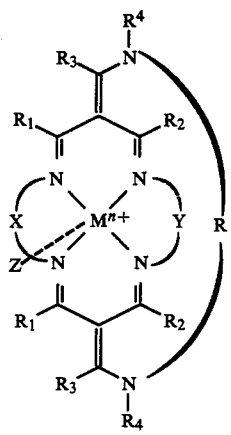

IA wherein:

M, n+, $R_1$, $R_2$, $R_4$, X, Y and Z are as defined in claim 64; each $R_3$ independently is hydrogen, an alkyl group containing not more than about 17 carbon atoms, a benzyl group, a phenyl group, or a phenyl group substituted by a halogen atom or by one or two methoxy groups;

R is a polymethylene group containing from 4 to about 12 carbon atoms, a polymethylene group containing from 4 to about 12 carbon atoms and substituted by a methoxycarbonyl group, or a grouping of the formula —$(CH_2)_a$—G—$(CH_2)_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4.

75. A salt according to claim 74 wherein the anion is selected from the group comprising hexafluorophosphate, tetrachlorozincate, perchlorate, hexafluoroarsenate, fluoroborate, trifluoromethylsulfonate and the halides.

76. A salt according to claim 74 wherein $M^{n+}$ is $Co^{2+}$, $Co^{3+}$, $Fe^{2+}$, $Fe^{3+}$, $Cu^{2+}$, $Mn^{2+}$ or $Mn^{3+}$.

77. A salt according to claim 74 wherein X and Y are each a trimethylene group.

78. A salt according to claim 74 wherein each $R_1$ is hydrogen.

79. A salt according to claim 74 wherein each $R_2$ is a methyl group.

80. A salt according to claim 74 wherein each $R_3$ is hydrogen, a methyl group, a phenyl group, a t-butyl group, an n-heptyl group, a 4-methoxyphenyl group, a 4-chlorophenyl group, a 4-fluorophenyl group or a 3,5-dimethoxyphenyl group.

81. A salt according to claim 74 wherein each $R_4$ is hydrogen, a methyl group or a benzyl group.

82. A salt according to claim 74 wherein R is a polymethylene bridge of 4 to about 8 carbon atoms, an m- or p-xylylene group or a —$(CH_2)_3$—(9,9-flourylene)—$(CH_2)_2)_3$— group.

83. A salt according to claim 74 wherein Z is chloride, cyanate, thiocyanate, azide, ethanol, acetonitrile, pyridine, 4-aminopyridine, imidazole or N-methylimidazole.

84. A salt according to claim 75 wherein said anion is hexafluorophosphate or chloride.

85. A salt according to claim 84 wherein $M^{n+}$ is $Co^{2+}$, $Co^{3+}$, $Fe^{2+}$, $Fe^{3+}$, $Mn^{2+}$, $Mn^{3+}$ or $Cu^{2+}$, X and Y are each a trimethylene group, each $R_1$ is hydrogen, each $R_2$ is a methyl group, each $R_3$ is hydrogen, a methyl group, a phenyl group, a t-butyl group, an n-heptyl group, a 4-methoxyphenyl group, a 4-chlorophenyl group, a 4-fluorophenyl group or a 3,5-dimethoxyphenyl group, each $R_4$ is hydrogen, a methyl group or a benzyl group, R is a polymethylene bridge of 4 to about 8 carbon atoms, an m- or p-xylylene group or a —$(CH_2)_3$—(9,9-fluorylene)—$(CH_2)_3$— group and Z is chloride, cyanate, thiocyanate, azide, ethanol, acetonitrile, pyridine, 4-aminopyridine, imidazole or N-methylimidazole.

86. A salt according to claim 64 wherein said cationic metal complex of the formula:

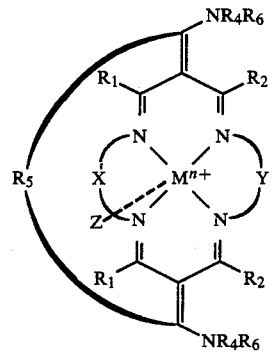

IIIA wherein M, n+, $R_1$, $R_2$, X, Y and Z are as defined in claim 64;

each $R_4$ independently is hydrogen; an alkyl group containing not more than about 4 carbon atoms or benzyl;

each $R_6$ independently is hydrogen or a methyl group; and $R_5$ is a polymethylene group containing from about 7 to about 12 carbon atoms or a m- or p-xylylene group.

87. A salt according to claim 86 wherein the anion is selected from the group comprising hexafluorophosphate, tetrachlorozincate, perchlorate, hexafluoroarsenate, fluoroborate, trifluoromethylsulfonate and the halides.

88. A salt according to claim 86 wherein M is cobalt or iron, n is 2, each $R_1$ is hydrogen, each $R_2$ and $R_4$ is hydrogen or a methyl group, each $R_3$ is hydrogen, a methyl group, an ethyl group, a n-propyl group or a benzyl group, X and Y are each a trimethylene group, $R_5$ is a polymethylene group containing 7 to 12 carbon atoms, Z is chloride, acetonitrile, or water and said anion is hexafluorophosphate.

89. A salt according to claim 64 wherein said cationic metal complex is of the formula:

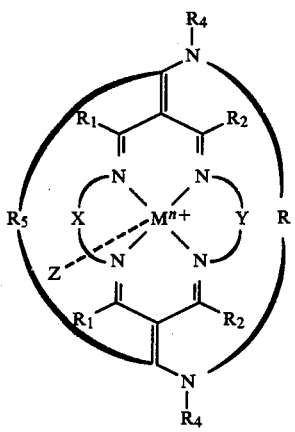

IIA wherein M, $n^{30}$, $R_1$, $R_2$, $R_4$, X, Y and Z are as defined in claim 64;

R is a polymethylene group containing from 4 to about 12 carbon atoms, a polymethylene group containing from 4 to about 12 carbon atoms and substituted by a methoxycarbonyl group, or a grouping of the formula —$(CH_2)_a$—G—$(CH_2)_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylane group, a sulfur atom, an imino group or a methylimino group, subject to the proviso that when G is a sulfur atom, a imino group or a methylimino group, the sum of a and b is at least 4; and $R_5$ is a polymethylene group containing from 7 to about 12 carbon atoms or an m- or p-xylylene group.

90. A salt according to claim 89 wherein the anion is selected from the group comprising hexafluorophosphate, tetrachlorozincate, perchlorate, hexafluoroarsenate, fluoroborate, trifluoromethylsulfonate and the halides.

91. A salt according to claim 64 wherein said cationic metal complex is of the formula:

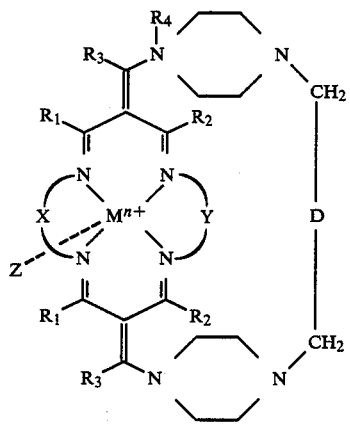

XVIIIA wherein M, $n^+$, $R_1$, $R_2$, $R_3$, X, Y and Z are as defined in claim 64; and D is a 1,3-phenylene group, a 1,4-phenylene group, a 1,4-phenylene group substituted by one or more methyl groups, a 9,10-anthracene group or a 2,6-pyridylene group.

92. A salt according to claim 91 wherein the anion is selected from the group comprising hexafluorophosphate, tetrachlorozincate, perchlorate, hexafluoroarsenate, fluoroborate, trifluoromethylsulfonate and the halides.

93. A salt according to claim 91 wherein $M^{n+}$ is $Co^{2+}$ or $Fe^{2+}$.

94. A salt according to claim 91 wherein X and Y are each a trimethylene group.

95. A salt according to claim 91 wherein each $R_1$ is hydrogen.

96. A salt according to claim 91 wherein each $R_2$ is a methyl group.

97. A salt according to claim 91 wherein each $R_3$ is a methyl group.

98. A salt according to claim 91 wherein each D is a 1,3-phenylene group, a tetramethyl-1,4-phenylene group or a 9,10-anthracene group 99. A salt according to claim 91 where Z is methanol, chloride or water.

100. A salt according to claim 92 wherein said anion is said hexafluorophosphate.

101. A salt according to claim 100, wherein each $R_1$ is hydrogen , each $R_2$ and $R_3$ is a methyl group, D is a 1,3-phenylene group, a tetramethyl-1,4-phenylene group or a 9,10-anthracene group and Z is methanol, chloride or water.

102. The salts according to claim 75 wherein M is iron, n is 2, X and Y are each a trimethylene group, each $R_1$ is hydrogen, each $R_2$ is a methyl group, each $R_3$ is a p-methoxypheny, p-chlorophenyl, p-fluorophenyl, n-heptyl or methyl group, each $R_4$ is a methyl group, R is m-xylylene, Z is chloride and the anion is hexafluorophosphate, namely:

[chloro(2,3,11,12,14,20-hexamethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-n-heptyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-p-methoxyphenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-p-chlorophenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate; and

[chloro(2,12-di-p-fluorophenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate.

103. The salt according to claim 75 wherein M is cobalt, n is 2, X and Y are each a trimethylene group, each $R_1$ is hydrogen, each $R_2$ is a methyl group, R is a phenyl group, each $R_4$ is hydrogen, R is a m-xylylene group, Z is acetonitrile and the anion is hexafluorophosphate, namely:

[acetonitrile(14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)cobalt(II)] hexafluorophosphate.

104. The salts according to claim 75 wherein M is iron, n is 2, X and Y are each a trimethylene group, each $R_1$ is hydrogen, each $R_2$ is a methyl group, each $R_3$ is a methyl group, each $R_4$ is a methyl or benzyl group, R is a m-xylylene group, Z is acetonitrile and the anion is hexafluorophosphate namely:

[acetonitrile(2,3,11,12,14,20-hexamethyl-3,11,15,19,22,26-hexaazatricyclo [11.7.7.1$^{5,9}$]octacosa-1,5,7,9(28),12,14,19,21,26-nonaene-κ$^4$N)iron(II)] hexafluorophosphate; and

[acetonitrile(3,11-dibenzyl-2,12,14,20-tetramethyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate.

105. The salts according to claim 75 wherein M is iron, n is 2, X and Y are each a trimethylene group, each $R_1$ is hydrogen, each $R_2$ is a methyl group, each $R_3$ is a phenyl group, each $R_4$ is a methyl or benzyl group, R is a m-xylylene group, Z is acetonitrite and the anion is hexafluorophosphate, namely:

[acetonitrile(3,11,14,20-tetramethyl-2,12-diphenyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate; and

[acetonitrile(3,11-dibenzyl-14,20-dimethyl-2,12-diphenyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate.

106. The salts according to claim 75 wherein M is cobalt, n is 2, X and Y are each a trimethylene group, each $R_1$ is hydrogen, each $R_2$ and $R_3$ is a methyl group, each $R_4$ is hydrogen, R is a heptamethylene or m-xylylene group, Z is acetonitrile and the anion is hexafluorophosphate, namely:

[acetonitrile(2,12,14,20-tetramethyl-3,11,15,19,22,26-hexaazabicyclo[11.7.7]heptacosa-1,12,14,19,21,26-hexaene-κ$^4$N)cobalt(II)] hexafluorophosphate; and

[acetonitrile(2,12,14,20-tetramethyl-3,11,15,19,22,26-hexaazatricyclo[11.7.7.1$^{5,9}$]octacosa-1,5,7,9(28),12,14,19,21,26-nonaene-κ$^4$N)cobalt(II)] hexafluorophosphate.

107. The salts according to claim 75 wherein M is cobalt, n is 2, X and Y are each a trimethylene group, each $R_1$ is hydrogen, each $R_2$ is a methyl group, each $R_3$ is hydrogen, each $R_4$ is a methyl group, R is a hexamethylene group, Z is acetonitrile and the anion is hexafluorophosphate, namely:

[acetonitrile(3,10,13,19-tetramethyl-3,10,14,18,21,25-hexaazabicyclo[10.7.7]hexacosa-1,11,13,18,20,25-hexaene-κ$^4$N)cobalt(II)] hexafluorophosphate.

108. The salts according to claim 87 wherein M is iron, n is 2, X and Y are each a trimethylene group, each $R_1$ is hydrogen, each $R_2$, $R_4$ and $R_6$ is a methyl group, $R_5$ is a heptamethylene or octamethylene group, Z is chloride and the anion is hexafluorophosphate, namely:

[chloro(2,10-bis-dimethylamino-12,18-dimethyl-13,17,20,24-tetraazabicyclo[9.7.7]pentacosa-1,10,12,17,19,24-hexaene-κ$^4$N)iron(II)] hexafluorophosphate; and

[chloro(2,11-bis-dimethylamino-13,19-dimethyl-14,18,21,25-tetraazabicyclo[10.7.7]hexacosa-1,11,13,18,20,25-hexaene-κ$^4$N)iron(II)] hexafluorophosphate.

109. The salt according to claim 87 where M is cobalt, n is 2, X and Y are each a trimethylene group, each $R_1$ is hydrogen, each $R_2$ is a methyl group, each $R_4$ is a n-propyl, $R_6$ is hydrogen, $R_5$ is a heptamethylene group, Z is acetonitrile and the anion is hexafluorophosphate, namely:

[acetonitrile(12,18-dimethyl-2,10-bis-propylamino-13,17,20,24-tetraazabicyclo[9.7.7]pentacosa-1,10,12,17,19,24-hexaene-κ$^4$N)cobalt(II)] hexafluorophosphate.

110. The salt according to claim 87 wherein M is cobalt, n is 2, X and Y are each a trimethylene group, each $R_1$ is hydrogen, each $R_2$, $R_4$ and $R_6$ is a methyl group, $R_5$ is an octamethylene group, Z is acetonitrile and the anion is hexafluorophosphate, namely:

[acetonitrile(2,11-bis-dimethylamino-13,19-dimethyl-14,18,21,25-tetraazabicyclo[10.7.7]hexacosa-1,11,13,18,20,25-hexaene-κ$^4$N)cobalt(II)] hexafluorophosphate.

111. A salt according to claim 64 dispersed in an aqueous solvent or an organic solvent which does not destroy the complex.

112. An adduct of a salt according to claim 64 and molecular oxygen or carbon monoxide.

113. A salt comprising a cationic metal complex of the formula:

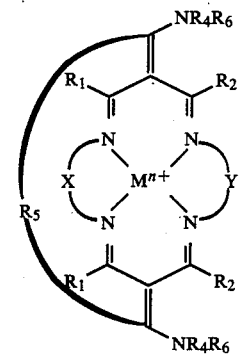

III wherein:
$M^{n+}$ is $Ni^{2+}$;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_4$ independently is hydrogen, an alkyl group containing not more than about 4 carbon atoms, a cyanoalkyl group containing not more than about four carbon atoms, a phenyl group or a benzyl group;

each $R_6$ independently is hydrogen or a methyl group; and $R_5$ is a polymethylene group containing from about 7 to about 12 carbon atoms or a m- or p-xylylene group.

114. A salt according to claim 113 wherein the anion is selected from the group comprising hexafluorophosphate, tetrachlorozincate, perchlorate, hexafluoroarsenate, fluoroborate, trifluoromethylsulfonate and the halides.

115. A salt comprising a cationic metal complex of the formula:

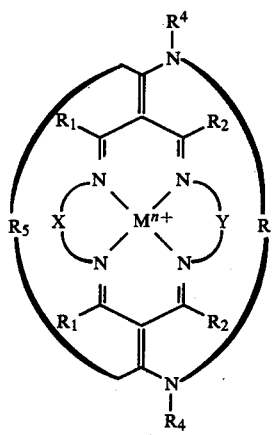

II wherein:

$M^{n+}$ is $Ni^{2+}$;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_4$ independently is hydrogen, an alkyl group containing not more than about 4 carbon atoms, a cyanoalkyl group containing not more than about four carbon atoms, a phenyl group or a benzyl group;

R is a polymethylene group containing from 4 to about 12 carbon atoms, a polymethylene group containing from 4 to about 12 carbon atoms and substituted by a methyoxycarbonyl group, or a grouping of the formula —$(CH_2)_a$—G—$(CH_2)_b$— where a and b are each independently 1, 2 or 3 G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4; and $R_5$ is a polymethylene group containing from 7 to about 12 carbon atoms or an m- or p-xylylene group.

116. A salt according to claim 115 wherein the anion is selected from the group comprising hexafluorophosphate, tetrachlorozincate, perchlorate, hexafluoroarsenate, fluoroborate, trifluoromethylsulfonate and the halides.

117. A salt comprising a cationic metal complex of the formula:

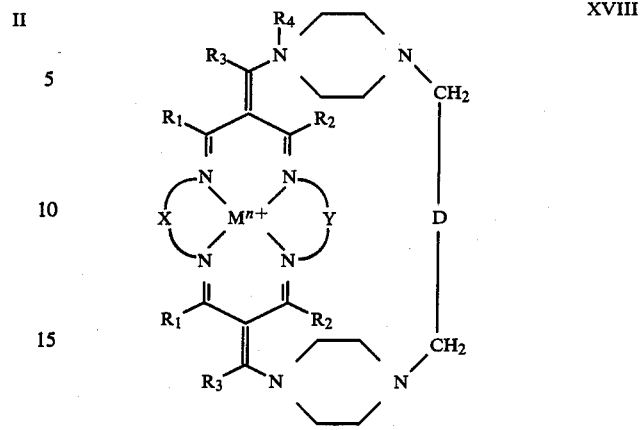

XVIII wherein:

$M^{n+}$ is $Ni^{2+}$;

X and Y are each independently an o-phenylene, ethylene, trimethylene, 2-(2-pyridyl)-trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group; and D is a 1,3-phenylene group, a 1,4-phenylene group, a 1,4-phenylene group substituted by one or more methyl groups, a 9,10-anthracene group or a 2,6-pyridylene group.

118. A salt according to claim 117 wherein the anion is selected from the group comprising hexafluorophosphate, tetrachlorozincate, perchlorate, hexafluoroarsenate, fluoroborate, trifluormethylsulfonate and the halides.

119. A method for removing molecular oxygen from a gaseous mixture which comprises:

exposing a salt of the formula:

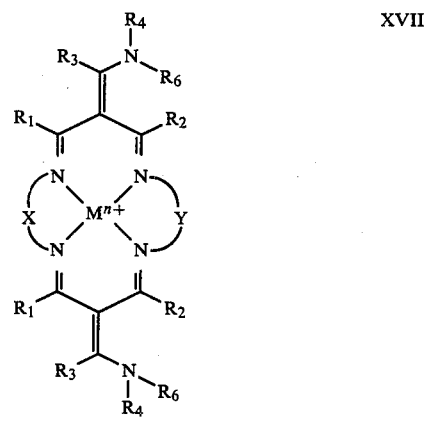

XVII wherein:

M is Co, Fe, Cu or Mn;

$n+$ is a positive oxidation state of M, n being not greater than 3;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;

each $R_4$ independently is hydrogen, an alkyl group containing not more than about 4 carbon atoms, a cyanoalkyl group containing not more than about four carbon atoms, a phenyl group or a benzyl group;

each $R_6$ independently is hydrogen or a methyl group; or the two $R_6$ groups together form a nitrogen-nitrogen bridge, said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula:

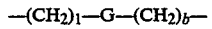

where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group, subject to the proviso that when G is a sulfur atom, a imino group or a methylimino group, the sum of a and b is at least 4;

or the two $NR_4R_6$ groups together form a bis-piperazino bridge of the formula

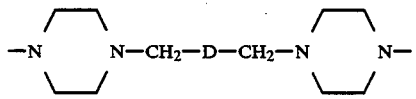

where D is a 1,3-phenylene group, a 1,4-phenylene group, a 1,4-phenylene group substituted by one or more methyl groups, a 9,10-anthracene group or a 2,6-pyridylene group, subject to the proviso that when the two $R_3$ groups do not form a carbon-carbon bridge, either the two $R_6$ groups must form a nitrogen-nitrogen bridge or the two $NR_4R_6$ groups must form a bis-piperazino group, to said mixture thereby allowing said cationic metal complex to complex molecular oxygen and thus to absorb oxygen from said gaseous mixture.

120. A method according to claim 119 wherein, after said cationic metal complex has complexed oxygen, and salt is withdrawn from contact with said gaseous mixture and is placed in a second environment wherein the oxygen partial pressure is less than the pressure in equilibrium with the oxygenated form of said salt under the conditions in said second environment, thereby allowing said cationic metal complex to decomplex molecular oxygen and thereby release oxygen into said second environment.

121. A method according to claim 120 wherein said oxygen partial pressure in said second environment is lower than the oxygen partial pressure in said first environment.

122. A method according to claim 121 wherein said first environment comprises the lungs of a mammal and said second environment comprises the non-lung tissues of said mammal.

123. A method according to claim 120 wherein said second environment is at a higher temperature than said first environment.

124. A method according to claim 120 wherein said salt comprises:

[(2,3,8,9,11,17-hexamethyl-3,8,12,16,19,23-hexaazabicyclo[8.7.7]tetracosa-1,9,11,16,18, 23-hexaene-$\kappa^4$N)cobalt(II)] hexafluorophosphate;

[(2,3,9,10,12,18-hexamethyl-3,9,13,17,20,24-hexaazabicyclo[9.7.7]-pentacosa-1,10,12, 17,19,24-hexaene-$\kappa^4$N)cobalt(II)] hexafluorophosphate;

[(2,3,10,11,13,19-hexamethyl-3,10,14,18,21,25-hexaazabicyclo[10.7.7]hexacosa-1,11,13,18, 20,25-hexaene-$\kappa^4$N)cobalt(II)] hexafluorophosphate;

[(3,8,11,17-tetramethyl-2,9-diphenyl-3,8,12,16,19,23-hexaazabicyclo[8.7.7]tetracosa-1,9,11,16,18,23-hexaene-$\kappa^4$N)cobalt(II)] hexafluorophosphate;

[(3,9,12,18-tetramethyl-2,10-diphenyl-3,9,13,17,20,24-hexaazabicyclo[9.7.7]pentacosa-1,10, 17,19,24-hexaene-$\kappa^4$N)cobalt(II)] hexafluorophosphate;

[(3,10,13,19-tetramethyl-2,11-diphenyl-3,10,14,18,21,25-hexaazabicyclo[10.7.7]hexacosa-1,11 18,20,25-hexaene-$\kappa^4$N)cobalt(II)] hexafluorophosphate;

[(2,10,12,18-tetramethyl-3,9,13,17,20,24-hexaazabicyclo[9.7.7]pentacosa-1,10,12,17,19, 24-hexaene-$\kappa^4$N)cobalt(II)] hexafluorophosphate;

[(2,11,13,19-tetramethyl-3,10,14,18,21,25-hexaazabicyclo[10.7.7]hexacosa-1,11,13,18, 20,25-hexaene-$\kappa^4$N)cobalt(II)] hexafluorophosphate;

[(2,7,12,14,20-pentamethyl-3,7,11,15,19,22,26-heptaazabicyclo[11.7.7]heptacosa-1,12,14, 19,21,26-hexaene-$\kappa^4$N)cobalt(II)] hexafluorophosphate;

[(12,18-dimethyl-2,10-diphenyl-3,9,13,17,20,24-hexaazabicyclo[9.7.7]pentacosa-1,10, 12,17,19,24-hexaene-$\kappa^4$N)cobalt(II)] hexafluorophosphate;

[13,19-dimethyl-2,11-diphenyl-3,10,14,18,21,25-hexaazabicyclo[10.7.7]hexacosa-1,11,13, 18,20,25-hexaene-$\kappa^4$N)cobalt(II)] hexafluorophosphate;

[(2,3,10,11,13,19-hexamethyl-23-(2-pyridyl)-3,10,14,18,21,25-hexaazabicyclo[10.7.7]hexacosa-1,11,13,18,20,25-hexaene-$\kappa^4$N)cobalt(II)] hexafluorophosphate;

[(12,18-dimethyl-2,10-bis-methylamino-13,17,20,24-tetraazabicyclo[9.7.7]pentacosa-1,10,12,17,19,24-hexaene-$\kappa^4$N)cobalt(II)] hexafluorophosphate; or

[(2,9,10,17,19,25,33,34-octamethyl-3,6,13,16,20,24,27,31-octaazapentacyclo[16.7.7.2$^{8,11}$.2$^{3,6}$.2$^{13,16}$]octatriaconta-1,8,10,17,19,24,26,31,33-nonaene-$\kappa^4$N)cobalt(II)] hexafluorophosphate.

125. A method for removing molecular oxygen from a gaseous mixture, which comprises:
exposing a salt of the formula:

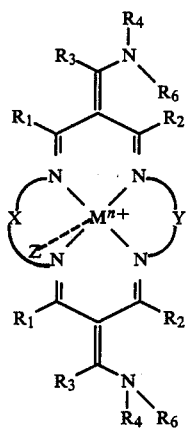

XVIIA wherein:

M is Co, Fe, Cu or Mn;

$n^+$ is a positive oxidation state of M, n being not greater than 3;

X and Y are each independently an o-phenylene, ethylene, trimethylene 2-(2-pyridyl)-trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;

each $R_4$ independently is hydrogen, an alkyl group containing not more than about 4 carbon atoms, a cyanoalkyl group containing not more than about four carbon atoms, a phenyl group or a benzyl group;

each $R_6$ independently is hydrogen or a methyl group; or the two $R_6$ groups together form a nitrogen-nitrogen bridge said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula —$(CH_2)_a$—G—$(CH_2)_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group or a methylimino group, subject to the proviso that when G is a sulfur atom, a imino group or a methylimino group, the sum of a and b is at least 4;

or the two $NR_4R_6$ groups together form a bis-piperazino bridge of the formula:

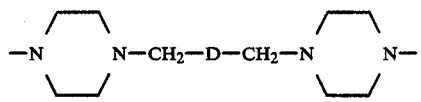

where D is a 1,3-phenylene group, a 1,4-phenylene group, a 1,4-phenylene group substituted by one or more methyl groups, a 9,10-anthracene group or a 2,6-pyridylene group, subject to the proviso that when the two $R_3$ groups do not form a carbon-carbon bridge, either the two $R_6$ groups must form a nitrogen-nitrogen bridge or the two $NR_4R_6$ groups must form a bis-piperazino group; and Z is an electron donor selected from the group consisting of the halide ions, cyanate, thiocyanate, azide, acetonitrile, water, an alkanol containing not more than about five carbon atoms, pyridine, 4-aminopyridine, imidazole and N-methylimidazole, to said mixture thereby allowing said cationic metal complex to complex molecular oxygen and thus to absorb oxygen from said gaseous mixture.

126. A method according to claim 125 wherein, after said cationic metal complex has complexed oxygen, said salt is withdrawn from contact with said gaseous mixture and is placed in a second environment wherein the oxygen partial pressure is less than the oxygen pressure in equilibrium with the oxygenated form of said salt under the conditions in said second environment, thereby allowing said cationic metal complex to decomplex molecular oxygen and thereby release oxygen into said second environment.

127. A method according to claim 126 wherein said oxygen partial pressure in said second environment is lower than the oxygen partial pressure in said first environment.

128. A method according to claim 127 wherein said first environment comprises the lungs of a mammal and said second environment comprises the non-lung tissues of said mammal.

129. A method according to claim 126 wherein said second environment is at a higher temperature than said first environment.

130. A method according to claim 125 wherein said salt comprises:

[chloro(2,3,11,12,14,20-hexamethyl-3,11,15,19,22,26-hexaazatricyclo[11.7.7.1$^{5,9}$]octacosa-1,5,7,9(28),12,14,19,21,26-nonaene-κ$^4$Niron(II)] hexafluorophosphate;

[chloro(2,12-di-n-heptyl-3,11,14,20-tetramethyl-3,11,15,19,22,26-hexaazatricyclo-[11.7.7.1$^{5,9}$]octacosa-1,5,7,9(28),12,14,19,21,26-nonaene-κ$^4$N)iron(II)] hexafluorophosphate;

[chloro(2,12-di-p-methoxyphenyl-3,11,14,20-tetramethyl-3,11,15,19,22,26-hexaazatricyclo[11.7.7.1$^{5,9}$]octacosa-1,5,7,9(28),12,14,19,21,26-nonaene-κ$^4$N)iron-(II)] hexafluorophosphate;

[chloro(2,12-di-p-chlorophenyl-3,11,14,20-tetramethyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate;

[chloro(2,12-di-p-fluorophenyl-3,11,14,20-tetramethyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate;

[acetonitrile(14,20-dimethyl-2,12-diphenyl-3,11,15,19,22,26-hexaazatricyclo[11.7.7.1$^{5,9}$]octacosa-1,5,7,9(28),12,14,19,21,26-nonaene-κ$^4$N)cobalt(II)] hexafluorophosphate;

[acetonitrile(2,3,11,12,14,20-hexamethyl-3,11,15,19,22,26-hexaazatricyclo [11.7.7.1$^{5,9}$]octacosa-1,5,7,9(28),12,14,19,21,26-nonaene-κ$^4$N)iron(II)] hexafluorophosphate;

[acetonitrile(3,11-dibenzyl-2,12,14,20-tetramethyl-3,11,15,19,22,26-hexaazatricyclo [11.7.7.1$^{5,9}$]octacosa-1,5,7,9(28),12,14,19,21,26-nonaene-κ$^4$N)iron(II)] hexafluorophosphate;

[acetonitrile(3,11,14,20-tetramethyl-2,12-diphenyl-3,11,15,19,22,26-hexaazatricyclo [11.7.7.1$^{5,9}$]octacosa-1,5,7,9(28),12,14,19,21,26-nonaene-κ$^4$N)iron(II)] hexafluorophosphate;

[acetonitrile(3,11-dibenzyl-14,20-dimethyl-2,12-diphenyl-3,11,15,19,22,26-hexaazatricyclo[11.7.7.1$^{5,9}$]octacosa-1,5,7,9(28),12,14,19,21,26-nonaene-κ$^4$N)iron(II)] hexafluorophosphate;

[acetonitrile(2,12,14,20-tetramethyl-3,11,15,19,22,26-hexaazabicyclo[11.7.7]heptacosa-1,12,14,19,21,26-hexaene-κ$^4$N)cobalt(II)] hexafluorophosphate;

[acetonitrile(2,12,14,20-tetramethyl-3,11,15,19,22,26-hexaazatricyclo[11.7.7.1$^{5,9}$]octacosa-1,5,7,9(28),12,14,19,21,26-nonaene-κ$^4$N)cobalt(II)] hexafluorophosphate;

[acetonitrile(3,10,13,19-tetramethyl-3,10,14,18,21,25-hexaazabicyclo[10.7.7]hexacosa-1,11,13,18,20,25-hexaene-κ$^4$N)cobalt(II)] hexafluorophosphate;

[chloro(2,10-bis-dimethylamino-12,18-dimethyl-13,17,20,24-tetraazabicyclo[9.7.7]pentacosa-1,10,12,17,19,24-hexaene-κ$^4$N)iron(II)] hexafluorophosphate;

[chloro(2,11-bis-dimethylamino-13,19-dimethyl-14,18,21,25-tetraazabicyclo[10.7.7]hexacosa-1,11,13,18,20,25-hexaene-κ$^4$N)iron(II)] hexafluorophosphate;

[acetonitrile(12,18-dimethyl-2,10-bis-propylamino-13,17,20,24-tetraazabicyclo[9.7.7]pentacosa-1,10,12,17,19,24-hexaene-κ$^4$N)cobalt(II)] hexafluorophosphate; or

[acetonitrile(2,11-bis-dimethylamino-13,19-dimethyl-14,18,21,25-tetraazabicyclo[10.7.7]hexacosa-1,11,13,18,20,25-hexaene-κ$^4$N)cobalt(II)] hexafluorophosphate.

131. In a method for increasing the proportion of a molecular oxygen in a gaseous mixture, which comprises:

passing said gaseous mixture over one face of an immobilized liquid membrane containing an oxygen-complexing compound;

allowing molecular oxygen to diffuse selectively through said liquid membrane;

removing from adjacent the opposed face of said liquid membrane an oxygen-enriched gas containing a higher proportion of molecular oxygen than said gaseous mixture, the improvement which comprises using as said liquid membrane a liquid membrane containing a solution of salt comprising a cationic metal complex of the formula:

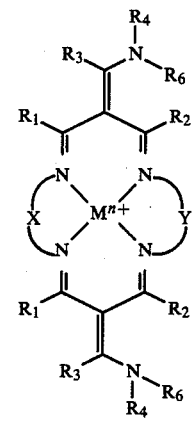

XVII wherein

M is Co, Fe, Cu or Mn;

$n^+$ is a positive oxidation state of M, n being not greater than 3;

X and Y are each independently an o-phenylene, ethylene, trimethylene, 2-(2-pyridyl)-trimethylene, 2-methyl substituted trimethylene, or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group consisting not more than about 17 carbon atoms, a benzyl group, a phenyl group, or a phenyl group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;

each $R_4$ independently is hydrogen, an alkyl group containing not more than about 4 carbon atoms, a cyanoalkyl group containing not more than about four carbon atoms, a phenyl group or a benzyl group;

each $R_6$ independently is hydrogen or a methyl group; or the two $R_6$ groups together form a nitrogen-nitrogen bridge, said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula:

—(CH$_2$)$_a$—G—(CH$_2$)$_b$— where a and b are each independently 1,2, or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, an imino group, or a methylimino group subject to the proviso that when G is a sulfur atom, a imino group or a methylimino group, the sum of a and b is at least 4;

or the two NR$_4$R$_6$ groups together form a bis-piperazino bridge of the formula:

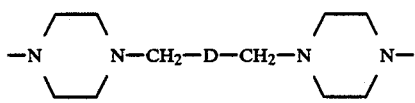

where D is a 1,3-phenylene group, a 1,4-phenylene group, a 1,4-phenylene group substituted by one or more methyl groups, a 9,10-anthracene group or a 2,6-pyridylene group, subject to the proviso that when the two R₃ groups do not form a carbon-carbon bridge, either the two R₆ groups must form a nitrogen-nitrogen bridge or the two NR₄R₆ groups must form a bis-piperazino bridge.

132. A method according to claim 131 wherein said salt comprises:

[(2,3,8,9,11,17-hexamethyl-3,8,12,16,19,23-hexaazabicyclo[8.7.7]tetracosa-1,9,11,16,18, 23-hexaene-$\kappa^4$N)cobalt(II)] hexafluorophosphate;

[(2,3,9,10,12,18-hexamethyl-3,9,13,17,20,24-hexaazabicyclo[9.7.7]-pentacosa-1,10,12, 17,19,24-hexaene-$\kappa^4$N)cobalt(II)] hexafluorophosphate;

[(2,3,10,11,13,19-hexamethyl-3,10,14,18,21,25-hexaazabicyclo[10.7.7]hexacosa-1,11,13,18, 20,25-hexaene-$\kappa^4$N)cobalt(II)] hexafluorophosphate;

[(3,8,11,17-tetramethyl-2,9-diphenyl-3,8,12,16,19,23-hexaazabicyclo[8.7.7]tetracosa-1,9,11,16,18,23-hexaene-$\kappa^4$N)cobalt(II)] hexafluorophosphate;

[(3,9,12,18-tetramethyl-2,10-diphenyl-3,9,13,17,20,24-hexaazabicyclo[9.7.7]pentacosa-1,10,12, 17,19,24-hexaene-78 $^4$N)cobalt(II)] hexafluorophosphate;

[(3,10,13,19-tetramethyl-2,11-diphenyl-3,10,14,18,21,25-hexaazabicyclo[10.7.7]hexacosa-1,11, 13,18,20,25-hexaene-$\kappa^4$N)cobalt(II)] hexafluorophosphate;

[(2,10,12,18-tetramethyl-3,9,13,17,20,24-hexaazabicyclo[9.7.7]pentacosa-1,10,12,17,19, 24-hexaene-$\kappa^4$N)cobalt(II)] hexafluorophosphate;

[(2,11,13,19-tetramethyl-3,10,14,18,21,25-hexaazabicyclo[10.7.7]hexacosa-1,11,13,18, 20,25-hexaene-$\kappa^4$N)cobalt(II)] hexafluorophosphate;

[(2,7,12,14,20-pentamethyl-3,7,11,15,19,22,26-heptaazabicyclo[11.7.7]heptacosa-1,12, 14,19,21,26-hexaene-$\kappa^4$N)cobalt(II)] hexafluorophosphate;

[(12,18-dimethyl-2,10-diphenyl-3,9,13,17,20,24-hexaazabicyclo[9.7.7]pentacosa-1,10, 12,17,19,24-hexaene-$\kappa^4$N)cobalt(II)] hexafluorophosphate;

[(13,19-dimethyl-2,11-diphenyl-3,10,14,18,21,25-hexaazabicyclo[10.7.7]hexacosa-1,11,13, 18,20,25-hexaene-$\kappa^4$N)cobalt(II)] hexafluorophosphate;

[(2,3,10,11,13,19-hexamethyl-23-(2-pyridyl)-3,10,14,18,21,25-hexaazabicyclo[10.7.7]hexacosa-1,11,13,18,20,25-hexaene-$\kappa^4$N)cobalt(II)] hexafluorophosphate;

[(12,18-dimethyl-2,10-bis-methylamino-13,17,20,24-tetraazabicyclo[9.7.7]pentacosa-1,10,12,17,19,24-hexaene-$\kappa^4$N)cobalt(II)] hexafluorophosphate; or

[(2,9,10,17,19,25,33,34-octamethyl-3,6,13,16,20,24,27,31-octaazapentacyclo[16.7.7.2$^{8,11}$.1$^{3,6}$.2$^{13,16}$]octatriaconta-1,8,10,17,19,24,26,31,33-nonaene-$\kappa^4$N)cobalt(II)] hexafluorophosphate.

133. In a method for increasing the proportion of a molecular oxygen in a gaseous mixture, which comprises:

passing said gaseous mixture over one face of an immobilized liquid membrane containing an oxygen-complexing compound;

allowing molecular oxygen to diffuse selectively through said liquid membrane;

removing from adjacent the opposed face of said liquid membrane an oxygen-enriched gas containing a higher proportion of molecular oxygen than said gaseous mixture, the improvement which comprises using as said liquid membrane a liquid membrane containing a solution of a salt comprising a cationic metal complex of the formula:

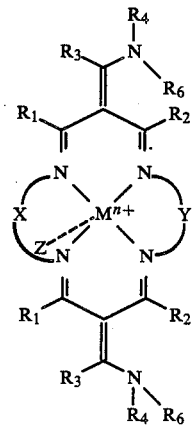

XVIIA wherein:

M is Co, Fe, Cu or Mn;

n+ is a positive oxidation state of M, n being not greater than 3;

X and Y are each independently an o-phenylene, ethylene, trimethylene, 2-(2-pyridyl)-trimethylene, 2-methyl substituted trimethylene or 2-(N-methyl-2-pyridino)-trimethylene group;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyul group substituted by a halogen atom or by one or two methoxy groups; or the two $R_3$ groups together form a carbon-carbon bridge, said carbon-carbon bridge comprising a polymethylene bridge containing from 7 to about 12 carbon atoms or an m- or p-xylylene group;

each $R_4$ independently is hydrogen, an alkyl group containing not more than about four carbon atoms, a phenyl group or a benzyl group;

$R_6$ independently is hydrogen or a methyl group, or the two $R_6$ groups together form a nitrogen-nitrogen bridge said nitrogen-nitrogen bridge comprising a polymethylene group containing from 4 to about 12 carbon atoms, a polymethylene group containing from 4 to about 12 carbon atoms and substituted by a methoxycarbonyl group, or a grouping of the formula —(CH$_2$)$_a$—G—(CH$_2$)$_b$— where a and b are each independently 1, 2 or 3 and G is a 1,3-phenylene group, a 1,4-phenylene group, a methoxy-substituted 1,4-phenylene group, a 9,9-fluorylene group, a 1,3-cyclohexylene group, a 1,4-cyclohexylene group, a sulfur atom, a imino group or a methylimino group, the sum of a and b is at least 4;

or the two $NR_4R_6$ groups together form a bis-piperazino bridge of the formula:

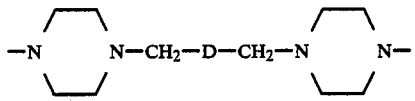

where D is a 1,3-phenylene group, a 1,4-phenylene group, a 1,4-phenylene group substituted by one or more methyl groups, a 9,10-anthracene group or a 2,6-pyridylene group subject to the proviso that when the two $R_3$ groups do not form a carbon-carbon bridge, either the two $R_6$ groups must form a nitrogen-nitrogen bridge or the two $NR_4R_6$ groups must form a bis-piperazino bridge; and Z is an electron donor selected from the group consisting of the halide ions, cyanate, thiocyanate, azide, acetonitrile, water, an alkanol containing not more than about five carbon atoms, pyridine, 4-aminopyridine, imidazole and N-methylimidazole.

134. A method according to claim 133 wherein said salt comprises:

[chloro(2,3,11,12,14,20-hexamethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-n-heptyl-3,11,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)iron(II)] hexafluorophosphate;

[chloro(2,12-di-p-methoxyphenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-p-chlorophenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[chloro(2,12-di-p-fluorophenyl-3,11,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[acetonitrile(14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)cobalt(II)] hexafluorophosphate;

[acetonitrile(2,3,11,12,14,20-hexamethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[acetonitrile (3,11-dibenzyl-2,12,14,20-tetramethyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[acetonitrile(3,11,14,20-tetramethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[acetonitrile(3,11-dibenzyl-14,20-dimethyl-2,12-diphenyl-3,11,15,19,22,26-hexaazatricyclo[11.7.7.1$^{5,9}$]octacosa-1,5,7,9(28),12,14,19,21,26-nonaene-$\kappa^4$N)iron(II)] hexafluorophosphate;

[acetonitrile(2,12,14,20-tetramethyl-3,11,15,19,22,26-hexaazabicyclo[11.7.7]heptacosa-1,12,14,19,21,26-hexaene-$\kappa^4$N)cobalt(II)] hexafluorophosphate;

[acetonitrile(2,12,14,20-tetramethyl-3,11,15,19,22,26-hexaazatricyclo-[11.7.7.1$^{5,9}$]octacosa-1,5,7,9(28),12,14,19,21,26-nonaene-$\kappa^4$N)cobalt(II)] hexafluorophosphate;

[acetonitrile(3,10,13,19-tetramethyl-3,10,14,18,21,25-hexaazabicyclo[10.7.7]hexacosa-1,11,13,18,20,25-hexaene-$\kappa^4$N)cobalt(II)] hexafluorophosphate;

[chloro(2,10-bis-dimethylamino-12,18-dimethyl-13,17,20,24-tetraazabicyclo[9.7.7]pentacosa-1,10,12,17,19,24-hexaene-$\kappa^4$N)iron(II)] hexafluorophosphate;

[chloro(2,11-bis-dimethylamino13,19dimethyl-14,18,21,25-tetraazabicyclo[10.7.7]hexacosa-1,11,13,18,20,25-hexaene-$\kappa^4$N)iron(II)] hexafluorophosphate;

[acetonitrile(12,18-dimethyl-2,10-bis-propylamino-13,17,20,24-tetraazabicyclo[9.7.7]pentacosa-1,10,12,17,19,24-hexaene-$\kappa^4$N)cobalt(II)] hexafluorophosphate; or

[acetonitrile(2,11-bis-dimethylamino-13,19-dimethyl-14,18,21,25-tetraazabicyclo[10.7.7]hexacosa-1,11,13,18,20,25-hexaene-$\kappa^4$N)cobalt(II)] hexafluorophosphate.

135. A process for the separation and purification of oxygen and nitrogen comprising:

(a) bringing an atmospheric air feed stream into contact with a solution containing a solvent or solvent mixture, an axial base and an oxygen carrier, said solvent or solvent mixture being capable of dissolving the axial base and the oxygen carrier when they are present together, when they are present together, said axial base being capable of providing a coordinating atom to the oxygen carrier, and said oxygen carrier being a metal-containing complex which is a salt of a cation having the structure

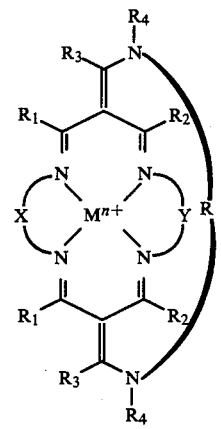

I wherein:

M is a metal selected from cobalt, iron, copper, nickel, manganese, ruthenium or rhodium;

n+ is a positive oxidation state of M, n being not greater than 3;

each $R_1$ independently is hydrogen or a methyl group;

each $R_2$ independently is hydrogen or a methyl group;

each R3 independently is hydrogen, an alkyl group containing not more than about 17 carbon atoms, a benzyl group, a phenyl group, or a phenyl group substituted by a halogen atom or by one or two methoxy groups;

each R4 independently is hydrogen, an alkyl group containing not more than about 4 carbon atoms, a cyanoalkyl group containing not more than about 4 carbon atoms, a phenyl group or a benzyl group;

R is a polymethylene group containing from about 4 to about 12 carbon atoms, or a grouping of the formula $-(CH_2)_a-G-(CH_2)_b-$ where a and b are each independently 1, 2 or 3 and G is a 1,3-phenylene group, a 1,4-phenylene group, a methoxy-substituted-1,4-phenylene group, a 9,9-fluorylene group, an imino group or a methylimino group, subject to the proviso that, when G is an imino group or a methylimino group, the sum of a and b is at least 4; and X and Y are each independently an o-phenylene, ethylene, trimethylene, 2-(2-pyridyl)-trimethylene, 2-methyl-substituted-trimethylene or 2-(N-methyl-2-2 pyridino)-trimethylene group, said solution adsorbing oxygen from said atmospheric air feed stream;

(b) collecting nitrogen from the atmospheric air feed stream after the oxygen has been adsorbed;

(c) desorbing oxygen from said solution to a gaseous product stream; and (d) collecting oxygen from the product stream after the oxygen has been desorbed.

136. A process for the separation and purification of oxygen comprising:

(a) bringing a gaseous, oxygen-containing feed stream into contact with a solution containing a solvent or solvent mixture, an axial base and an oxygen carrier, said solvent mixture being capable of dissolving the axial base and the oxygen carrier when they are present together, said axial base being capable of providing a coordinating atom to the oxygen carrier, and said oxygen carrier being a metal-containing complex which is a salt of a cation having the formula

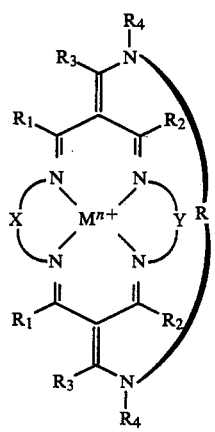

I wherein:

M is a metal selected from cobalt, iron, copper, nickel, manganese, ruthenium or rhodium;

n+ is a positive oxidation state of M, n being not greater than 3;

each R1 independently is hydrogen or a methyl group;

each R2 independently is hydrogen or a methyl group;

each R3 independently is hydrogen, an alkyl group containing not more than about 17 carbon atoms, a benzyl group, a phenyl group, or a phenyl group substituted by a halogen atom or by one or two methoxy groups;

each R4 independently is hydrogen, an alkyl group containing not more than about 4 carbon atoms, a cyanoalkyl group containing not more than about 4 carbon atoms, a phenyl group or a benzyl group;

R is a polymethylene group containing from about 4 to about 12 carbon atoms, or a grouping of the formula $-(CH_2)_a-G-(CH_2)_b-$ where a and b are each independently 1, 2 or 3 and G is a 1,3-phenylene group, a 1,4-phenylene group, a methoxy-substituted-1,4-phenylene group, a 9,9-fluorylene group, an imino group or a methylimino group, subject to the proviso that when G is an imino group or a methylimino group, the sum of a and b is at least 4; and X and Y are each independently an o-phenylene, ethylene, trimethylene, 2-(2-pyridyl)-trimethylene, 2-methyl-substituted-trimethylene or 2-(N-methyl-2-2-pyridino)-trimethylene group, said solution adsorbing oxygen from said gaseous oxygen-containing feed stream;

(b) desorbing oxygen from said solution to a gaseous product stream; and (c) collecting oxygen from the product stream after the oxygen has been desorbed.

137. The process of claim 135 wherein said desorption of oxygen is accomplished by bringing said solution into contact with a gaseous product stream with an oxygen partial pressure substantially less than that of said feed stream.

138. The process of claim 136 wherein said desorption of oxygen is accomplished by bringing said solution into contact with a gaseous product stream with an oxygen partial pressure substantially less than that of said feed stream.

139. The process of claim 135 wherein said desorption of oxygen is accomplished by heating said solution and bringing it into contact with said gaseous product stream.

140. The process of claim 136 wherein said desorption of oxygen is accomplished by heating said solution and bringing it into contact with said gaseous product stream.

141. The process of claim 139 wherein the temperature of said feed stream is between about −41.5° C. and +40° C. and the temperature of the product stream is at least about 30° C. higher than the temperature of the product stream.

142. The process of claim 140 wherein the temperature of said feed stream is between about −41.5° C. and +40° C. and the temperature of the product stream is at least about 30° C. higher than the temperature of the product stream.

143. The process of claim 135 wherein the metal is cobalt.

144. The process of claim 136 wherein the metal is cobalt.

145. The process of claim 137 wherein the oxygen partial pressure of the product steam is at least about 110 mm. Hg. less than the partial pressure of the feed stream.

146. The process of claim 138 wherein the oxygen partial pressure of the product steam is at least about 110 mm. Hg. less than the partial pressure of the feed stream.

147. The process of claim 145 wherein the oxygen partial pressure of the feed stream is substantially atmospheric.

148. The process of claim 146 wherein the oxygen partial pressure of the feed stream is substantially atmospheric.

149. The process of claim 136 wherein the rates of absorption of oxygen into or desorption of oxygen are increased by agitating said solution or by increasing the interfacial area between said feed stream and said solution, said interfacial area being increased by any of the following methods:
   (a) bubbling said feed stream through said solution;
   (b) spraying said solution through said feed stream; or
   (c) contacting said solution with said feed stream in a packed column.

150. The process of claim 136 wherein the rates of absorption of oxygen into or desorption of oxygen are increased by agitating said solution or by increasing the interfacial area between said feed stream and said solution, said interfacial area being increased by any of the following methods:
   (a) bubbling said feed stream through said solution;
   (b) spraying said solution through said feed stream; or
   (c) contacting said solution with said feed stream in a packed column.

151. The process of claim 135 conducted at a temperature of between about −41.5° C. and +40° C.

152. The process of claim 136 conducted at a temperature of between about −41.5° C. and +40° C.

153. The process of claim 135 wherein the solvent is selected from nitriles, amines, water and mixtures thereof, and
   the axial base is selected from imidazoles and pyridines.

154. The process of claim 136 wherein the solvent is selected from nitriles, amines, water and mixtures thereof, and
   the axial base is selected from imidazoles and pyridines.

155. The process of claim 153 wherein the solvent is dimethylformamide and the axial base is selected from at least one of 1-methylimidazole and pyridine.

156. The process of claim 154 wherein the solvent is dimethylformamide and the axial base is selected from at least one of 1-methylimidazole and pyridine.

157. The process of claim 155 wherein the oxygen carrier is a salt of a cation having the formula

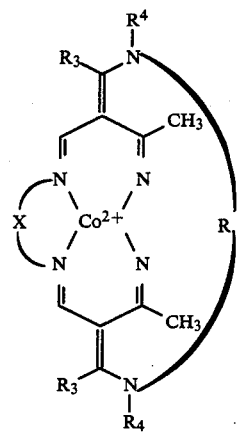

wherein:
   R is as defined in claim 135;
   $R_3$ is methyl or benzyl; and
   $R_4$ is hydrogen or methyl;
   X is an ethylene or trimethylene group.

158. The process of claim 156 wherein the oxygen carrier is a salt of a cation having the formula

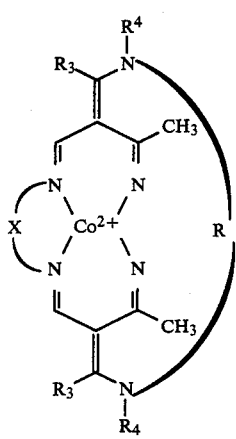

wherein:
   R is as defined in claim 151;
   $R_3$ is methyl or benzyl; and
   $R_4$ is hydrogen or methyl;
   X is an ethylene or trimethylene group.

159. A solution useful for the separation of oxygen and nitrogen from atmospheric air comprising a solvent or solvent mixture, an axial base and an oxygen carrier, said solvent or solvent mixture being capable of dissolving said axial base and said oxygen carrier when they are present together, said axial base being capable of providing a coordinating atom to the oxygen carrier, and said oxygen carrier being a metal-containing complex which is a salt of a cation having the structure wherein:

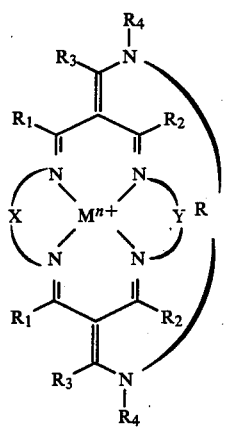

I

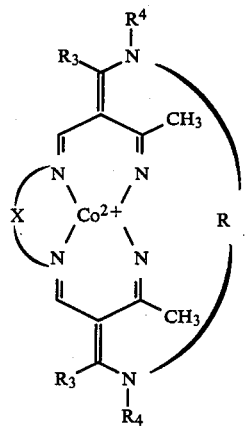

M is a metal selected from cobalt, iron, copper, nickel, manganese, ruthenium or rhodium;

n+ is a positive oxidation state of M, n being not greater than 3;

each $R_1$ independently is hydrogen or a methyl group;

each $R_2$ independently is hydrogen or a methyl group;

each $R_3$ independently is hydrogen, an alkyl group containing not more than about 17 carbon atoms, a benzyl group, a phenyl group, or a phenyl group substituted by a halogen atom or by one or two methoxy groups;

each $R_4$ independently is hydrogen, an alkyl group containing not more than about 4 carbon atoms, a cyanoalkyl group containing not more than about 4 carbon atoms, a phenyl group or a benzyl group;

R is a polymethylene group containing from about 4 to about 12 carbon atoms, or a grouping of the formula —$(CH_2)_a$—G—$(CH_2)_b$— where a and b are each independently 1, 2 or 3 and G is a 1,3-phenylene group, a 1,4-phenylene group, a methoxy-substituted-1,4-phenylene group, a 9,9-fluorylene group, an imino group or a methylimino group, subject to the proviso that when G is an imino group or a methylimino group, the sum of a and b is at least 4; and X and Y are each independently an o-phenylene, ethylene, trimethylene, 2-(2-pyridyl)-trimethylene, 2-methyl-substituted-trimethylene or 2-(N-methyl-2-2 pyridino)-trimethylene group.

160. The solution of claim 159 wherein the solvent is selected from nitriles, amines, water and mixtures thereof, and the axial base is selected from imidazoles and pyridines.

161. The solution of claim 160 wherein the solvent is dimethylformamide, the axial base is selected from at least one of 1-methylimidazole and pyridine, and the oxygen carrier is a salt of a cation having the formula wherein:

R is as defined in claim 135;

$R_3$ is methyl or benzyl; and $R_4$ is hydrogen or methyl;

X is an ethylene or trimethylene group.

162. A process for the separation and purification of oxygen and nitrogen comprising:

(a) bring an atmospheric air feed stream into contact with a solution containing a solvent or solvent mixture, an axial base and an oxygen carrier when they are present together, said axial ase being capable of providing a coordinating atom to the oxygen carrier, and said oxygen carrier being a metal-containing complex which is a salt of a cation having the structure

III wherein:

M is a metal selected from cobalt, iron, copper, nickel, manganese, ruthenium or rhodium;

n+is a positive oxidation state of M, n being not greater than 3;

each $R_1$ independently is hydrogen or a methyl group;

each $R_2$ independently is hydrogen or a methyl group;

each $R_4$ independently is hydrogen, an alkyl group containing not more than about 4 carbon atoms, a cyanoalkyl group containing not more than about 4 carbon atoms, a phenyl group or a benzyl group;

R5 is a polymethylene group containing from 7 to about 12 carbon atoms or a m- or p-xylylene group; and each R6 independently is hydrogen or a methyl group.

163. A process for the separation and purification of oxygen comprising:

bringing a gaseous, oxygen-containing feed stream into contact with a solution containing a solvent or solvent mixture, an axial base and an oxygen carrier, said solvent mixture being capable of dissolving the axial base and the oxygen carrier when they are present together, said axial base being capable of providing a coordinating atom to the oxygen carrier, and said oxygen carrier being a metal-containing complex which is a salt of a cation having the formula

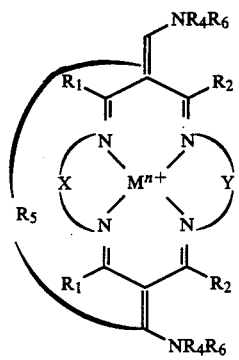

III wherein:

M is a metal selected from cobalt, iron, copper, nickel, manganese, ruthenium or rhodium;

$n+$ is a positive oxidation state of M, n being not greater than 3;

each $R_1$ independently is hydrogen or a methyl group;

each $R_2$ independently is hydrogen or a methyl group;

each $R_4$ independently is hydrogen, an alkyl group containing not more than about 4 carbon atoms, a cyanoalkyl group containing not more than about 4 carbon atoms, a phenyl group or a benzyl group;

$R_5$ is a polymethylene group containing from 7 to about 12 carbon atoms or a m- or p-xylylene group; and each $R_6$ independently is hydrogen or a methyl group.

164. The process of claim 162 wherein said desorption of oxygen is accomplished by bringing said solution into contact with a gaseous product stream with an oxygen partial pressure substantially less than that of said feed stream.

165. The process of claim 163 wherein said desorption of oxygen is accomplished by bringing said solution into contact with a gaseous product stream with an oxygen partial pressure substantially less than that of said feed stream.

166. The process of claim 162 wherein said desorption of oxygen is accomplished by heating said solution and bringing it into contact with said gaseous product stream.

167. The process of claim 162 wherein said desorption of oxygen is accomplished by heating said solution and bringing it into contact with said gaseous product stream.

168. The process of claim 166 wherein the temperature of said feed stream is between about −41.5° C. and +40° C. and the temperature of the product stream is at least about 30° C. higher than the temperature of the product stream.

169. The process of claim 167 wherein the temperature of said feed stream is between about −41.5° C. and +40° C. and the temperature of the product stream is at least about 30° C. higher than the temperature of the product stream.

170. The process of claim 162 wherein the metal is cobalt.

171. The process of claim 163 wherein the metal is cobalt.

172. The process of claim 164 wherein the oxygen partial pressure of the product steam is at least about 110 mm. Hg. less than the partial pressure of the feed stream.

173. The process of claim 165 wherein the oxygen partial pressure of the product steam is at least about 110 mm. Hg. less than the partial pressure of the feed stream.

174. The process of claim 164 wherein the oxygen partial pressure of the feed stream is substantially atmospheric.

175. The process of claim 165 wherein the oxygen partial pressure of the feed stream is substantially atmospheric.

176. The process of claim 162 wherein the rates of absorption of oxygen into or desorption of oxygen are increased by agitating said solution or by increasing the interfacial area between said feed stream and said solution, said interfacial area being increased by any of the following methods:

(a) bubbling said feed stream through said solution;
(b) spraying said solution through said feed stream; or
(c) contacting said solution with said feed stream in a packed column.

177. The process of claim 163 wherein the rates of absorption of oxygen into or desorption of oxygen are increased by agitating said solution or by increasing the interfacial area between said feed stream and said solution, said interfacial area being increased by any of the following methods:

(a) bubbling said feed stream through said solution;
(b) spraying said solution through said feed stream; or
(c) contacting said solution with said feed stream in a packed column.

178. The process of claim 162 conducted at a temperature of between about −41.5° C. and +40° C.

179. The process of claim 163 conducted at a temperature of between about −41.5° C. and +40° C.

180. The process of claim 162 wherein the solvent is selected from nitriles, amines, water and mixtures thereof, and the axial base is selected from imidazoles and pyridines.

181. The process of claim 163 wherein the solvent is selected from nitriles, amines, water and mixtures thereof, and the axial base is selected from imidazoles and pyridines.

182. The process of claim 180 wherein the solvent is dimethylformamide and the axial base is selected from at least one of 1-methylimidazole and pyridine.

183. The process of claim 181 wherein the solvent is dimethylformamide and the axial base is selected from at least one of 1-methylimidazole and pyridine.

184. A solution useful for the separation of oxygen and nitrogen from atmospheric air comprising a solvent or solvent mixture, an axial base and an oxygen carrier, said solvent or solvent mixture being capable of dissolving said axial base and said oxygen carrier when they are present together, said axial base being capable of providing a coordinating atom to the oxygen carrier, and said oxygen carrier being a metal-containing complex which is a salt of a cation having the structure

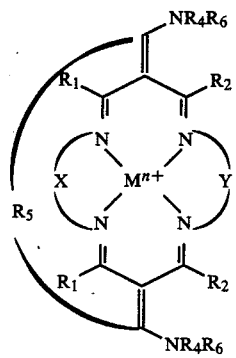

III wherein:
  M is a metal selected from cobalt, iron, copper, nickel, manganese, ruthenium or rhodium;
  n+ is a positive oxidation state of M, n being not greater than 3;
  each $R_1$ independently is hydrogen or a methyl group;
  each $R_2$ independently is hydrogen or a methyl group;
  each $R_4$ independently is hydrogen, an alkyl group containing not more than about 4 carbon atoms, a cyanoalkyl group containing not more than about 4 carbon atoms, a phenyl group or a benzyl group;
  $R_5$ is a polymethylene group containing from 7 to about 12 carbon atoms or a m- or p-xylylene group; and
  each $R_6$ independently is hydrogen or a methyl group.

185. The solution of claim 184 wherein the solvent is selected from nitriles, amines, water and mixtures thereof, and the axial base is selected from imidazoles and pyridines.

186. A solution useful for the separation of oxygen and nitrogen from atmospheric air comprising a solvent or solvent mixture, an axial base and an oxygen carrier, said solvent or solvent mixture being capable of dissolvent the axial based and the oxygen carrier when they are present together, said axial base being capable of providing a coordinating atom to the oxygen carrier, and said oxygen carrier being a mutual-containing complex having any of the structures:

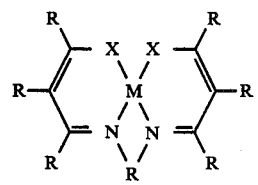

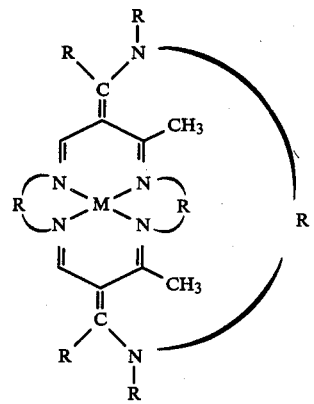

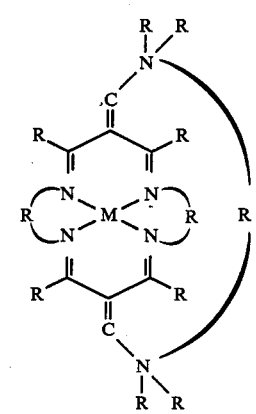

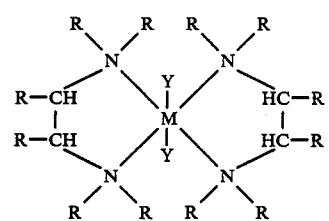

wherein
  M is metal selected from cobalt, iron, copper, nickel, manganese, ruthenium or rhodium; X is —O—, —S—

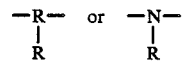

R is hydrogen alkyl, aryl, halogen, alkoxy or a nitrogen-containing moiety; and Y is halide, nitrate, thiocyanate or cyanide.

187. A process for the separation and purification of oxygen and nitrogen comprising:
  (a) bringing atmospheric air into contact with a membrane, said membrane separating said atmospheric air into a feed stream on one side of said membrane and a product stream on the other side of said membrane, (b) maintaining the oxygen partial pressure on the product-stream side of said membrane lower than the oxygen partial pressure on the feed-stream side of said membrane, (c) collecting oxygen from the product-stream side of said membrane, (d) said membrane comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

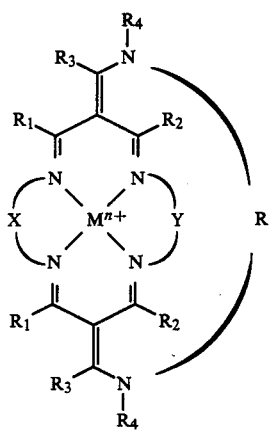

I

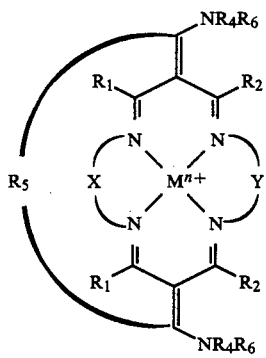

III wherein
M is a metal selected from cobalt, iron, copper, nickel, manganese, ruthenium or rhodium;
n+ is a positive oxidation state of M, n being not greater than 3: in Formula I, each $R_1$ is hydrogen and each $R_2$ is methyl, while in Formula III, each $R_1$ and $R_2$ independently is hydrogen or a methyl group;
each $R_3$ independently is hydrogen, alkyl or aryl;
each $R_4$ independently is hydrogen, or an alkyl or aryl group;
R is an alkylene or arylene group or a nitrogen-containing moiety;
$R_5$ is an alkylene or arylene group;
each $R_6$ independently is hydrogen or an alkyl group; and
X and Y are each independently an alkylene or arylene group or a nitrogen-containing moiety.

188. A process for the separation and purification of oxygen comprising:

(a) bringing a gaseous oxygen-containing stream into contact with a membrane, said membrane separating said gaseous oxygen-containing stream into a feed stream on one side of said membrane and a product stream on the other side of said membrane, (b) maintaining the oxygen partial pressure on the product-stream side of said membrane lower than the oxygen partial pressure on the feed-stream side of said membrane, (c) collecting oxygen from the product-stream side of said membrane, (d) said membrane comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

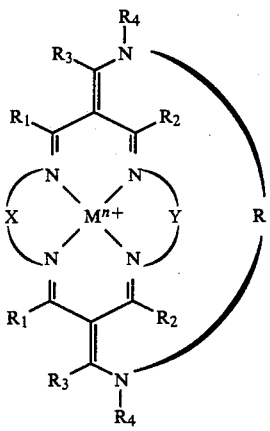

I

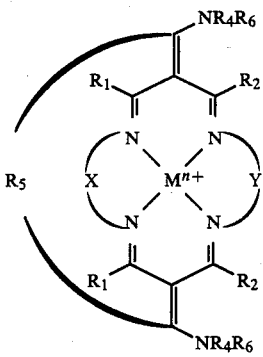

III wherein
m is a metal selected from cobalt, iron, copper, nickel, manganese, ruthenium or rhodium;
n+ is a positive oxidation state of M, n being not greater than 3: in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

189. A process for the separation and purification of oxygen and nitrogen comprising:

(a) bringing atmospheric air into contact with a membrane, said membrane separating said atmospheric air into a feed stream on one side of said membrane and a product stream on the other side of said membrane, (b) maintaining the temperature on the product-stream side of said membrane higher than the temperature on the feed-stream side of said membrane, (c) collecting oxygen from the product-stream side of said membrane, (d) said membrane comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

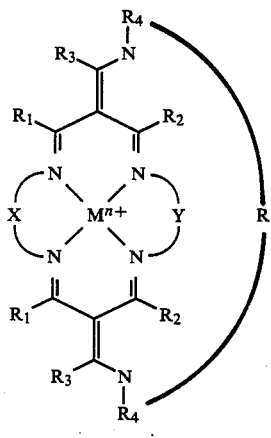

I

-continued

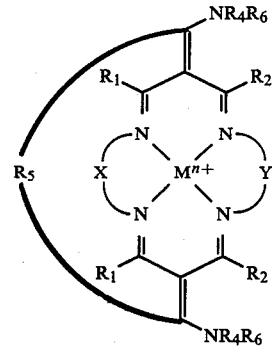

III wherein

M is a metal selected from cobalt, iron, copper, nickel, manganese, ruthenium or rhodium;

n+ is a positive oxidation state of M, n being not greater than 3: in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

190. A process for the separation and purification of oxygen comprising:

(a) bringing a gaseous oxygen-containing stream into contact with a membrane, said membrane separating said gaseous oxygen-containing stream into a feed stream on one side of said membrane and a product stream on the other side of said membrane, (b) maintaining the temperature on the product-stream side of said membrane higher than the temperature on the feed-stream side of said membrane, (c) collecting oxygen from the product-stream side of said membrane, (d) said membrane comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

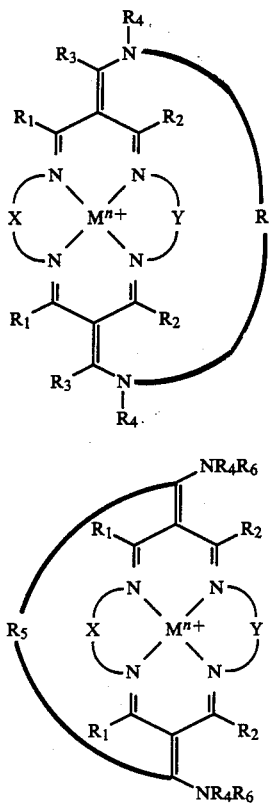

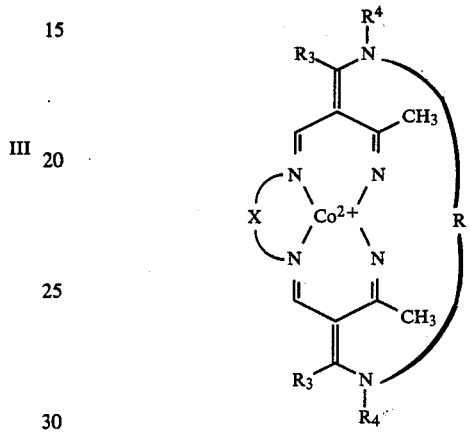

wherein

M is a metal selected from cobalt, iron, copper, nickel, manganese, ruthenium or rhodium;

$n^+$ is a positive oxidation state of M, n being not greater than 3: in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

191. The process of claim 187 or 188 wherein the oxygen partial pressure on the feed-stream side of said membrane is substantially atmospheric or less than atmospheric.

192. The process of claim 187 or 188 wherein the oxygen partial pressure on the feed-stream side of said membrane is at least about 10 mm Hg high than atmospheric.

193. The process of claim 187 or 188 conducted at a temperature of between about $-50°$ C. and $+100°$ C.

194. The process of claim 189 or 190 wherein the temperature on the feed-stream side of said membrane is between about $-50°$ C and $+95°$ C.

195. The process of claim 187, 188, 189 or 190 wherein the metal is cobalt.

196. The process of claim 187 or 188 wherein the solvent or solvent mixture is selected from nitriles, amines, water and mixtures thereof, and the axial base is selected from imidazoles and pyridines.

197. The process of claim 187 or 188 wherein the solvent is dimethylformamide, and the axial base is selected from at least one of 1-methylimidazole and pyridine.

198. The process of claim 187 or 188 wherein the oxygen carrier is

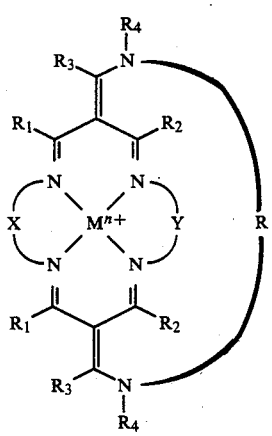

wherein

R is as defined in claim 203;

$R_4$ is hydrogen or methyl;

$R_3$ is methyl or benzyl; and

X is alkyl containing 2 to 3 carbon atoms.

199. A membrane useful for the separation of oxygen and nitrogen from atmospheric air comprising a membrane support, said membrane support containing a solvent or solvent mixture, axial base, and oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures -continued

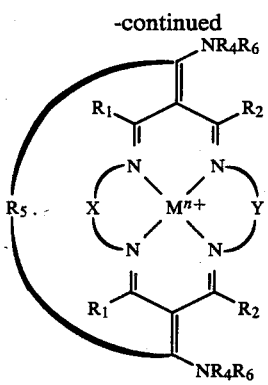

wherein
M is a metal selected from cobalt, iron, copper, nickel, manganese, ruthenium or rhodium;

$n^+$ is a positive oxidation state of M, n being not greater than 3:

in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

200. The membrane of claim 199 wherein the solvent or solvent mixture is selected from nitriles, amines, water and mixtures thereof, and the axial base is selected from imidazoles and pyridines.

201. The membrane of claim 199 wherein the solvent is dimethylformamide, the axial base is selected from at least one of 1-methylimidazole and pyridine, and the oxygen carrier is

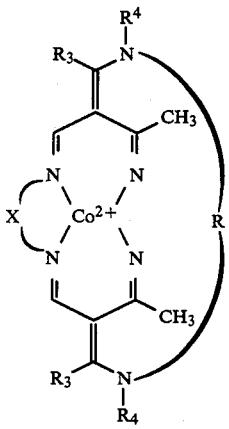

wherein
R is as defined in claim 203;
$R_4$ is hydrogen or methyl;
$R_3$ is methyl or benzyl; and
X is alkyl containing 2 to 3 carbon atoms.

202. The membrane of claim 199 wherein the solvent or solvent mixture contains an additive selected from the group consisting of less than or equal to 20% by weight of water or an inorganic acid or base.

203. Apparatus for the separation and purification of oxygen and nitrogen comprising:
 (a) membrane means,
 (b) means for bringing atmospheric air into contact with said membrane means, said membrane means separating said atmospheric air into a feed stream on one side of said membrane means and a product stream on the other side of said membrane means,
 (c) means for maintaining the oxygen partial pressure on the product-stream side of said membrane means lower than the oxygen partial pressure on the feed-stream side of said membrane means,
 (d) means for collecting oxygen from the product-stream side of said membrane means,
 (e) said membrane means comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

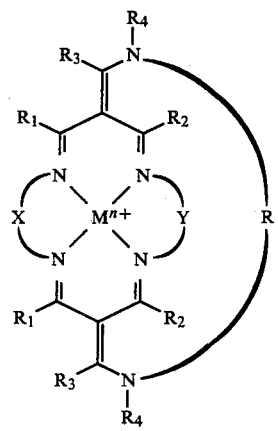

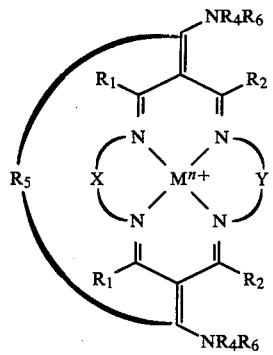

wherein
M is a metal selected from cobalt, iron, copper, nickel, manganese, ruthenium or rhodium;
$n^+$ is a positive oxidation state of M, n being not greater than 3:

in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

204. Apparatus for the separation and purification of oxygen comprising:

(a) a membrane means, (b) means for bringing a gaseous oxygen-containing stream into contact with said membrane means, said membrane means separating said gaseous oxygen-containing stream into a feed stream on one side of said membrane means and a product stream on the other side of said membrane means, (c) means for maintaining the oxygen partial pressure on the product-stream side of said membrane means lower than the oxygen partial pressure on the feed-stream side of said membrane means.

(d) means for collecting oxygen from the product-stream side of said membrane means, (e) said membrane means comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

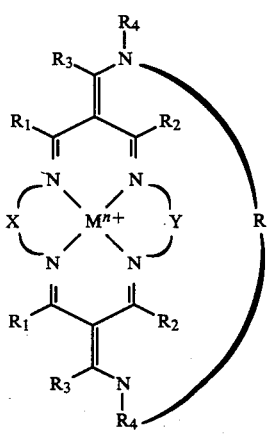

I

-continued

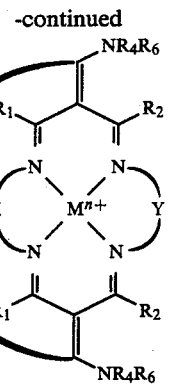

III wherein

M is a metal selected from cobalt, iron, copper, nickel, manganese, ruthenium or rhodium;

n+ is a positive oxidation state of M, n being not greater than 3:

in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group, and

X and Y are each independently an alkylene or arylene group or a nitrogen-containing moiety.

205. Apparatus for the separation and purification of oxygen and nitrogen comprising:

(a) membrane means, (b) means for bringing atmospheric air into contact with said membrane means, said membrane means separating said atmospheric air into a feed stream on one side of said membrane means and a product stream on the other side of said membrane means, (c) temperature maintenance means for maintaining the temperature on the product-stream side of said membrane means higher than the temperature on the feed-stream side of said membrane means, (d) means for collecting oxygen from the product-stream side of said membrane means, (e) said membrane means comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures

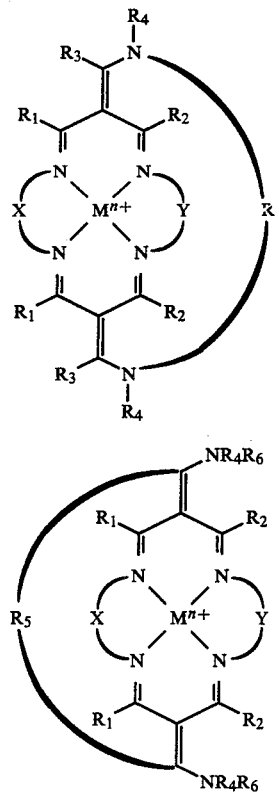

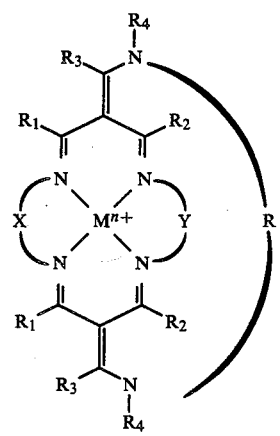

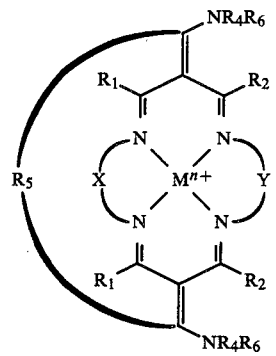

wherein

M is a metal selected from cobalt, iron, copper, nickel, manganese, ruthenium or rhodium;

$n^+$ is a positive oxidation state of M, n being not greater than 3:

in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

206. Apparatus for the separation and purification of oxygen comprising:

(a) membrane means, (b) means for bringing a gaseous oxygen-containing stream into contact with said membrane means, said membrane means separating said gaseous oxygen-containing stream into a feed stream on one side of said membrane means and a product stream on the other side of said membrane means, (c) temperature maintenance means for maintaining the temperature on the product-stream side of said membrane means higher than the temperature on the feed-stream side of said membrane means, (d) means for collecting oxygen from the product-stream side of said membrane means, (e) said membrane means comprising a membrane support, said membrane support containing a solvent or solvent mixture, an axial base, and an oxygen carrier, said solvent or solvent mixture, axial base, and oxygen carrier being in the liquid phase when present together, said solvent or solvent mixture being capable of dissolving the axial base and the oxygen carrier when they are present together, said axial base being capable of providing a coordinating atom to the oxygen carrier, and said oxygen carrier being a metal-containing complex having either of the structures wherein M is a metal selected from cobalt, iron, copper, nickel, manganese, ruthenium or rhodium;

$n^+$ is a positive oxidation state of M, n being not greater than 3:

in Formula I, each $R_1$ is hydrogen and each $R_2$ is methyl, while in Formula III, each $R_1$ and $R_2$ independently is hydrogen or a methyl group;

each $R_3$ independently is hydrogen, alkyl or aryl;

each $R_4$ independently is hydrogen, or an alkyl or aryl group;

R is an alkylene or arylene group or a nitrogen-containing moiety;

$R_5$ is an alkylene or arylene group;

each $R_6$ independently is hydrogen or an alkyl group; and

X and Y are each independently an alkylene or arylene group or a nitrogen-containing moiety.

207. The apparatus of claim 203, 204, 205 or 206 wherein the metal is cobalt.

208. The apparatus of claim 203, 204, 205 or 206 wherein the solvent or solvent mixture is dimethylformamide, the axial base is selected from at least one of 1-methylimidazole and pyridine, and the oxygen carrier is
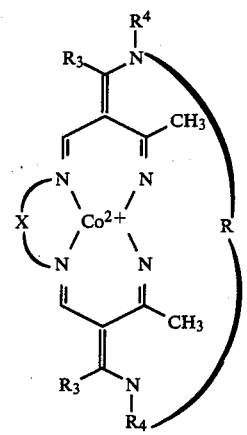
wherein
R is as defined in claim 203;
$R_4$ is hydrogen or methyl;
$R_3$ is methyl or benzyl; and
X is alkyl containing 2 to 3 carbon atoms.
* * * * *